United States Patent
Adamovich et al.

(10) Patent No.: US 10,749,114 B2
(45) Date of Patent: Aug. 18, 2020

(54) ORGANIC ELECTROLUMINESCENT MATERIALS AND DEVICES

(71) Applicant: Universal Display Corporation, Ewing, NJ (US)

(72) Inventors: Vadim Adamovich, Yardley, PA (US); Hitoshi Yamamoto, Pennington, NJ (US); Ting-Chih Wang, Lawrenceville, NJ (US); Michael S. Weaver, Princeton, NJ (US); Chuanjun Xia, Lawrenceville, NJ (US); Bert Alleyne, Newtown, PA (US); Pierre-Luc T. Boudreault, Pennington, NJ (US); Alexey Borisovich Dyatkin, Ambler, PA (US); Scott Joseph, Ewing, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 16/047,123

(22) Filed: Jul. 27, 2018

(65) Prior Publication Data
US 2018/0342680 A1 Nov. 29, 2018

Related U.S. Application Data

(62) Division of application No. 14/253,505, filed on Apr. 15, 2014, now Pat. No. 10,074,806.

(60) Provisional application No. 61/940,603, filed on Feb. 17, 2014, provisional application No. 61/920,544, filed on Dec. 24, 2013, provisional application No. 61/894,160, filed on Oct. 22, 2013, provisional application No. 61/874,444, filed on Sep. 6, 2013, provisional application No. 61/867,858, filed on Aug. 20, 2013.

(51) Int. Cl.
| | | |
|---|---|---|
| H01L 51/00 | (2006.01) | |
| C07F 15/00 | (2006.01) | |
| C07D 403/04 | (2006.01) | |
| C07D 403/10 | (2006.01) | |
| C07D 471/04 | (2006.01) | |
| H01L 51/50 | (2006.01) | |
| C07D 215/06 | (2006.01) | |
| C07D 401/04 | (2006.01) | |
| C07D 403/14 | (2006.01) | |
| C07D 487/04 | (2006.01) | |
| C07D 491/048 | (2006.01) | |
| C07D 495/04 | (2006.01) | |
| C07D 213/06 | (2006.01) | |
| C07D 213/22 | (2006.01) | |
| C07D 213/26 | (2006.01) | |
| H01L 51/56 | (2006.01) | |

(52) U.S. Cl.
CPC ........ *H01L 51/0054* (2013.01); *C07D 213/06* (2013.01); *C07D 213/22* (2013.01); *C07D 213/26* (2013.01); *C07D 215/06* (2013.01); *C07D 401/04* (2013.01); *C07D 403/04* (2013.01); *C07D 403/10* (2013.01); *C07D 403/14* (2013.01); *C07D 471/04* (2013.01); *C07D 487/04* (2013.01); *C07D 491/048* (2013.01); *C07D 495/04* (2013.01); *C07F 15/0033* (2013.01); *H01L 51/0052* (2013.01); *H01L 51/0067* (2013.01); *H01L 51/0071* (2013.01); *H01L 51/0072* (2013.01); *H01L 51/0085* (2013.01); *H01L 51/5012* (2013.01); *H01L 51/5016* (2013.01); *H01L 51/56* (2013.01)

(58) Field of Classification Search
CPC .................................................. C07F 15/0033
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 5,981,092 | A | 11/1999 | Arai et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |

(Continued)

FOREIGN PATENT DOCUMENTS

| | | |
|---|---|---|
| CN | 101657518 | 2/2010 |
| CN | 102898477 | 1/2013 |

(Continued)

OTHER PUBLICATIONS

Chang, Mei-Ying et al., "High-Brightness White Organic Light-Emitting Diodes Featuring a Single Emission Layer," Journal of the Electrochemical Society (2009), 156(1), J1-J5.

(Continued)

*Primary Examiner* — Joseph R Kosack
(74) *Attorney, Agent, or Firm* — Duane Morris LLP

(57) ABSTRACT

A composition formed of a mixture of two compounds having similar thermal evaporation properties that are premixed into an evaporation source that can be used to co-evaporate the two compounds into an emission layer in OLEDs via vacuum thermal evaporation process is disclosed.

7 Claims, 7 Drawing Sheets

(56) References Cited

U.S. PATENT DOCUMENTS

| | | |
|---|---|---|
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,252,859 B2 | 8/2007 | Ng et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 9,340,728 B2 | 5/2016 | Ise et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0247061 A1 | 10/2007 | Adamovich et al. |
| 2007/0249148 A1 | 10/2007 | Werner et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0177641 A1 | 7/2011 | Cheon et al. |
| 2012/0181511 A1 | 7/2012 | Ma et al. |
| 2012/0241732 A1 | 9/2012 | Endo et al. |
| 2012/0319146 A1 | 12/2012 | Adamovich et al. |
| 2013/0112952 A1 | 5/2013 | Adamovich et al. |
| 2013/0207082 A1 | 8/2013 | Cho et al. |
| 2013/0248849 A1 | 9/2013 | Feldman et al. |
| 2013/0264561 A1 | 10/2013 | Dobbs et al. |
| 2014/0054564 A1 | 2/2014 | Kim et al. |
| 2015/0001471 A1 | 1/2015 | Boudreault et al. |
| 2015/0171341 A1 | 6/2015 | Lee et al. |
| 2015/0357588 A1 | 12/2015 | Kwong et al. |
| 2016/0099425 A1 | 4/2016 | Kottas et al. |

FOREIGN PATENT DOCUMENTS

| | | |
|---|---|---|
| CN | 102918134 | 2/2013 |
| CN | 104250244 | 12/2014 |
| EP | 0650955 | 5/1995 |
| EP | 1156536 | 11/2001 |
| EP | 1725079 | 11/2006 |
| EP | 2034538 | 3/2009 |
| EP | 2166592 | 3/2010 |
| EP | 2461390 | 6/2012 |
| JP | 200511610 | 1/2005 |
| JP | 2007123392 | 5/2007 |
| JP | 2007254297 | 10/2007 |
| JP | 2008074939 | 4/2008 |
| JP | 2011-091366 | 5/2011 |
| JP | 2012056880 | 3/2012 |
| JP | 2012-195140 | 10/2012 |
| JP | 2012216801 | 11/2012 |
| WO | 1999/053724 | 10/1999 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004/070787 | 8/2004 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009/030981 | 3/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010107244 | 9/2010 |
| WO | 2011013843 | 2/2011 |
| WO | 2011081423 | 7/2011 |
| WO | 2011136755 | 11/2011 |
| WO | 2012005363 | 1/2012 |
| WO | 2012015274 | 2/2012 |
| WO | 2012023947 | 2/2012 |
| WO | 2012064499 | 5/2012 |
| WO | 2012108879 | 8/2012 |

(56) References Cited

FOREIGN PATENT DOCUMENTS

| WO | 2012165844 | 12/2012 |
|---|---|---|
| WO | 2012166101 | 12/2012 |

OTHER PUBLICATIONS

Wang, D. et al., "Broad wavelength modulating and design of organic white diode based on lighting by using exciplex emission from mixed acceptors," Applied Physics Letters (2006), 89(23), 233511/1-233511/3.
Adamovich, Adam et al., "High-efficiency single dopant white electrophosphorescent light-emitting diodes," New Journal of Chemistry (2002), 26(9), 1171-1178.
Coya, Carmen et al., "White emission from a single-component single-layer solution processed OLED," SPIE (2009), 7415(Organic Light Emitting Materials and Devices XIII), 74151P/1-74151P/12.
Jou, Jwo-Huei et al., "Efficient, color-stable fluorescent white organic light-emitting diodes with single emission layer by vapor deposition from solvent premixed deposition source," Applied Physics Letters (2006), 88(19), 193501/1-193501/3.
Jou, Jwo-Huei et al., "Efficient pure-white organic light-emitting diodes with a solution-processed, binary-host employing single emission layer," Applied Physics Letters (2006), 88(14), 141101/1-141101/3.
Yang, J.P. et al., "White light emission from a single layer organic light emitting diode fabricated by spincoating," Chemical Physics Letters 325 (2000) 251-256.
Notice of Reasons for Rejection dated Jan. 16, 2018 for corresponding JP Application No. 2014-166272.
EP Search Report dated May 19, 2015 for corresponding EP Patent Application No. 14181083.8.
Office Action dated Jan. 25, 2017 for corresponding Chinese Patent Application No. 201410412431.9.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).

(56) References Cited

OTHER PUBLICATIONS

Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing N∧C∧N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Notice of Reasons for Rejection dated Jan. 7, 2020 in corresponding Japanese patent application No. JP 2019-008238.

ORGANIC ELECTROLUMINESCENT MATERIALS AND DEVICES

CROSS-REFERENCE TO RELATED APPLICATIONS

This application is a divisional application of U.S. patent application Ser. No. 14/253,505, filed on Apr. 15, 2014, which claims priority under 35 U.S.C. § 119(e) to U.S. Provisional Applications No. 61/940,603, filed on Feb. 17, 2014, No. 61/920,544, filed on Dec. 24, 2013, No. 61/894,160, filed on Oct. 22, 2013, No. 61/874,444, filed on Sep. 6, 2013, and No. 61/867,858, filed on Aug. 20, 2013, the entire contents of which are incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to organic materials used in such devices. More specifically, the present invention relates to novel premixed host systems for phosphorescent OLEDs. At least one emitter and at least another material can be mixed and co-evaporated from one sublimation crucible in a vacuum thermal evaporation (VTE) process and achieve stable evaporation.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

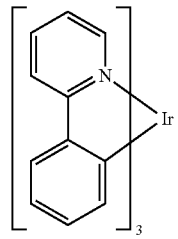

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

The present disclosure provides a novel composition comprising a mixture of a first compound and a second compound, wherein the first compound has different chemical structure than the second compound; wherein the first compound is capable of functioning as a phosphorescent emitter in an organic light emitting device at room temperature. The first compound can have an evaporation temperature T1 of 150 to 350° C. The second compound can have an evaporation temperature T2 of 150 to 350° C. In order to form the inventive composition comprising a mixture of the first compound and the second compound, the absolute value of T1−T2, the difference between T1 and T2, should be less than 20° C. The first compound has a concentration C1 in the mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predetermined distance away from the mixture being evaporated, and wherein the absolute value of (C1−C2)/C1 is less than 5%.

According to an embodiment of the present disclosure, a first device comprising a first organic light emitting device, the first organic light emitting device comprising: an anode; a cathode; and an organic layer, disposed between the anode and the cathode, comprising a first composition further comprising a mixture of a first compound and a second compound, wherein the first compound has different chemical structure than the second compound;
wherein the first compound is capable of functioning as a phosphorescent emitter in an organic light emitting device at room temperature;
wherein the first compound has an evaporation temperature T1 of 150 to 350° C.;
wherein the second compound has an evaporation temperature T2 of 150 to 350° C.;
wherein the absolute value of T1−T2 is less than 20° C.;
wherein the first compound has a concentration C1 in said mixture, a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predetermined distance away from the mixture being evaporated and wherein the absolute value of (C1−C2)/C1 is less than 5%.

According to an embodiment of the present disclosure, a method of fabricating an organic light emitting device comprising a first electrode, a second electrode, and a first organic layer disposed between the first electrode and the second electrode, wherein the first organic layer comprises a first organic composition further comprising a mixture of a first compound and a second compound, is disclosed. The method comprises:
providing a substrate having the first electrode disposed thereon;
depositing the first composition over the first electrode; and
depositing the second electrode over the first organic layer, wherein the first compound has different chemical structure than the second compound;
wherein the first compound is capable of functioning as a phosphorescent emitter in an organic light emitting device at room temperature;
wherein the first compound has an evaporation temperature T1 of 150 to 350° C.;
wherein the second compound has an evaporation temperature T2 of 150 to 350° C.;
wherein the absolute value of T1−T2 is less than 20° C.;
wherein the first compound has a concentration C1 in said mixture, and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predefined distance away from the mixture being evaporate; and wherein the absolute value of (C1−C2)/C1 is less than 5%.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
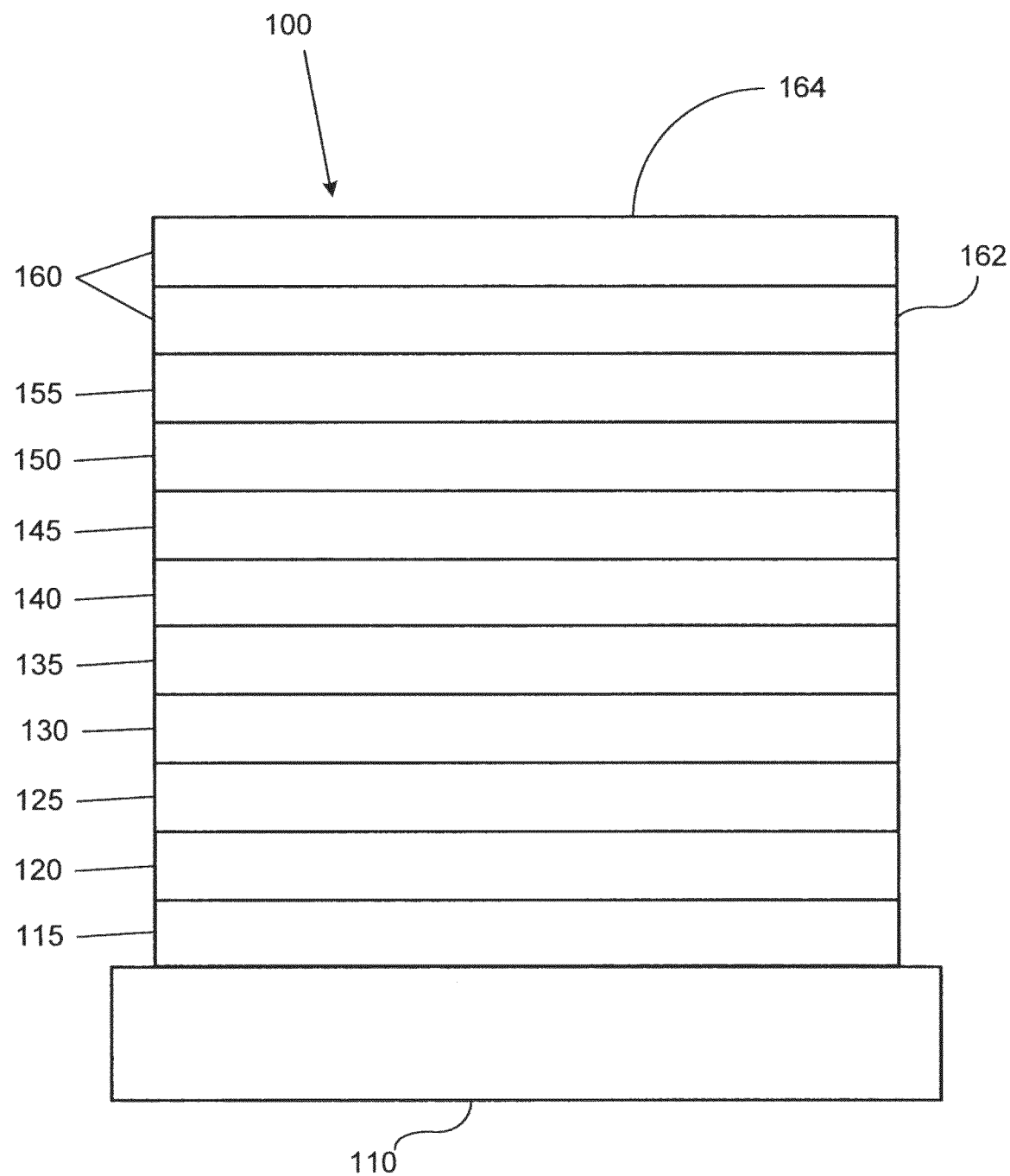
FIG. 1 shows an organic light emitting device that can incorporate the inventive host material disclosed herein.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
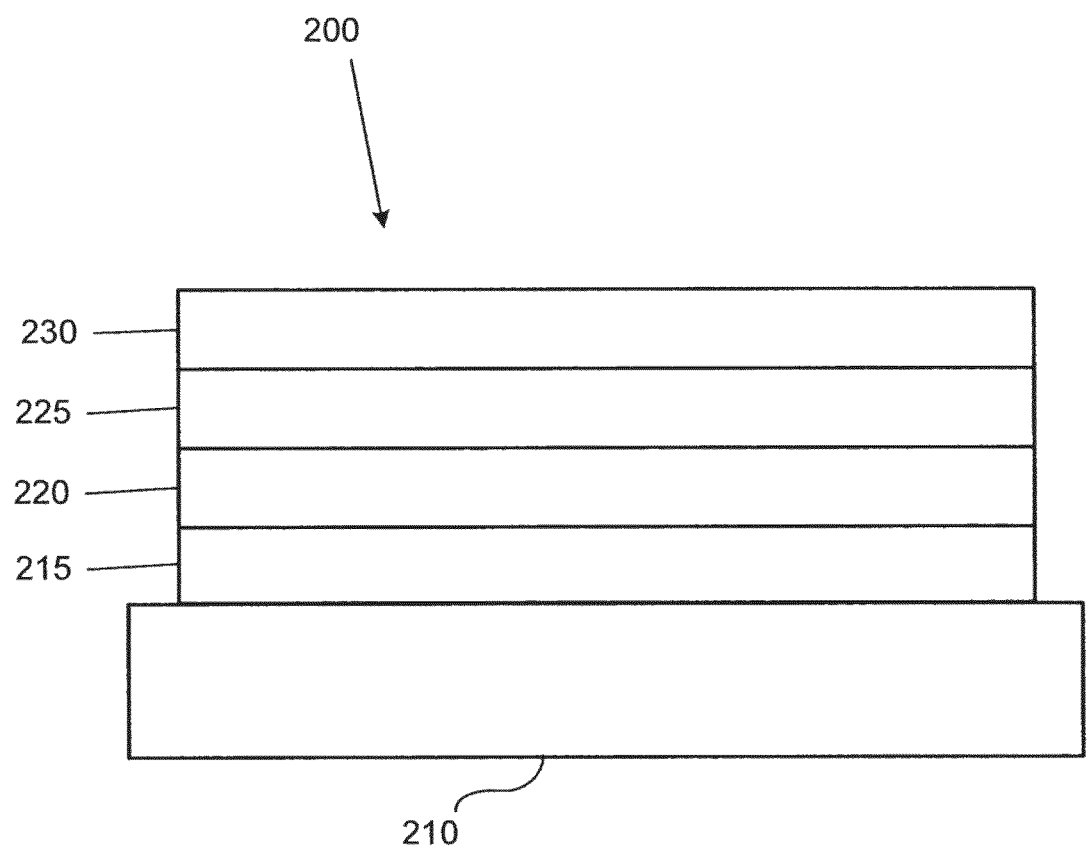
FIG. 2 shows an inverted organic light emitting device that can incorporate the inventive host material disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al., which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also refer to heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

Often, the emissive layer (EML) of OLED devices exhibiting good lifetime and efficiency requires more than two components (e.g. 3 or 4 components). Fabricating such EMLs using vacuum thermal evaporation (VTE) process then requires evaporating 3 or 4 evaporation source materials in separate VTE sublimation crucibles, which is very complicated and costly compared to a standard two-component EML with a single host and an emitter, which requires only two evaporation sources.

Premixing two or more materials and evaporating them from one VTE sublimation crucible can reduce the complexity of the fabrication process. However, the co-evaporation must be stable and produce an evaporated film having a composition that remains constant through the evaporation process. Variations in the film's composition may adversely affect the device performance. In order to obtain a stable co-evaporation from a mixture of compounds under vacuum, one would assume that the materials must have the same evaporation temperature under the same condition. However, this may not be the only parameter one has to consider. When two compounds are mixed together, they may interact with each other and the evaporation property of the mixture may differ from their individual properties. On the other hand, materials with slightly different evaporation temperatures may form a stable co-evaporation mixture. Therefore, it is extremely difficult to achieve a stable co-evaporation mixture. So far, there have been very few stable co-evaporation mixture examples. "Evaporation temperature" of a material is measured in a vacuum deposition tool at a constant pressure, normally between $1\times10^{-7}$ Torr to $1\times10^{-8}$ Torr, at a 2 Å/sec deposition rate on a surface positioned at a set distance away from the evaporation source of the material being evaporated, e.g. sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

Many factors other than temperature can contribute to the ability to achieve stable co-evaporation, such as the miscibility of the different materials and the phase transition temperatures of the different materials. The inventors found that when two materials have similar evaporation temperatures, and similar mass loss rate or similar vapor pressures, the two materials can co-evaporate consistently. "Mass loss rate" of a material is defined as the percentage of mass lost over time ("percentage/minute" or "%/min") and is determined by measuring the time it takes to lose the first 10% of the mass of a sample of the material as measured by thermal gravity analysis (TGA) under a given experimental condition at a given constant temperature for a given material after the a steady evaporation state is reached. The given constant temperature is one temperature point that is chosen so that the value of mass loss rate is between about 0.05 to 0.50%/min. A skilled person in this field should appreciate that in order to compare two parameters, the experimental condition should be consistent. The method of measuring mass loss rate and vapor pressure is well known in the art and can be found, for example, in Bull. et al. Mater. Sci. 2011, 34, 7.

In the state of the art phosphorescent OLED devices, the EML may consist of three or more components. In one example, the EML can consist of two host-type compounds and an emitter combination (e.g. a hole transporting cohost (h-host), an electron transporting cohost (e-host), and a compound capable of functioning as a phosphorescent emitter in an OLED at room temperature). In another example, the EML can consist of one host-type compound and two emitter-type compounds (e.g., a host compound and two compounds each capable of functioning as a phosphorescent emitter in an OLED at room temperature). Conventionally, in order to fabricate such EMLs having three or more components using VTE process, three or more evaporation sources are required, one for each of the components. Because the concentration of the components are important for the device performance, typically, the rate of deposition of each component is measured individually during the deposition process. This makes the VTE process complicated and costly. Thus, it is desired to premix at least two of the components of such EMLs to reduce the number of VTE evaporation sources.

As used herein, an "emitter-type compound" refers to a compound that is capable of functioning as a phosphorescent emitter in the EML of an OLED at room temperature. A "host-type compound" refers to a compound that is capable of functioning as a host material in the EML of an OLED at room temperature.

If any two of the three or more components of the EMLs can be premixed and form a stable mixture of co-evaporation source, then the number of evaporation sources required for EML layer fabrication would be reduced. In order for materials to be premixable into an evaporation source, they should co-evaporate and deposit uniformly without changing the ratio. The ratio of the components in the mixture should be the same as the ratio of the components in the evaporation deposited films from these premixed materials. Therefore, the concentration of the two components in the deposited film is controlled by their concentration in the premixed evaporation source.

The present disclosure describes a new class of emitters and another class of materials (such as host-type materials) which can be premixed to provide a VTE co-evaporation source that can be used for a stable co-evaporation of the two materials.

Maximizing the efficiency of a phosphorescent emitter in an OLED may involve narrowing the emission spectrum. This side effect of narrowed emission is not desirable in some applications, such as, when the emitter is used as part of a white emitting OLED. In applications such as for white emitting OLEDs, often a broad full width half maximum (FWHM) spectrum is preferred.

One possible approach to achieving both high efficiency and a broad FWHM spectrum is to incorporate two emitters within a device. This can be done by incorporating the emitters in separate EMLs or depositing two emitters into one layer. The inventors have discovered that by premixing two emitters that have similar thermal evaporation properties in a desired ratio and depositing the material by evaporation using a VTE process from one evaporation sublimation crucible containing the mixed composition source material, the manufacturing of OLEDs having an EML comprising the two emitters can be simplified.

The combination of premixed compounds described in this disclosure, where at least one of the compounds is an emitter-type compound, can be used for fine tuning device emission spectra for a specific spectral width without compromising the device efficiency. Premixing allows for a greater control of the ratio of the components of the EML layer thereby more accurately enabling the desired/resultant spectral shape than when evaporating the components of the EML layer from separate evaporation sources. This provides a more robust manufacturing process for OLEDs.

According to the present disclosure, the composition of the film deposited by VTE from a premixed emitter evaporation source material is determined in advance at the mixing stage. The composition of the premixed emitter evaporation source material is determined by the desired contribution of the two emitter-type compounds used. The ratio of the two emitter-type compounds in the composition of the premix may be between 1:1 to 200:1. Preferably, the ratio is between 1:1 to 50:1, more preferably between 1:1 and 20:1, more preferably between 1:1 to 5:1, and most preferably between 1:1 to 2:1.

EXAMPLES

In a first example, a novel combination of two emitter-type compounds, Compound 20 and Compound 145, having very similar sublimation properties are premixed together, placed in a single deposition source and evaporated into a device EML with a variable ratio. For example, a mixture of these two emitters was deposited at 0.2 Å/s for a film 2000 Å thick. Material was then deposited onto a substrate at a deposition rate of 1 Å/s to yield a film of 70 nm thick. The ratio of the two emitters in the premixture, as measured by weight prior to mixing, was 85% (Compound 20) to 15% (Compound 145). The composition of the premixture, as measured by high pressure liquid chromatography (HPLC), was 84.5% (Compound 20) to 15.5% (Compound 145). Because mixing can lead to non-uniformities within the total premixture, an error bar of 1% is given for the measured % of the premixture components when a small sample is analyzed by HPLC. The composition of the deposited film, as measured by HPLC, was 85.3% (Compound 20) to 14.7% (Compound 145). Therefore, the compositions of the premixture and deposited material are equivalent.

The novel two-compound mixture combinations disclosed herein can be used in making various white OLED configurations. For example, the two-compound mixture combinations disclosed herein can be used to make premixed emitter evaporation source materials that can be used in depositing broad yellow EML layers in blue-yellow white OLEDs.

Examples of the various configurations for such blue-yellow white OLEDs are illustrated in FIGS. 3A through 6C. The layers "Y EML," "Y1 EML," and "Y2 EML" in the figures are the broad yellow EMLs and as well known in the art, the broad yellow EML layers often consist of two emitter-type compounds in order to achieve the desired emission spectrum required for producing white light in conjunction with the blue EML layers. The layers "Ph B EML," "F1 B EML," "B EML," "B1 EML," and "B2 EML" in the figures are the blue EMLs.

In these examples, the broad yellow EML layers are made of two emitter-type compounds to produce light in desired red-green, red-yellow, or yellow spectrum that when combined with the blue emission from the blue EML to produce white light emitting OLEDs. The premixed emitter evaporation source materials disclosed herein is useful for depositing these broad yellow EML layers by VTE process.

Figure 3A:
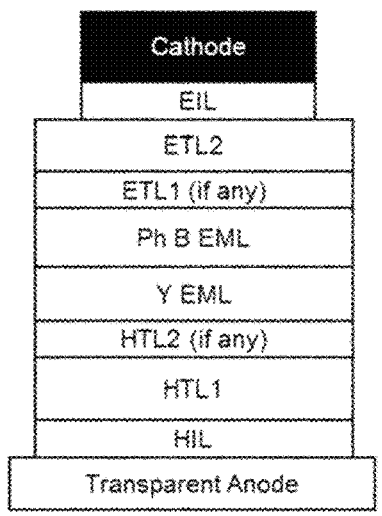
FIGS. 3A through 3C show examples of white OLEDs in top emission, bottom emission and transparent OLEDs (TOLED) configurations.
Figure 3B:
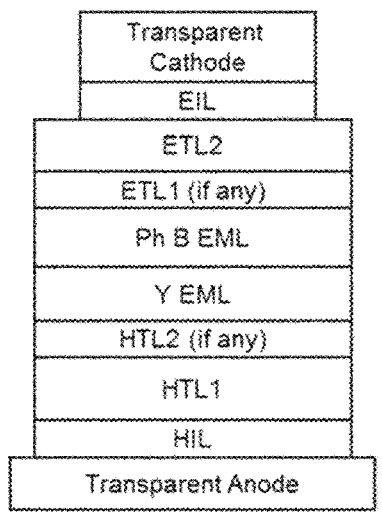
Figure 3C:
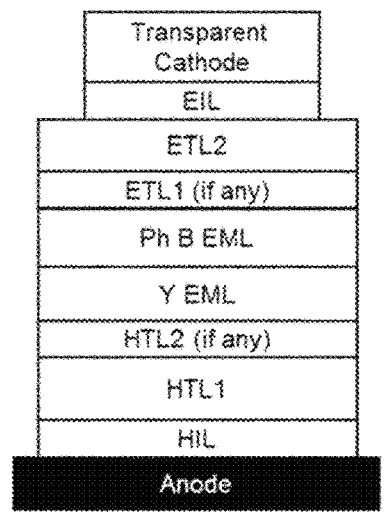
Figure 4A:
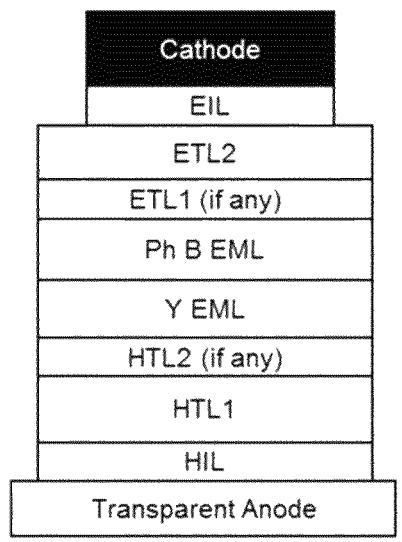
FIGS. 4A through 4D show examples of blue yellow white OLED structures.
Figure 4B:
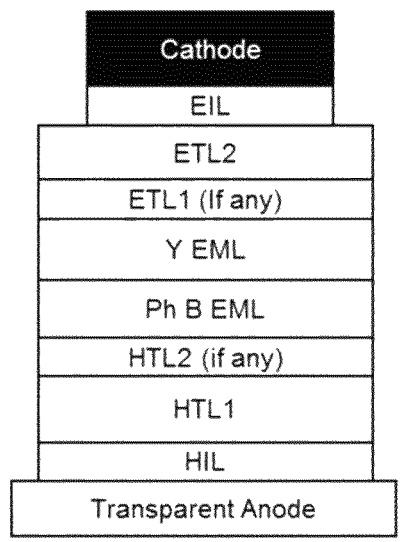
Figure 4C:
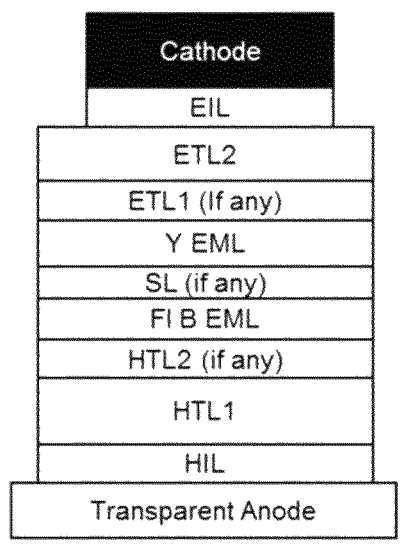
Figure 4D:
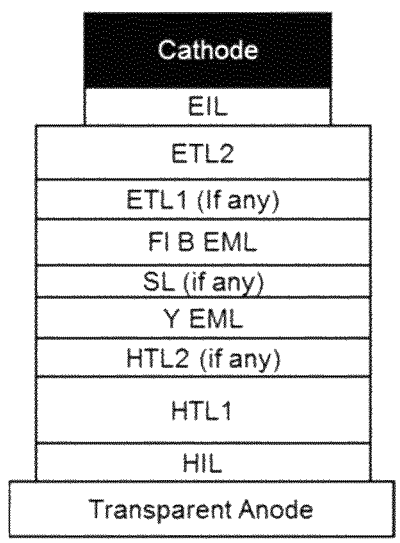
Figure 5A:
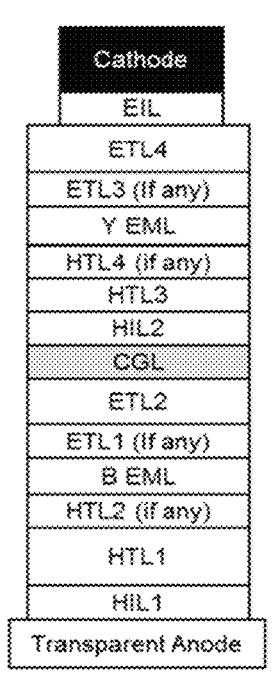
FIGS. 5A through 5G show examples of two-unit white stacked OLED structures.
Figure 5B:
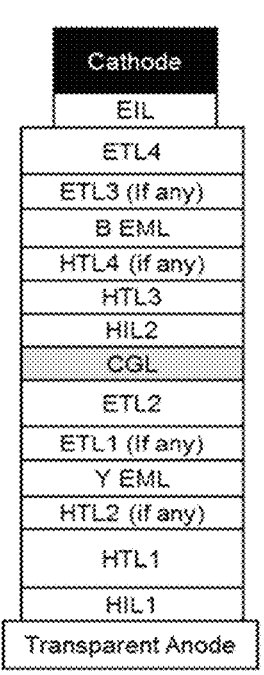
Figure 5C:
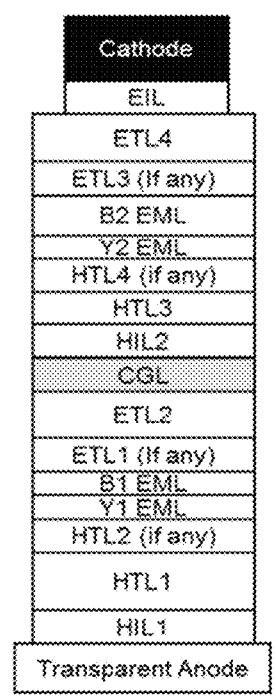
Figure 5D:
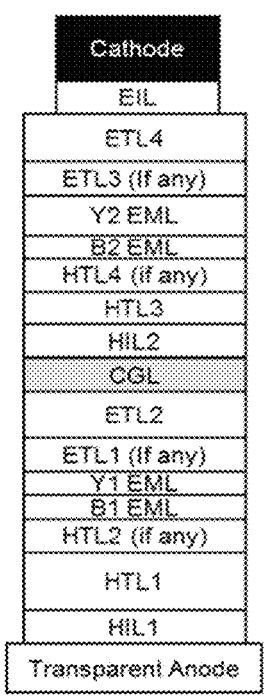
Figure 5E:
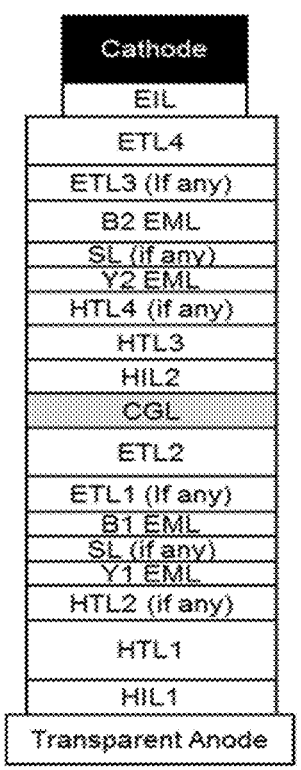
Figure 5F:
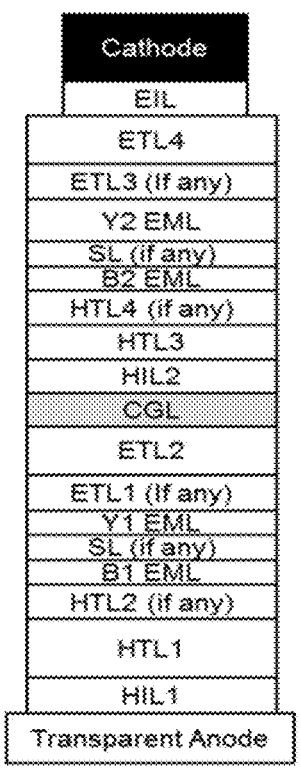
Figure 5G:
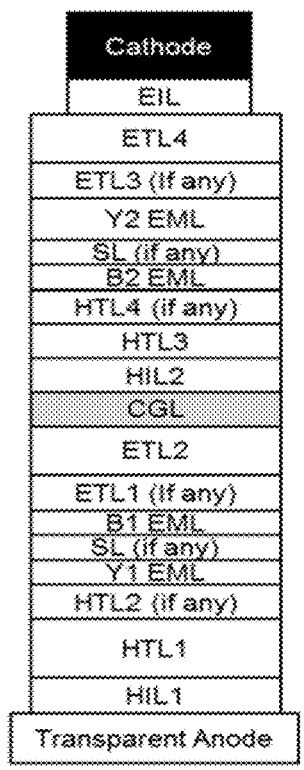

FIGS. 3A through 3C show basic configurations for blue-yellow white OLEDs. FIG. 3A shows an example of blue-yellow white OLEDs in a bottom emission configuration (anode is transparent). FIG. 3B shows an example of a blue-yellow white OLED in a transparent OLED configuration (both anode and cathode are transparent). FIG. 3C shows an example of a blue-yellow white OLED in a top emission configuration (cathode is transparent). The examples shown in FIGS. 4A through 6C are all shown in the bottom emission configuration but one skilled in the art would readily understand that the examples shown in FIGS. 4A through 6C are equally applicable to the top emission configuration and transparent OLED configurations.

Figure 6A:
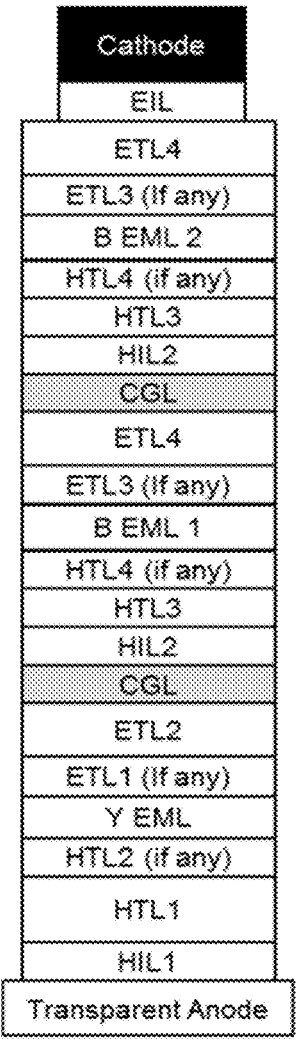
FIGS. 6A through 6C show examples of white stacked OLED structures having three or more units.
Figure 6B:
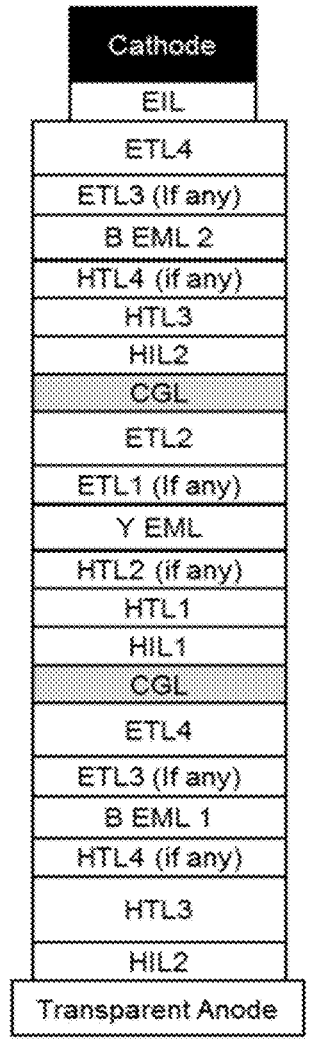
Figure 6C:
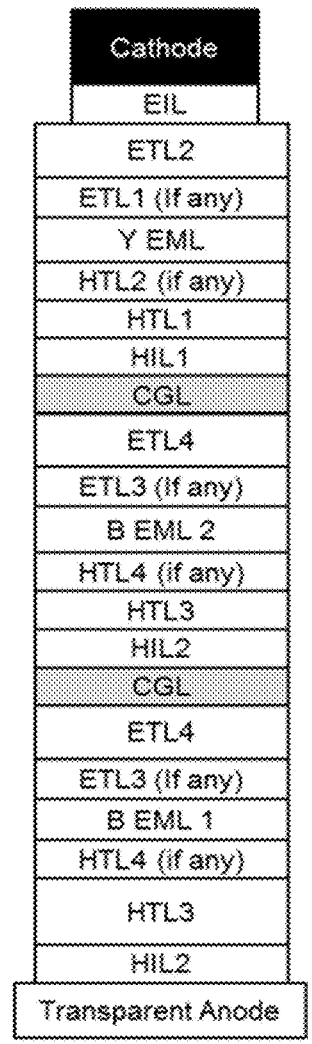

FIGS. 4A through 4D show examples of single-unit blue-yellow white OLED structures. FIGS. 5A through 5G show examples of two-unit blue-yellow white stacked OLED structures. FIGS. 6A through 6C show examples of three-unit blue-yellow white stacked OLED structures. One skilled in the art would readily understand that these stacked OLED configurations can be applied to embodiments having more than three light emitting units. In these figures, the following abbreviations are used: HIL—hole injection layer, HTL—hole transporter layer, EML—emissive layer, ETL—, electron transporter layer, EIL—electron injection layer, SL—separation layer, CGL—charge generation layer, Ph—phosphorescent, Fl—fluorescent. In these configurations, HIL2 can be the same material as HIL1 or a different material, HTL3 can be the same material as HTL1 or a different material, HTL4 can be the same material as HTL2 or a different material, ETL3 can be the same material as ETL1 or a different material, and ETL4 can be the same material as ETL2 or a different material. B EML, B1 EML and B2 EML are blue EMLs and they can be either fluorescent or phosphorescent. B2 EML can be the same material as B1 EML or a different material. Y EML, Y1 EML, and Y2 EML are yellow EMLs and they can be either fluorescent or phosphorescent. Y2 EML can be the same material as Y1 EML or a different material.

In the white stacked OLED structures of FIGS. 6A through 6C, HIL2 can be the same material as HIL1 or a different material, HTL3 can be the same material as HTL1 or a different material, HTL4 can be the same material as HTL2 or a different material, ETL3 can be the same material as ETL1 or a different material, and ETL4 can be the same material as ETL2 or a different material. B EML1 and B EML2 represent blue EMLs and can be either fluorescent or phosphorescent. B EML1 can be the same material as B EML2 or a different material. Y EML represent yellow EML. The number of stacked units can be any number greater than or equal to 3. The number of blue and yellow EML units can be any number. The stacked units can be in any order, e.g. B/Y/B/Y or B/B/Y/Y, or B/Y/B/Y/B, etc., where B denotes blue and Y denotes broad yellow.

According to another aspect of the present disclosure, a second example of premixed emitter evaporation source is disclosed. The premixed mixture according to this second example, comprises one emitter-type compound, Compound E5, and one host compound, Compound H1. Compound H1 and Compound E5 demonstrated premixability, which means they can be premixed and codeposited from one evaporation source without changing the composition. Uniform coevaporation of host:emitter pair is desired for the consistency of the device performance fabricated from this premixed precursor. The structures of Compound H1 and Compound E5 are shown below:

Compound H1

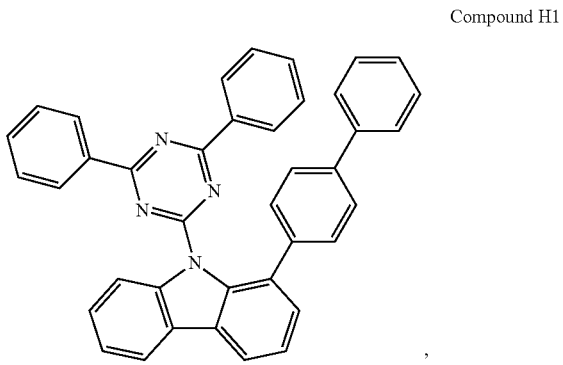

Compound E5

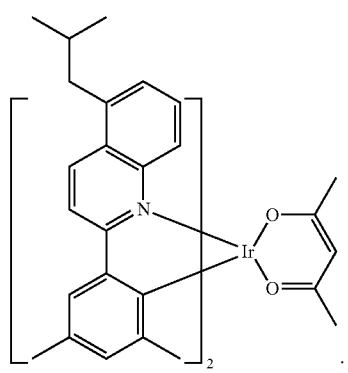

The premixability of Compound H1 and Compound E5 was tested by HPLC analysis of evaporated films. For this purpose the host Compound H1 (0.485 g) and emitter Compound E5 (0.015 g) were mixed and grinded to form 0.5 g of the mixture. The mixture was loaded into the evaporation source of the vacuum VTE chamber. The chamber was pumped down to $10^{-7}$ Torr pressure. The premixed components were deposited at rate 2 Å/s onto glass substrates. The substrates were replaced continuously after deposition of 1100 Å of film without stopping the deposition and cooling the source. The premixed material was evaporated until depletion.

The deposited films were analyzed by HPLC (HPLC Conditions C18, 80-100 (CH$_3$CN concentration in CH$_3$CN and H$_2$O), 30 min, detected wavelength 254 nm) and results are shown in Table 1 below. The composition of the host Compound H1 and emitter Compound E5 did not change significantly from Plate 1 to Plate 3. Each of the sample substrates are labeled Plate 1, Plate 2, and Plate 3. Some fluctuations in the concentration do not reveal any trend and can be explained by the accuracy of HPLC analysis.

TABLE 1

HPLC composition (%) of sequentially deposited films from a premixed host: emitter pair (host Compound H1 and emitter Compound E5) evaporation source.

| Films (1100Å) Plate # | H1 [%] | E5 [%] |
|---|---|---|
| 1 | 98.0 | 2.0 |
| 2 | 98.1 | 1.9 |
| 3 | 97.8 | 2.2 |

This data shows that host Compound H1 and emitter Compound E5 and potentially the other hosts and emitters from these families can be premixed to be used as single evaporation sources for an EML or part of the EML for PHOLEDs.

Examples of other possible premixed host:emitter pairs are provided in Table 2 below.

TABLE 2

Examples of possible premix pairs

| Mixture number | Electron transporting host | Emitter Metal complex |
|---|---|---|
| 1 | Compound H1 | Compound E5 |
| 2 | Compound H14 | Compound E1 |
| 3 | Compound H21 | Compound E4 |
| 4 | Compound H30 | Compound E9 |
| 5 | Compound H21 | Compound E17 |
| 6 | Compound H33 | Compound E13 |

Host Compound EH40 and emitter Compound 97 show premixability also. It means that they can be premixed and codeposited from one source without changing the composition. Uniform coevaporation of host:emitter is critical for the consistency of the devices performance fabricated from this premixed precursor. The structures of host Compound EH40 and emitter Compound 97 are shown below.

Compound EH40

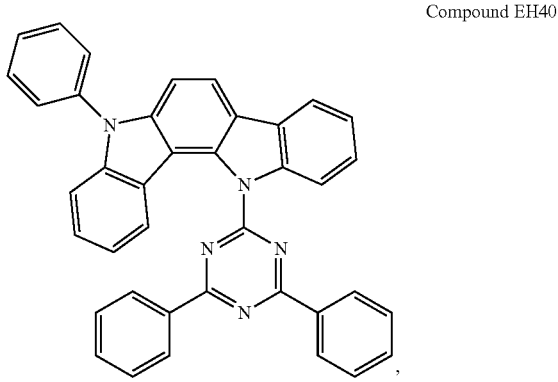

Compound 97

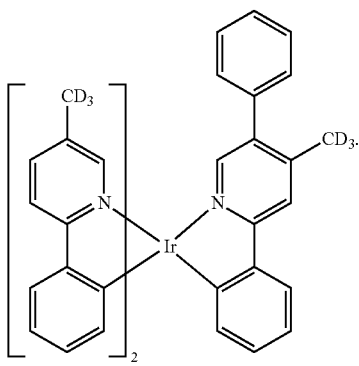

The premixability of Compound EH40 and Compound 97 was tested by HPLC analysis of evaporated films. For this purpose the host Compound EH40 and emitter Compound 97 were mixed in the ratio ~7:1 and grinded to form 0.2 g of the mixture. The mixture was loaded into the evaporation source of the vacuum VTE chamber. The chamber was pumped down to $10^{-7}$ Torr pressure. The premixed components were deposited at rate 2 Å/s onto glass substrates. The substrates were replaced continuously after deposition of 500 Å of film without stopping the deposition and cooling the source. The premixed material was evaporated until depletion.

The films were analyzed by HPLC (HPLC Conditions C18, 100% $CH_3CN$, 30 min, detected wavelength 254 nm) and results are shown in Table 3. The composition of the host Compound EH40 and emitter Compound 97 did not change significantly from Plate 1 to Plate 5. Each of the sample substrates are labeled Plate 1, Plate 2, and Plate 3. Some fluctuations in the concentration do not reveal any trend and can be explained by the accuracy of HPLC analysis.

TABLE 3

HPLC composition (%) of sequentially deposited films from premixed host: emitter (Host Compound EH40: Emitter Compound 97 in ratio of ~7:1) evaporation source.

| Films (500Å) | Host Compound EH40 (%) | Emitter Compound 97 (%) |
| --- | --- | --- |
| Plate 1 | 87.2 | 12.8 |
| Plate 2 | 87.1 | 12.9 |
| Plate 3 | 87.5 | 12.5 |
| Plate 4 | 87.6 | 12.4 |
| Plate 5 | 87.9 | 12.1 |

This is the evidence that host Compound EH40 and emitter Compound 97, and potentially the other hosts and emitters from these families can be premixed to be used as single evaporation sources for an EML or part of the EML for PHOLEDs. Examples of other possible premixed host:emitter pairs are provided in Table 4 below.

TABLE 4

Examples of possible premix pairs of host:emitter.

| Mixture number | Electron transporting host | Emitter Metal complex |
| --- | --- | --- |
| 1 | Compound EH1 | Compound 4 |
| 2 | Compound EH2 | Compound 7 |
| 3 | Compound EH4 | Compound 3 |
| 4 | Compound EH5 | Compound 11 |
| 5 | Compound EH8 | Compound 1 |
| 6 | Compound EH8 | Compound 67 |
| 7 | Compound EH16 | Compound 21 |
| 8 | Compound EH28 | Compound 29 |
| 9 | Compound EH40 | Compound 34 |
| 10 | Compound EH40 | Compound 97 |

According to an aspect of the present disclosure, a composition comprising a mixture of a first compound and a second compound is now described. In the mixture, the first compound has a different chemical structure than the second compound. The first compound is capable of functioning as a phosphorescent emitter in an OLED at room temperature. The first compound has an evaporation temperature T1 of 150 to 350° C. and the second compound has an evaporation temperature T2 of 150 to 350° C., wherein the absolute value of T1–T2, i.e. the difference between T1 and T2, is less than 20° C. Preferably, the absolute value of T1–T2 is less than 10° C. and more preferably less than 5° C.

The first compound has a concentration C1 in the mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predefined distance away from the evaporation source of the mixture being evaporated, and wherein the absolute value of (C1–C2)/C1 is less than 5%. Preferably, the absolute value of (C1–C2)/C1 is less than 3%.

The concentrations C1 and C2 are relative concentrations of the first compound. Therefore, the conditional requirement for the two compounds forming the mixture described above means that the relative concentration of the first compound in the as-deposited film (C2) should be as close to the original relative concentration of the first compound (C1) in the evaporation source mixture. One of ordinary skill in this field should realize that the concentration of each component in the mixture is expressed as relative percentage. The concentration of each component in the mixture can be measured by a suitable analytical methods well known to those skilled in the art. Examples of such methods are high pressure liquid chromatography (HPLC) and nuclear magnetic resonance spectroscopy (NMR). The percentage was calculated by dividing the integration area under the HPLC trace of each component by the total integration area. HPLC can use different detectors such as UV-vis, photo diode array detector, refractive index detector, fluorescence detector, and light scattering detector. Due to different materials properties, each component in the mixture may respond differently. Therefore, the measured concentration may differ from their real concentration in the mixture, however the relative ratio value of (C1–C2)/C1 is independent of these variables as long as the experimental condition keeps consistent, for example, all concentrations should be calculated under the exact same HPLC parameters for each component. It is sometimes preferred to select a measurement condition that gives calculated concentration close to the real concentration. However, it is not necessary. It is important to select a detecting condition that accurately detects each component. For example, fluorescence detector should not be used if one of the components does not fluoresce.

In one embodiment, the first compound has evaporation temperature T1 of 200 to 350° C. and the second compound has evaporation temperature T2 of 200 to 350° C.

In one embodiment, the first compound has a vapor pressure of P1 at T1 at 1 atm, and the second compound has a vapor pressure of P2 at T2 at 1 atm. The ratio of P1/P2 is desirably within the range of 0.90 to 1.10.

The first compound has a first mass loss rate and the second compound has a second mass loss rate, wherein the ratio between the first mass loss rate and the second mass loss rate is desirably within the range of 0.90 to 1.10. Preferably, the ratio between the first mass loss rate and the second mass loss rate is within the range of 0.95 to 1.05. More preferably, the ratio between the first mass loss rate and the second mass loss rate is within the range of 0.97 to 1.03.

The phosphorescent emitter component in the composition is capable of emitting light from a triplet excited state to a ground singlet state at room temperature. In one embodiment of the composition, the first compound is a metal coordination complex having a metal-carbon bond. The metal in the metal-carbon bond can be selected from the group consisting of Ir, Rh, Re, Ru, Os, Pt, Au, and Cu. In another embodiment, the metal is Ir (iridium). In another embodiment, the metal is Pt (platinum).

In one embodiment of the composition, the second compound is also capable of functioning as a phosphorescent emitter in an OLED at room temperature.

In another embodiment, the second compound is capable of functioning as a host in the EML of an OLED at room temperature. In one embodiment, the host is a hole transporting host. In another embodiment, the host is an electron transporting host.

According to an aspect of the present disclosure, the lowest triplet energy TE1 of the first compound is lower than that of the second compound. Triplet energy is determined by phosphorescence in an organic solvent glass at 77° K.

In one embodiment of the composition, the second compound comprises at least one chemical group selected from the group consisting of triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

In one embodiment of the composition, the first compound and the second compound each has a purity in excess of 99% as determined by HPLC.

According to another aspect, the mixture in the composition further comprises a third compound. The third compound has a different chemical structure than the first compound and the second compound, wherein the third compound has an evaporation temperature T3 of 150 to 350° C.; and wherein the absolute value of T1−T3 is less than 20° C. Preferably, the absolute value of T1−T3 is less than 10° C., and more preferably less than 5° C.

In one embodiment, the composition is in a liquid form at a temperature less than T1 (the evaporation temperature of the first compound) and T2 (the evaporation temperature of the second compound).

In one embodiment of the composition, the first compound has the formula of

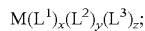

wherein $L^1$, $L^2$ and $L^3$ can be the same or different;
wherein x is 1, 2, or 3;
wherein y is 0, 1, or 2;
wherein z is 0, 1, or 2;
wherein x+y+z is the oxidation state of the metal M;
wherein $L^1$, $L^2$, and $L^3$ are independently selected from the group consisting of:

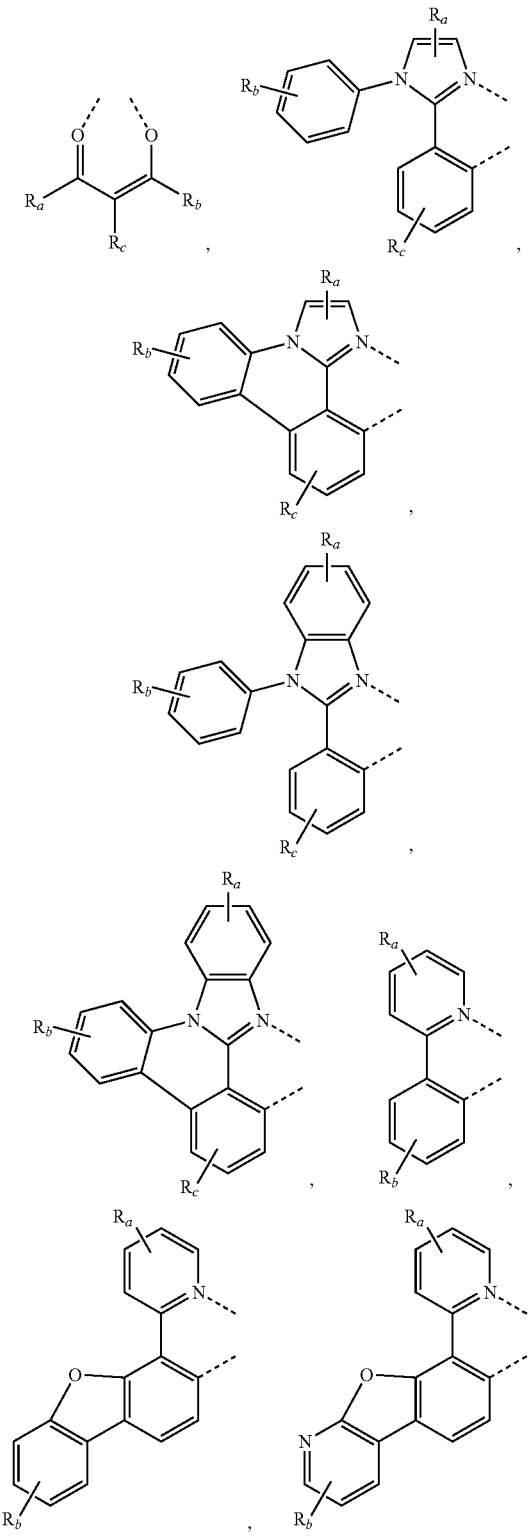

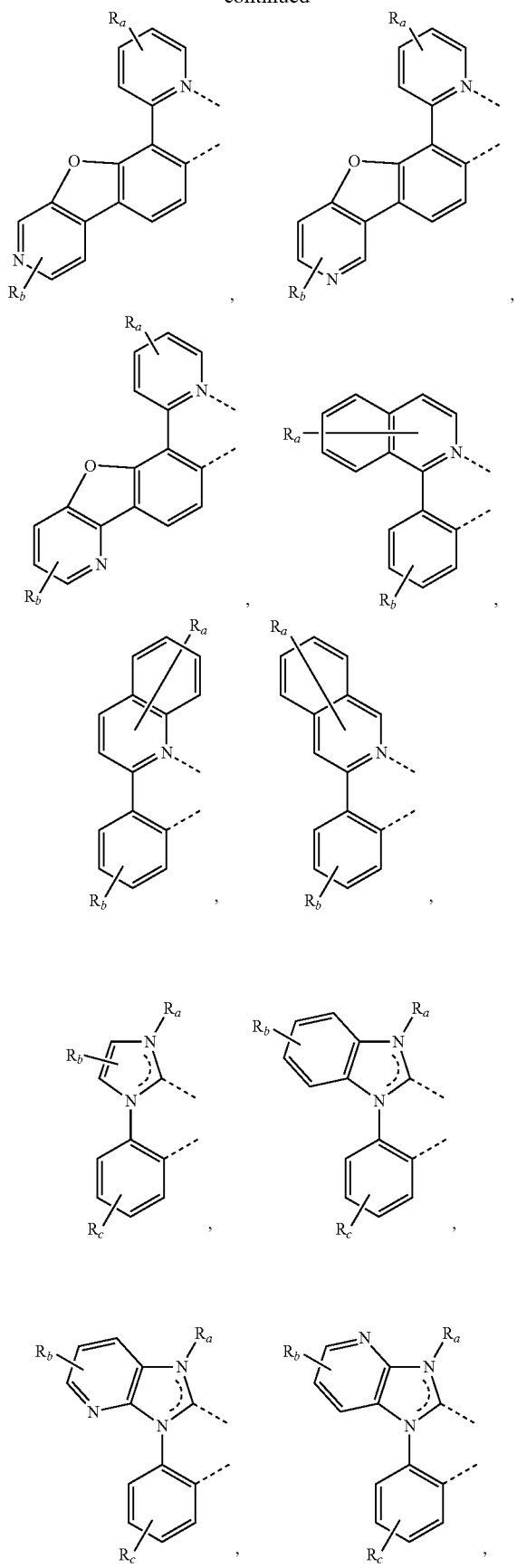

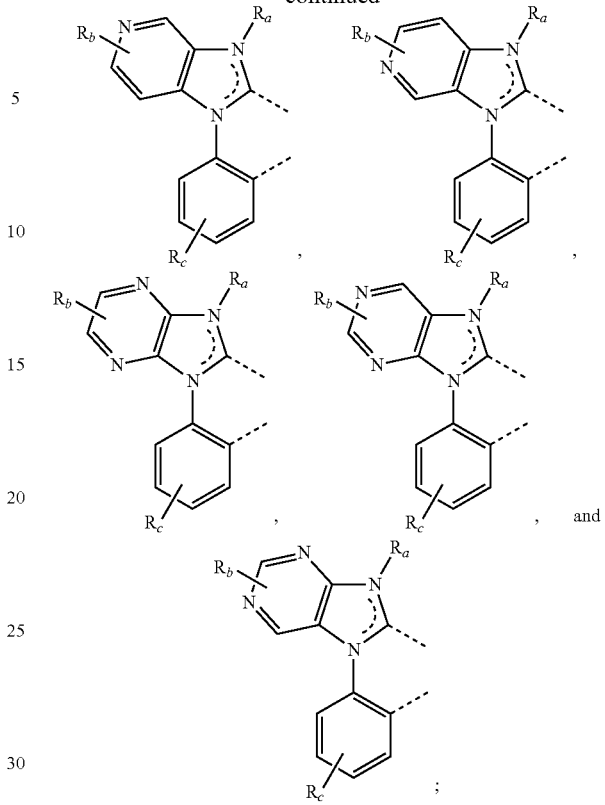

wherein $R_a$, $R_b$, $R_c$, and $R_d$ may represent mono, di, tri, or tetra substitution, or no substitution; wherein $R_a$, $R_b$, $R_c$, and $R_d$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

According to another embodiment, where the first compound has the formula of $M(L^1)_x(L^2)_y(L^3)_z$ as defined above, the first compound has the formula of $Ir(L^1)_2(L^2)$.

In one embodiment, where the first compound has the formula of $Ir(L^1)_2(L^2)$, $L^2$ has the formula:

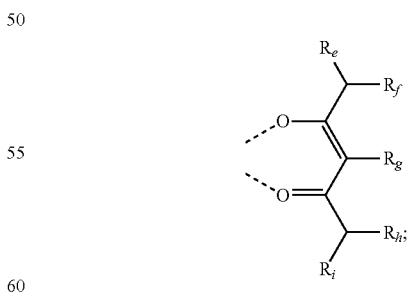

wherein $R_e$, $R_f$, $R_h$, and $R_i$ are independently selected from group consisting of alkyl, cycloalkyl, aryl, and heteroaryl; wherein at least one of $R_e$, $R_f$, $R_h$, and $R_i$ has at least two carbon atoms;
wherein $R_g$ is selected from group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In one embodiment, where the first compound has the formula of Ir(L¹)₂(L²), L² has the formula selected from the group consisting of:

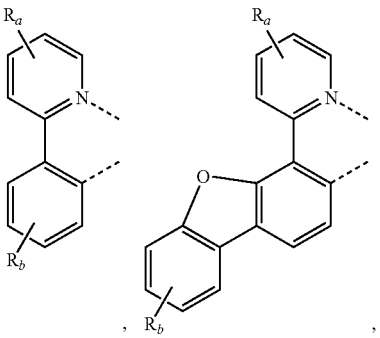

,

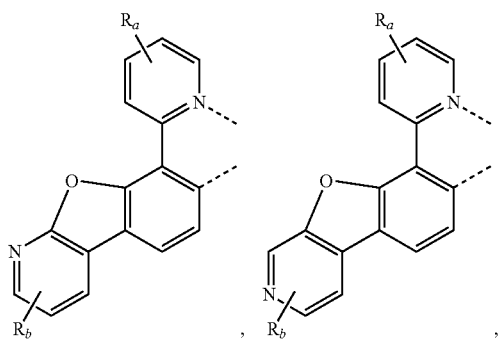

,

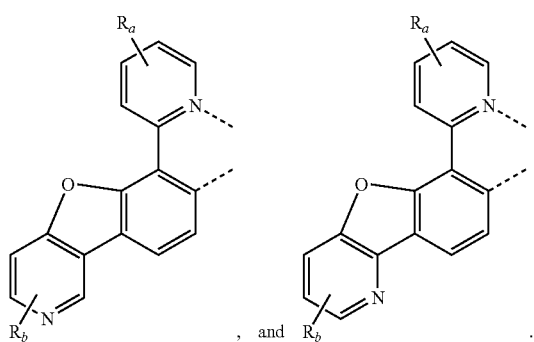

, and

.

In another embodiment, where the first compound has the formula of M(L¹)ₓ(L²)ᵧ(L³)_z as defined above, the first compound has the formula of Pt(L¹)₂ or Pt(L¹)(L²). L¹ can be connected to the other L¹ or L² to form a tetradentate ligand.

In one embodiment of the composition, the first compound has the Formula I:

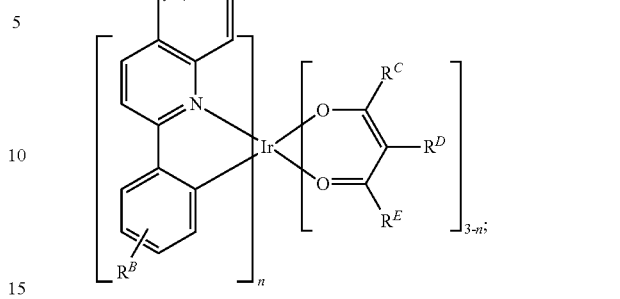

Formula I wherein $R^A$ represents mono, di, tri, tetra, penta, hexa substitutions, or no substitution;
$R^B$ represents mono, di, tri, tetra substitutions, or no substitution;
$R_A$, $R^B$, $R^C$, $R^D$, and $R^E$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;
wherein n is 1 or 2;
wherein the second compound has the Formula II:

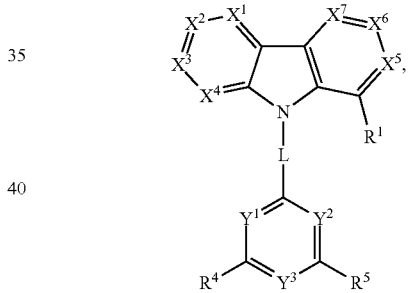

Formula II wherein $R^1$, $R^4$, and $R^5$ are independently selected from group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; wherein L is selected from the group consisting of a direct bond, aryl, substituted aryl, heteroaryl, substituted heteroaryl, and combinations thereof;
wherein $X^1$, $X^2$, $X^3$, $X^4$, $X^5$, $X^6$, $X^7$, $Y^1$, $Y^2$, and $Y^3$ are each independently selected from the group consisting of CR and N;
wherein at least two of $Y^1$, $Y^2$, and $Y^3$ are N; and
wherein each R can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In another embodiment, $R^1$, $R^4$, and $R^5$ in Formula II are independently selected from group consisting of non-fused aryl, non-fused heteroaryl, and combinations thereof; wherein L is selected from the group consisting of a direct bond, non-fused aryl, non-fused heteroaryl, and combinations thereof and wherein each of R is independently selected from the group consisting of hydrogen, deuterium, non-fused aryl, non-fused heteroaryl and combinations thereof.

In another embodiment, $R^1$ in Formula II is selected from the group consisting of phenyl, biphenyl, terphenyl, tetraphenyl, pentaphenyl, pyridine, phenyl pyridine and pyridyl phenyl.

In another embodiment, L in Formula II is selected from the group consisting of phenyl, pyridyl, biphenyl, terphenyl and a direct bond.

In another embodiment, $R^4$ and $R^5$ in Formula II are each independently selected from the group consisting of phenyl, pyridyl, biphenyl, and terphenyl.

In another embodiment of the composition, where the first compound has the structure according to Formula I as defined above, the second compound has a structure according to Formula III:

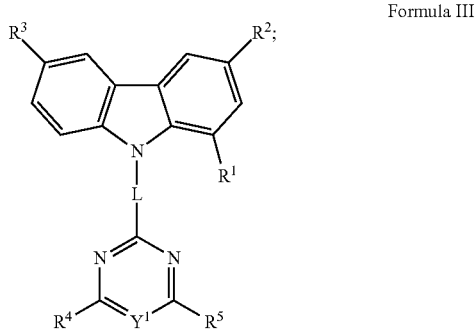

Formula III wherein $R^2$ and $R^3$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In one embodiment, $R^1$ and $R^3$ of Formula III are each independently selected from the group consisting of hydrogen, deuterium, non-fused aryl, non-fused heteroaryl and combinations thereof.

In one embodiment, where the second compound has the structure of Formula III, the second compound can have a structure selected from the group consisting of:

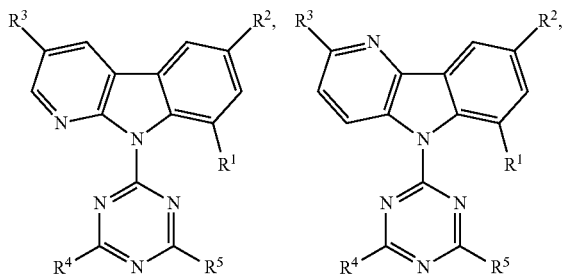

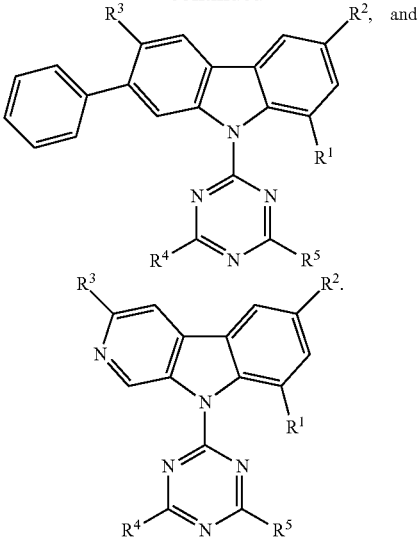

In one embodiment of the composition where the first compound has the structure of Formula I, n is 1. In another embodiment, $R^A$, $R^B$, $R^C$, and $R^E$ are each independently selected from the group consisting of hydrogen, deuterium, alkyl, cycloalkyl, and combinations thereof. In another embodiment, at least one of $R^C$ and $R^E$ contains a branched alkyl moiety with branching at a position further than the a position to the carbonyl group. In another embodiment, $R^D$ is hydrogen.

In one embodiment of the composition where the first compound has the structure of Formula I, at least one of $R^C$ and $R^E$ has the following structure:

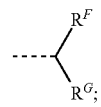

wherein $R^F$, and $R^G$ are independently selected from group consisting of alkyl and cycloalkyl; and wherein at least one of $R^F$, and $R^G$ has at least two C.

In one embodiment of the composition where the second compound has the structure according to Formula II defined above, the first compound has a structure according to Formula IV:

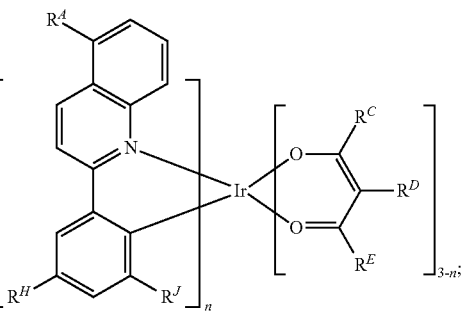

Formula IV wherein $R^H$ and $R^J$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In another embodiment of the composition where the first compound has a structure according to Formula IV as defined above, $R^H$ and $R^J$ are each independently selected from the group consisting of hydrogen, deuterium, alkyl, cycloalkyl, and combinations thereof.

In another embodiment of the composition where the first compound has a structure according to Formula IV as defined above, $R^H$ and $R^J$ are methyl.

In an embodiment of the composition where the second compound has a structure according to Formula II, the second compound can be selected from the group consisting of:

Compound H1

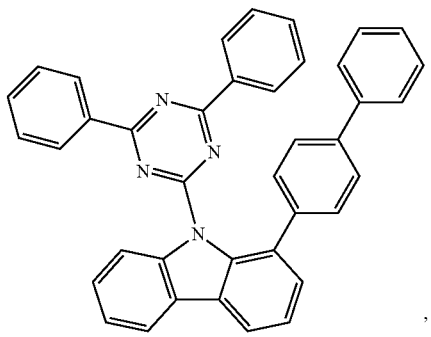

Compound H2

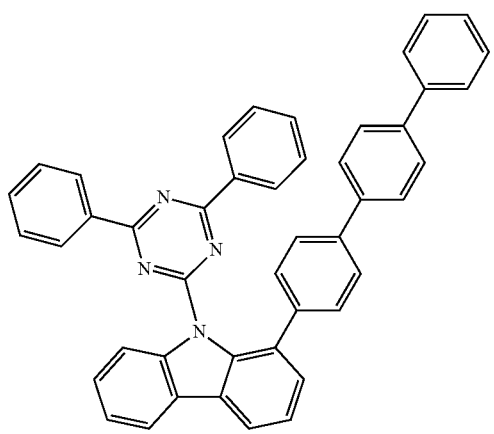

Compound H3

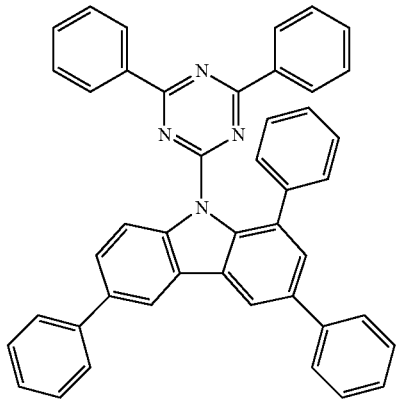

Compound H4

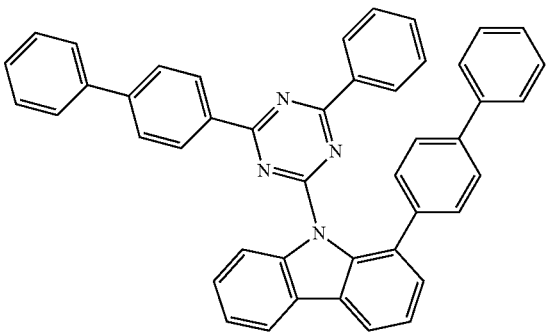

Compound H5

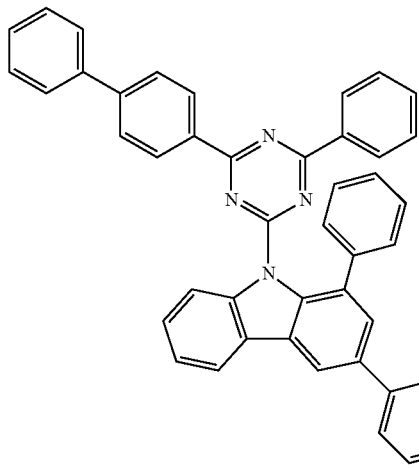

Compound H6

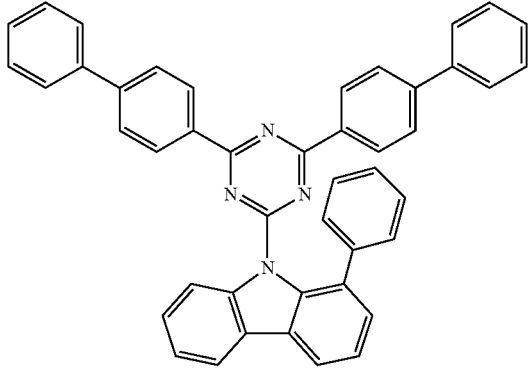

Compound H7
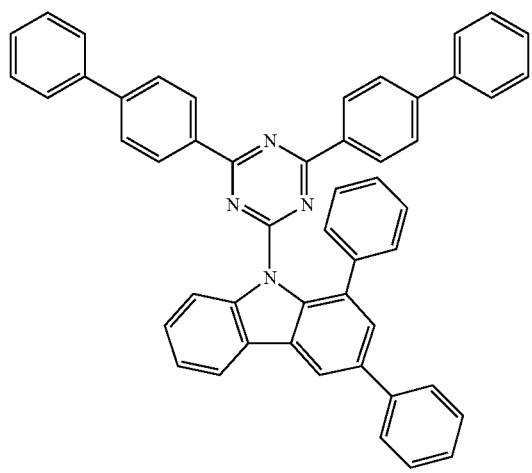
Compound H8
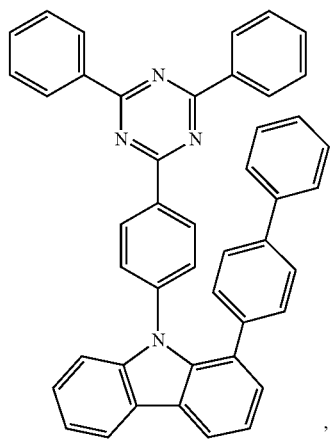
Compound H9
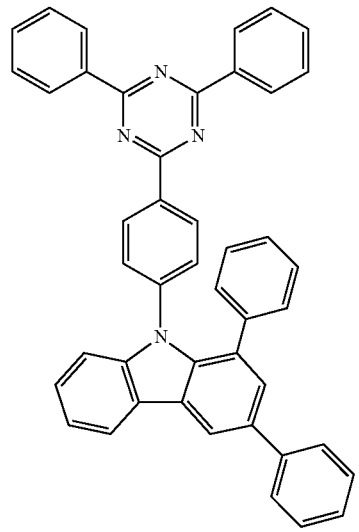
Compound H10
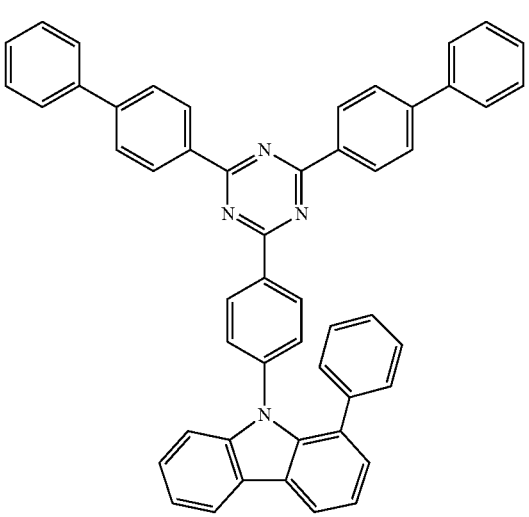
Compound H11
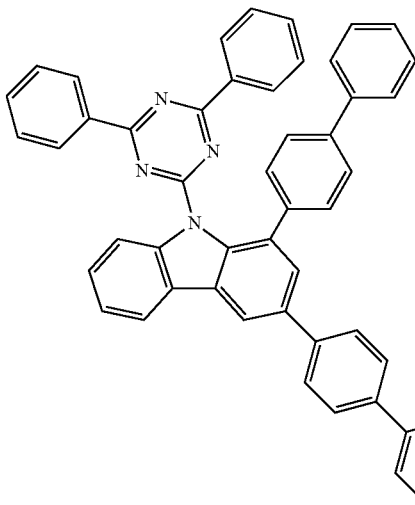
Compound H12
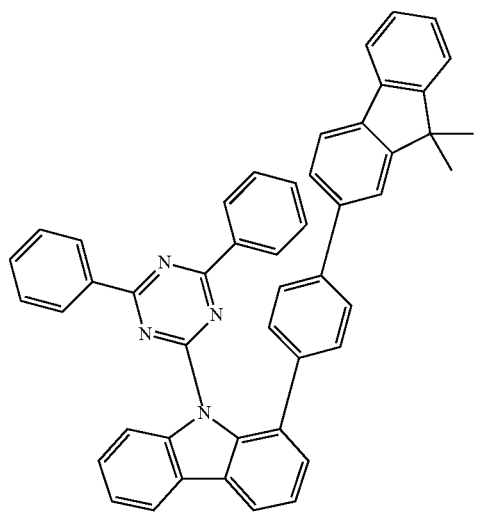

Compound H13
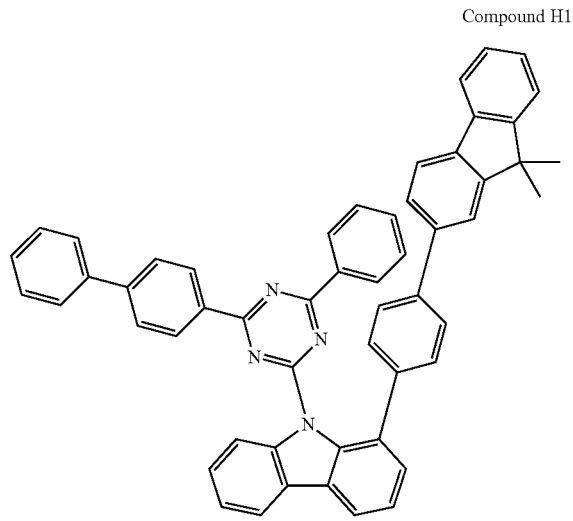
Compound H14
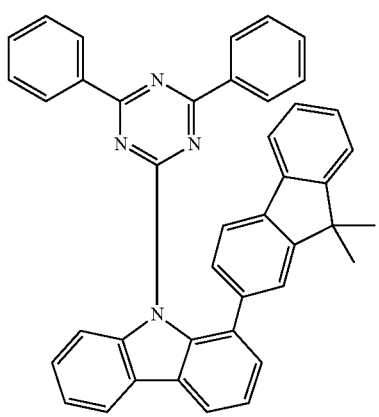
Compound H15
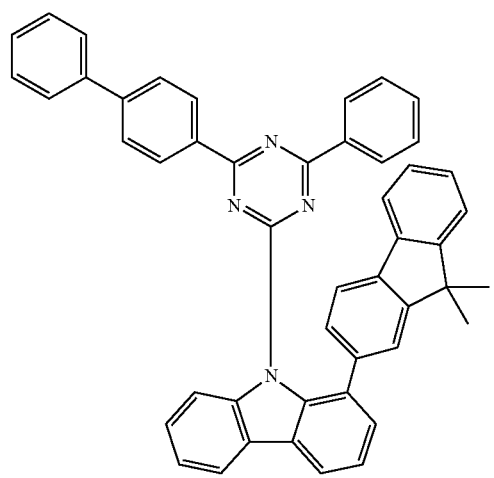
Compound H16
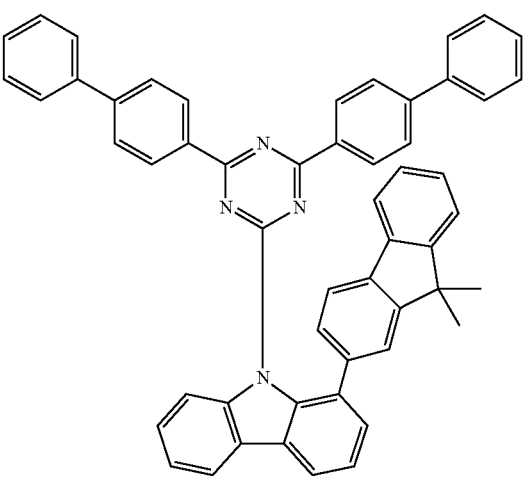
Compound H17
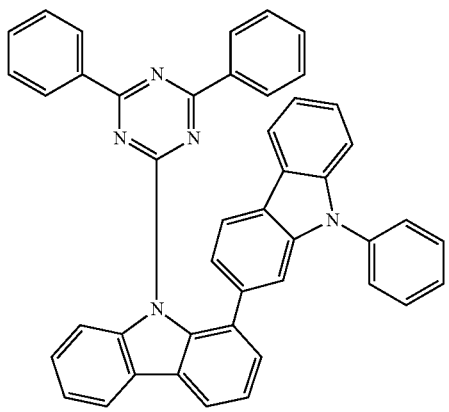
Compound H18
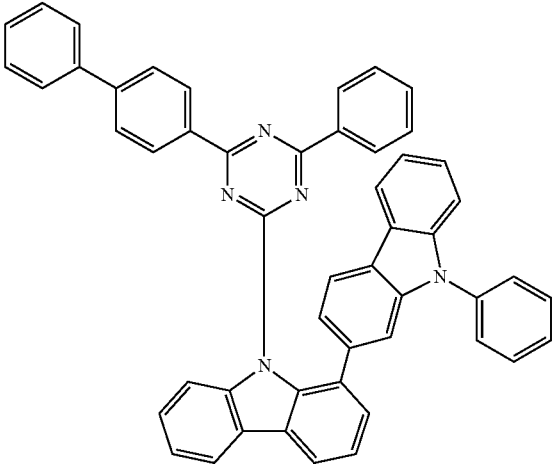

Compound H19
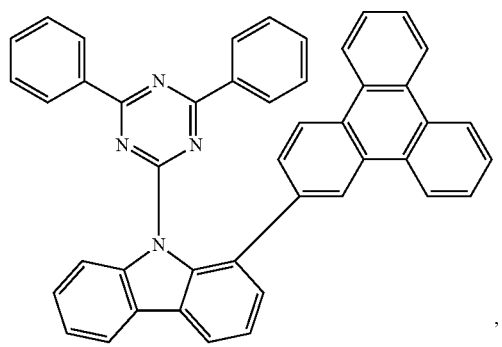
Compound H20
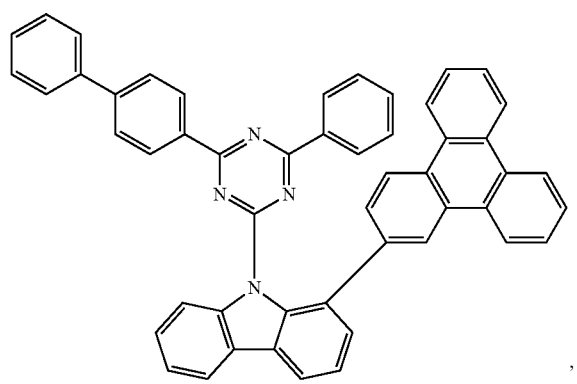
Compound H21
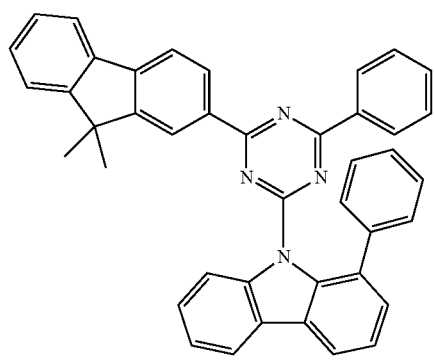
Compound H22
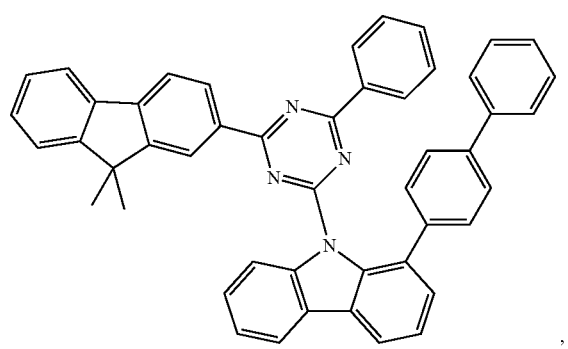
Compound H23
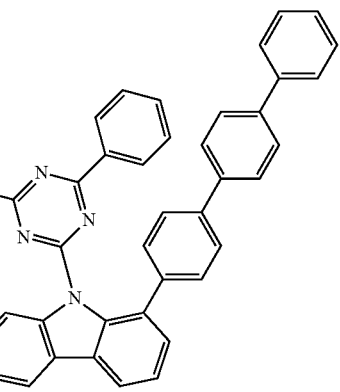
Compound H24
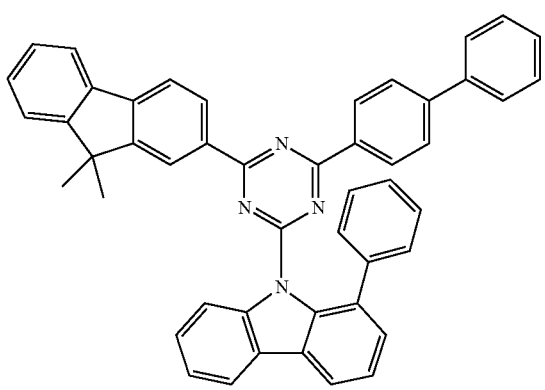
Compound H25
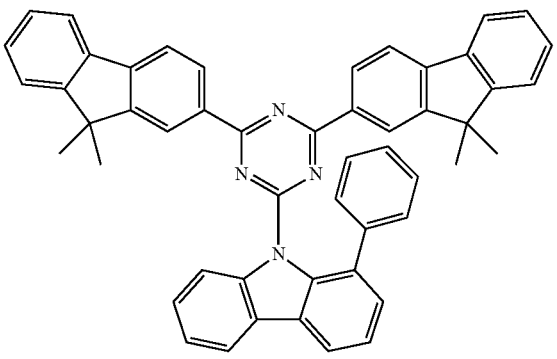
Compound H26
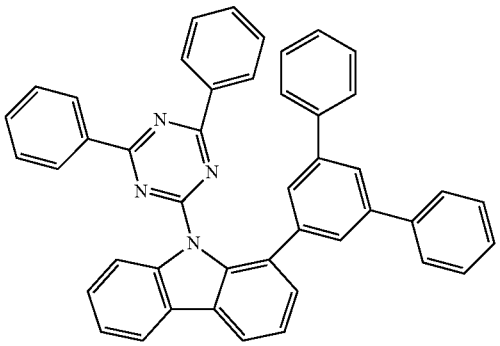

Compound H27
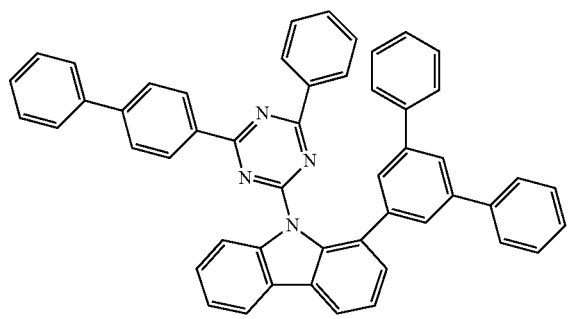
Compound H31
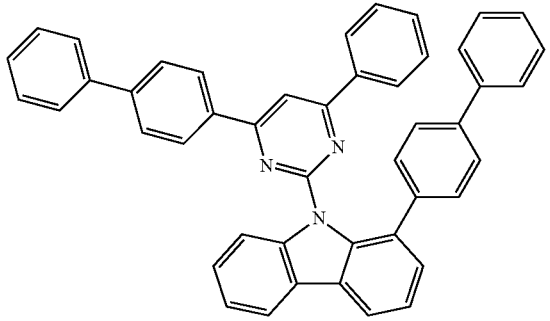
Compound H28
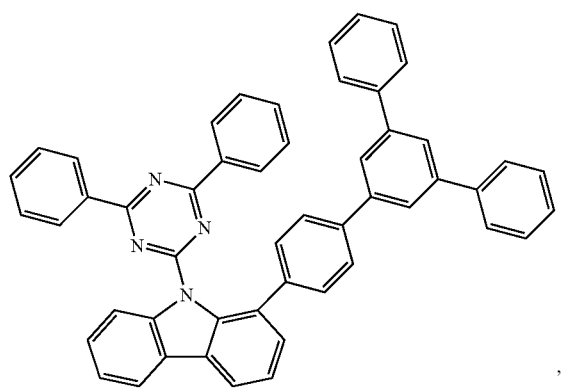
Compound H32
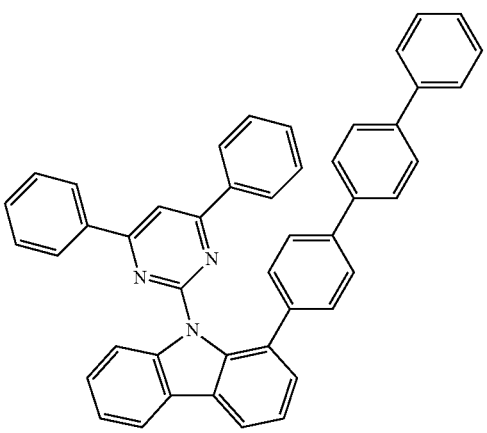
Compound H29
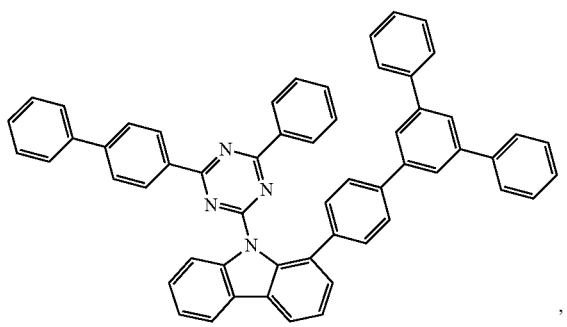
Compound H33
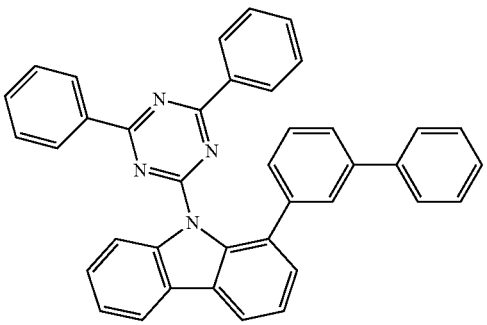
Compound H30
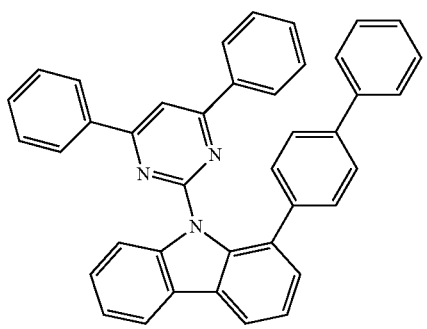
Compound H34
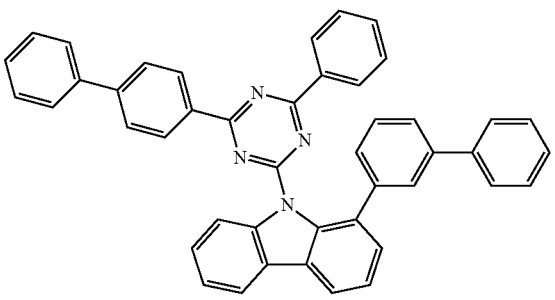

Compound H35
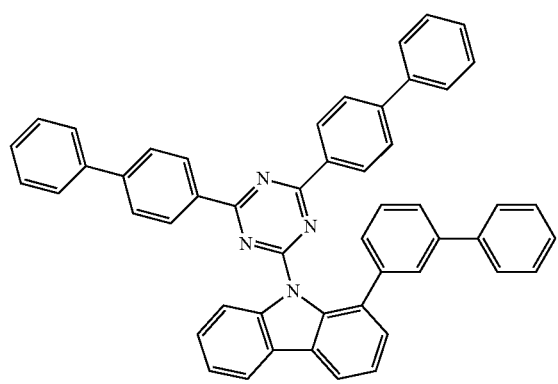
Compound H36
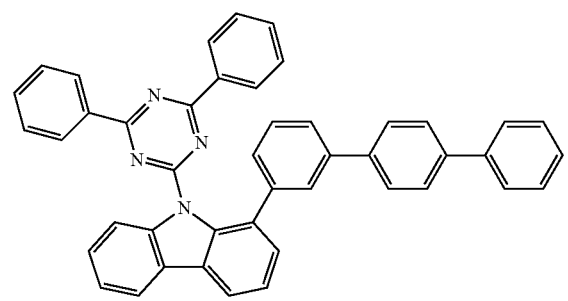
Compound H37
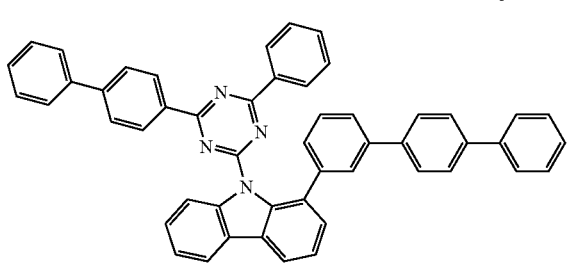
Compound H38
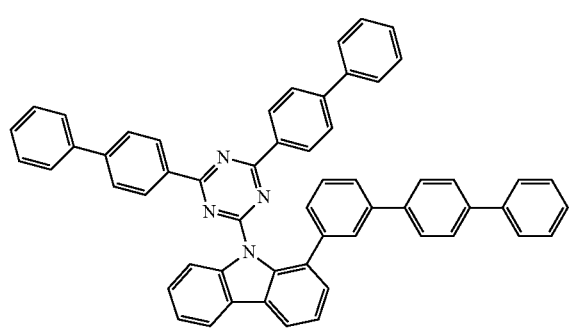
Compound H39
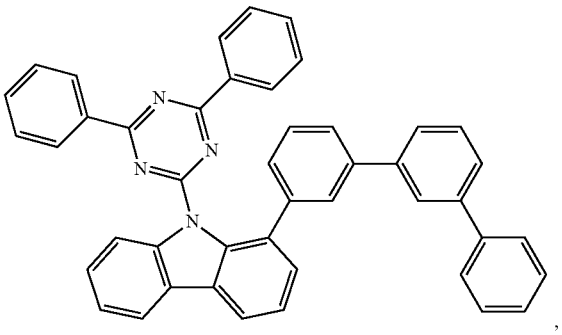
Compound H40
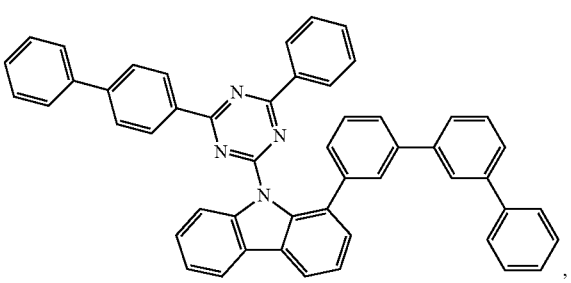
Compound H41
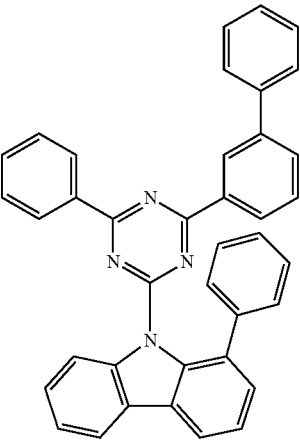
Compound H42
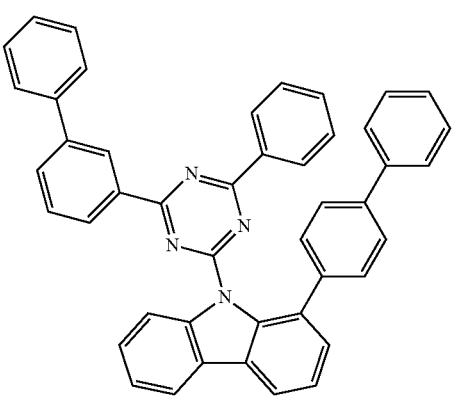

Compound H43
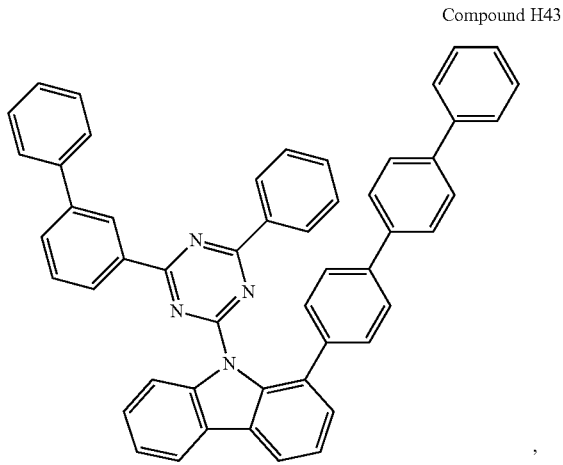
Compound H46
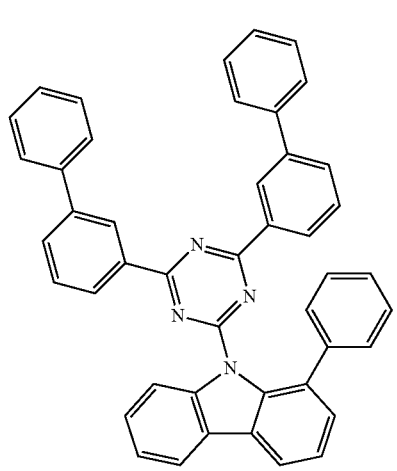
Compound H44
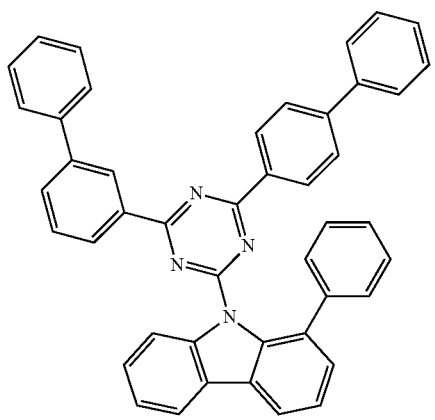
Compound H47
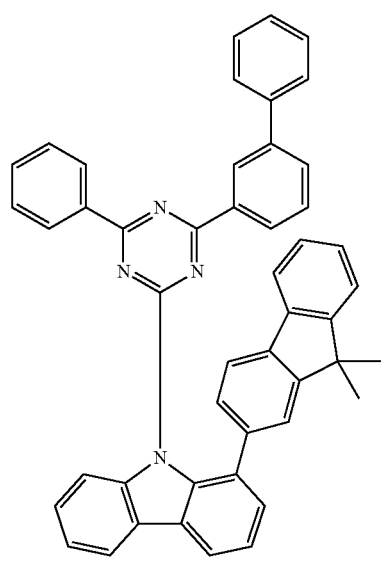
Compound H45
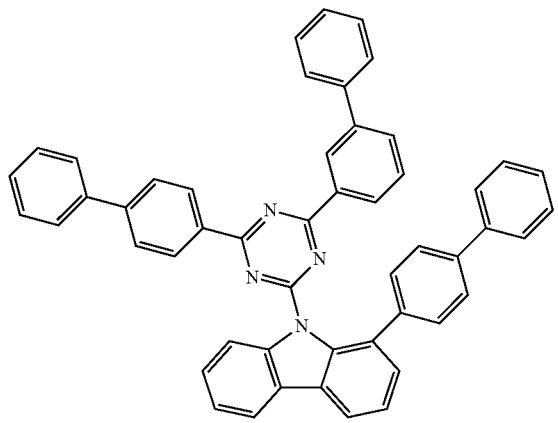
Compound H48
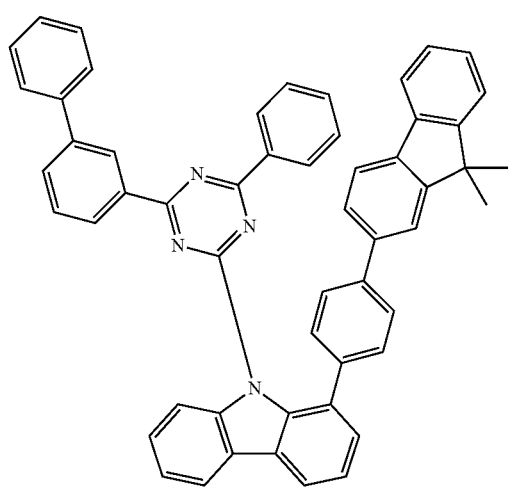

Compound H49
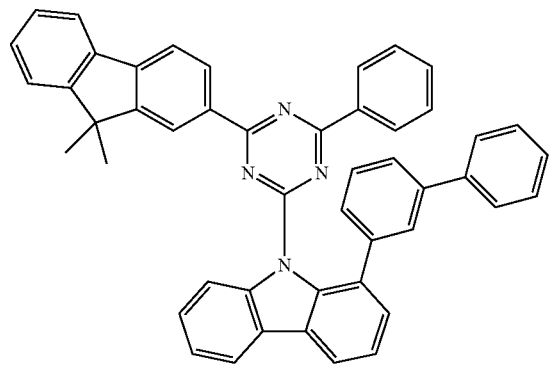
and
Compound H50
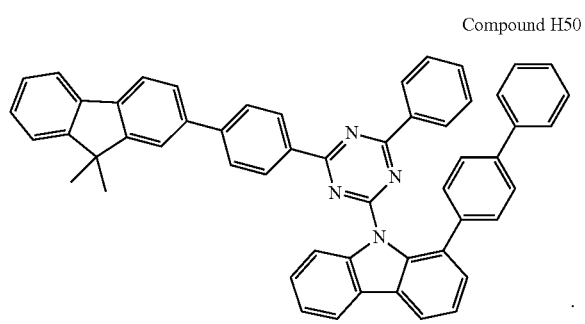 [SMILES: CC1(C)c2ccccc2-c2ccc(-c3ccc(-c4nc(-c5ccccc5)nc(-n5c6ccccc6c6cccc(-c7ccc(-c8ccccc8)cc7)c65)n4)cc3)cc21]
In another embodiment of the composition where the first compound has a structure according to Formula I as defined above, the first compound can be selected from the group consisting of:
Compound E1
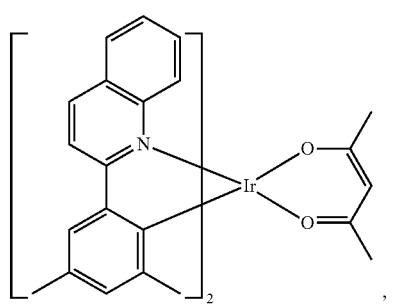
Compound E2
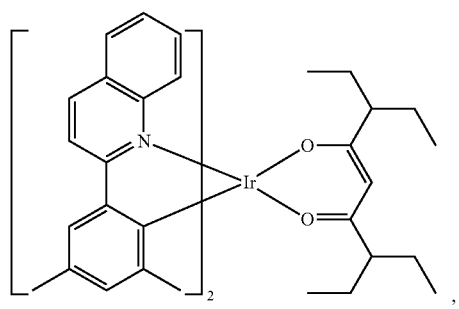
Compound E3
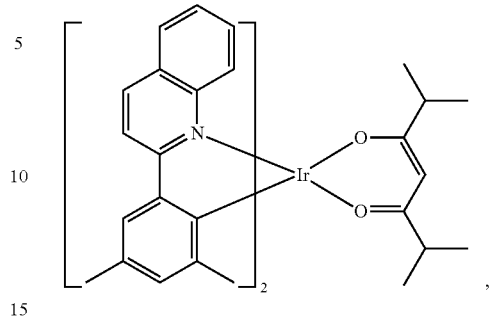
Compound E4
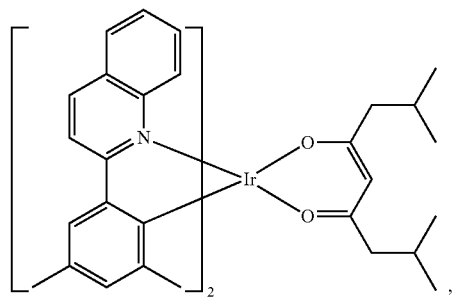
Compound E5
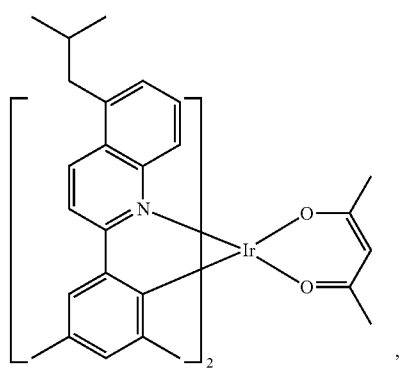
Compound E6
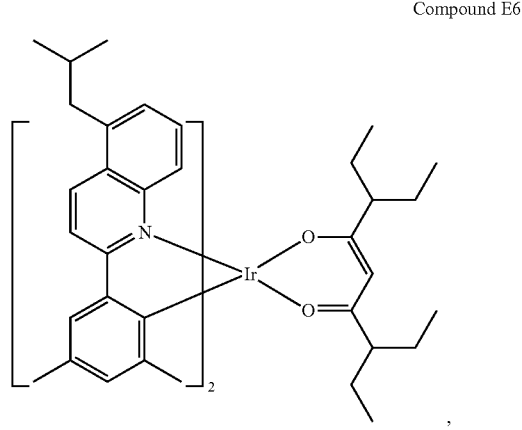

Compound E7
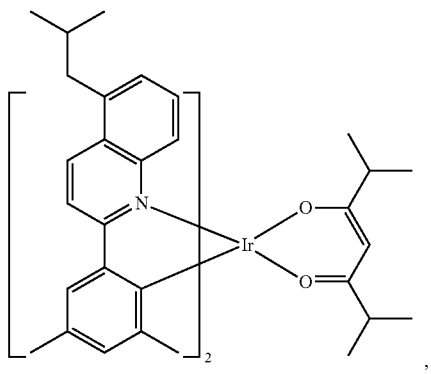
Compound E8
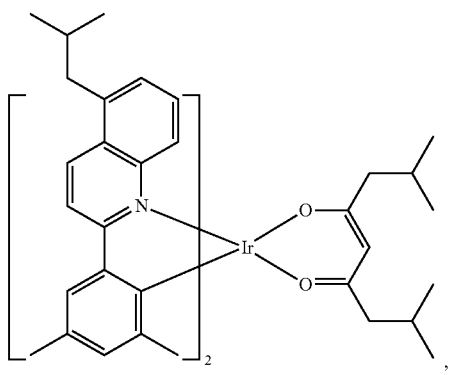
Compound E9
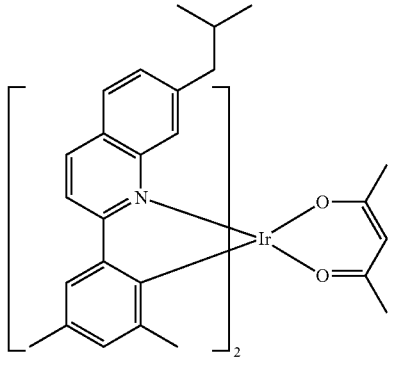
Compound E10
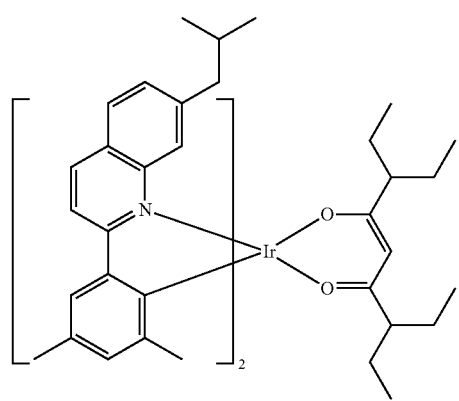
Compound E11
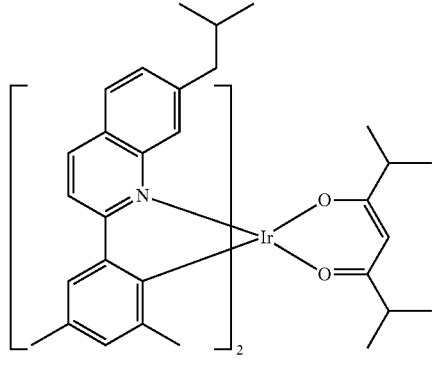
Compound E12
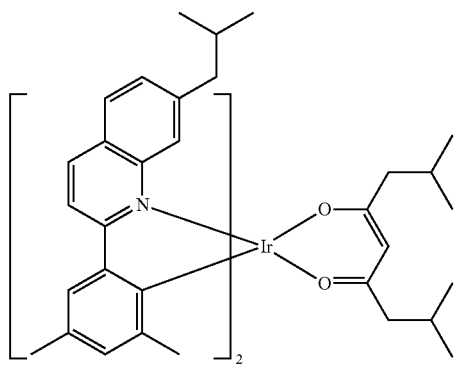
Compound E13
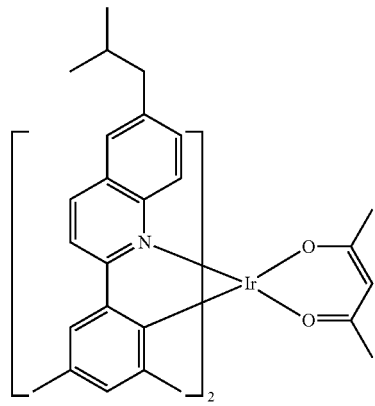
Compound E14
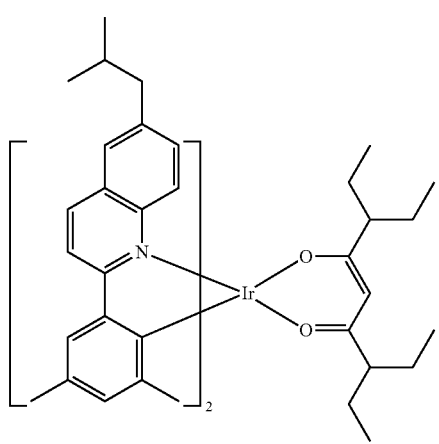

Compound E15
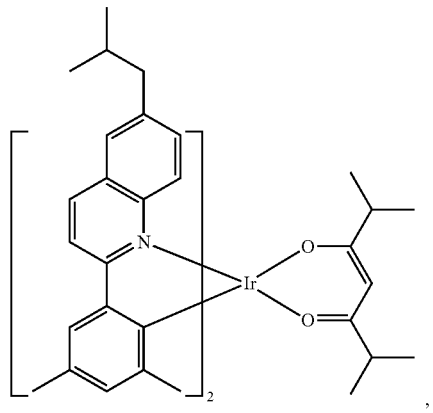
Compound E16
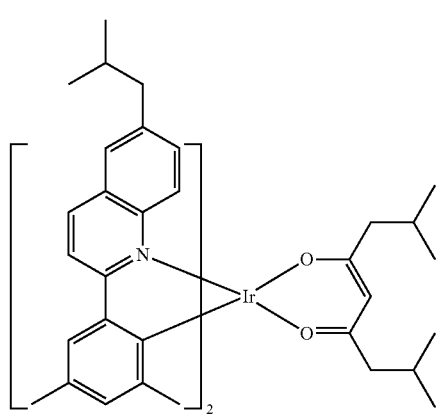
Compound E17
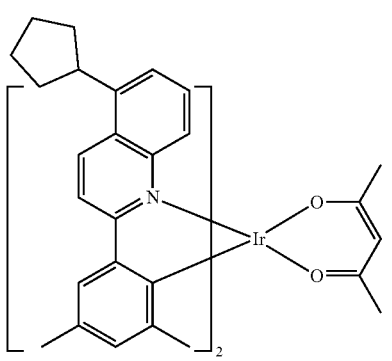
Compound E18
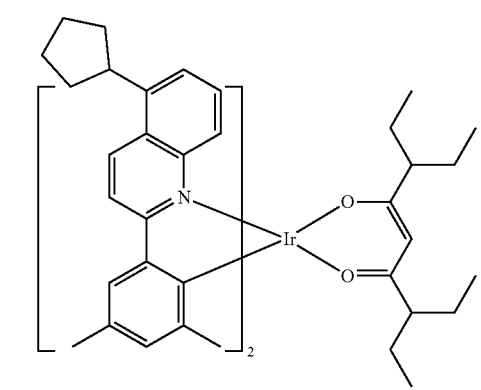
Compound E19
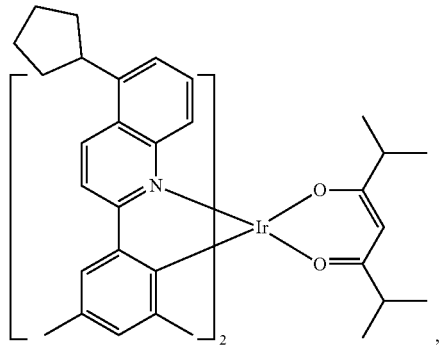
Compound E20
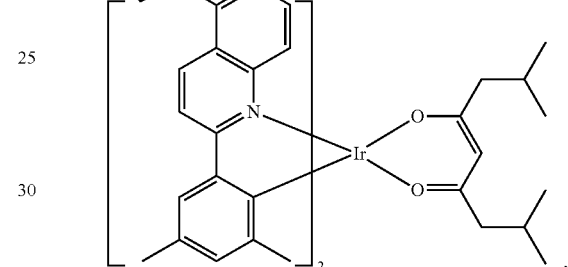
Compound E21
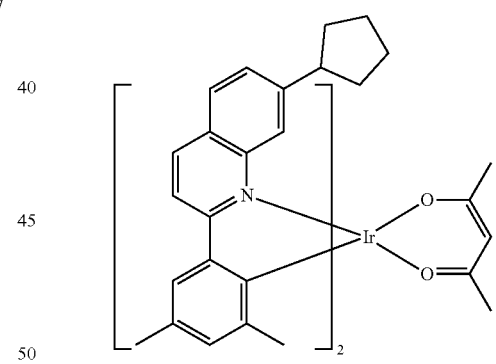
Compound E22
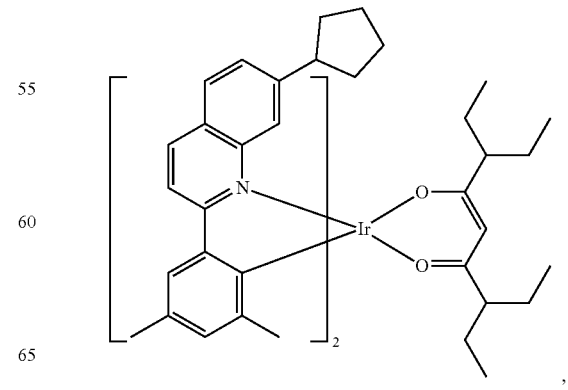

Compound E23
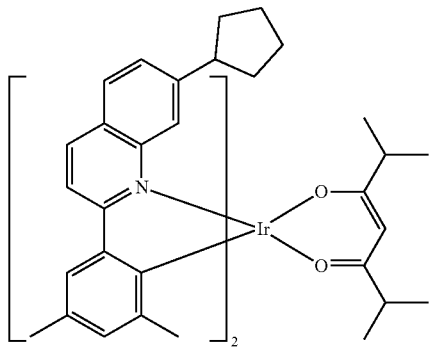
Compound E24
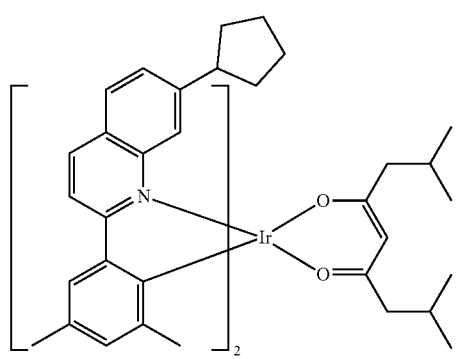
Compound E25
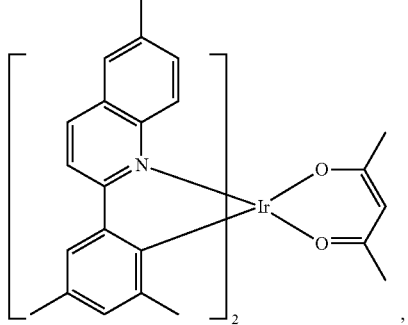
Compound E26
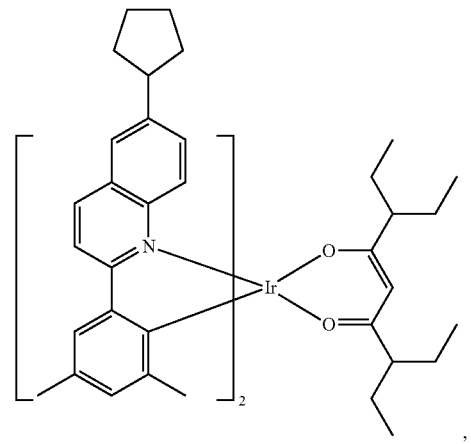
Compound E27
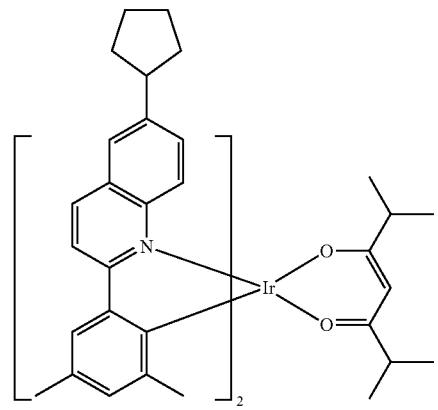
Compound E28
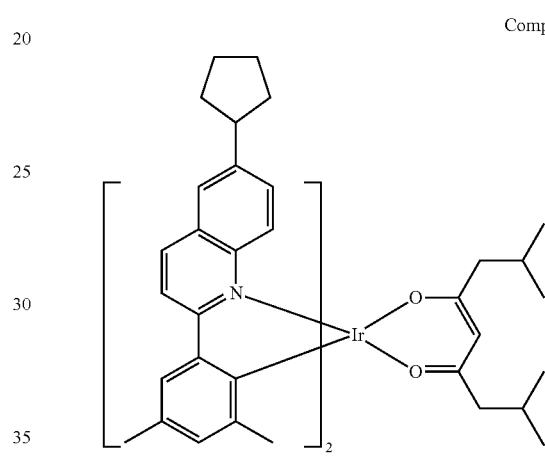
Compound E29
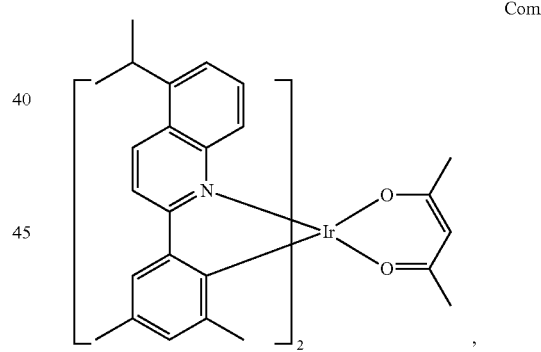
Compound E30
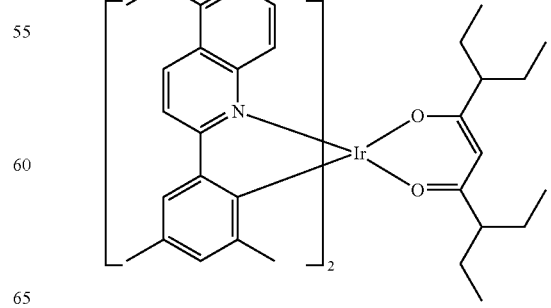

Compound E31
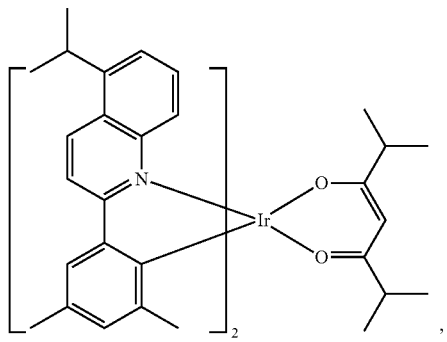
Compound E32
Compound E33
Compound E34
Compound E35
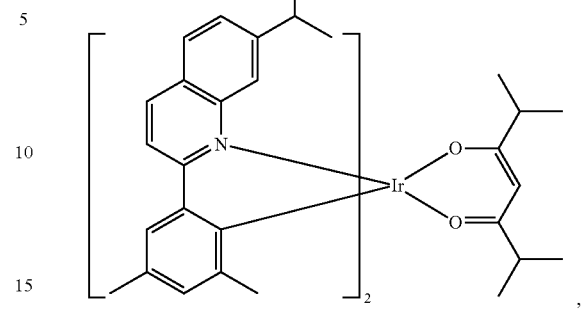
Compound E36
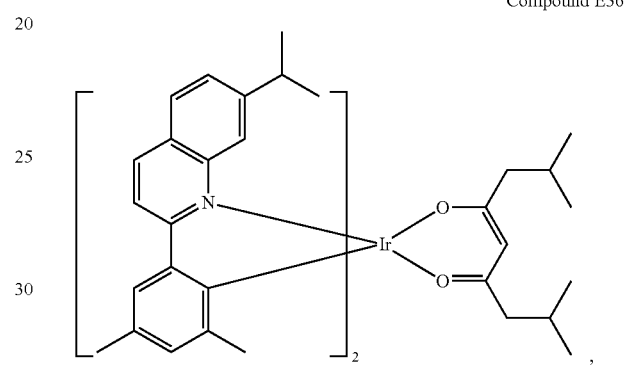
Compound E37
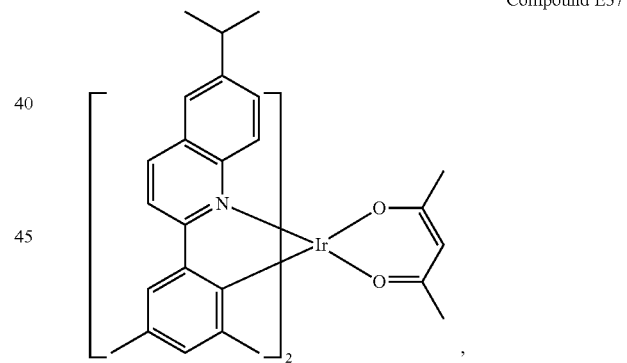
Compound E38
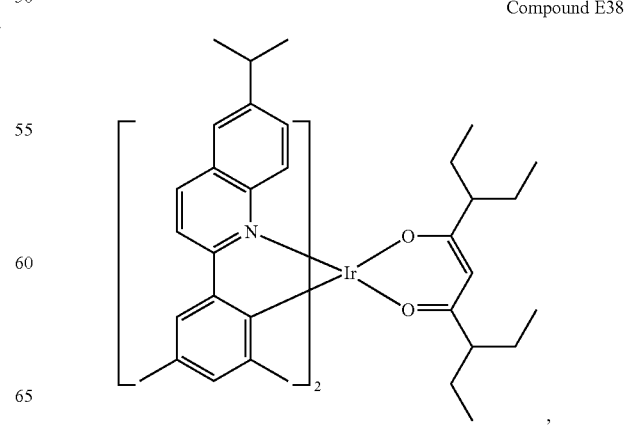

Compound E39

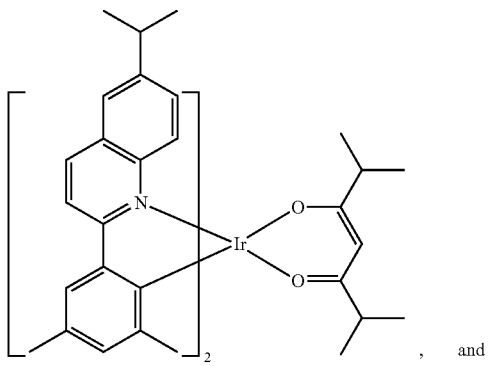

, and

Compound E40

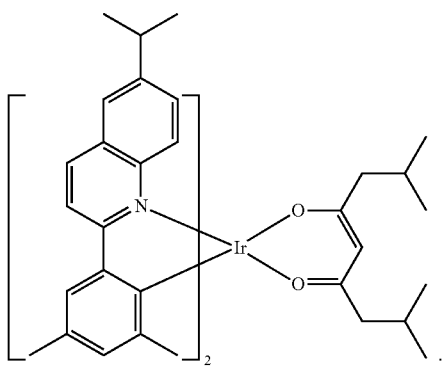

.

In another embodiment of the composition where the first compound has a structure according to Formula I and the second compound has a structure according to Formula II as defined above, the mixture of the first compound and the second compound is selected from the group consisting of: (Compound E5 and Compound H1), (Compound E1 and Compound H14), (Compound E4 and Compound H21), (Compound E9 and Compound H30), (Compound E17 and Compound H21), and (Compound E13 and Compound H33).

In another embodiment of the composition where the first compound has a structure according to Formula I and the second compound has a structure according to Formula II as defined above, the mixture of the first compound and the second compound is (Compound E5 and Compound H1).

In an embodiment of the composition comprising a mixture of a first compound and a second compound, wherein the first compound has a difference chemical structure than the second compound, wherein the first compound is capable of functioning as a phosphorescent emitter in an OLED at room temperature, the first compound and the second compound each independently has the formula of $Ir(L^1)_2(L^2)$, wherein $L^1$ has the formula:

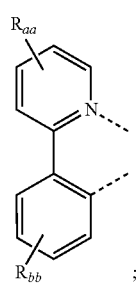

wherein $L^2$ has the formula:

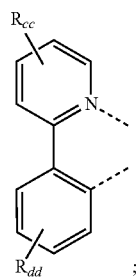

wherein $L^1$ is different from $L^2$;

wherein $R_{aa}$, $R_{bb}$, $R_{cc}$, and $R_{dd}$ may represent mono, di, tri, or tetra substitution, or no substitution;

wherein $R_{aa}$, $R_{bb}$, $R_{cc}$, and $R_{dd}$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; wherein two adjacent substituents of $R_{aa}$, $R_{bb}$, $R_{cc}$, and $R_{dd}$ are optionally joined to form a fused ring or form a multidentate ligand; and wherein at least one of $R_{cc}$ is a 5 or 6-membered carbocyclic or heterocyclic ring.

In one embodiment of the composition where the first compound and the second compound each independently has the formula of $Ir(L^1)_2(L^2)$ as defined above, at least one of $R_{cc}$ is benzene or pyridine.

In one embodiment of the composition where the first compound and the second compound each independently has the formula of $Ir(L^1)_2(L^2)$ as defined above, $L^1$ is selected from the group consisting of:

$L_{1-1}$

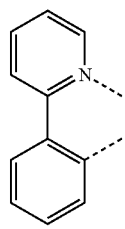

L1-2 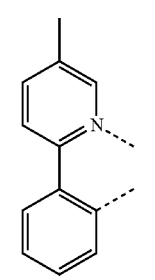
L1-3 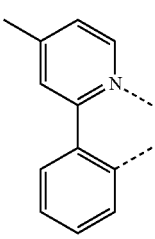
L1-4 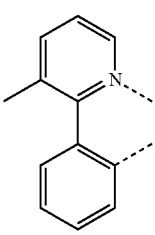
L1-5 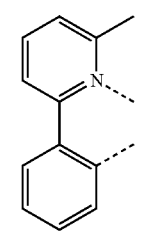
L1-6 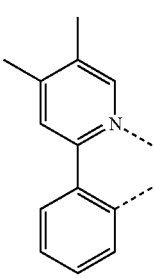
L1-7 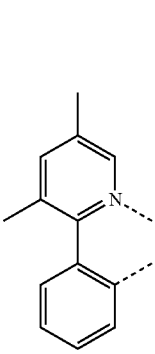
L1-8 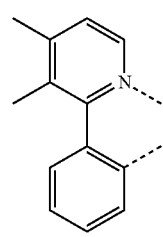
L1-9 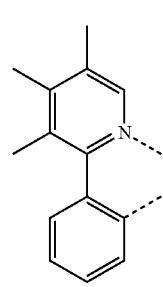
L1-10 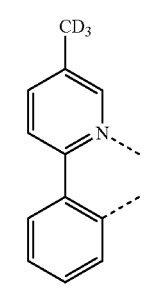
L1-11 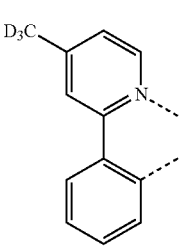
L1-12 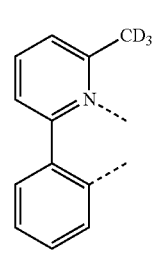
L1-13 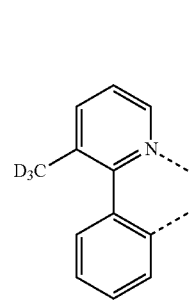

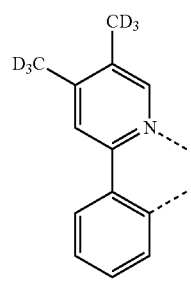 L1-14
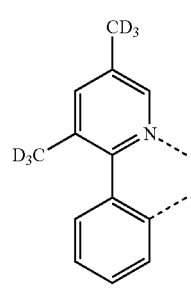 L1-15
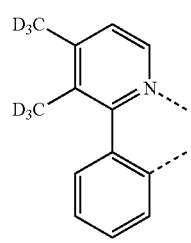 L1-16
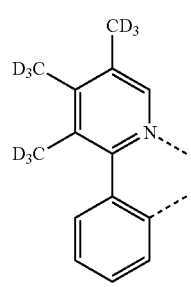 L1-17
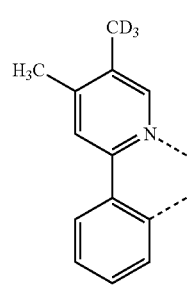 L1-18
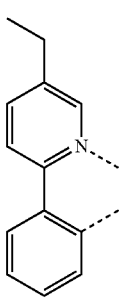 L1-19
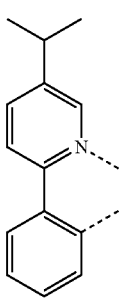 L1-20
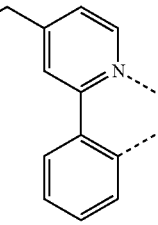 L1-21
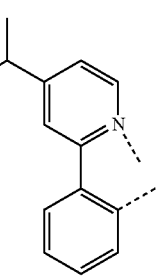 L1-22
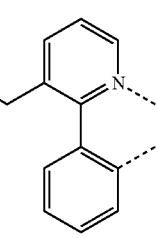 L1-23
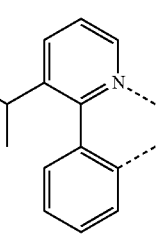 L1-24

| | | | |
|---|---|---|---|
| L₁-25 | | L₁-31 | |
| L₁-26 | | L₁-32 | |
| L₁-27 | | L₁-33 | |
| L₁-28 | | L₁-34 | |
| L₁-29 | | L₁-35 | |
| L₁-30 | | | |

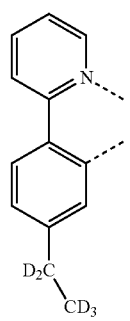 L1-36
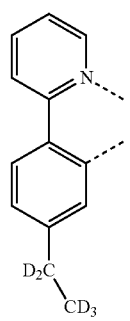 L1-37
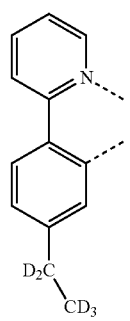 L1-38
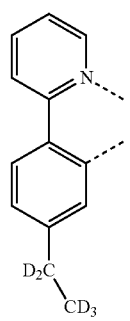 L1-39
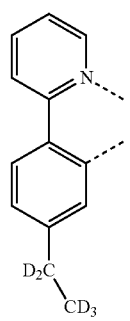 L1-40
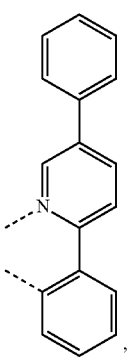 L2-1
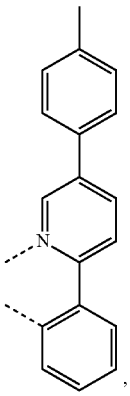 L2-2
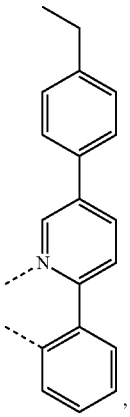 L2-3
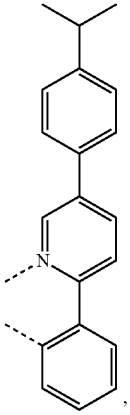 L2-4
In one embodiment of the composition where the first compound and the second compound each independently has the formula of Ir(L$^1$)$_2$(L$^2$) as defined above, L$^2$ is selected from the group consisting of:

L2-5
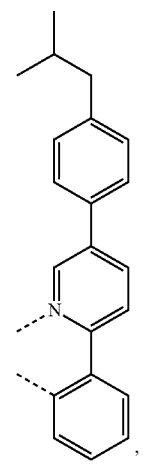
L2-6
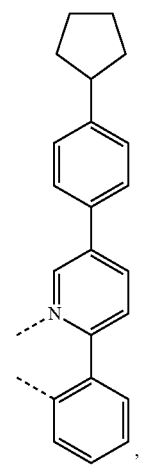
L2-7
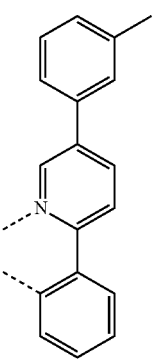
L2-8
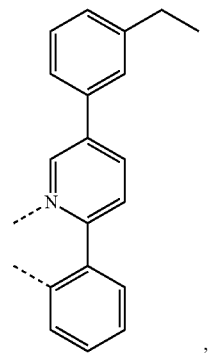
L2-9
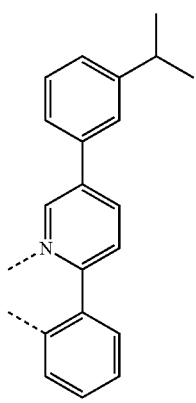
,
L2-10
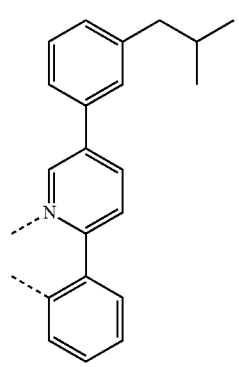
,
L2-11
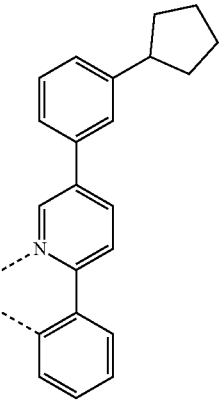
,
L2-12
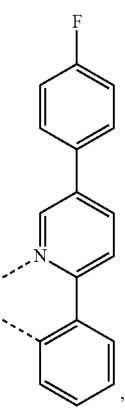
, L2-13 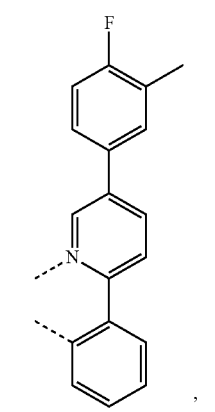
L2-14 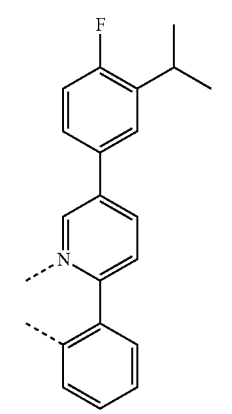
L2-15 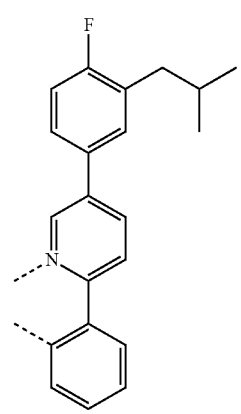
L2-16
L2-17 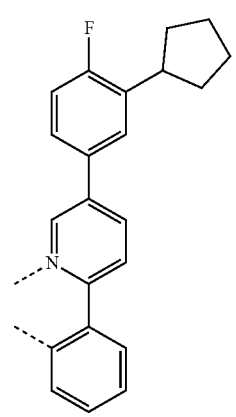
L2-18 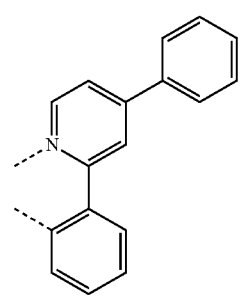
L2-19 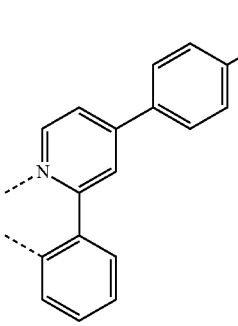
L2-20 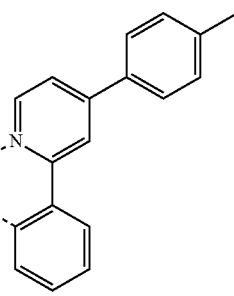

-continued

L2-21

L2-22

L2-23

L2-24

L2-25

L2-26

L2-27

L2-28

-continued
L2-29
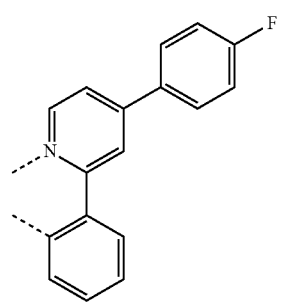
L2-30
L2-31
L2-32
-continued
L2-33
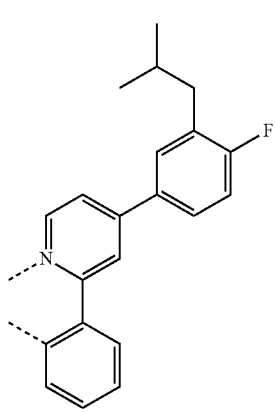
L2-34
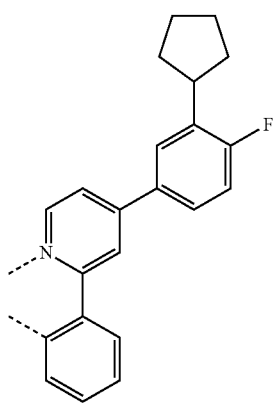
L2-35
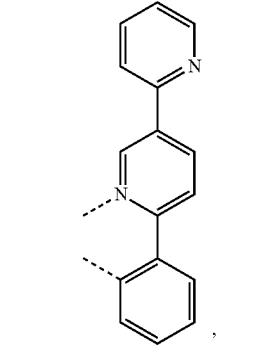
L2-36
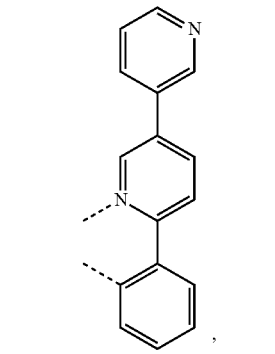

L2-37 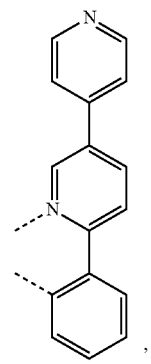
L2-38 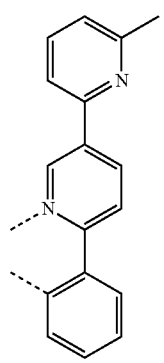
L2-39 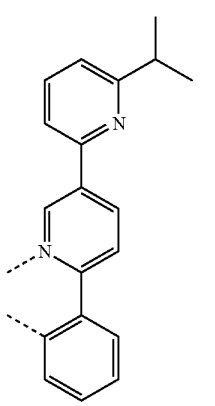
L2-40 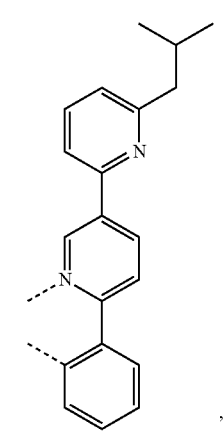
L2-41 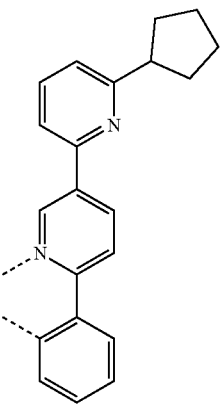
L2-42 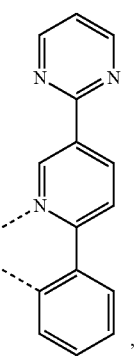
L2-43 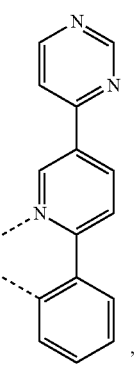
L2-44 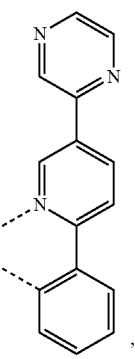

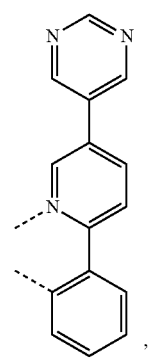
L2-45
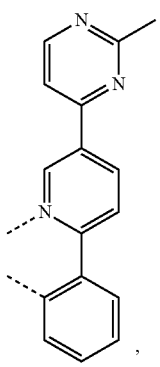
L2-46
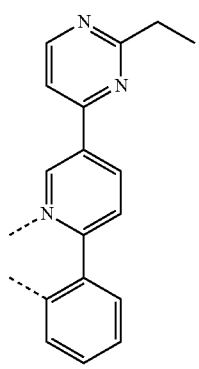
L2-47
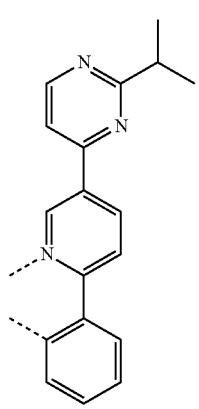
L2-48
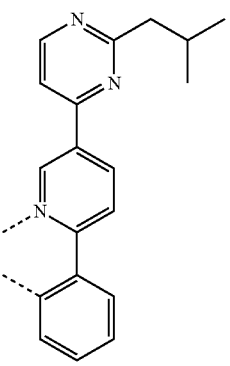
L2-49
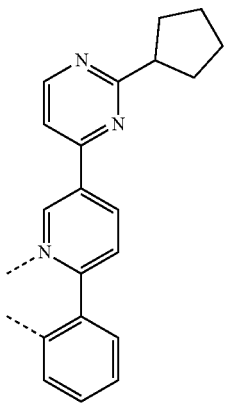
L2-50
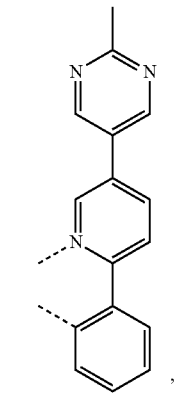
L2-51
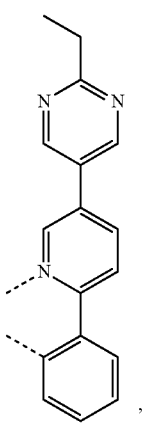
L2-52

-continued
L2-53 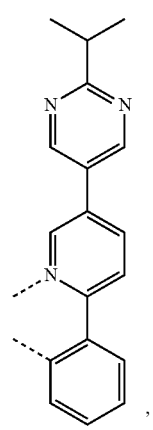,
L2-54 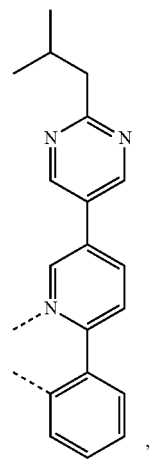,
L2-55 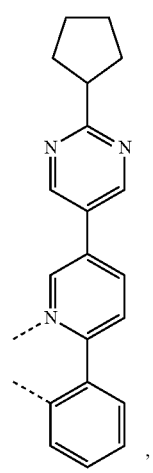,
-continued
L2-56 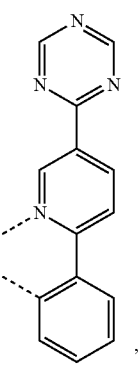,
L2-57 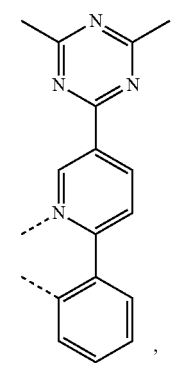,
L2-58 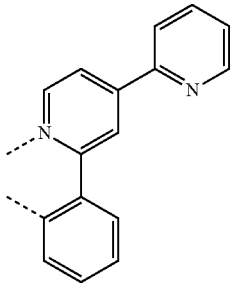,
L2-59 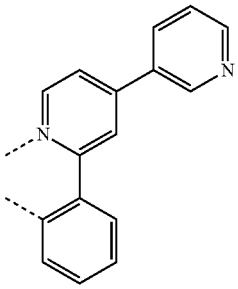,
L2-60 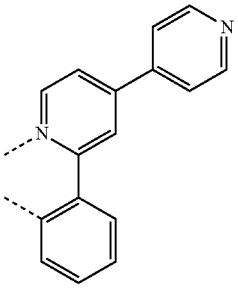, L2-61 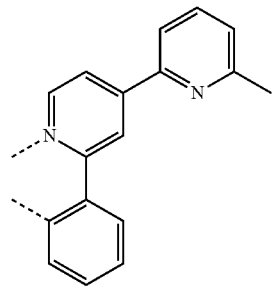
L2-62 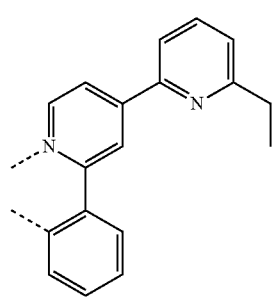
L2-63 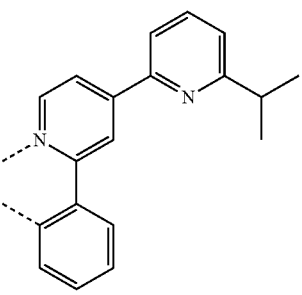
L2-64 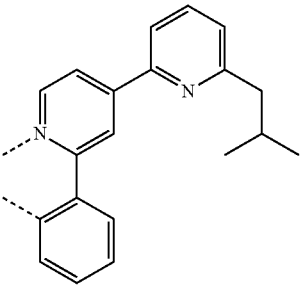
L2-65 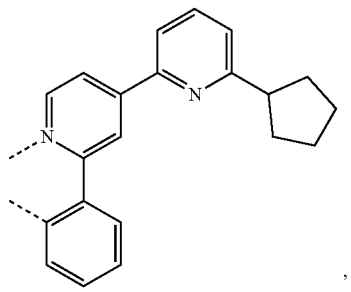
L2-66 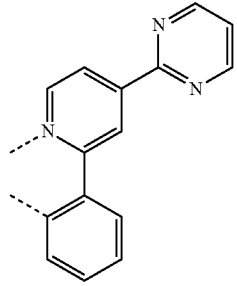
L2-67 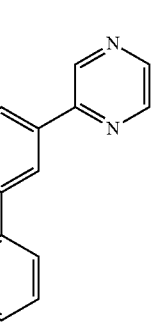
L2-68 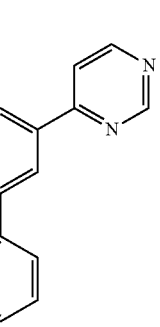
L2-69 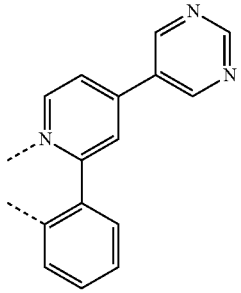
L2-70 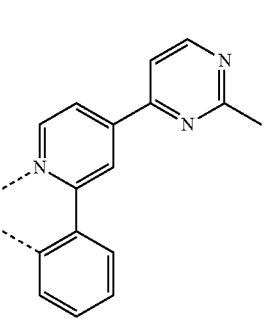

75
-continued
L2-71
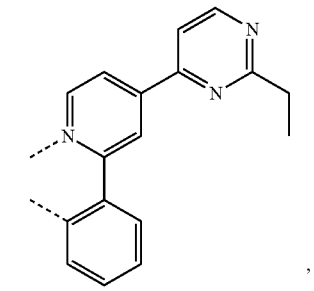
L2-72
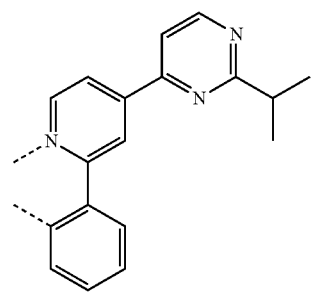
L2-73
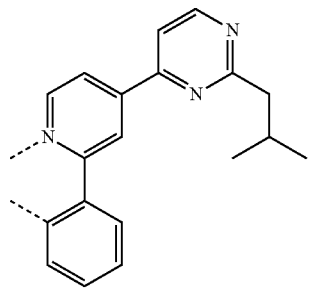
L2-74
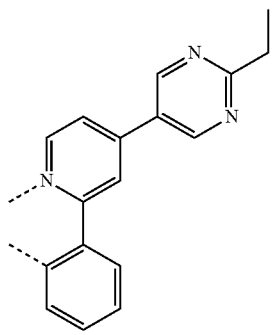
L2-75
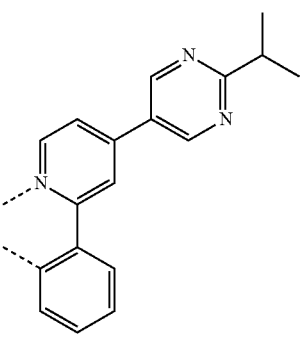
76
-continued
L2-76
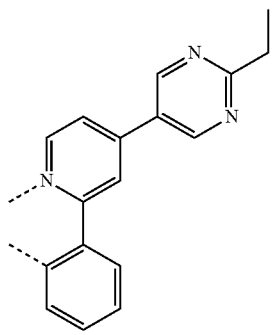
L2-77
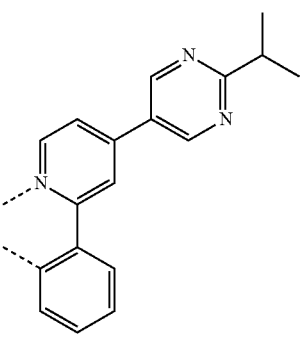
L2-78
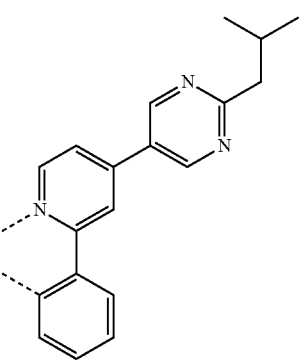
L2-79
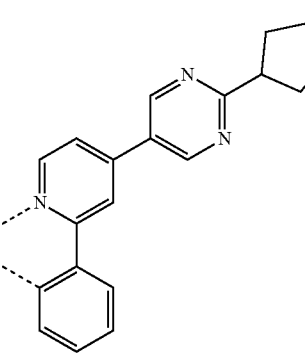

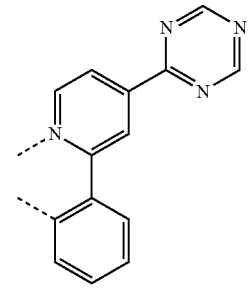 L2-80
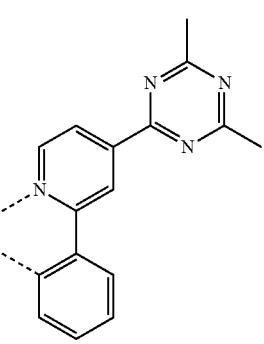 L2-81
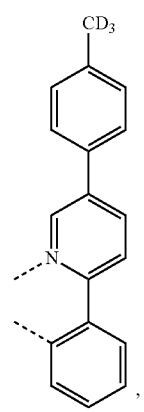 L2-82
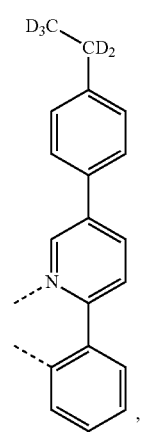 L2-83
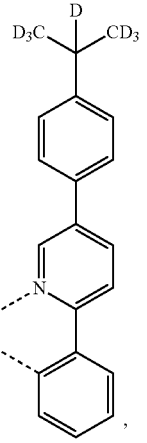 L2-84
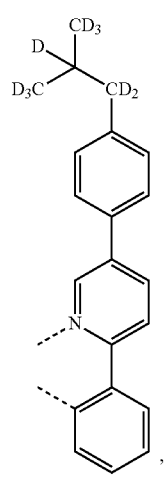 L2-85
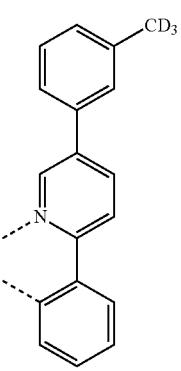 L2-86

L2-87 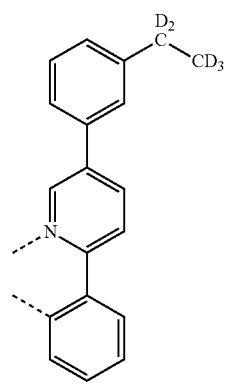
L2-88 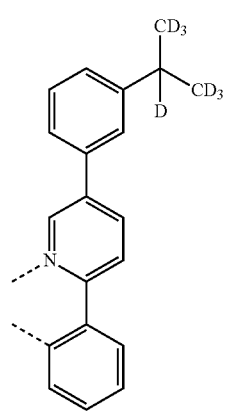
L2-89 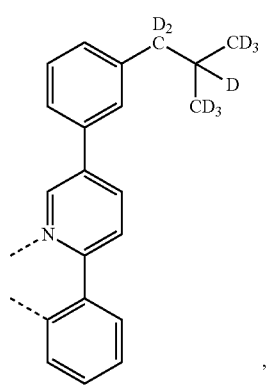
L2-90 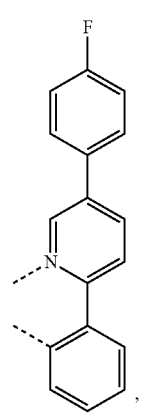
L2-91 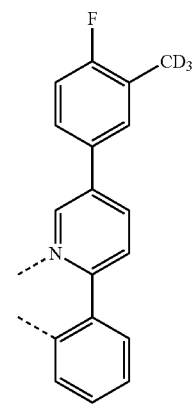
L2-92 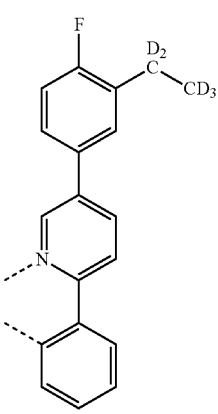
L2-93 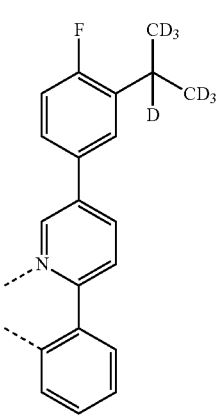
L2-94

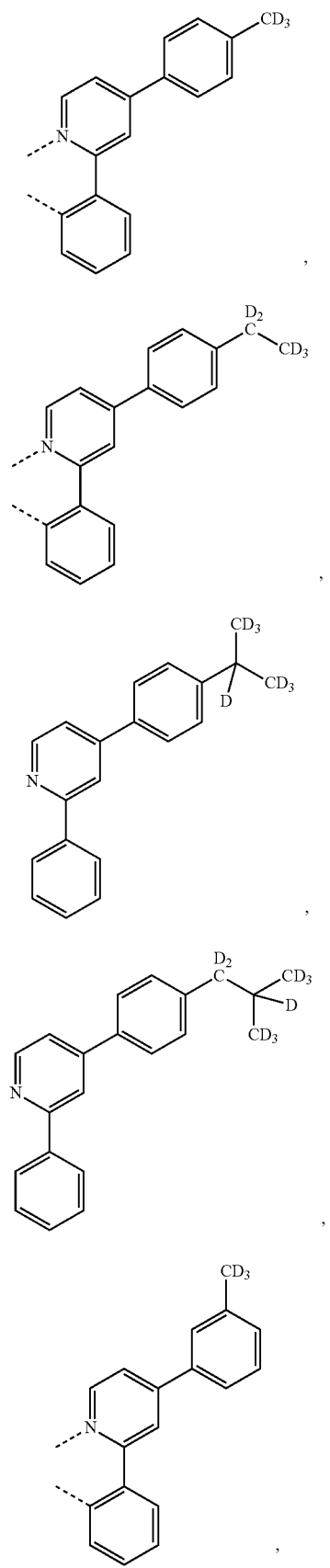

L2-104, L2-105, L2-106, L2-107, L2-108, L2-109, L2-110, L2-111

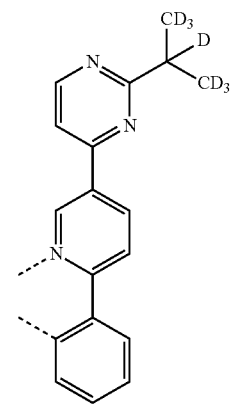 L2-112,
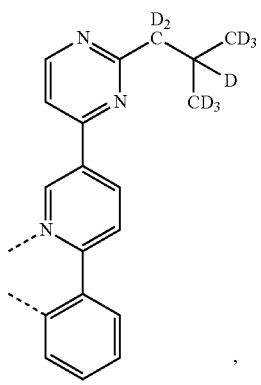 L2-113,
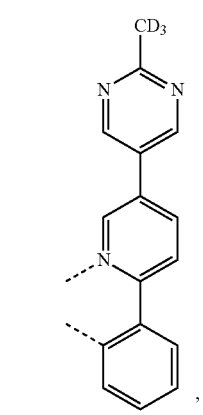 L2-114,
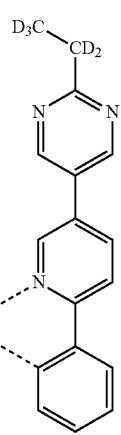
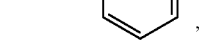 L2-115,
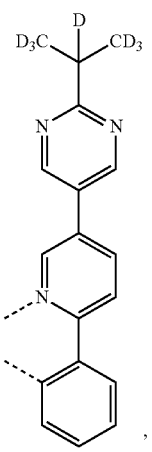 L2-116,
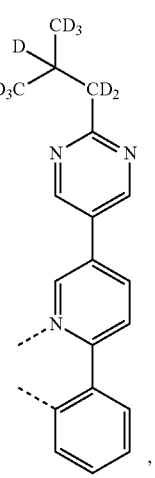 L2-117,
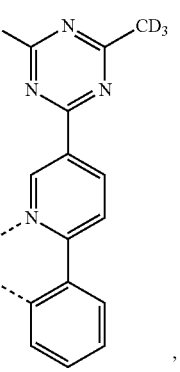 L2-118,
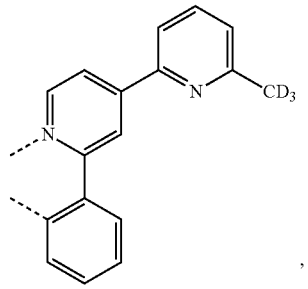 L2-119,

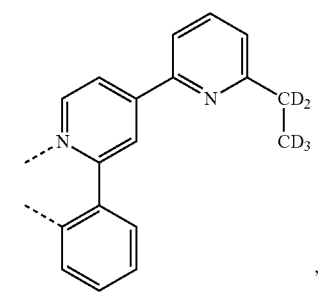 L2-120
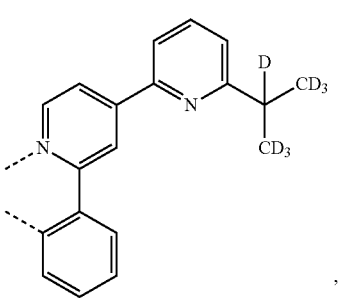 L2-121
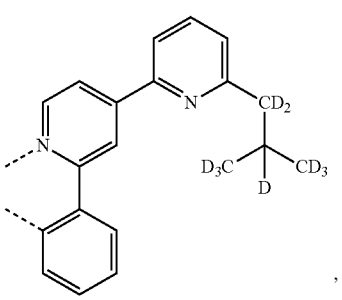 L2-122
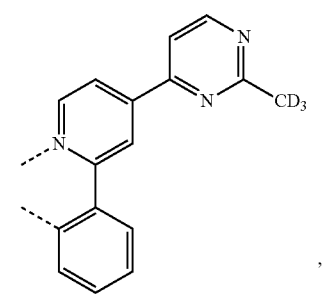 L2-123
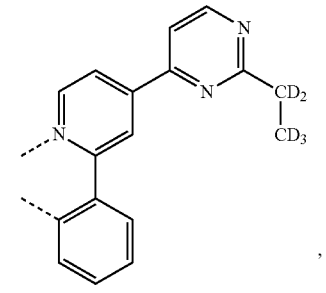 L2-124
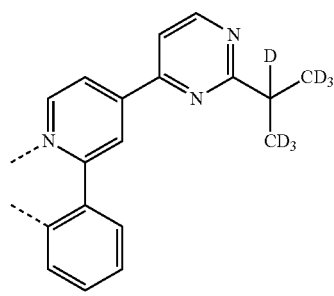 L2-125
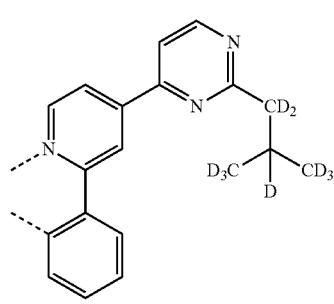 L2-126
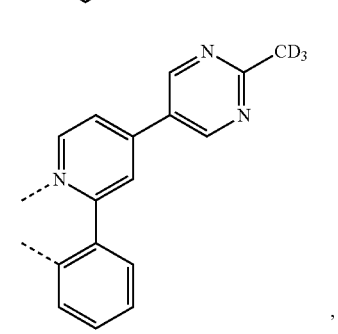 L2-127
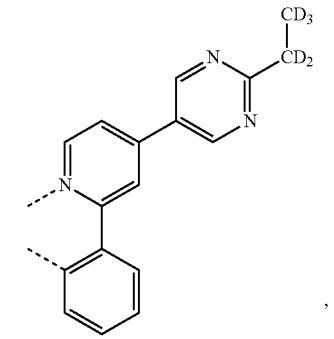 L2-128
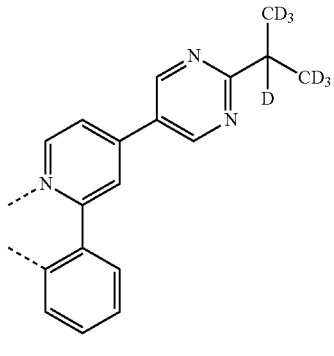 L2-129

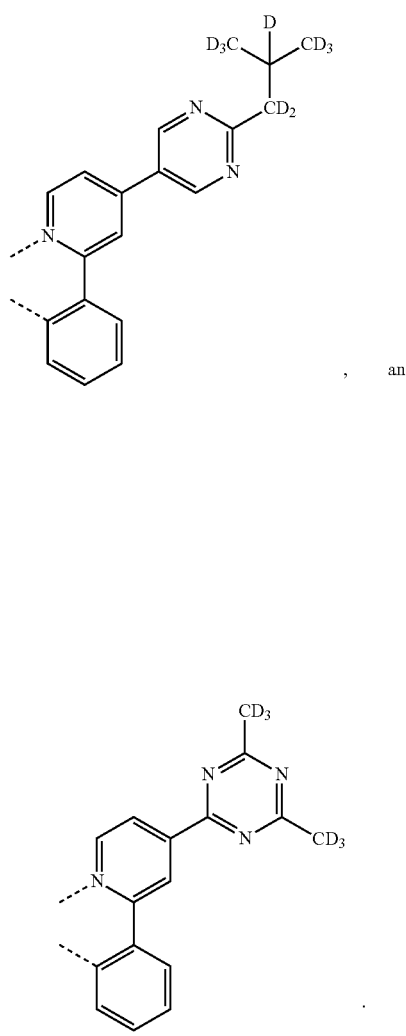
, and
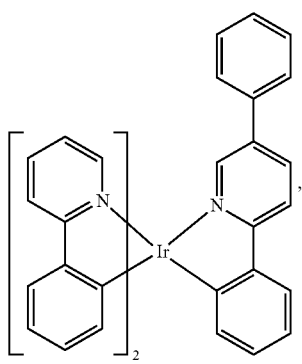
In one embodiment of the composition where the first compound and the second compound each independently has the formula of Ir(L¹)₂(L²) as defined above, the first compound and the second compound are each independently selected from the group consisting of:
Compound 7
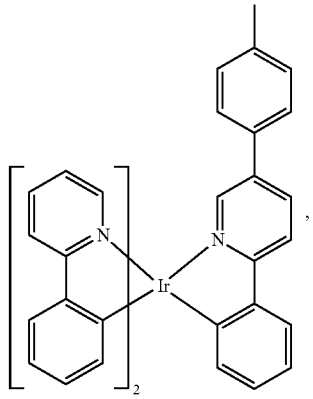
Compound 8
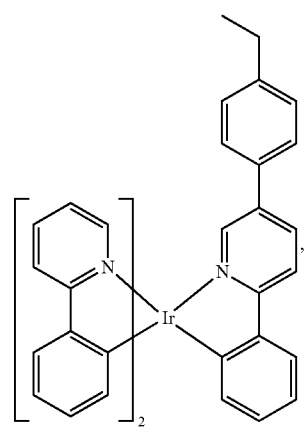
Compound 9
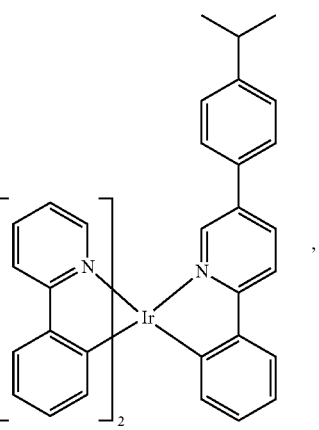
Compound 10
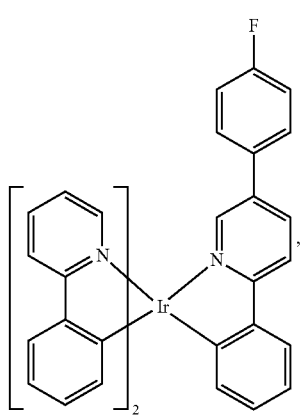
Compound 11

Compound 12
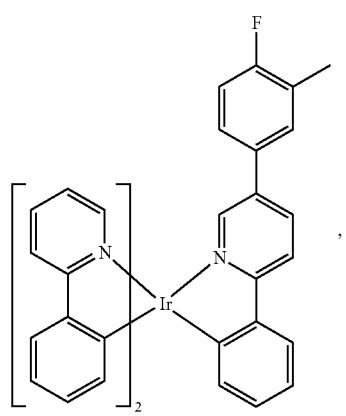
Compound 13
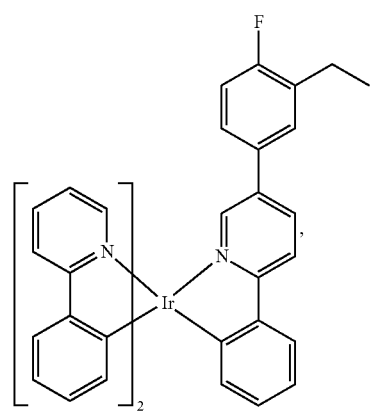
Compound 14
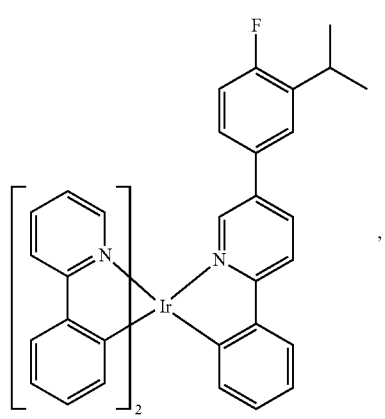
Compound 15
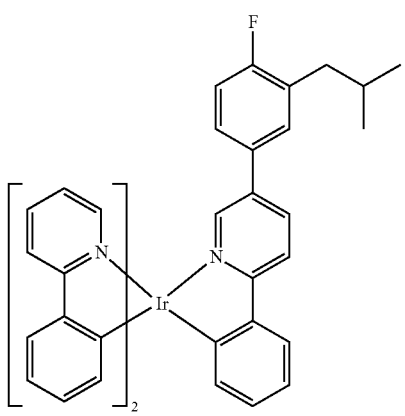
Compound 20
Compound 21
Compound 22
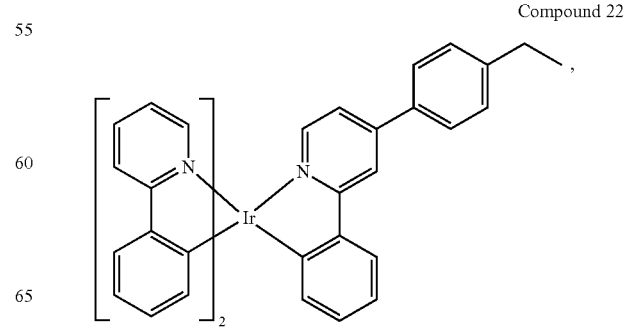

Compound 23
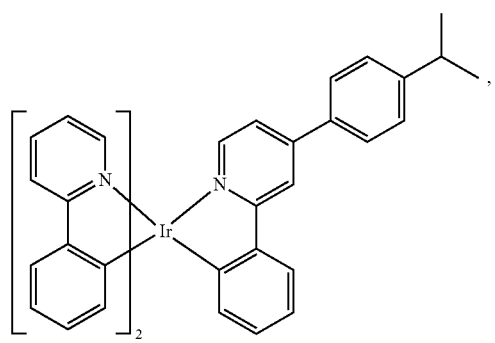
Compound 24
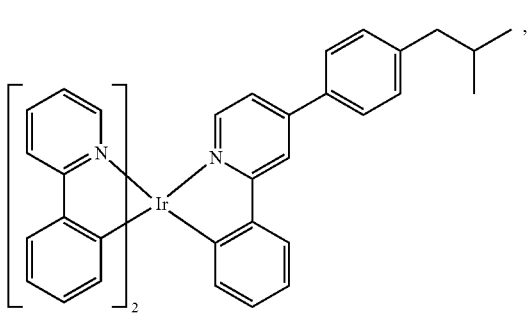
Compound 25
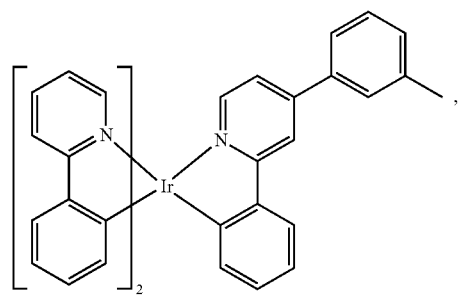
Compound 26
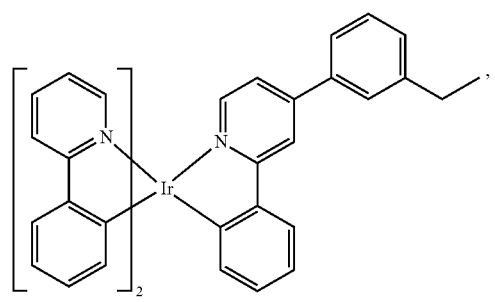
Compound 27
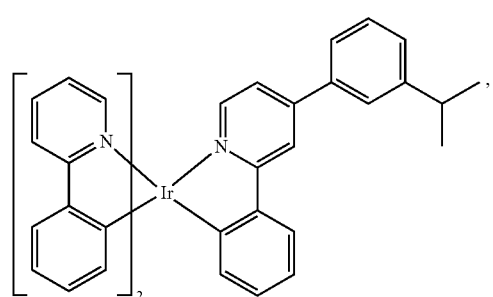
Compound 28
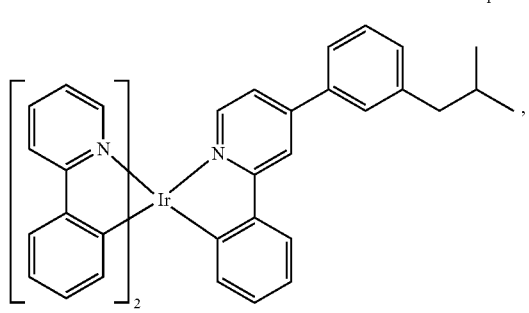
Compound 29
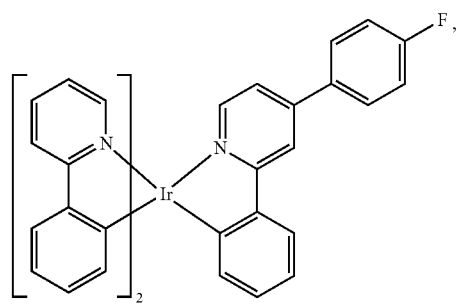
Compound 30
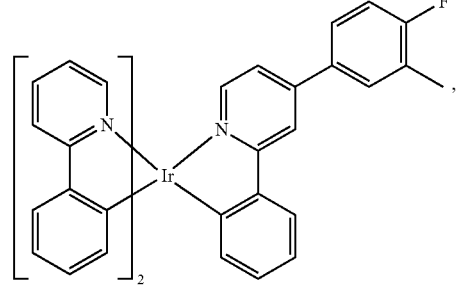
Compound 31
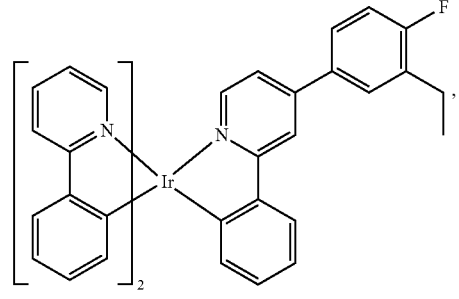
Compound 32
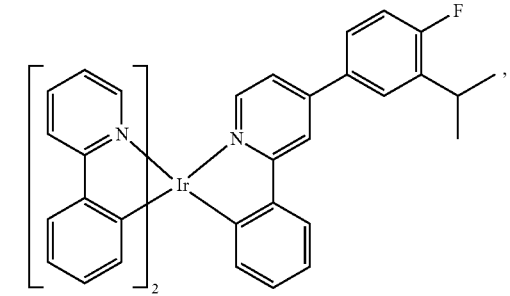

Compound 33
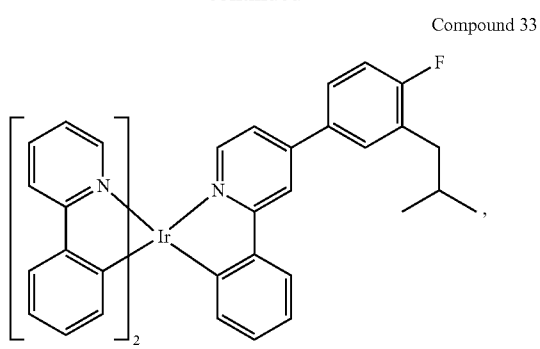
Compound 40
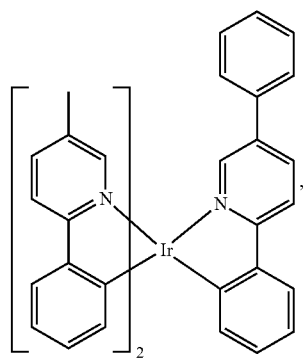
Compound 41
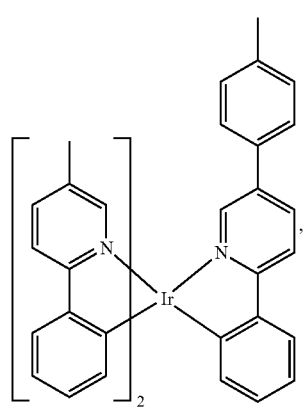
Compound 42
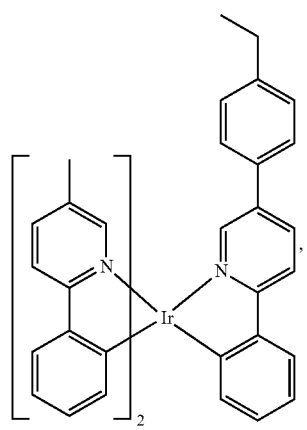
Compound 43
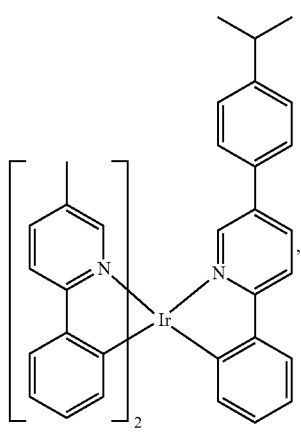
Compound 44
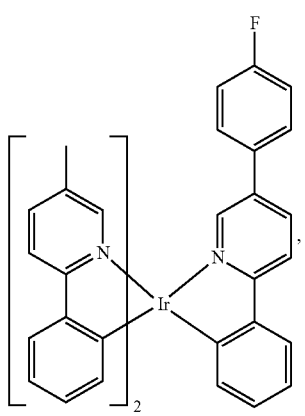
Compound 45
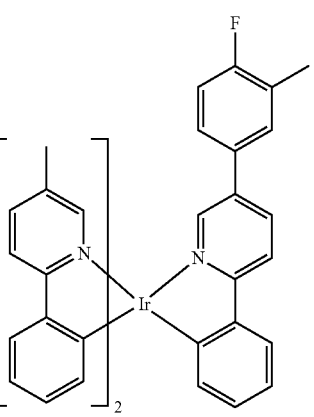

Compound 46
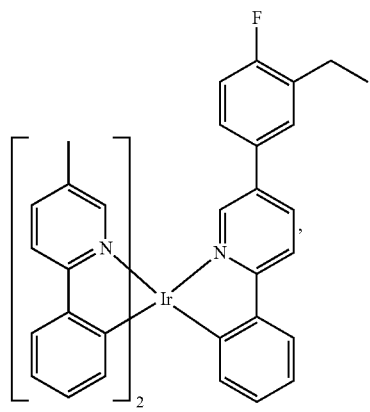
Compound 47
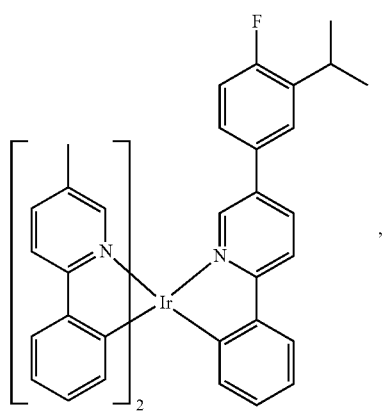
Compound 48
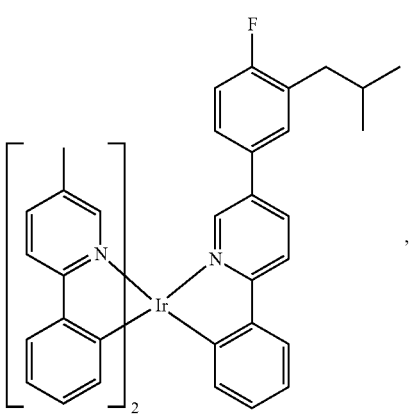
Compound 53
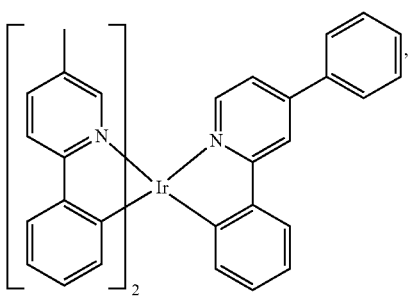
Compound 54
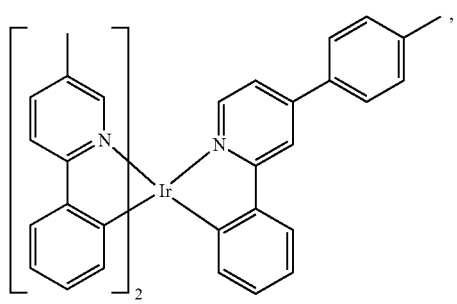
Compound 55
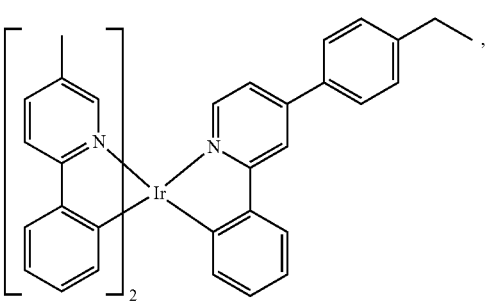
Compound 56
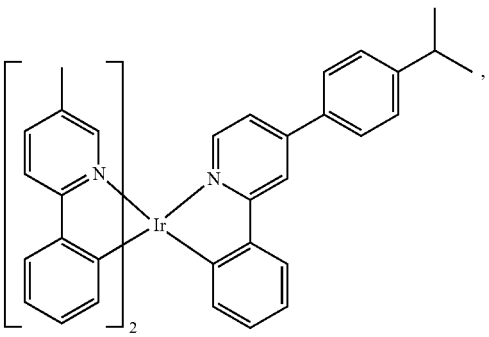
Compound 57
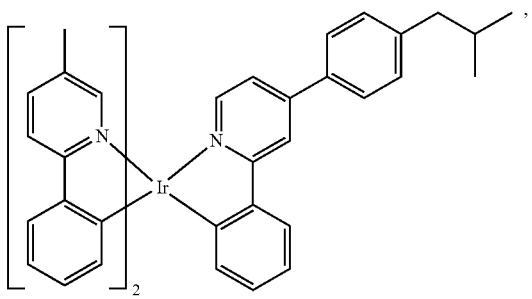

Compound 58
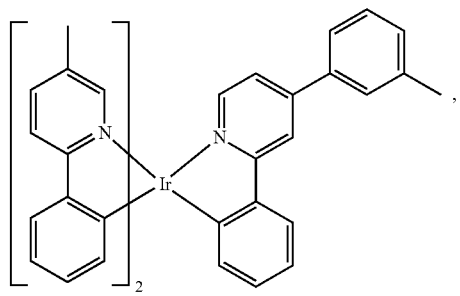
Compound 59
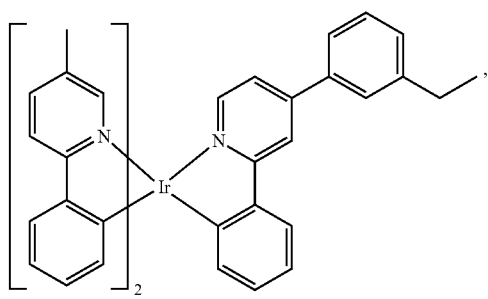
Compound 60
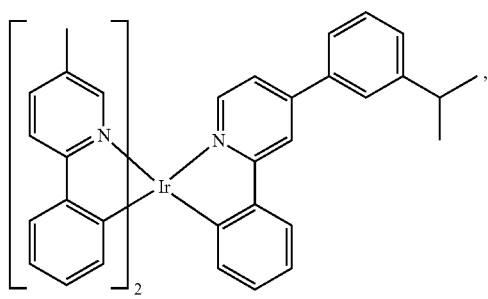
Compound 61
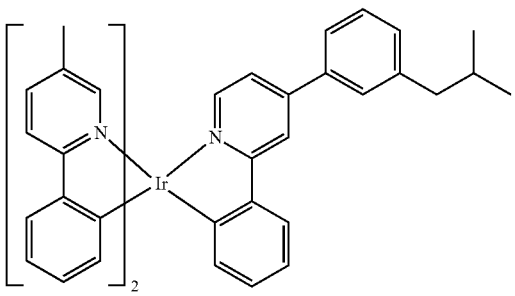
Compound 62
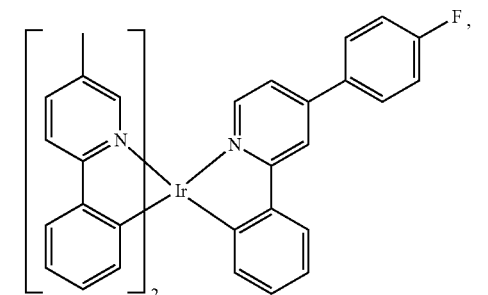
Compound 63
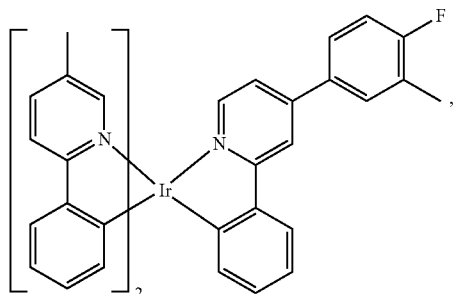
Compound 64
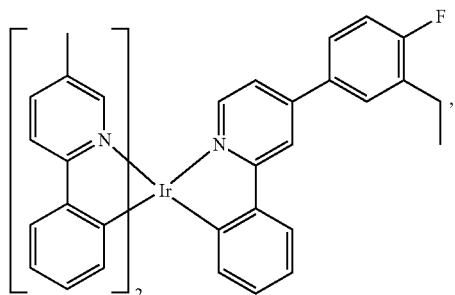
Compound 65
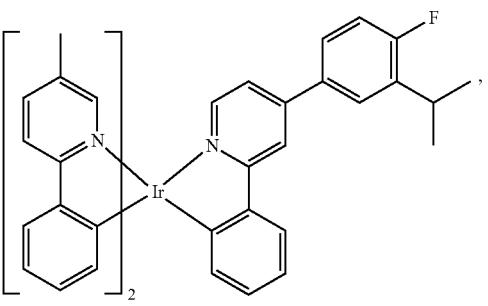
Compound 66
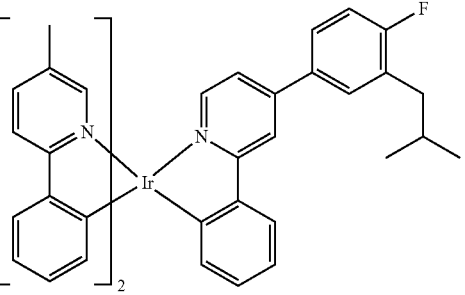

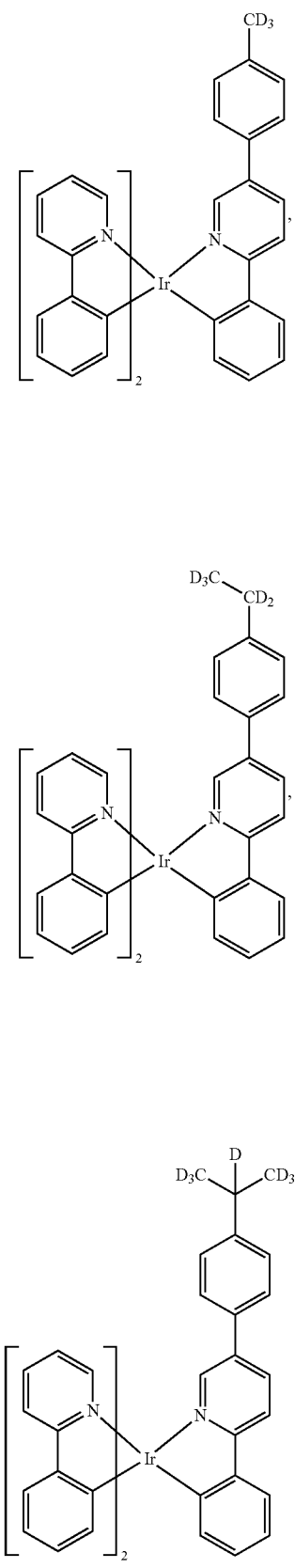
Compound 73
Compound 74
Compound 75
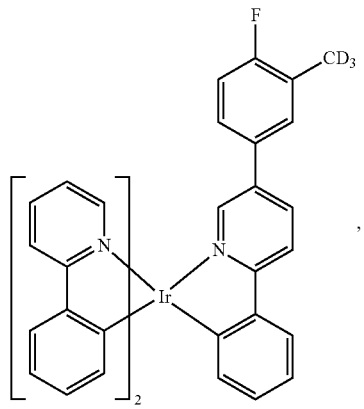
Compound 76
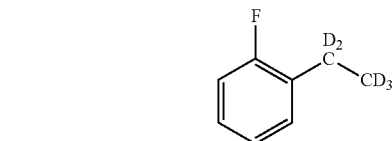
Compound 77
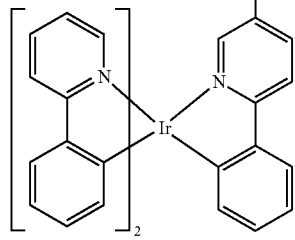
Compound 78
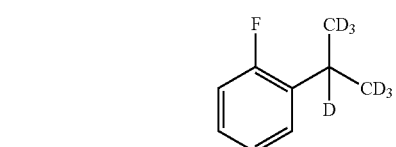
Compound 79
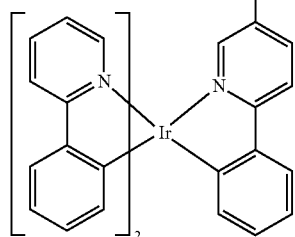

Compound 84
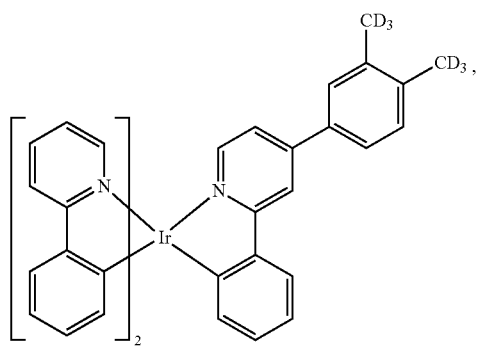
Compound 85
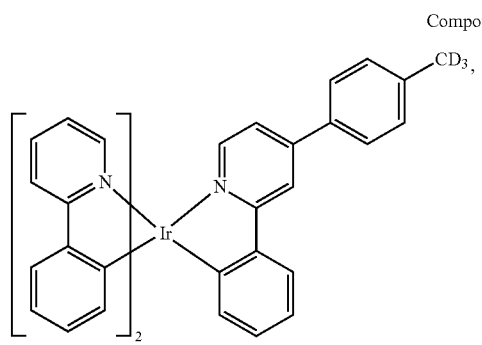
Compound 86
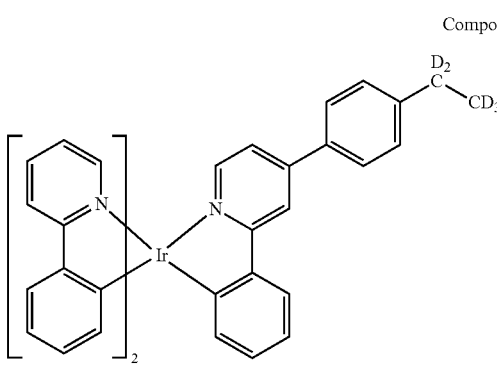
Compound 87
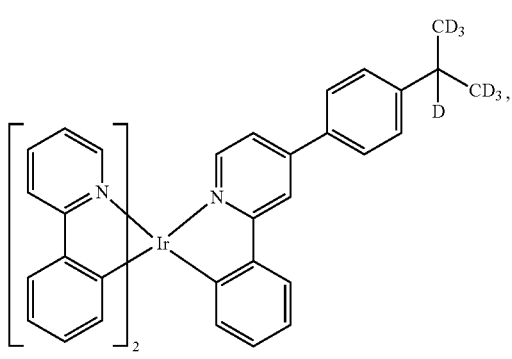
Compound 88
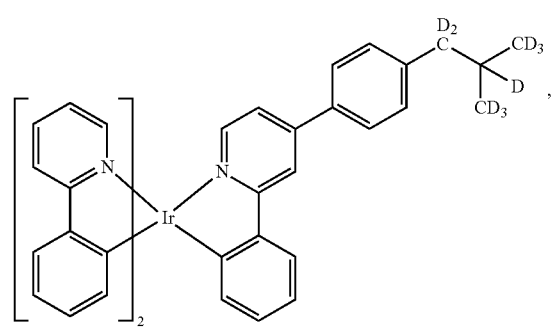
Compound 89
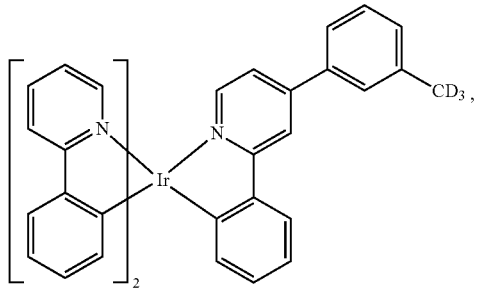
Compound 90
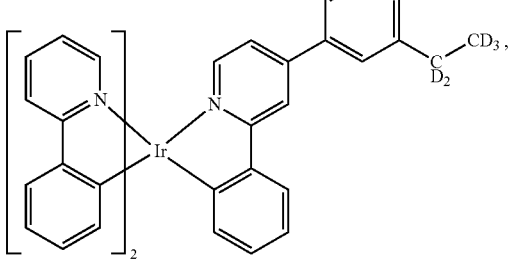
Compound 91
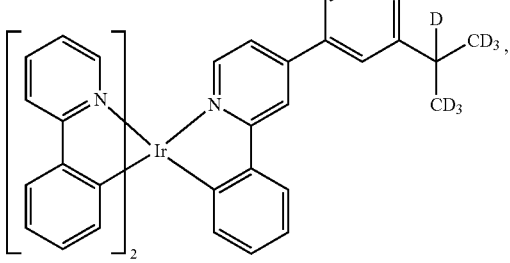
Compound 92
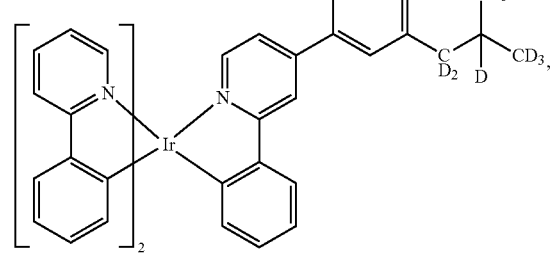

Compound 93
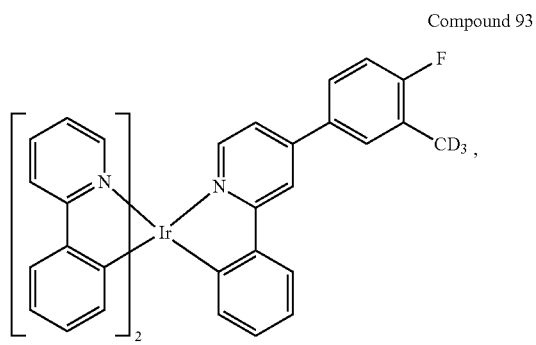
Compound 94
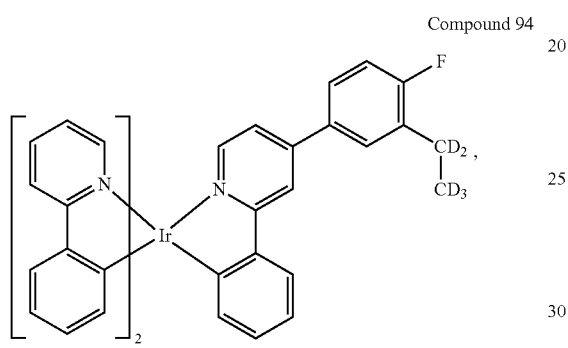
Compound 95
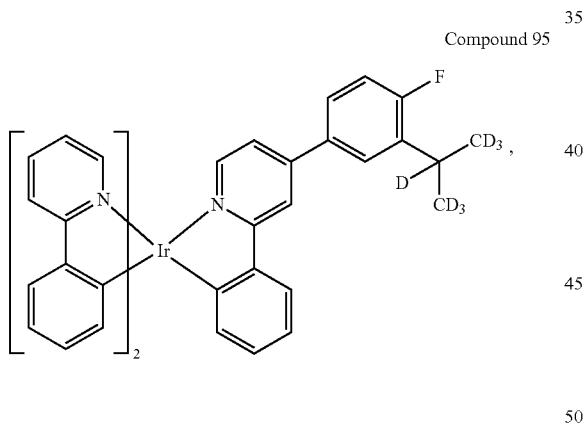
Compound 96
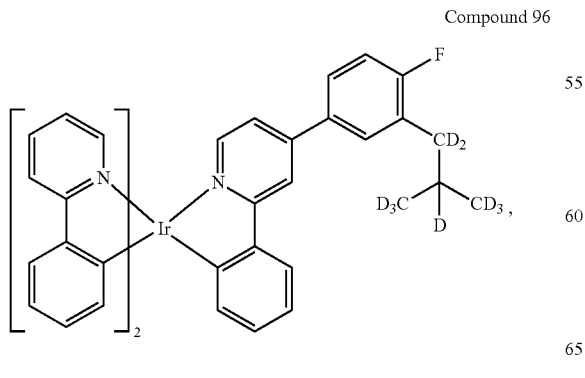
Compound 103
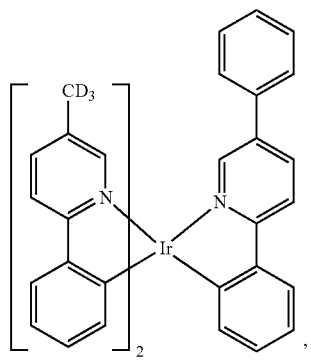
Compound 104
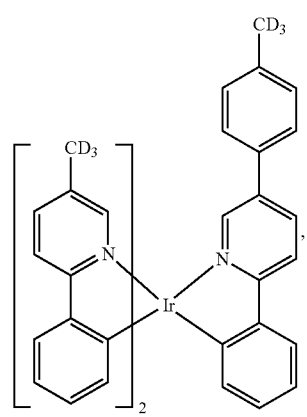
Compound 105
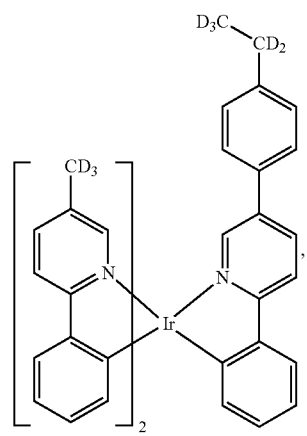
Compound 106
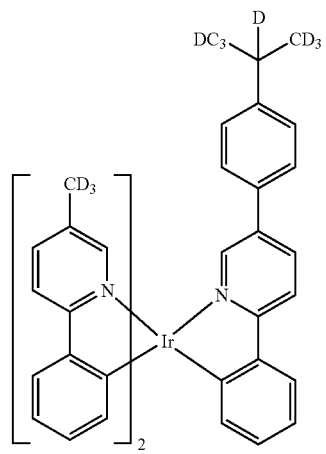

Compound 107
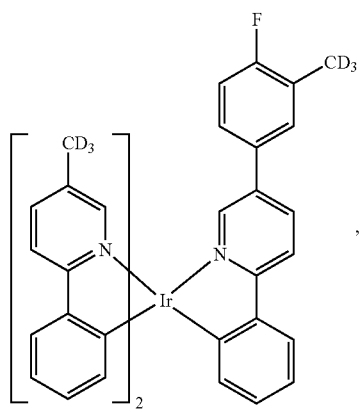
Compound 111
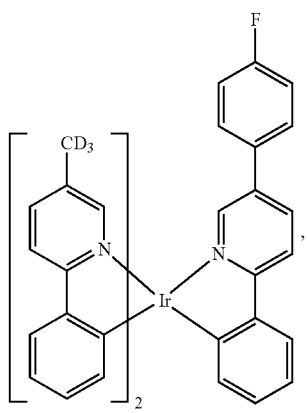
Compound 108
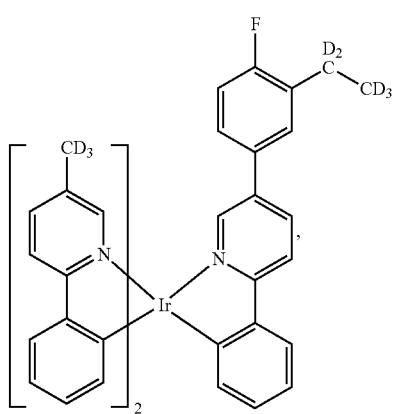
Compound 116
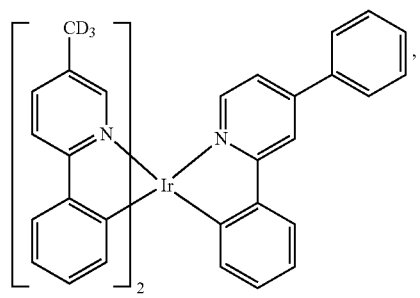
Compound 109
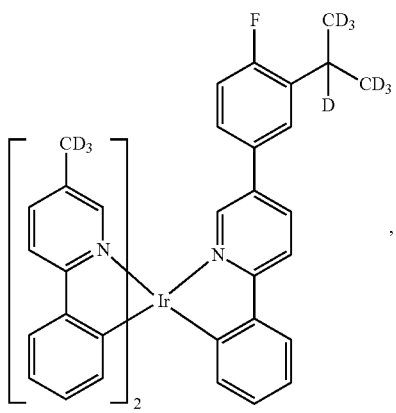
Compound 117
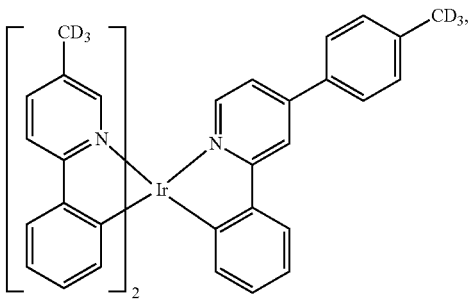
Compound 110
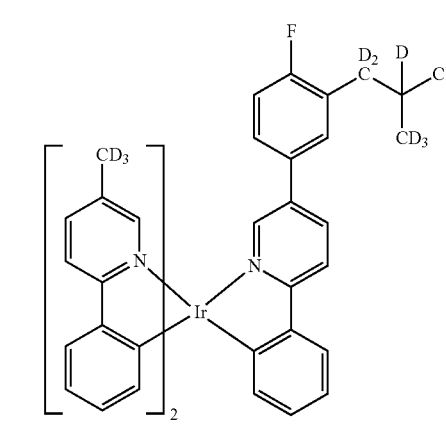
Compound 118
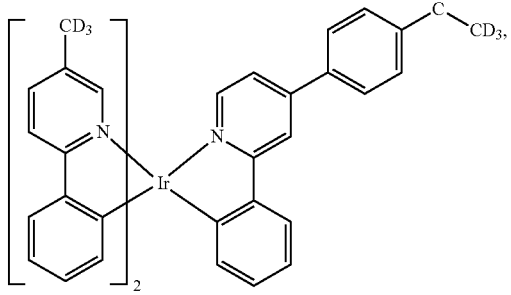

-continued
Compound 119
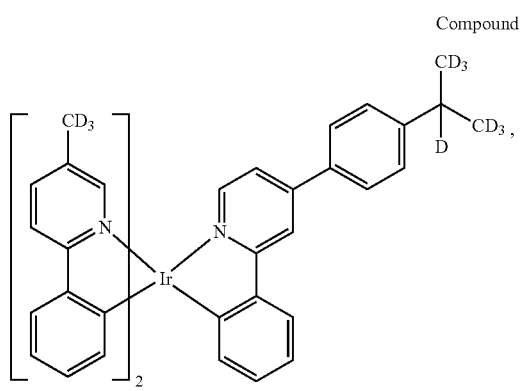
Compound 120
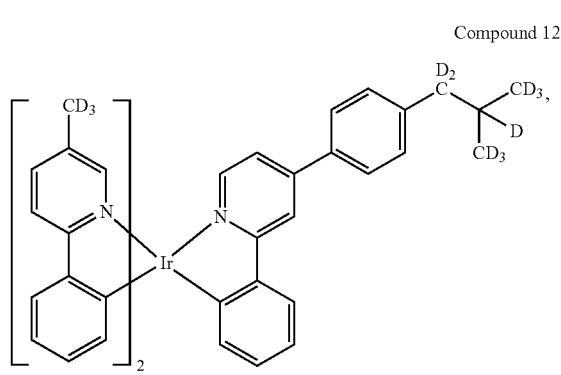
Compound 121
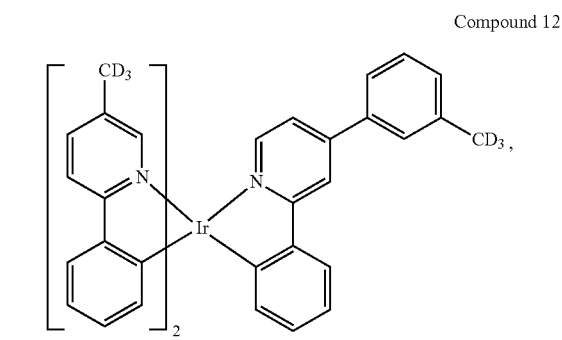
Compound 122
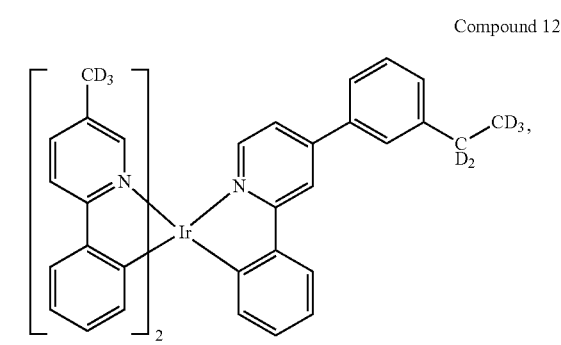
-continued
Compound 123
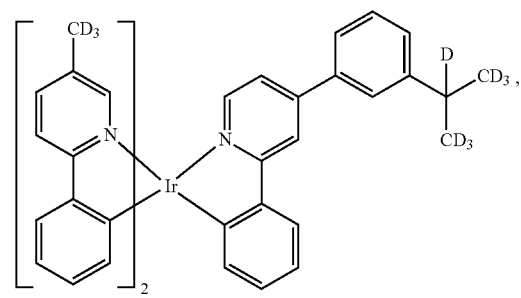
Compound 124
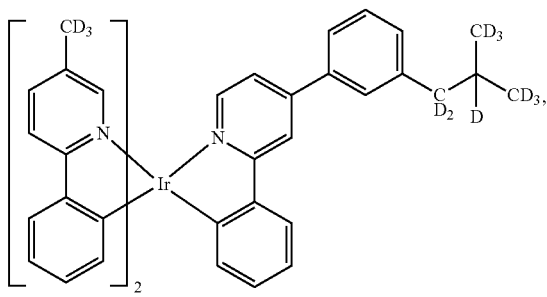
Compound 125
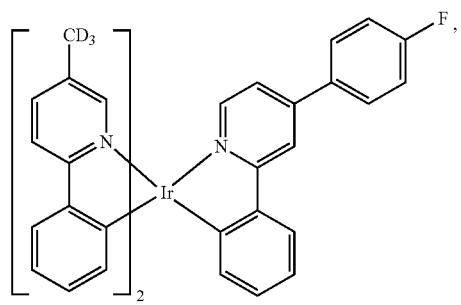
Compound 126
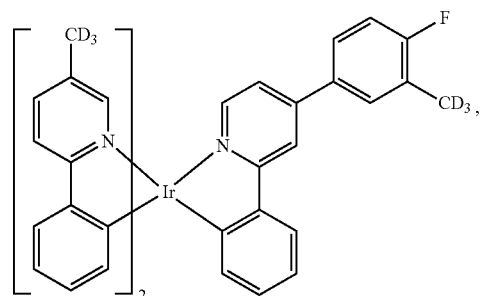
Compound 127
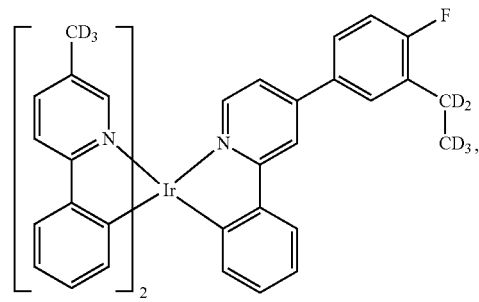

Compound 128
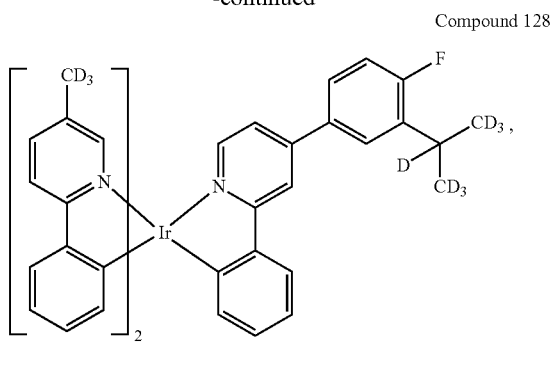
Compound 132
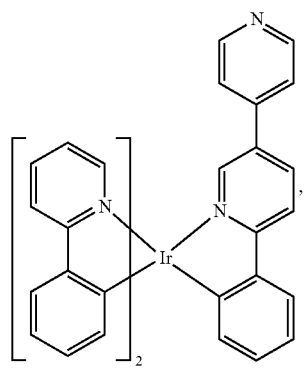
Compound 129
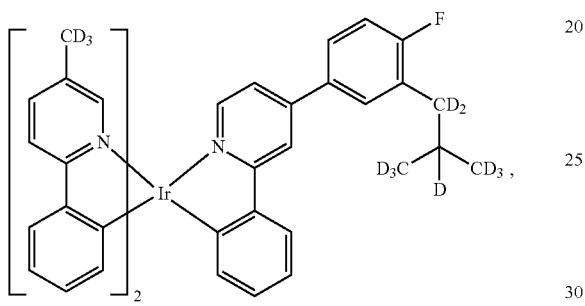
Compound 133
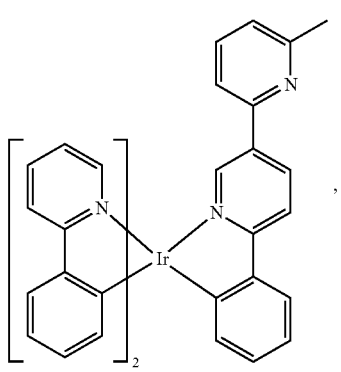
Compound 130
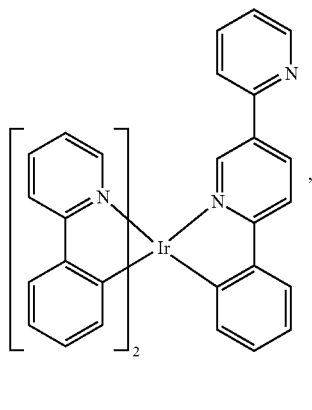
Compound 134
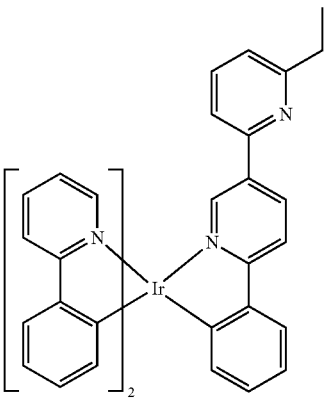
Compound 131
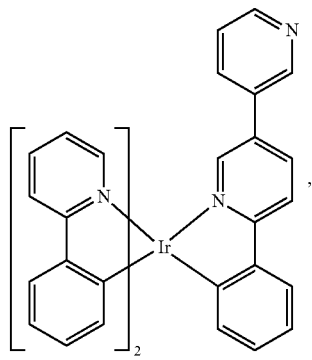
Compound 135
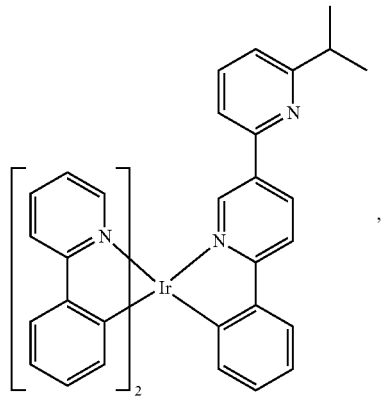

Compound 136
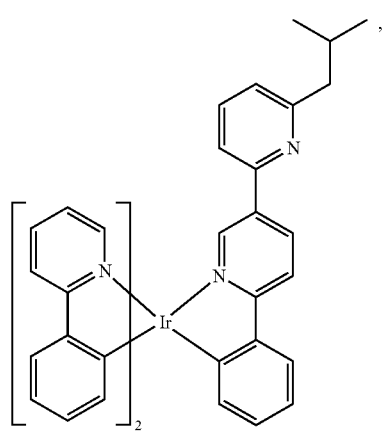
Compound 137
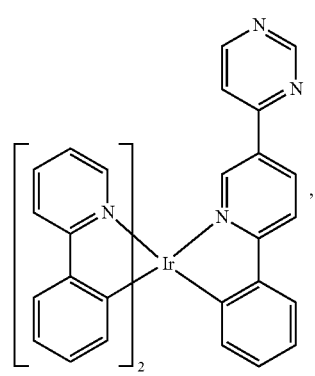
Compound 138
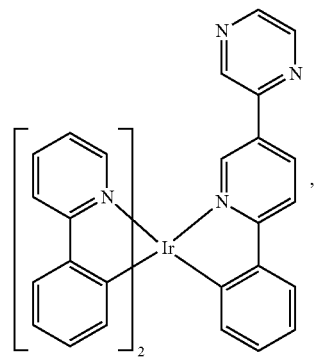
Compound 139
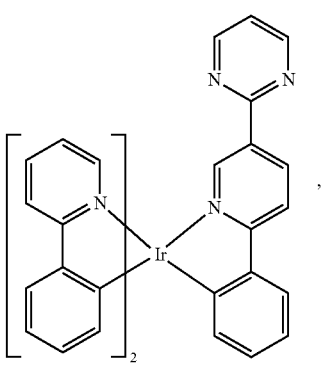
Compound 140
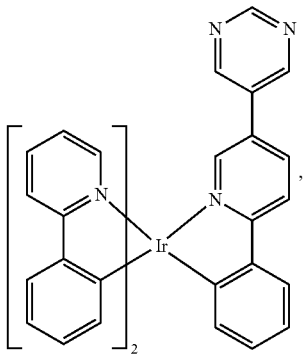
Compound 141
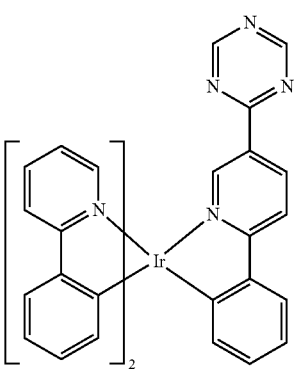
Compound 142
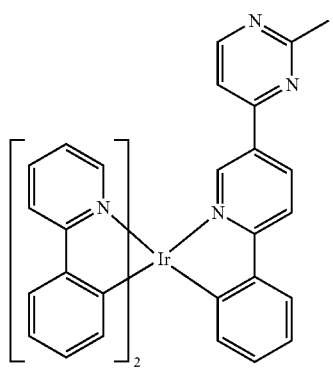
Compound 143
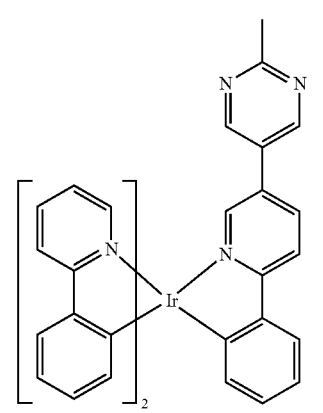

Compound 144
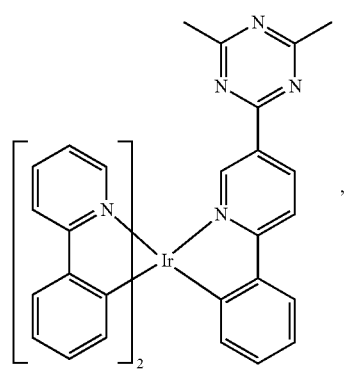
Compound 145
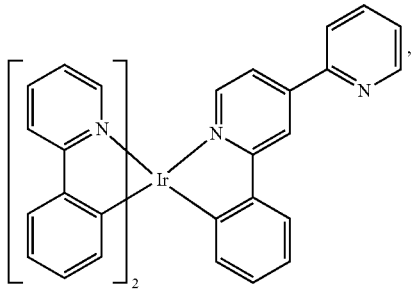
Compound 146
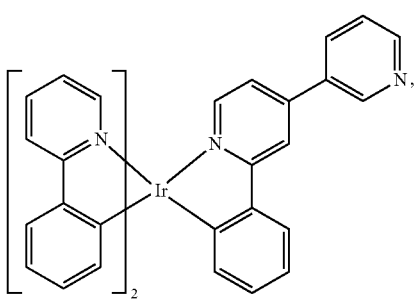
Compound 147
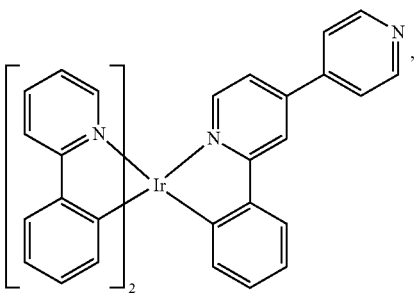
Compound 148
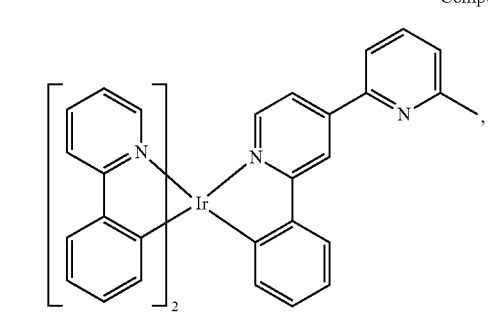
Compound 149
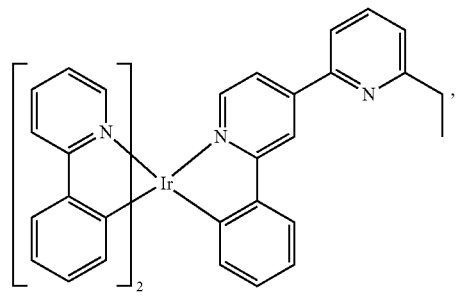
Compound 150
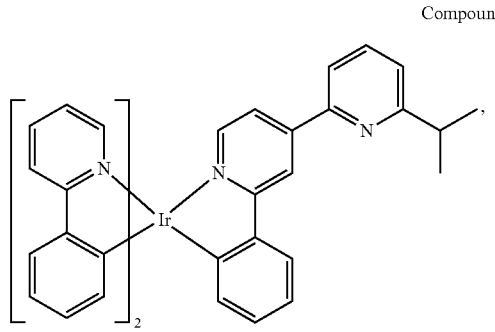
Compound 151
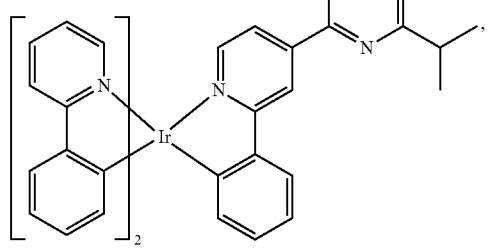
Compound 152
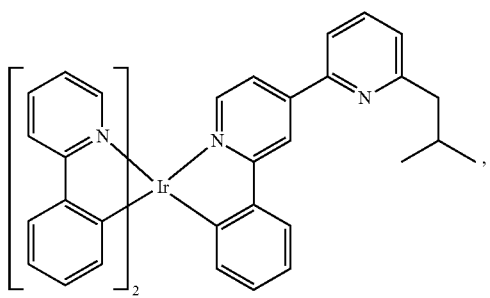
Compound 153
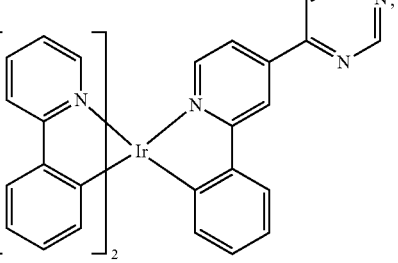

Compound 154
Compound 155
Compound 156
Compound 157
Compound 158
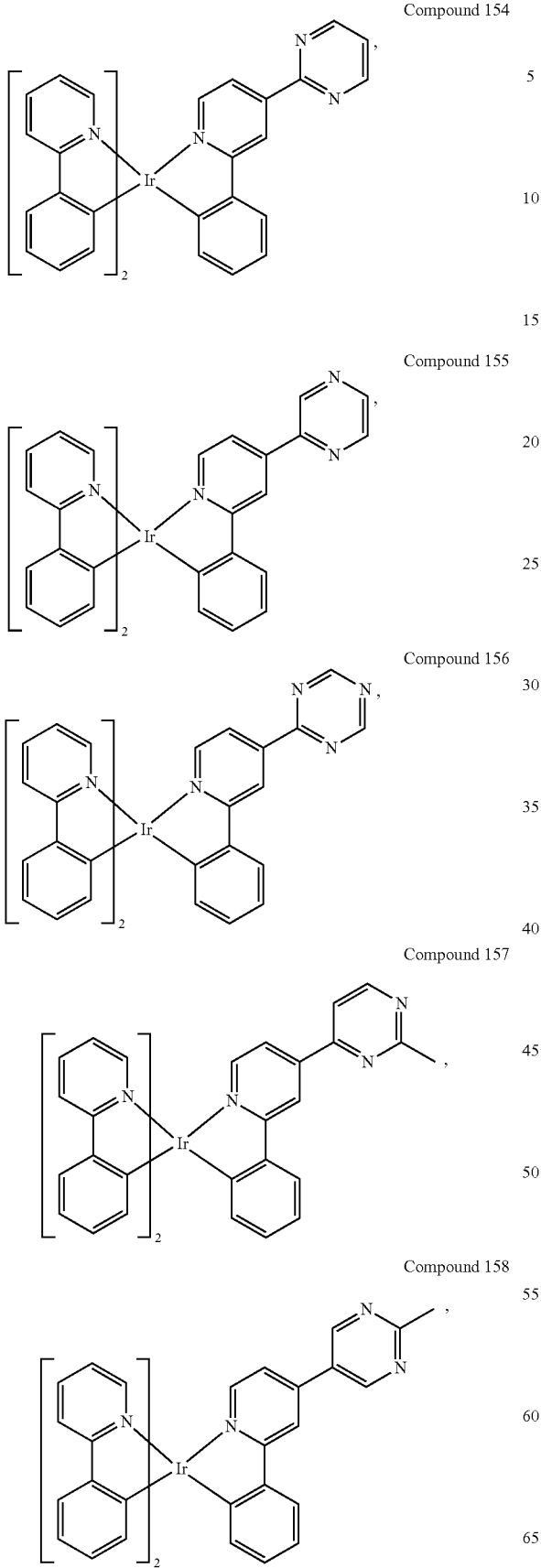
Compound 159
Compound 160
Compound 161
Compound 162
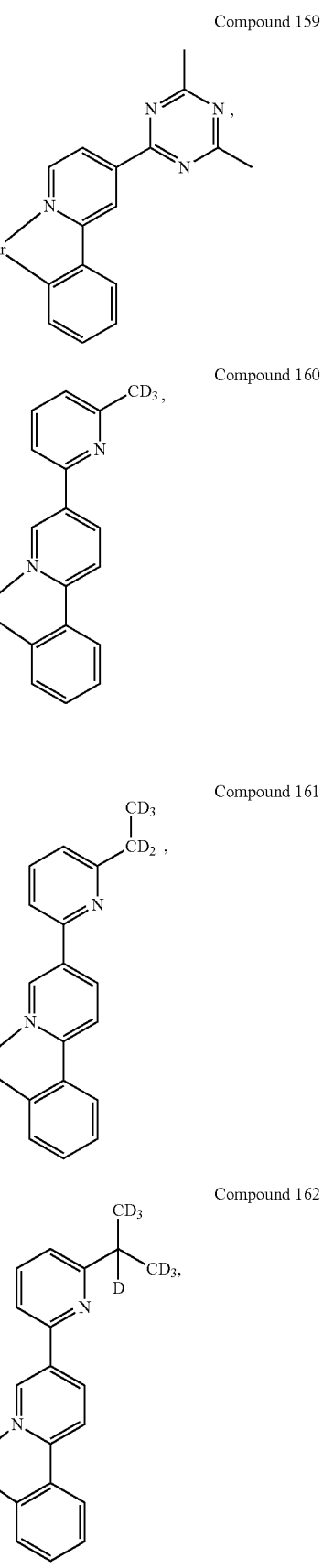

Compound 163
Compound 164
Compound 165
Compound 166
Compound 167
Compound 168
Compound 169
Compound 170
Compound 171
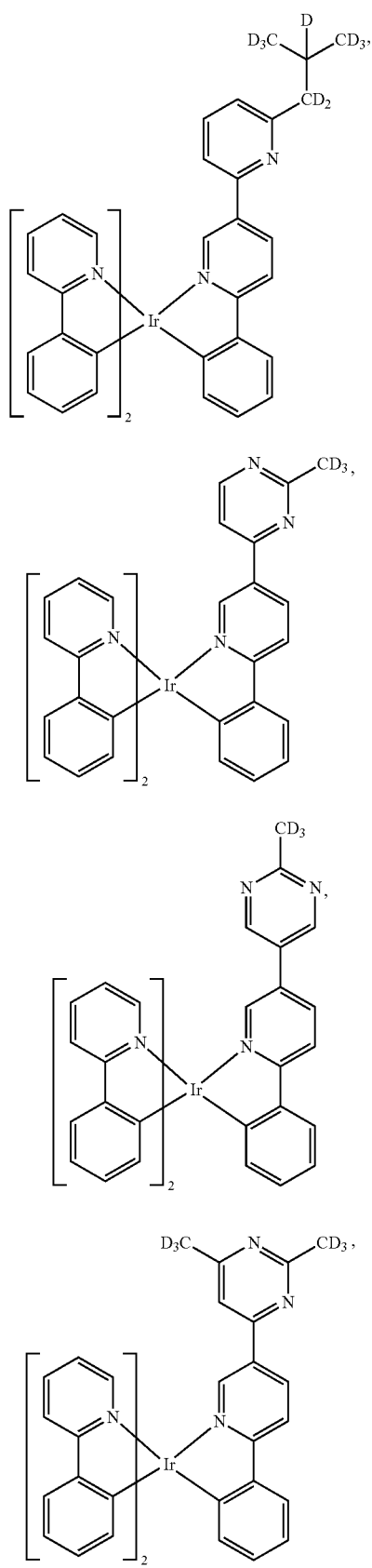
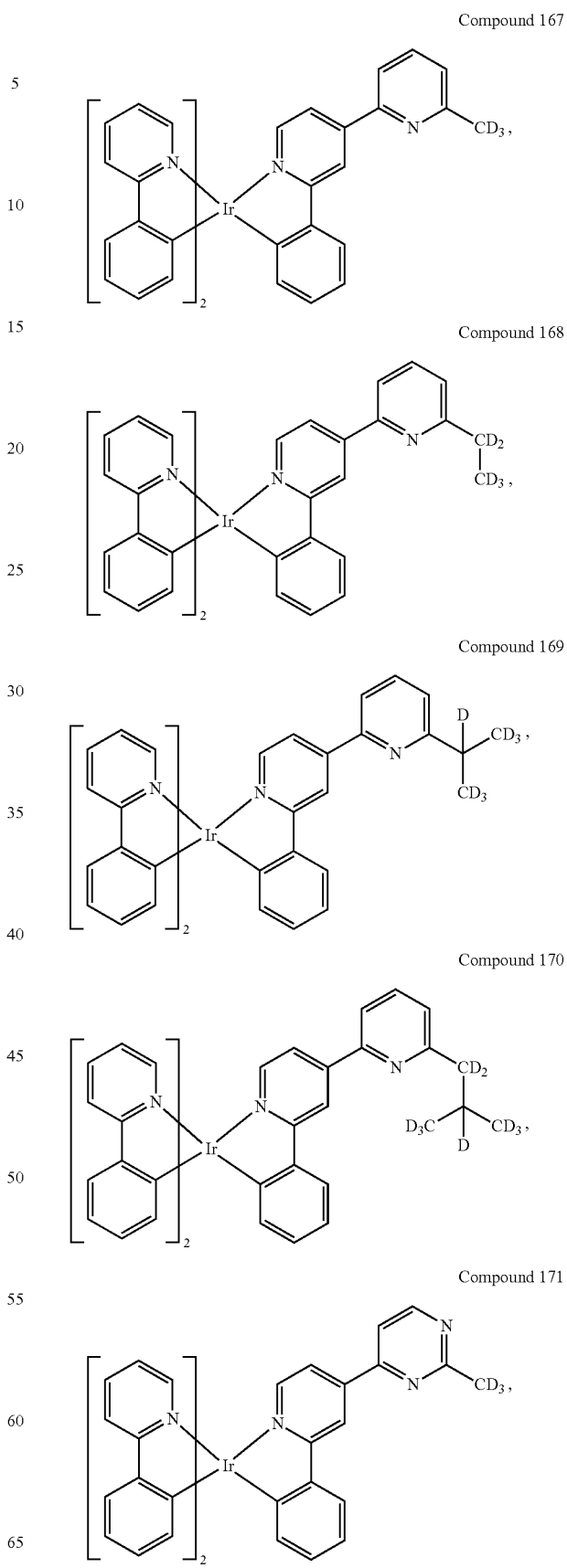

Compound 172
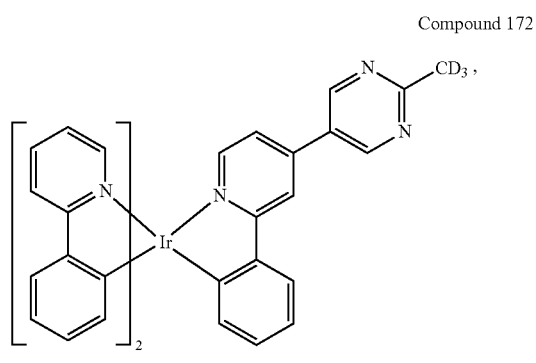
Compound 173
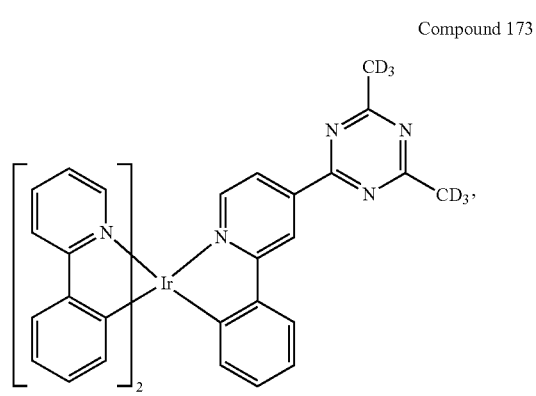
Compound 174
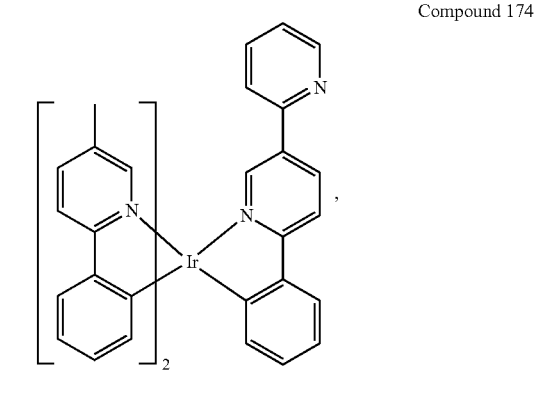
Compound 175
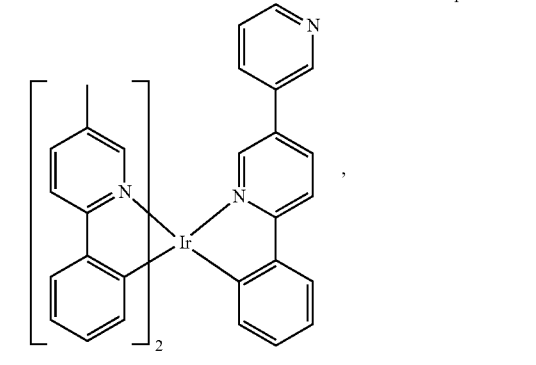
Compound 176
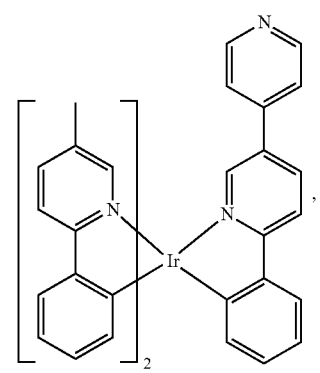
Compound 177
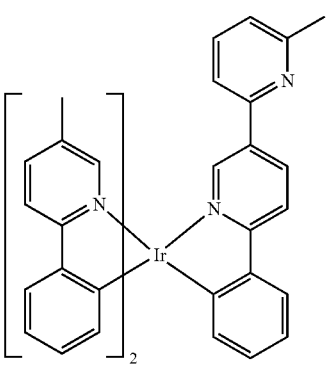
Compound 178
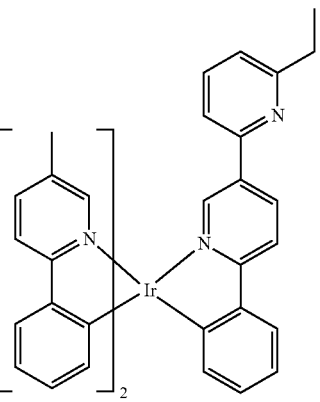
Compound 179
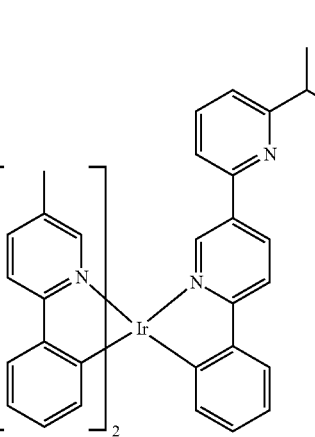

Compound 180
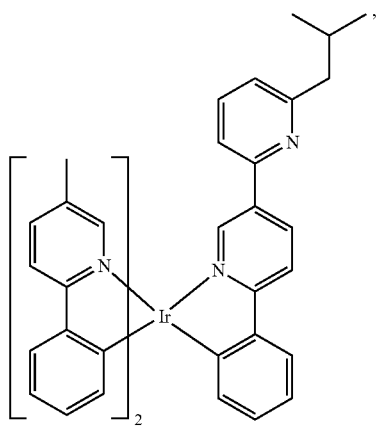
Compound 181
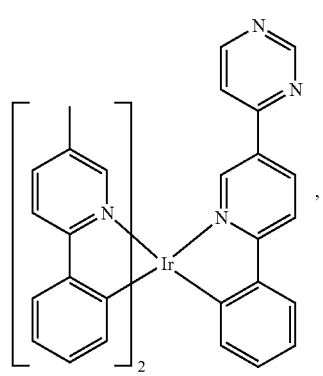
Compound 182
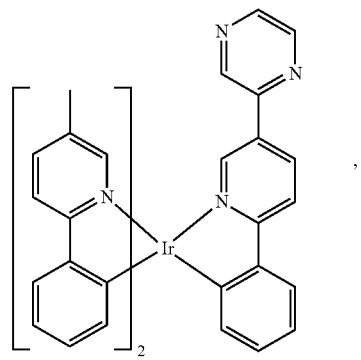
Compound 183
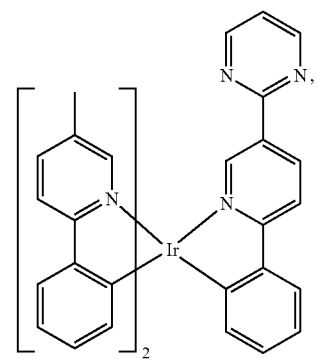
Compound 184
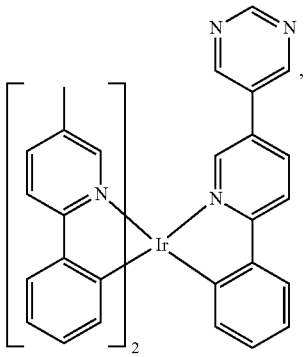
Compound 185
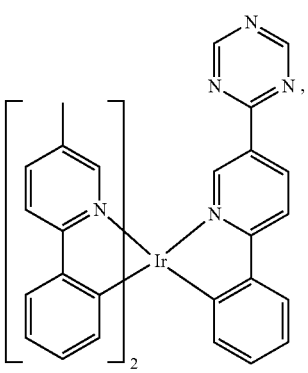
Compound 186
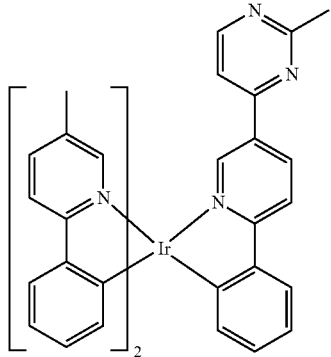

Compound 187
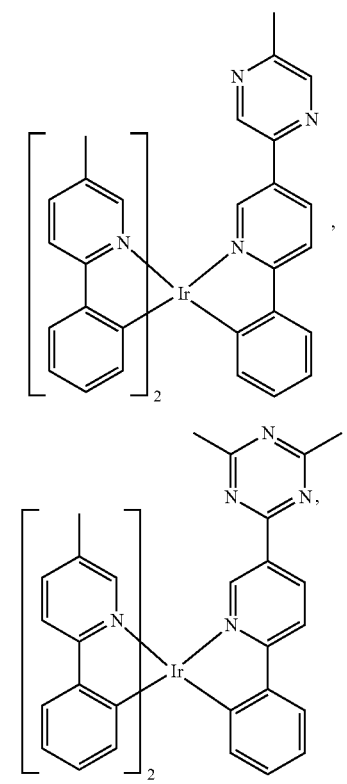
Compound 189
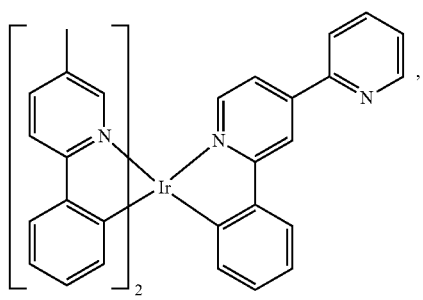
Compound 190
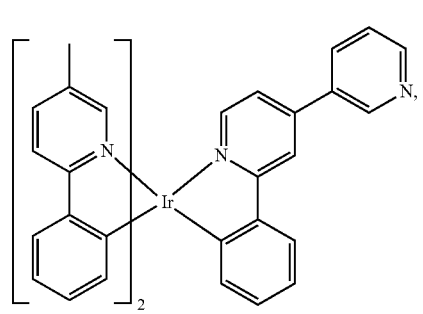
Compound 191
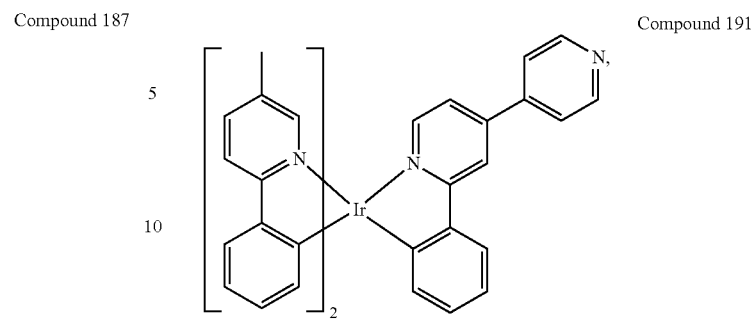
Compound 192
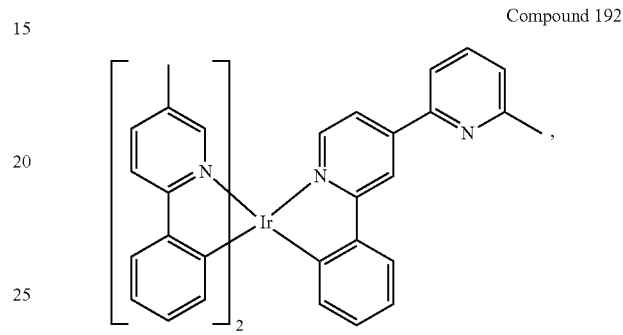
Compound 193
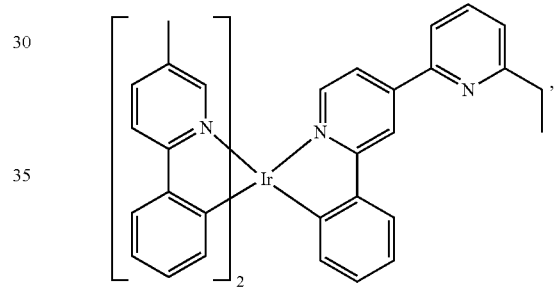
Compound 194
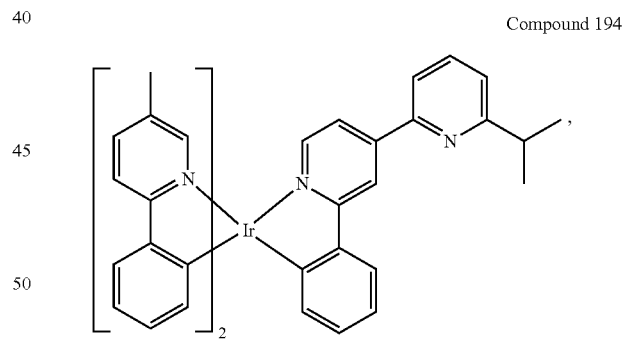
Compound 195
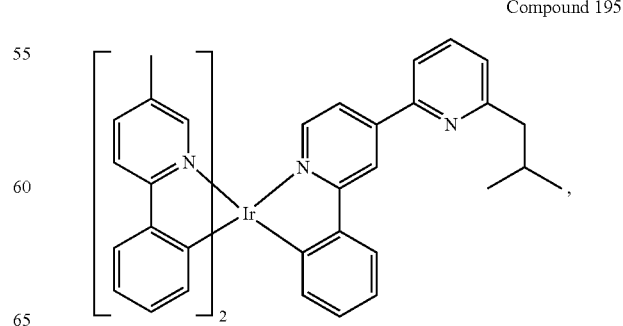

Compound 196
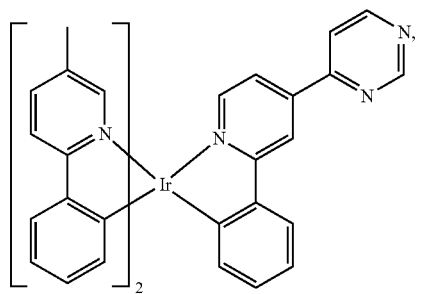
Compound 197
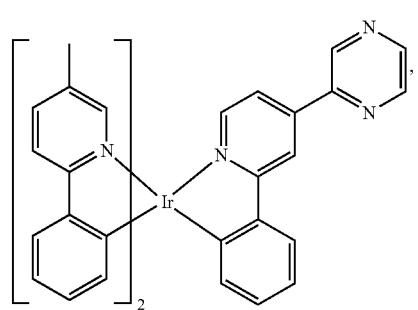
Compound 198
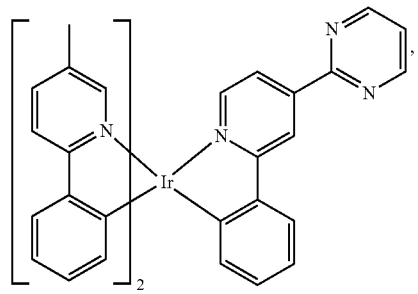
Compound 199
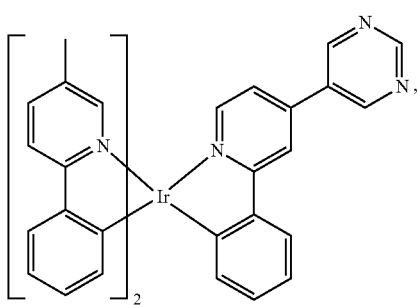
Compound 200
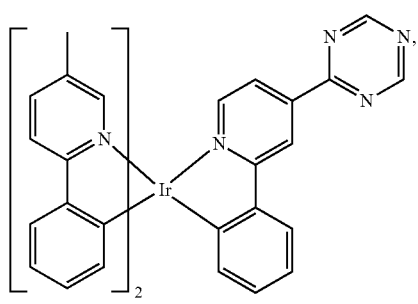
Compound 201
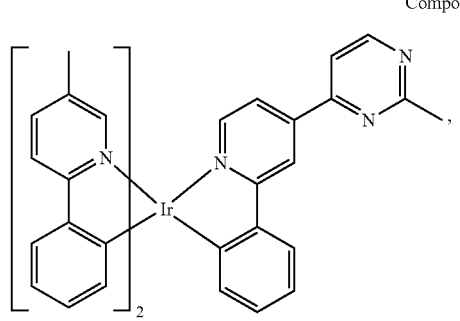
Compound 202
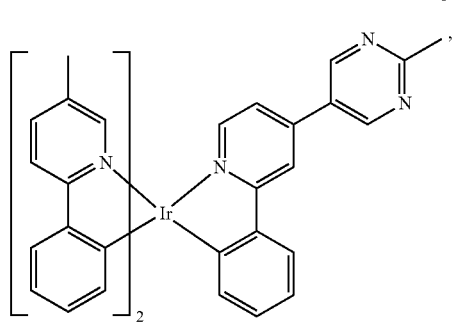
Compound 203
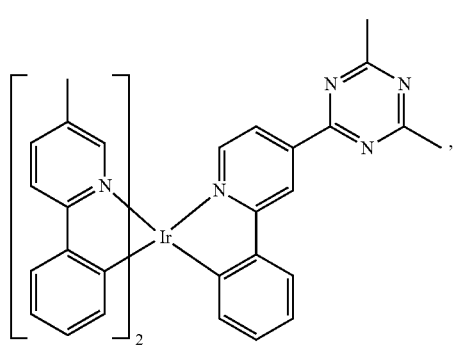
Compound 204
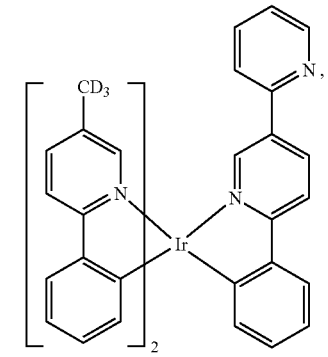

Compound 205
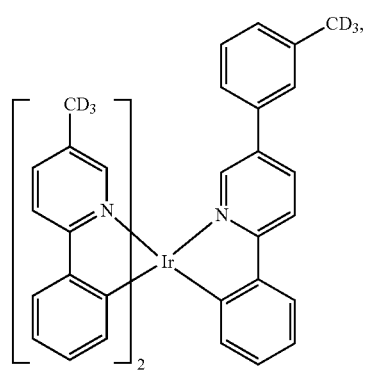
Compound 206
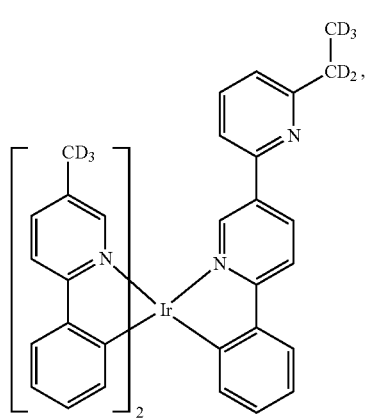
Compound 207
Compound 208
Compound 209
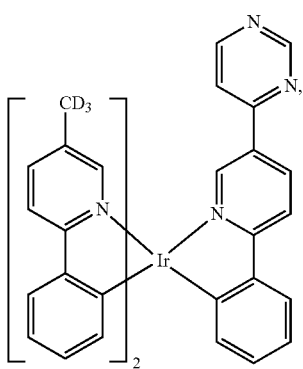
Compound 210
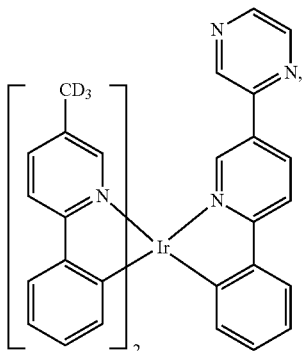
Compound 211
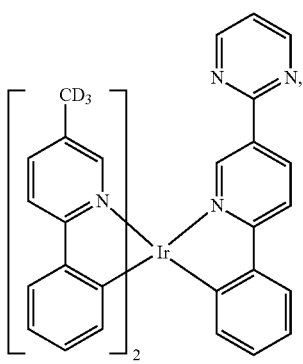
Compound 212
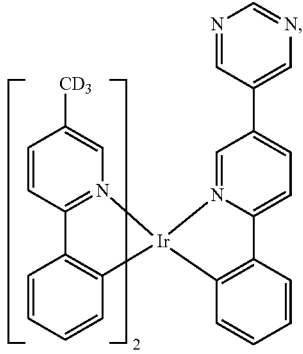

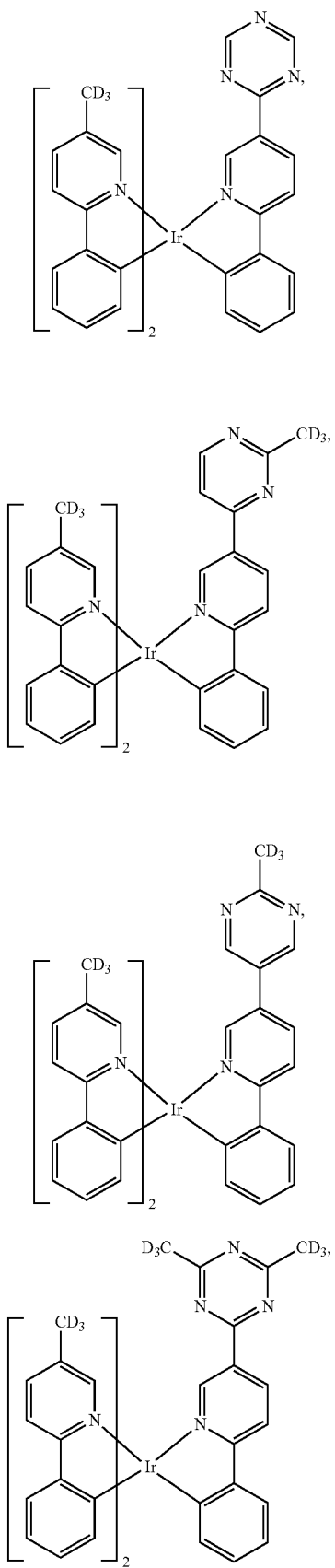
Compound 213
Compound 214
Compound 215
Compound 216
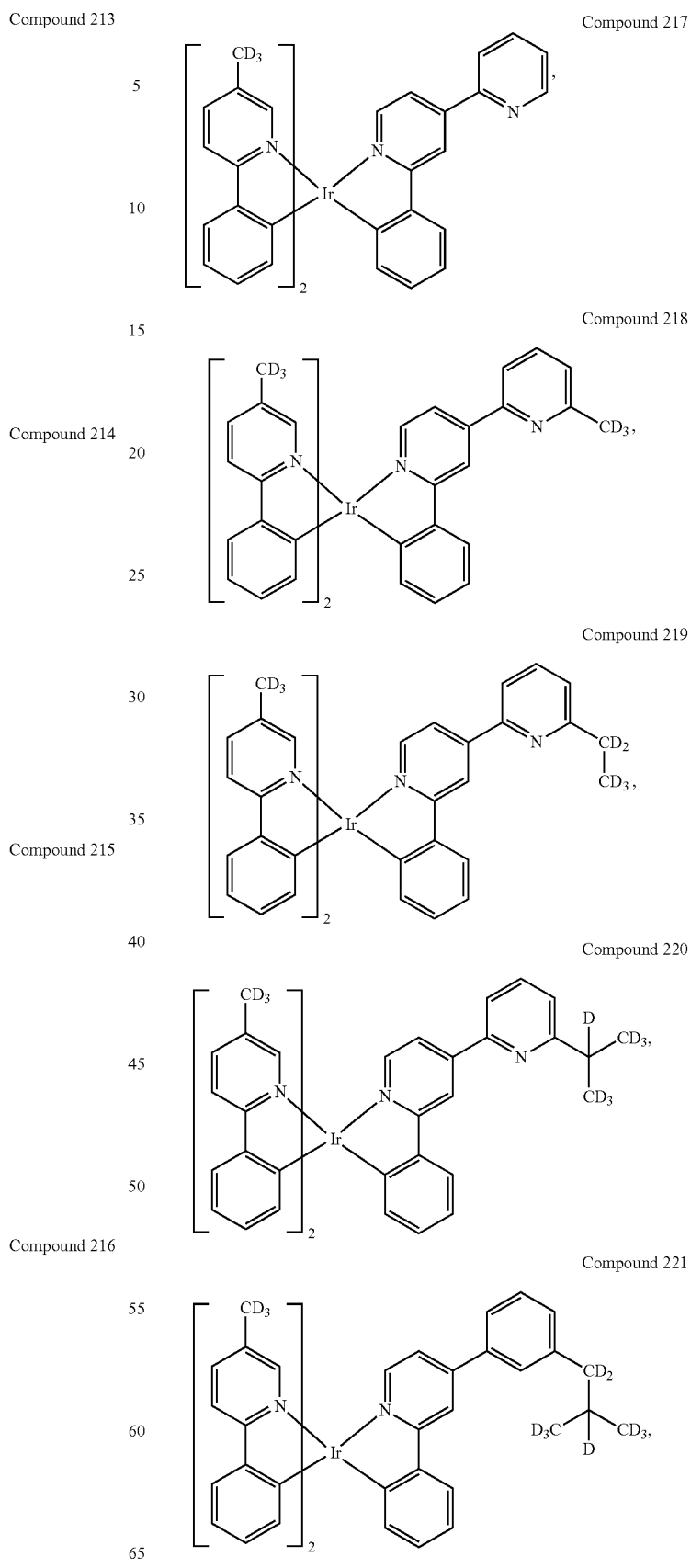
Compound 217
Compound 218
Compound 219
Compound 220
Compound 221

Compound 222

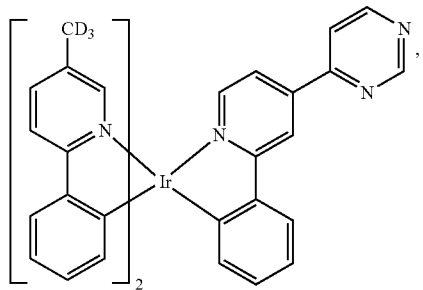

Compound 223

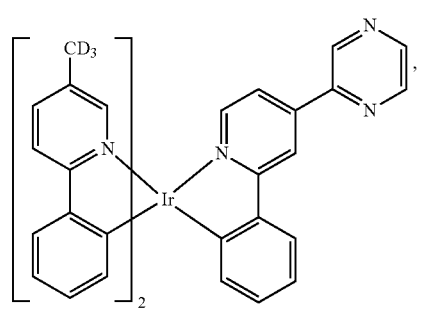

Compound 224

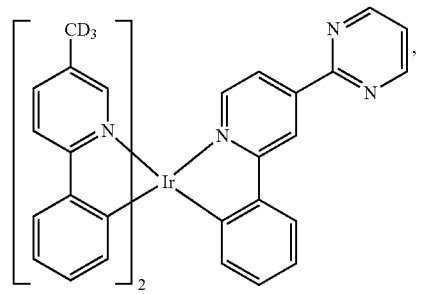

Compound 225

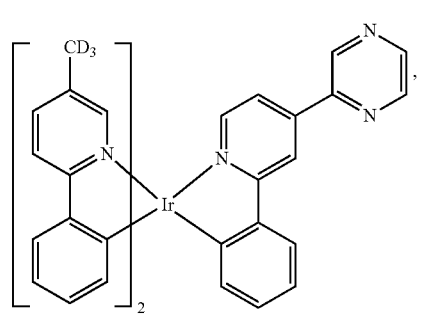

Compound 226

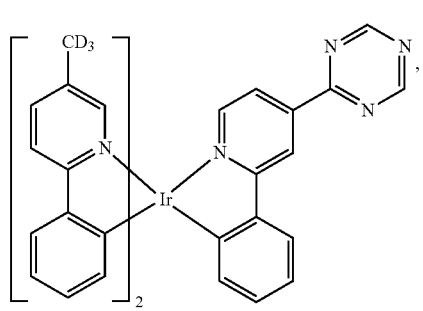

Compound 227

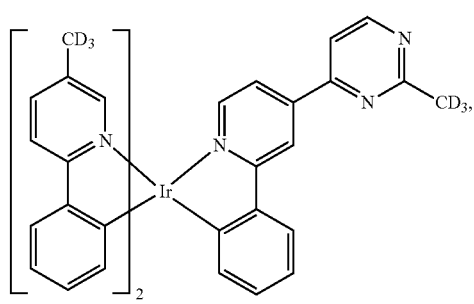

Compound 228

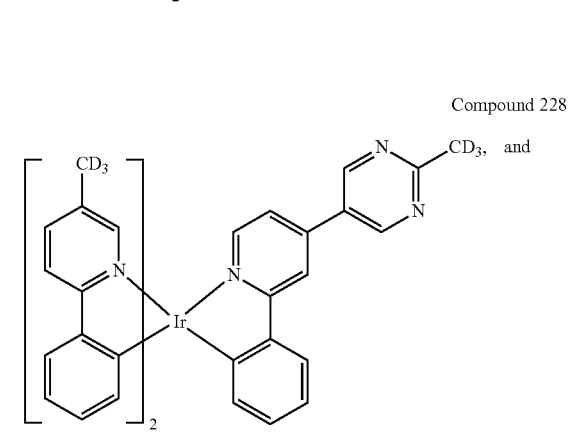

Compound 229

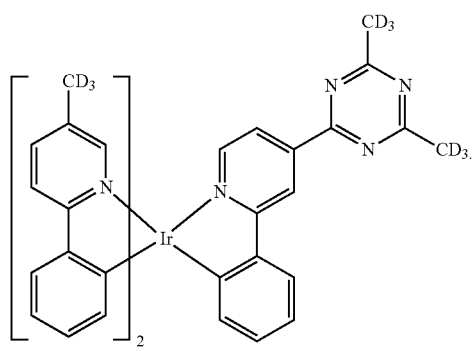

In one embodiment of the composition wherein the first compound and the second compound each independently has the formula of $Ir(L^1)_2(L^2)$ as defined above, the mixture of the first compound and the second compound is selected from the group consisting of: (Compound 7 and Compound 130), (Compound 8 and Compound 131), (Compound 25 and Compound 131), (Compound 27 and Compound 135), (Compound 20 and Compound 145), (Compound 25 and Compound 148), (Compound 40 and Compound 174), (Compound 103 and Compound 204), and (Compound 116 and Compound 217).

In one embodiment of the composition comprising a mixture of a first compound and a second compound, wherein the first compound has a difference chemical structure than the second compound, wherein the first compound is capable of functioning as a phosphorescent emitter in an OLED at room temperature, the second compound has a structure according to Formula V:

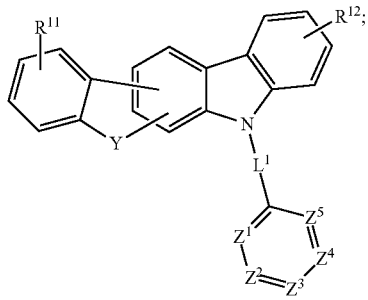

Formula V wherein $R^{11}$ and $R^{12}$ each independently represent mono, di, tri, tetra substitutions, or no substitution; Y is selected from the group consisting of O, S, Se, NR' and CR"R"';
$L^1$ is a single bond or comprises an aryl or heteroaryl group having from 5-24 carbon atoms, which is optionally further substituted; $Z^1$, $Z^2$, $Z^3$, $Z^4$ and $Z^5$ are each independently selected from group consisting of CR"" and N; at least one of $Z^1$, $Z^2$, $Z^3$, $Z^4$ and $Z^5$ is N; and $R^{11}$, $R^{12}$, R', R", R"', and R"" are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein the first compound has the Formula VI:

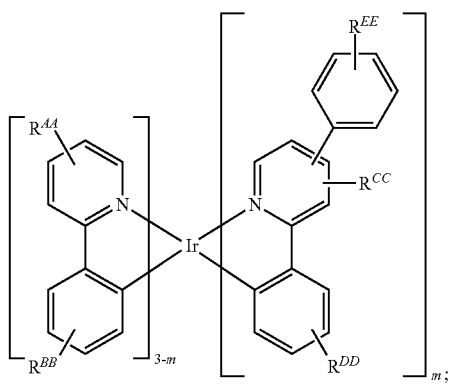

Formula VI wherein $R^{AA}$, $R^{BB}$, $R^{DD}$, and $R^{EE}$ each independently represent mono, di, tri, tetra substitutions, or no substitution; $R^{CC}$ represent mono, di, tri substitutions, or no substitution; $R^{AA}$, $R^{BB}$, $R^{CC}$, $R^{DD}$, and $R^{EE}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
and m is 1 or 2.

In one embodiment, where the second compound has the structure according to Formula II defined above, $X^1$, $X^3$ and $X^5$ are N; and $X^2$ and $X^4$ are CR"".

In one embodiment, where the second compound has the structure according to Formula VI, m is 1. In another embodiment, $R^{AA}$, $R^{BB}$, $R^{CC}$, and $R^{DD}$ are each independently selected from the group consisting of hydrogen, deuterium, alkyl, cycloalkyl, and combinations thereof. In another embodiment, $R^{EE}$ is selected from the group consisting of hydrogen, deuterium, halide, alkyl, cycloalkyl, and combinations thereof.

In another embodiment, where the first compound has the structure according to Formula VI defined above, the first compound is selected from the group consisting of:

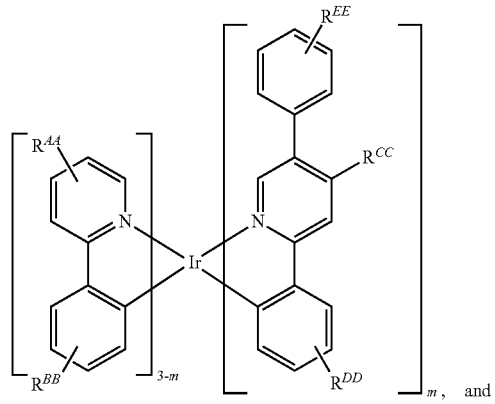

, and

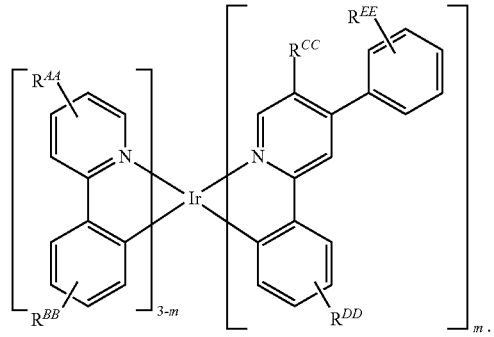

.

In another embodiment, where the second compound has the structure according to Formula V defined above, the second compound is selected from the group consisting of:

Compound EH1

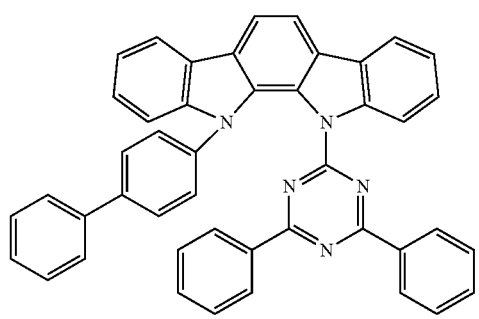

-continued
Compound EH2
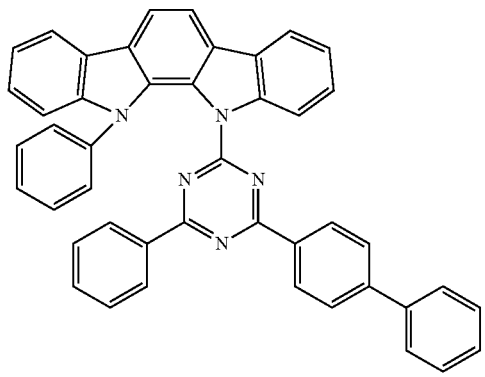
Compound EH3
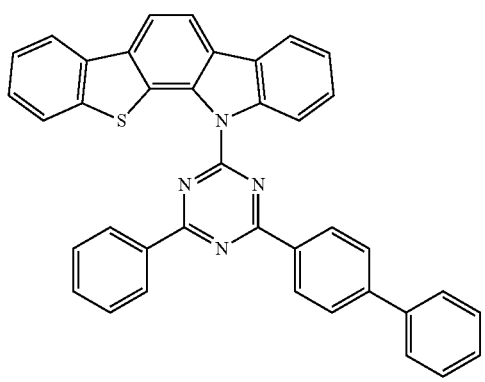
Compound EH4
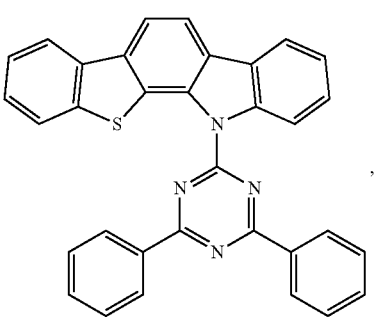
Compound EH5
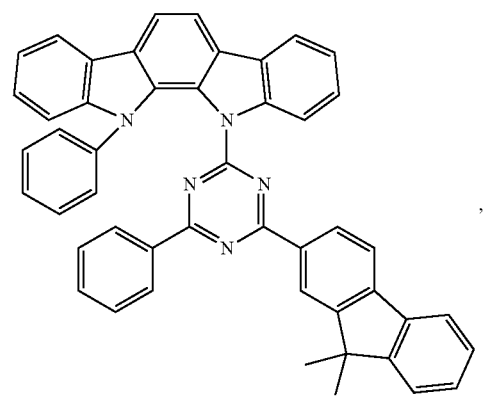
-continued
Compound EH6
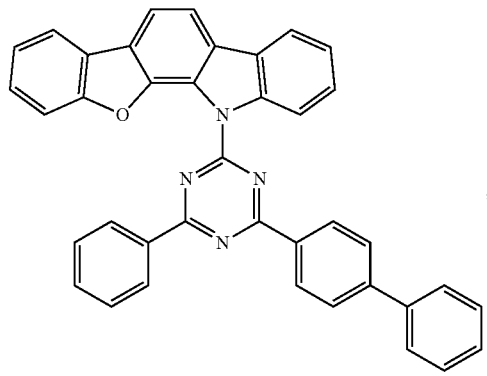
Compound EH7
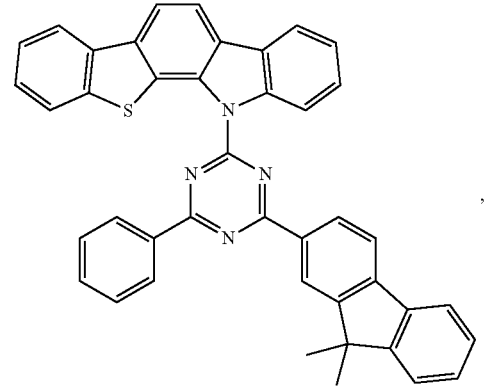
Compound EH8
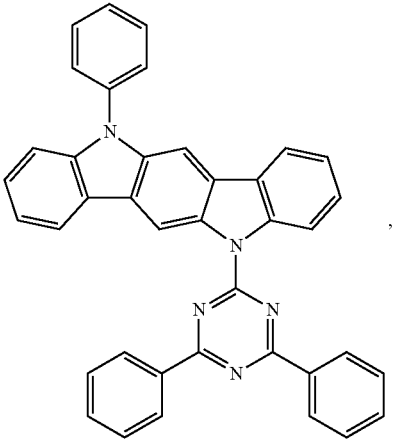

Compound EH9
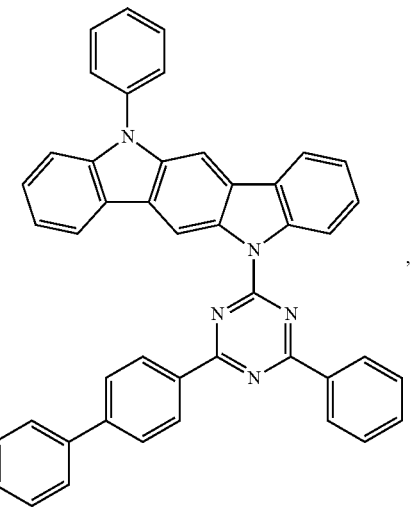
Compound EH13
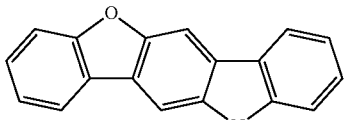
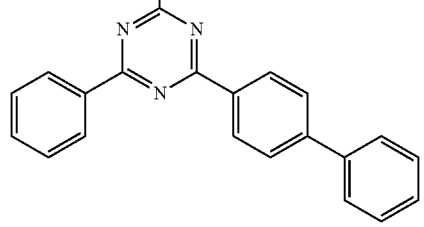
Compound EH10
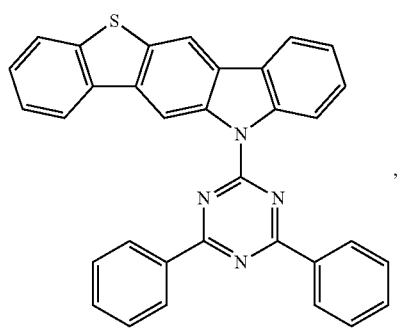
Compound EH14
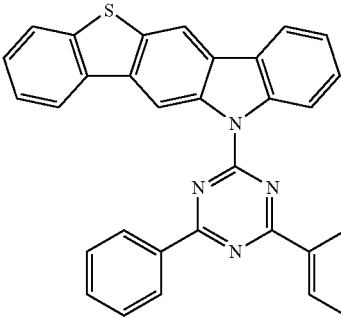
Compound EH11
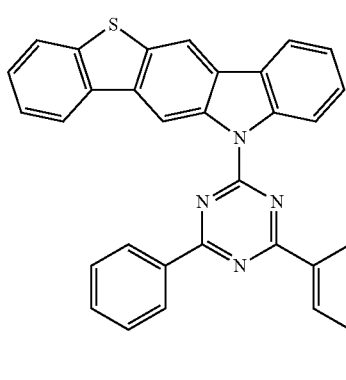
Compound EH12
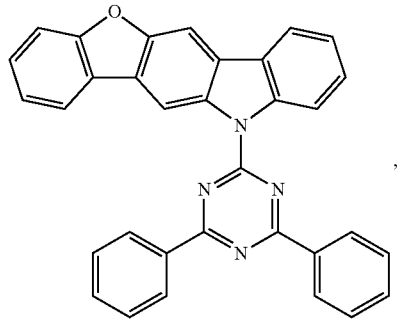
Compound EH15
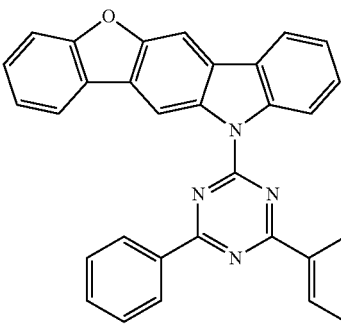

Compound EH16
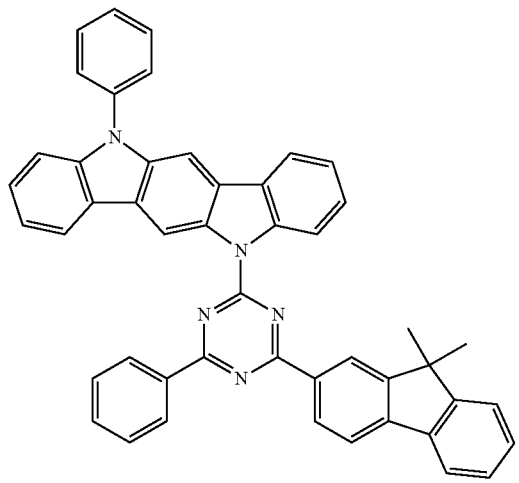
Compound EH17
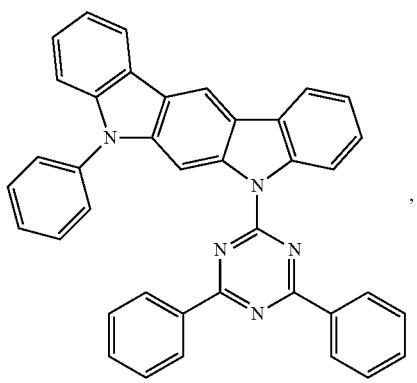
Compound EH18
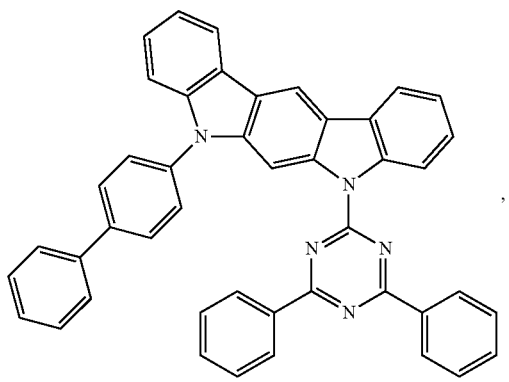
Compound EH19
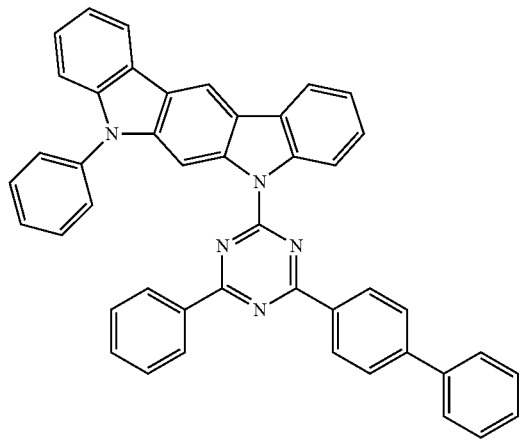
Compound EH20
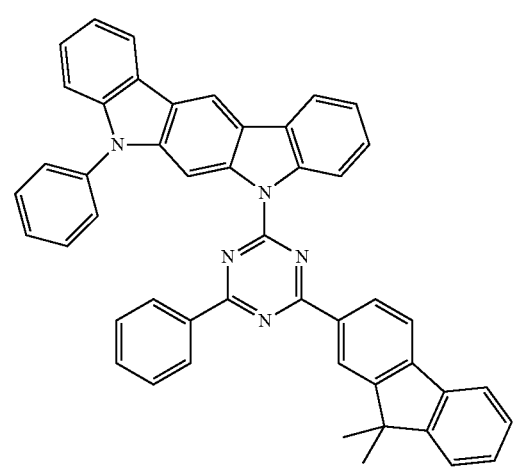
Compound EH21
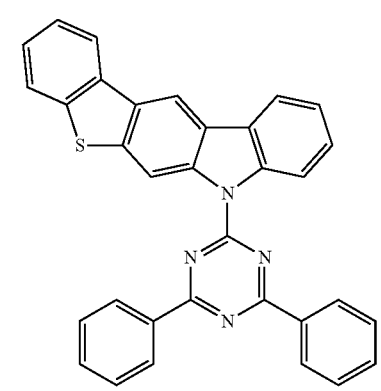

Compound EH22
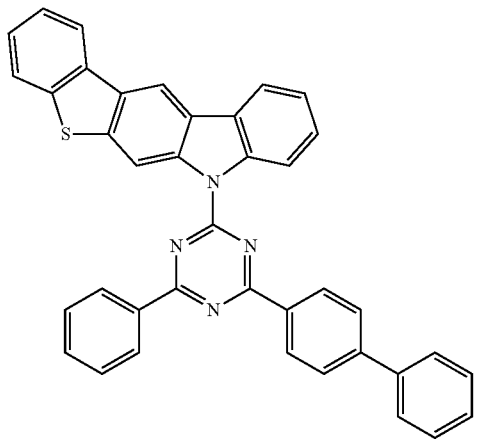
Compound EH23
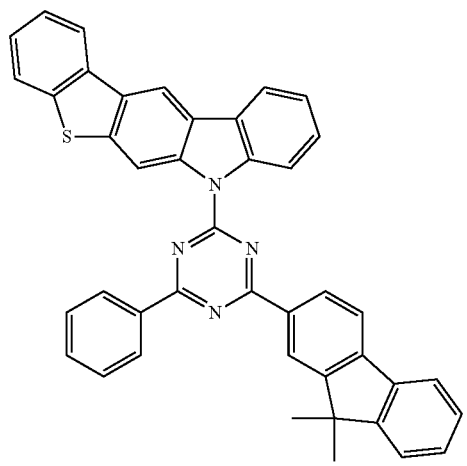
Compound EH24
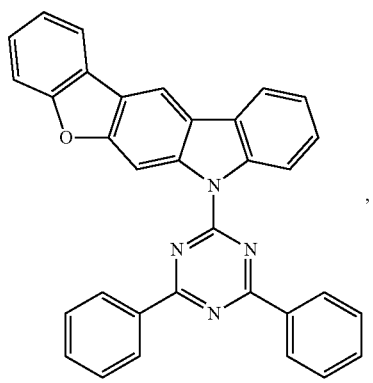
Compound EH25
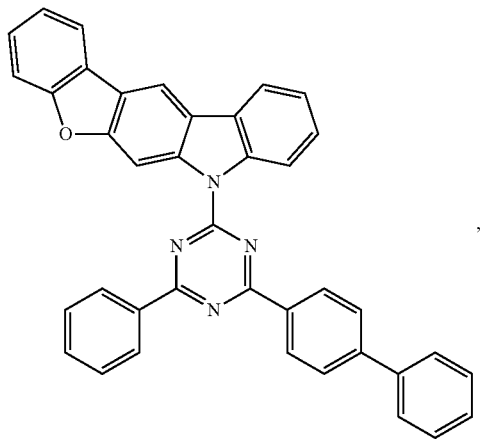
Compound EH26
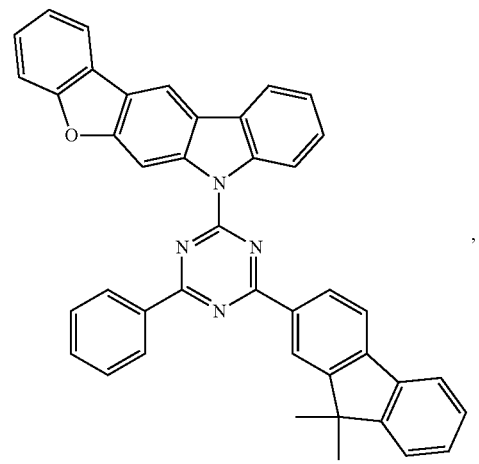
Compound EH27
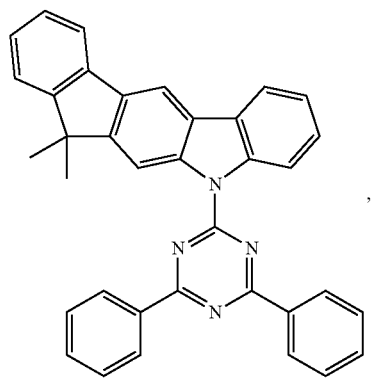

-continued
Compound EH28
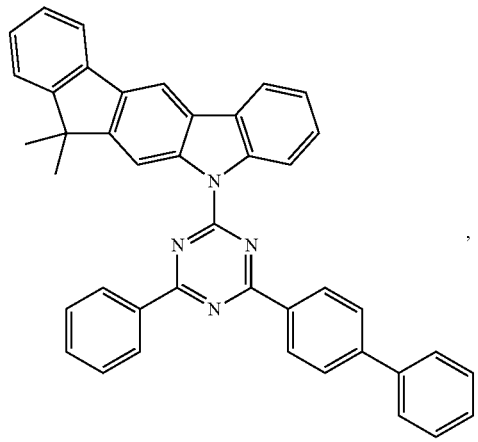
Compound EH29
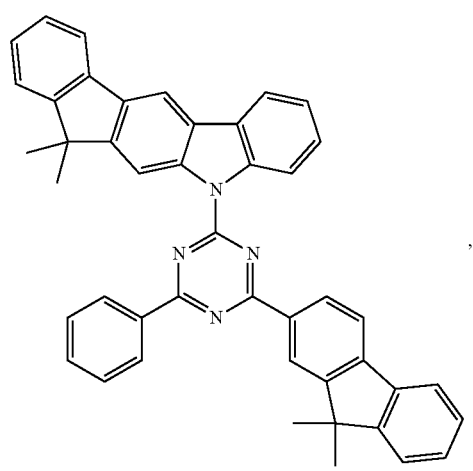
Compound EH30
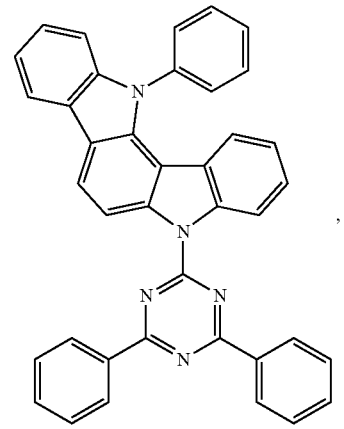
-continued
Compound EH31
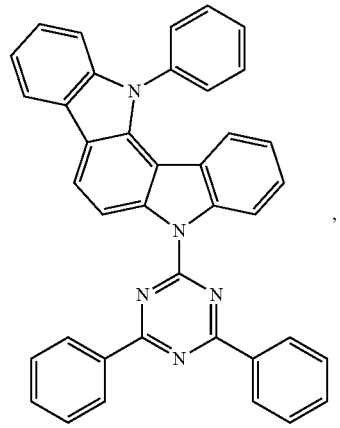
Compound EH32
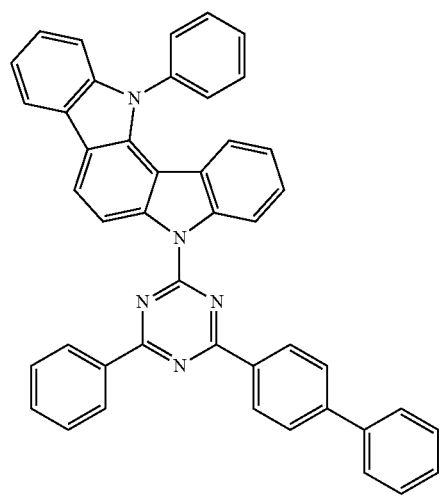
Compound EH33
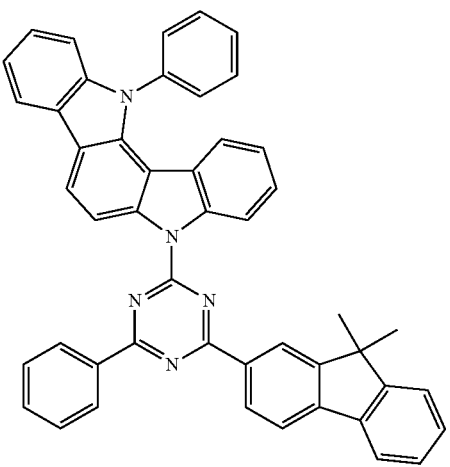

Compound EH34
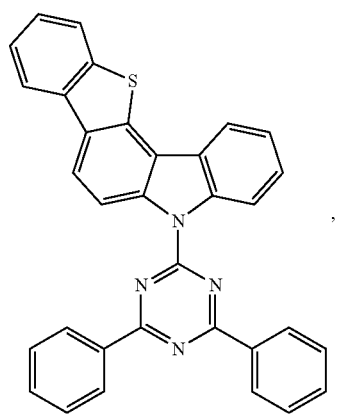
Compound EH37
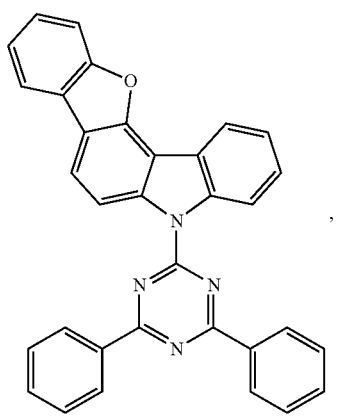
Compound EH35
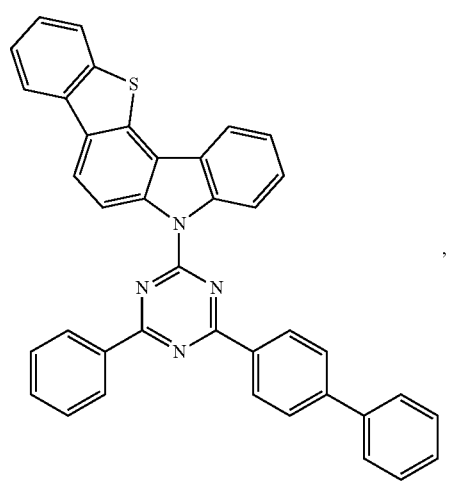
Compound EH38
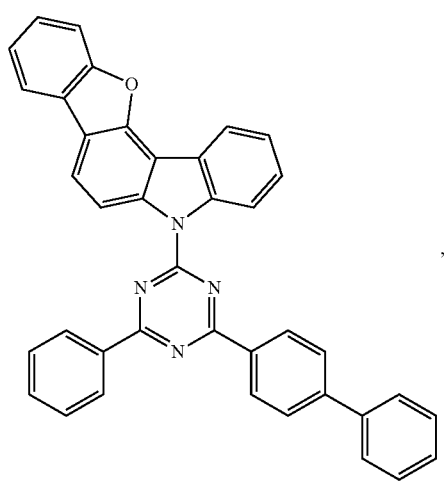
Compound EH36
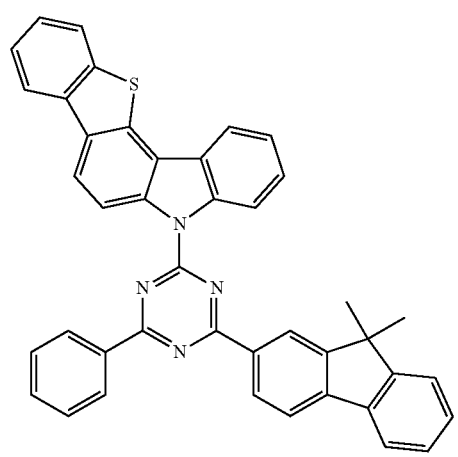
Compound EH39
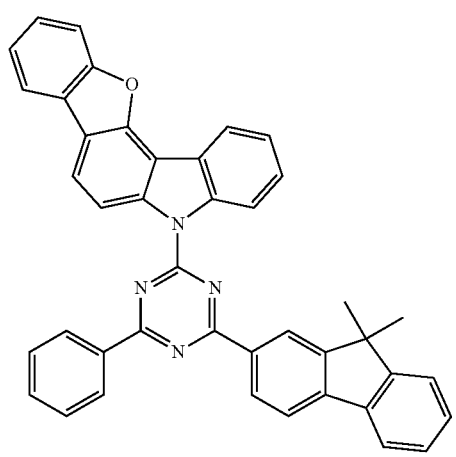

Compound EH40
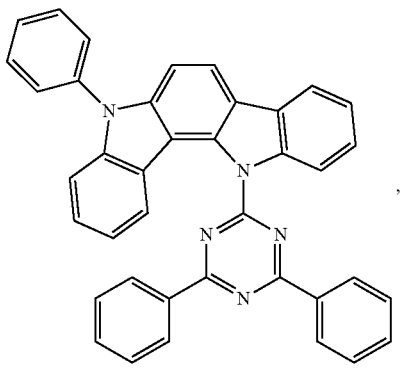
Compound EH41
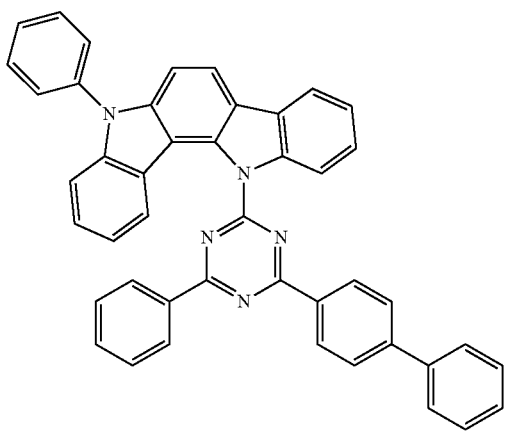
Compound EH42
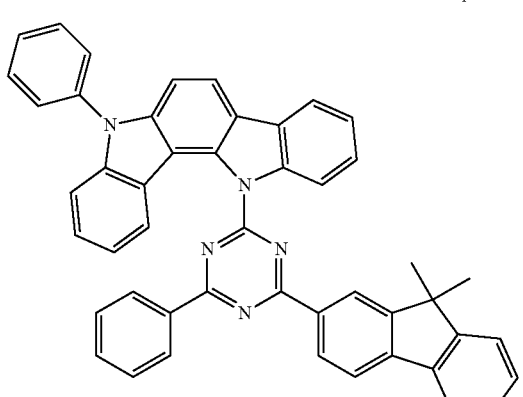
Compound EH43
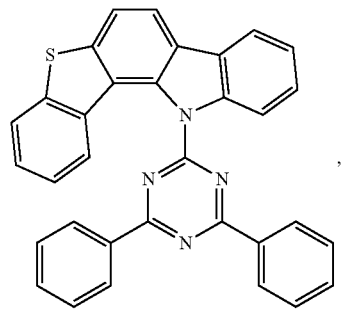
Compound EH44
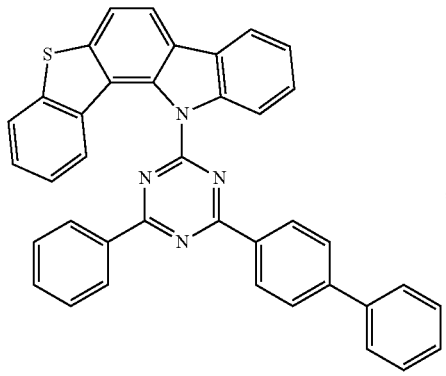
Compound EH45
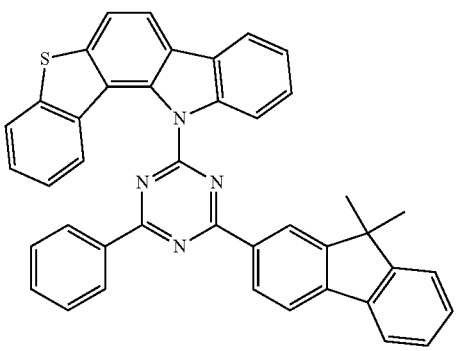
Compound EH46
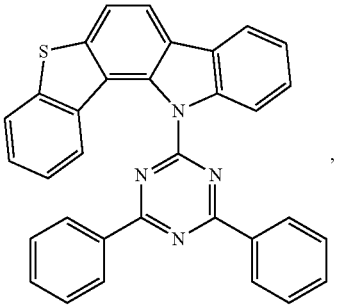
Compound EH47
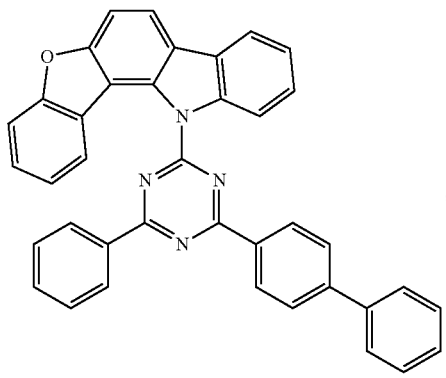

Compound EH48
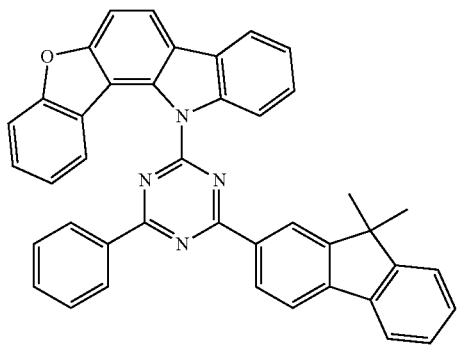
Compound EH49
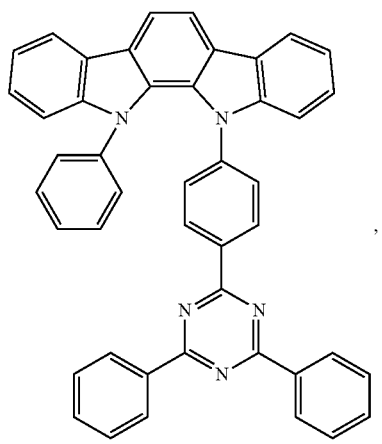
Compound EH50
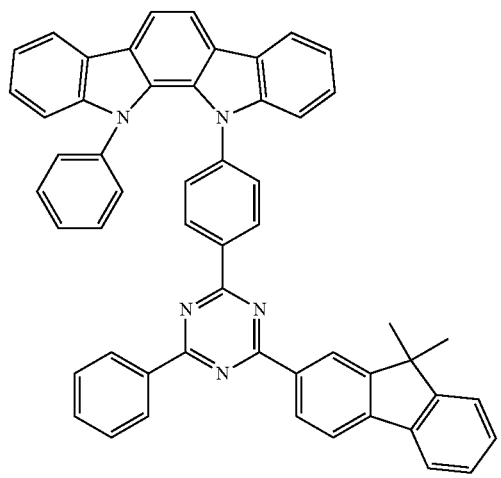
Compound EH51
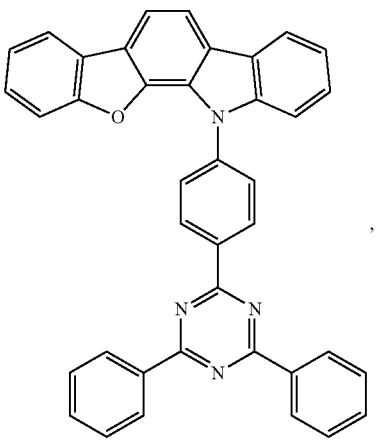
, 
Compound EH52
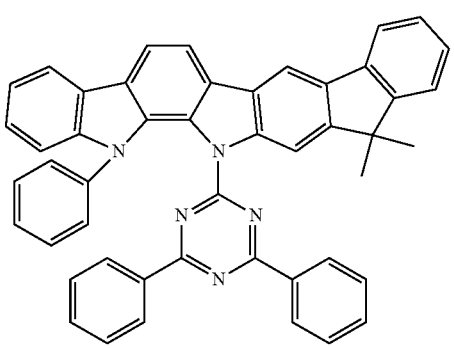
, and
Compound EH53
In one embodiment of the composition, where the first compound has the structure according to Formula VI, the first compound is selected from the group consisting of:

-continued
Compound 1
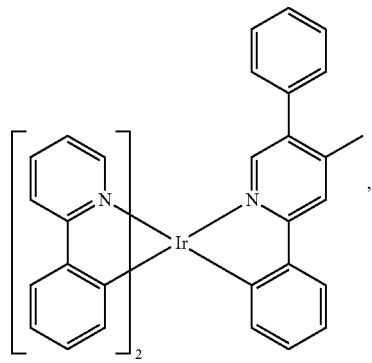
Compound 2
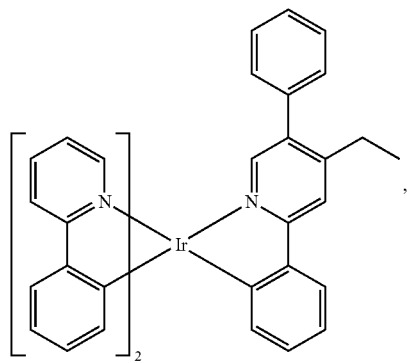
Compound 3
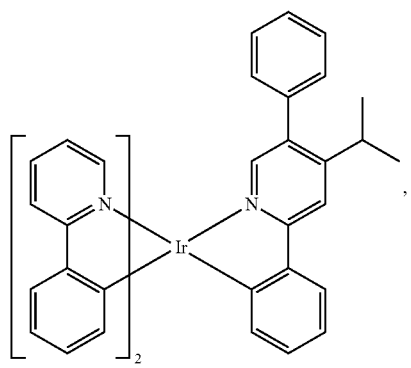
Compound 4
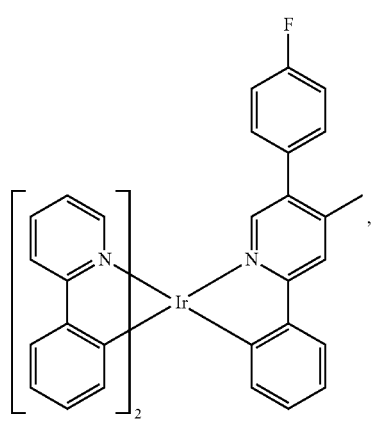
Compound 5
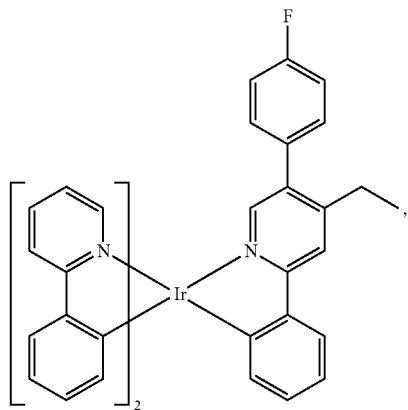
Compound 6
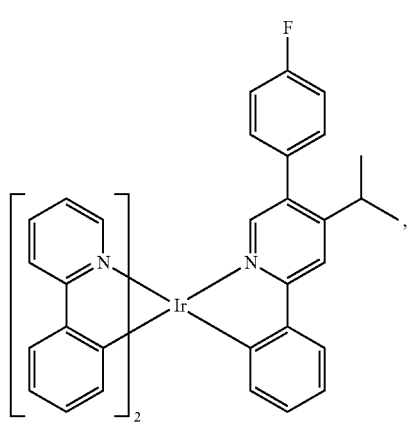
Compound 7
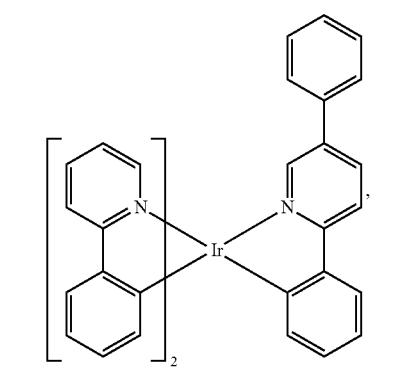
Compound 8
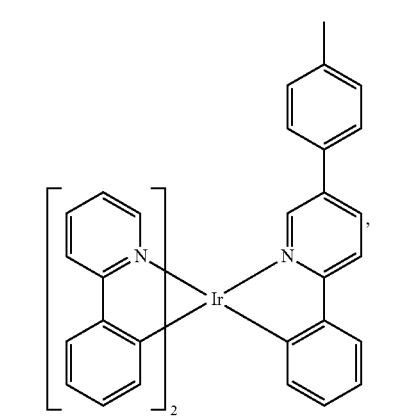

Compound 9
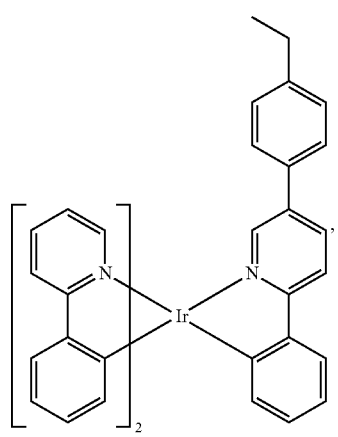
Compound 10
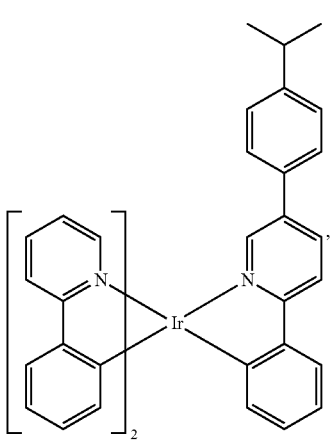
Compound 11
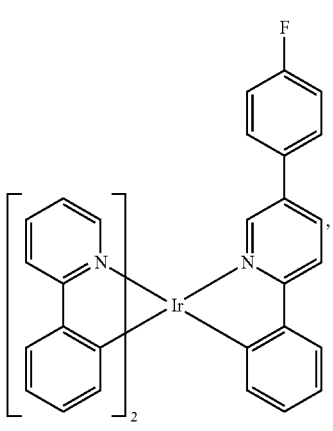
Compound 12
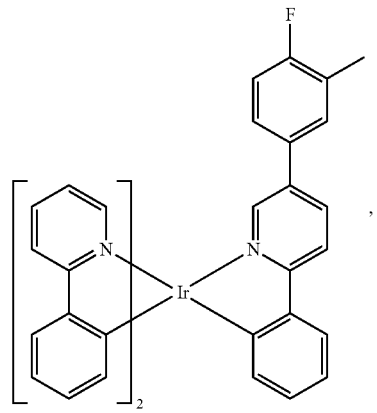
Compound 13
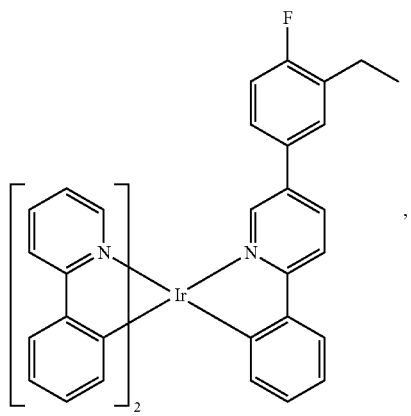
Compound 14
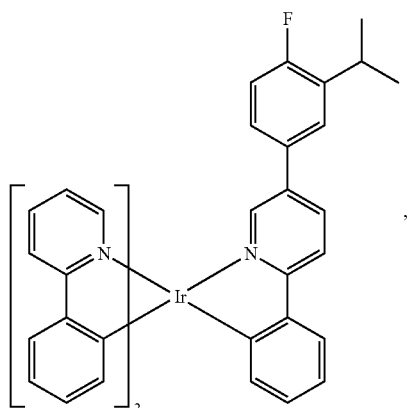
Compound 15
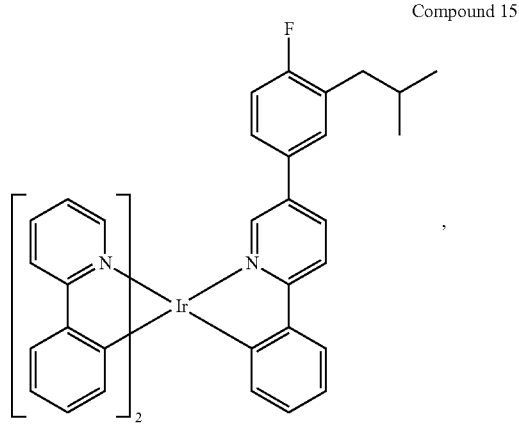

Compound 16
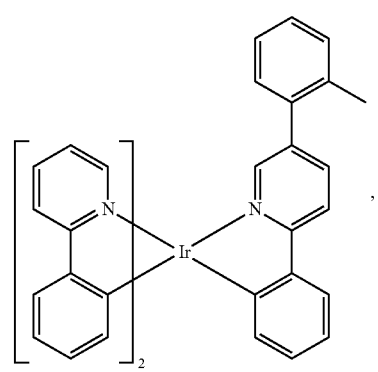
Compound 17
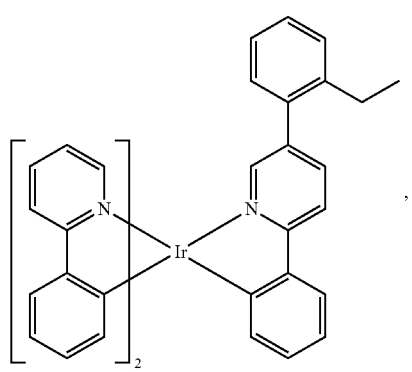
Compound 18
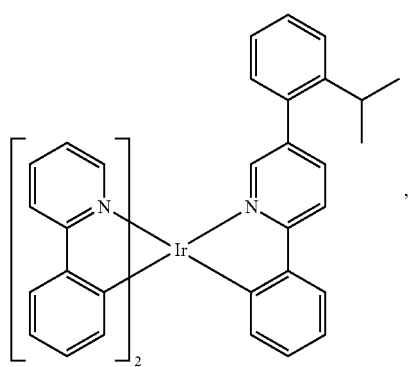
Compound 19
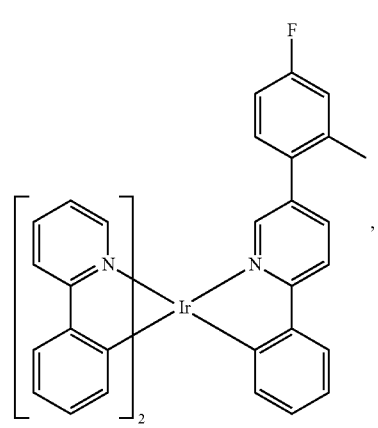
Compound 20
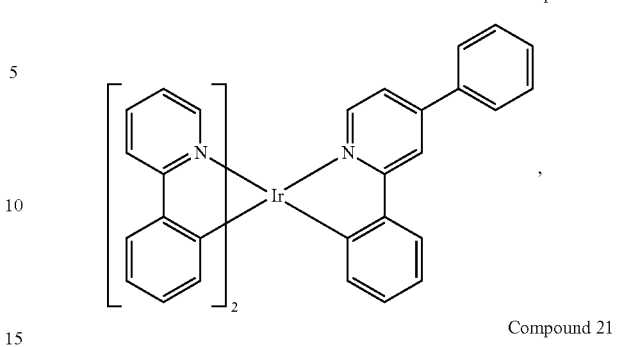
Compound 21
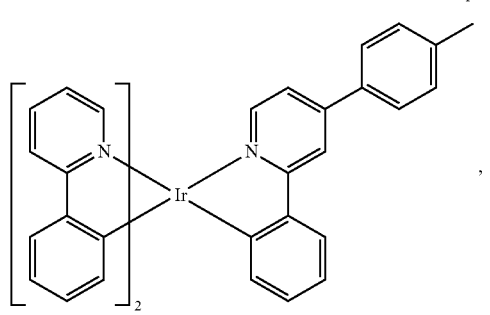
Compound 22
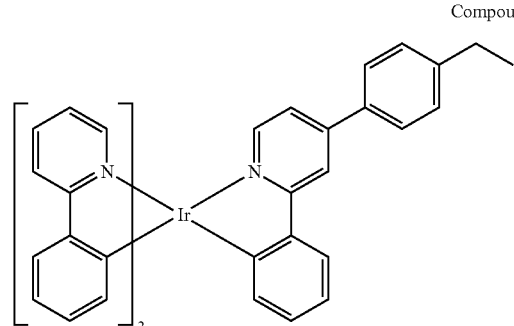
Compound 23
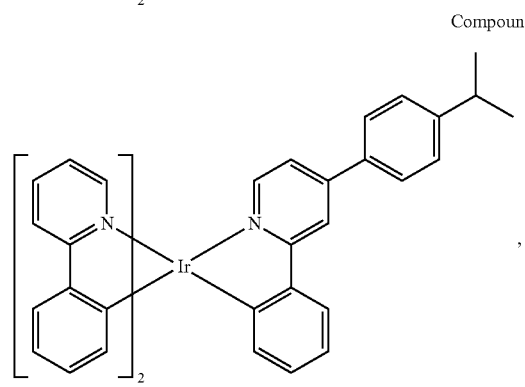
Compound 24
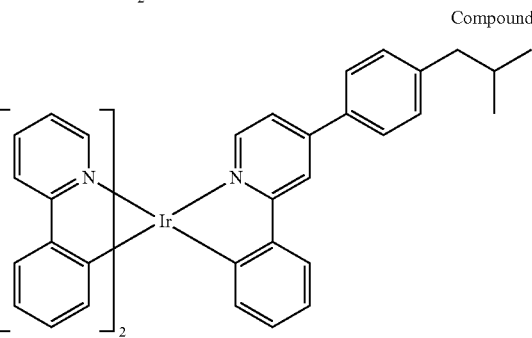

Compound 25
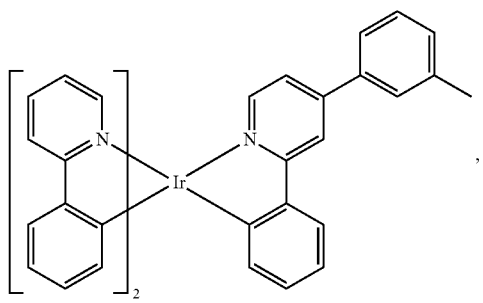
Compound 26
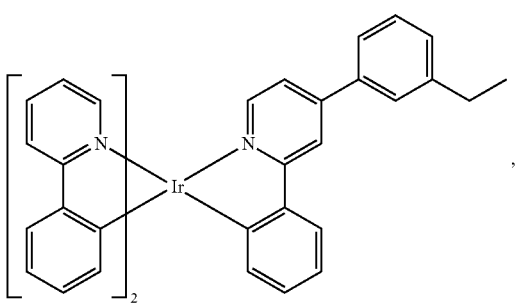
Compound 27
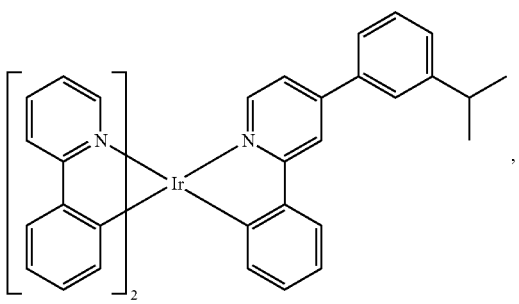
Compound 28
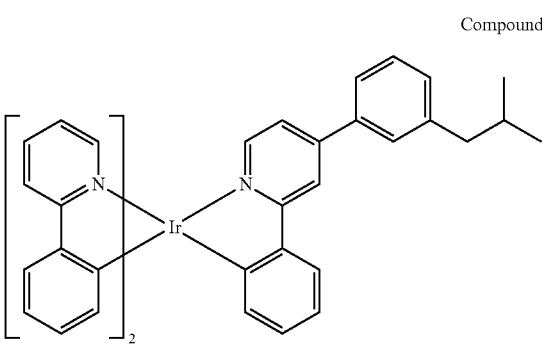
Compound 29
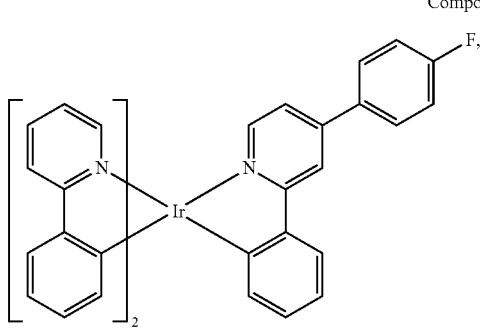
Compound 30
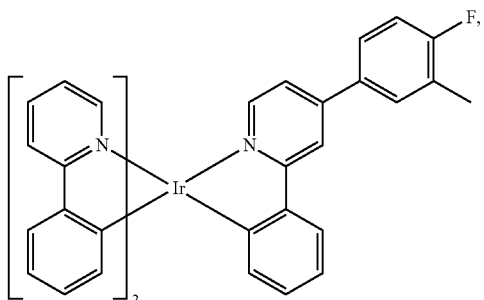
Compound 31
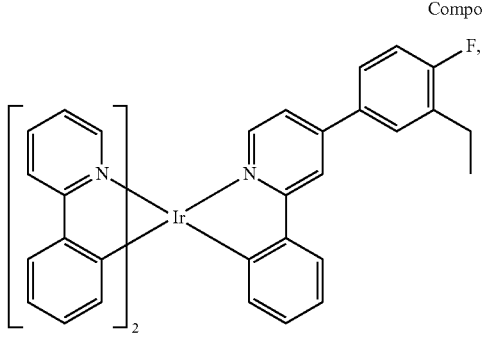
Compound 32
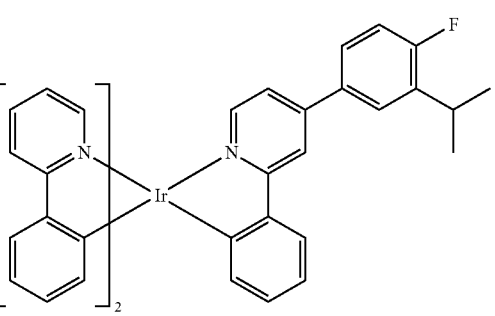
Compound 33
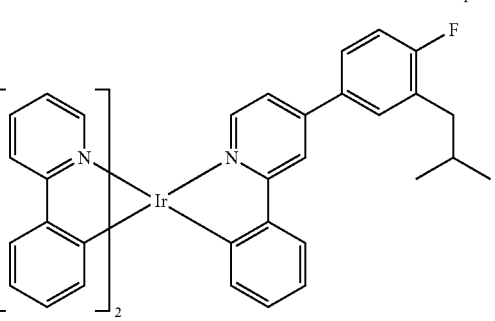

Compound 34
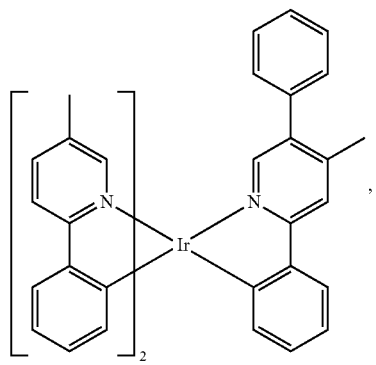
Compound 35
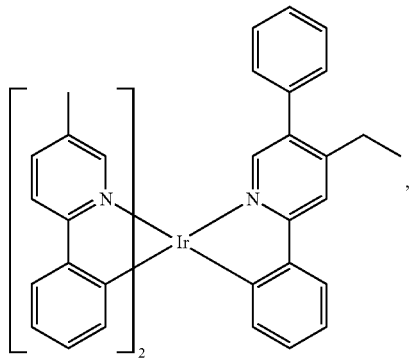
Compound 36
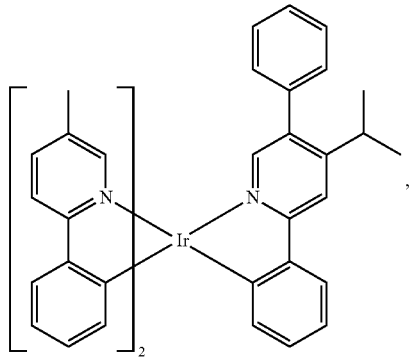
Compound 37
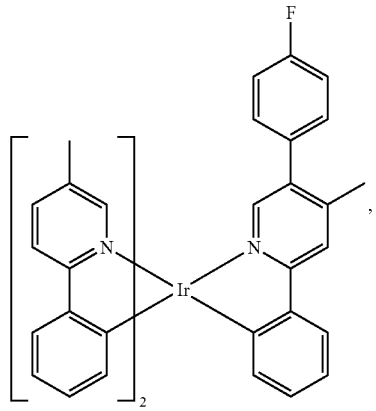
Compound 38
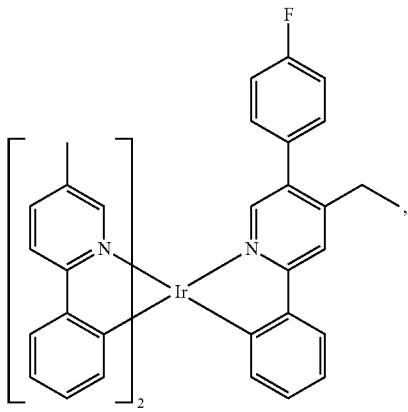
Compound 39
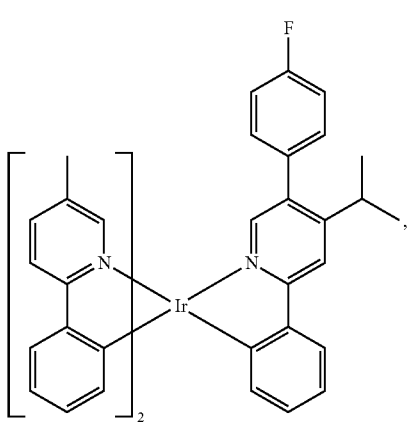
Compound 40
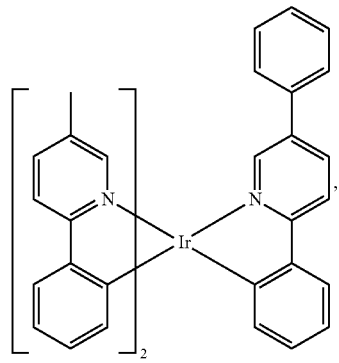
Compound 41
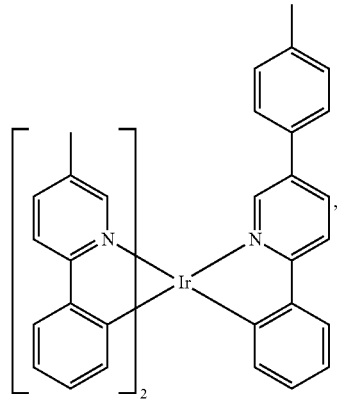

Compound 42
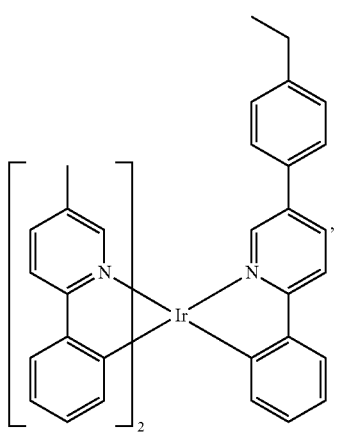
Compound 43
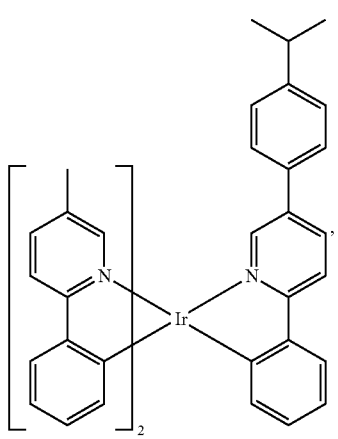
Compound 44
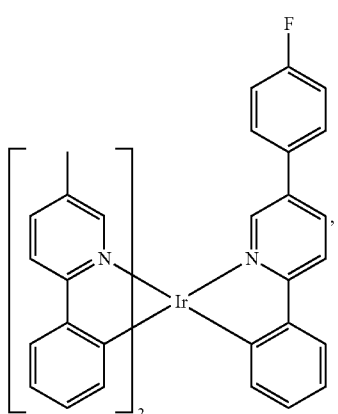
Compound 45
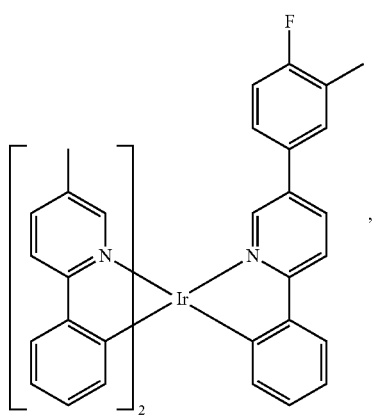
Compound 46
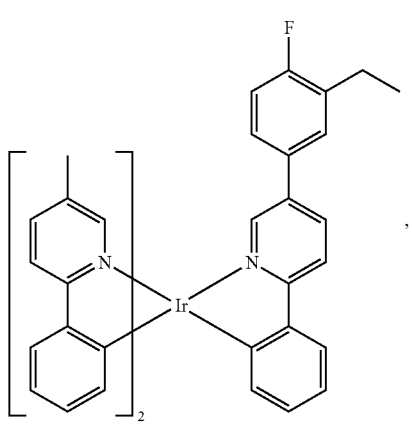
Compound 47
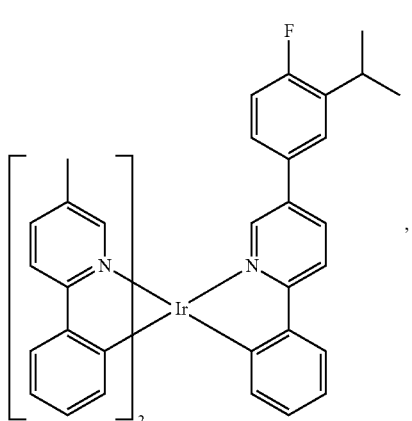

Compound 48
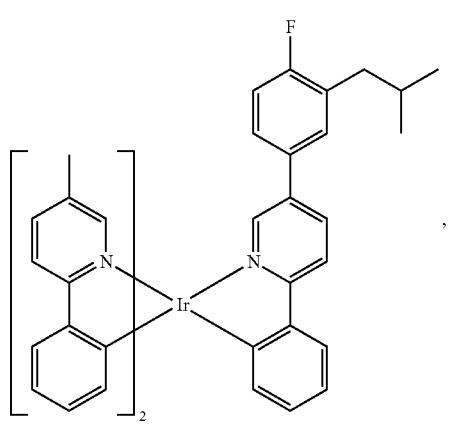
Compound 49
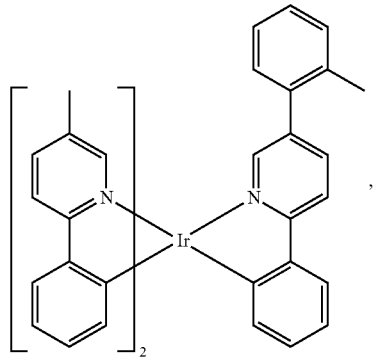
Compound 50
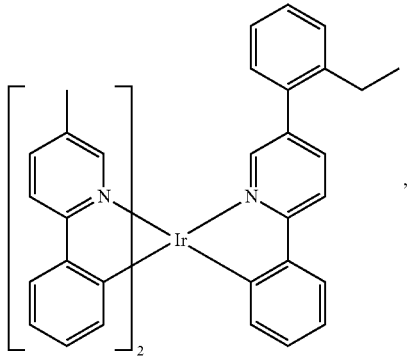
Compound 51
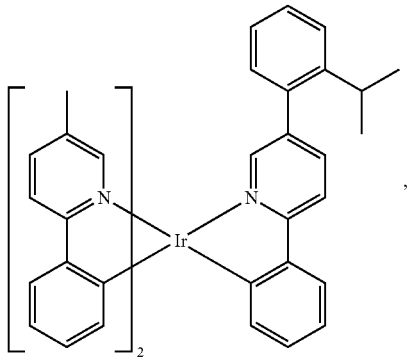
Compound 52
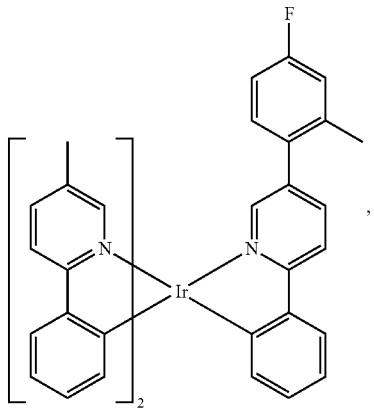
Compound 53
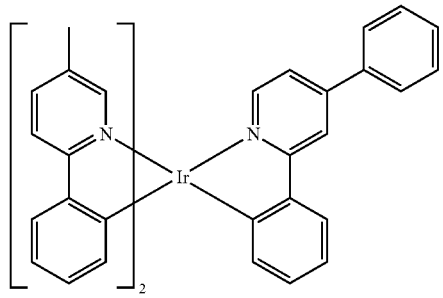
Compound 54
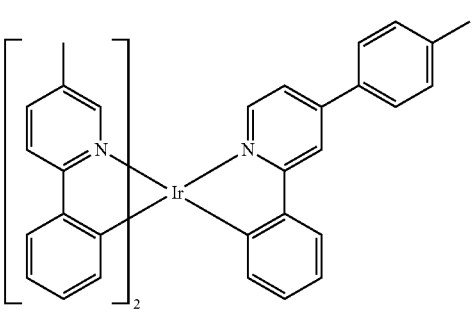
Compound 55
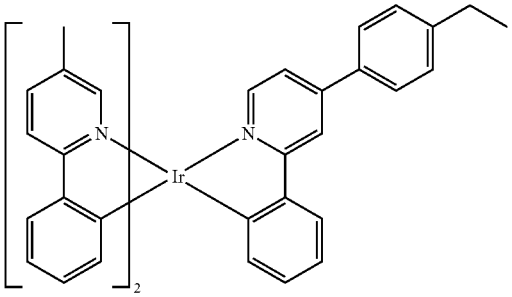

Compound 56
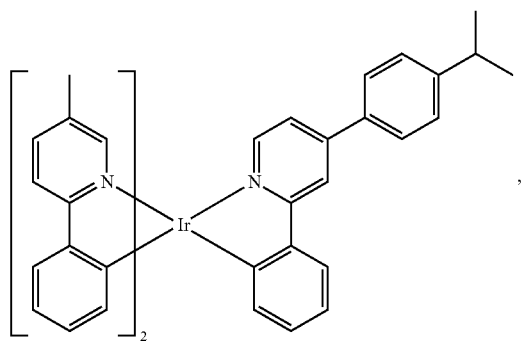
Compound 57
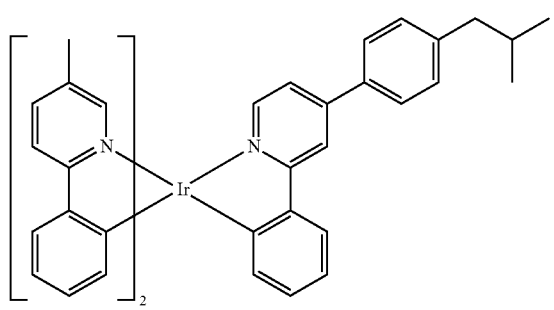
Compound 58
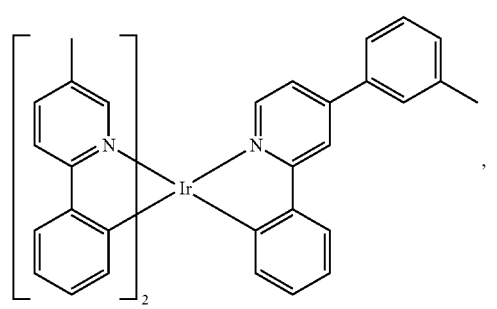
Compound 59
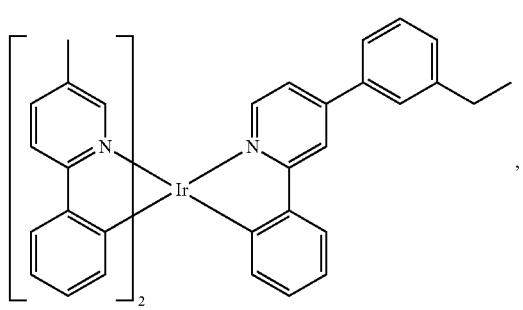
Compound 60
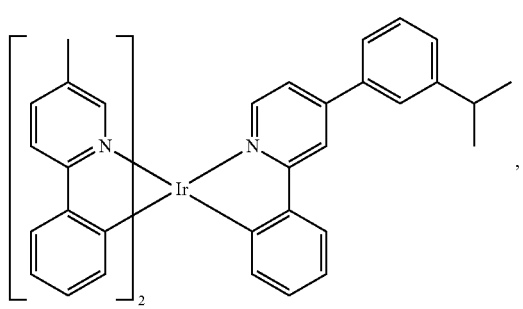
Compound 61
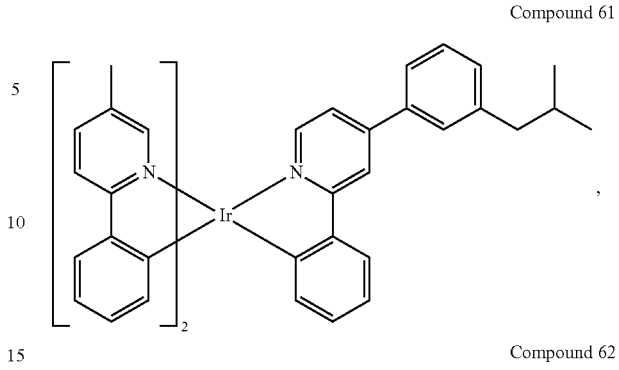
Compound 62
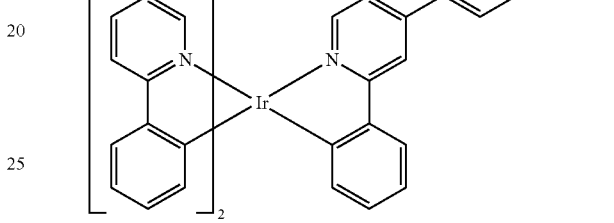
Compound 63
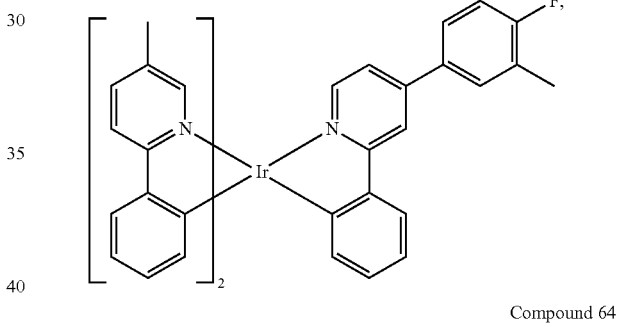
Compound 64
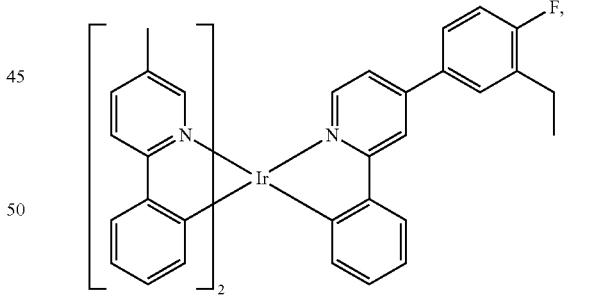
Compound 65
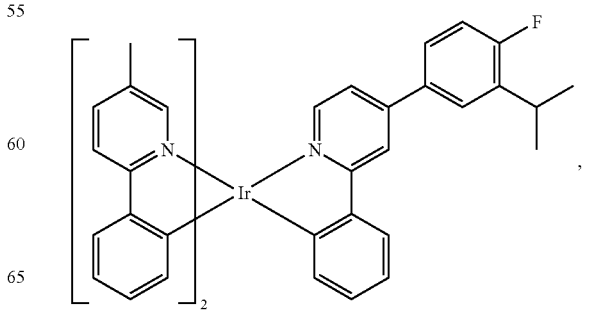

Compound 66
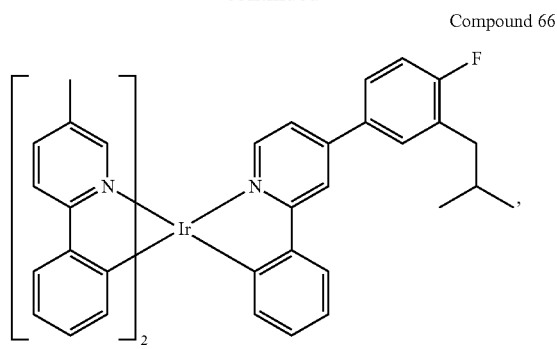
Compound 67
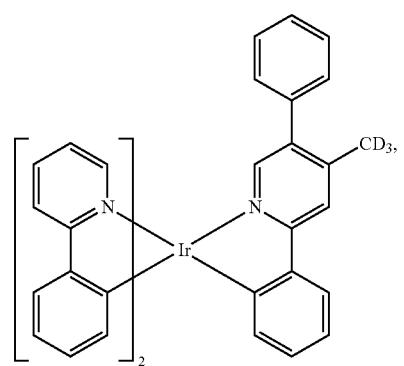
Compound 68
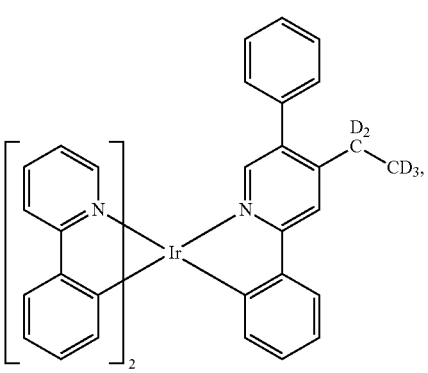
Compound 69
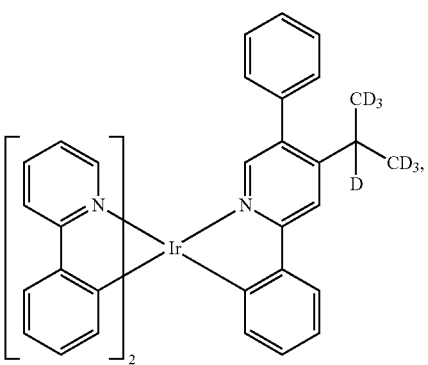
Compound 70
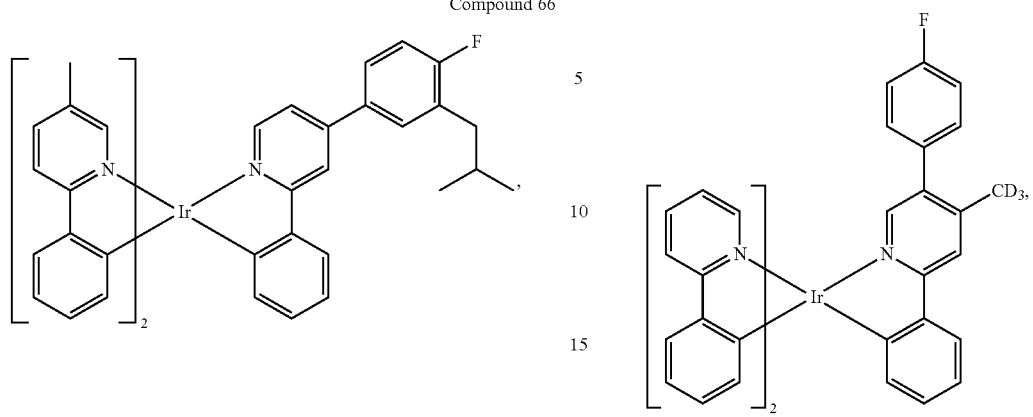
Compound 71
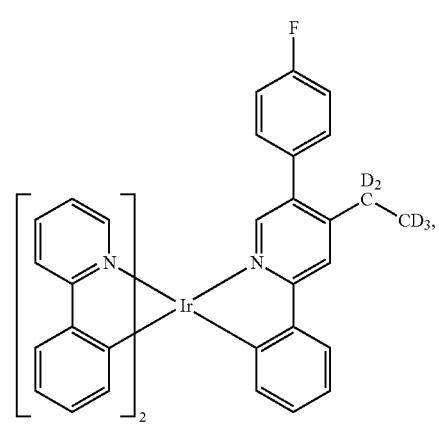
Compound 72
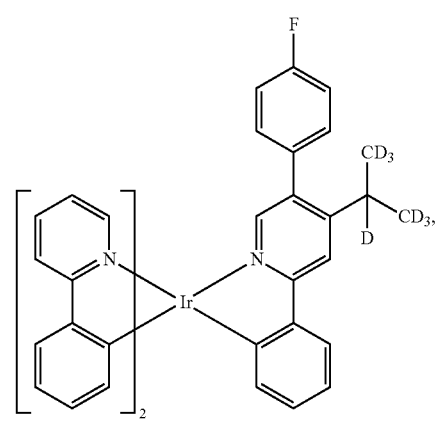
Compound 73
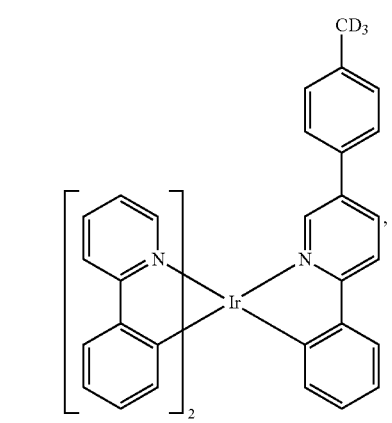

Compound 74
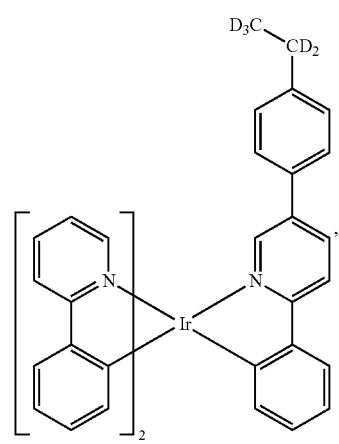
Compound 75
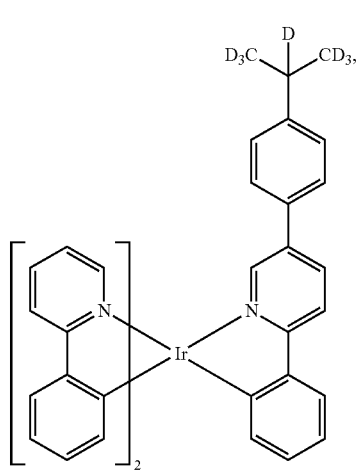
Compound 76
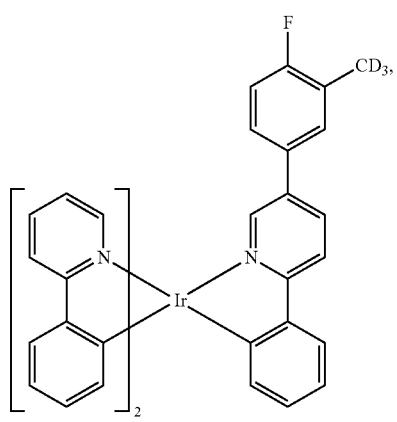
Compound 77
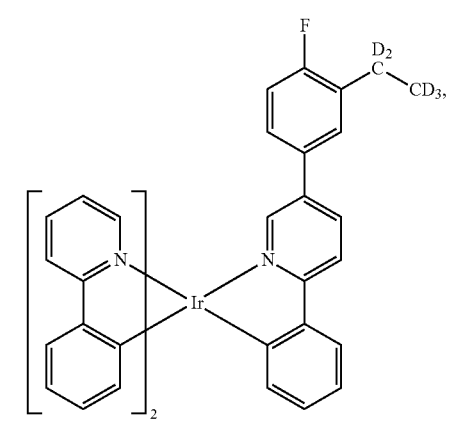
Compound 78
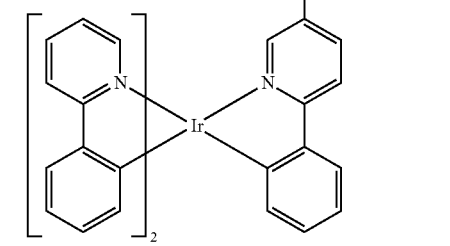
Compound 79
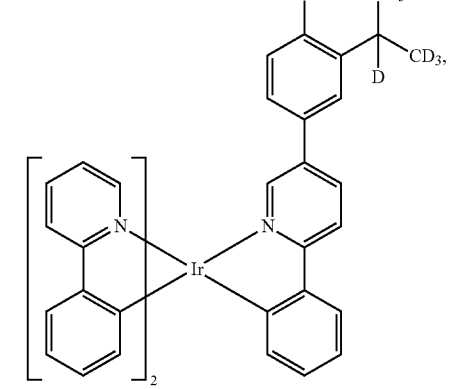
Compound 80
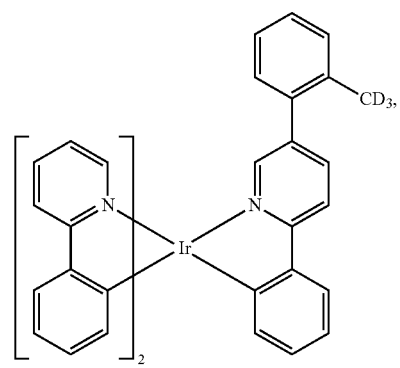

Compound 81
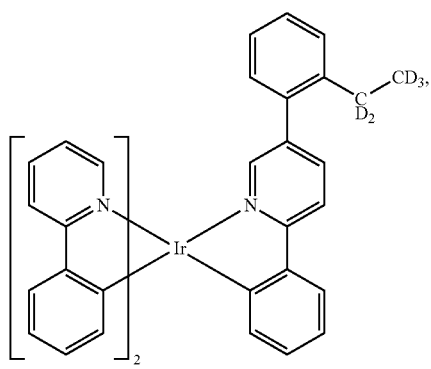
Compound 82
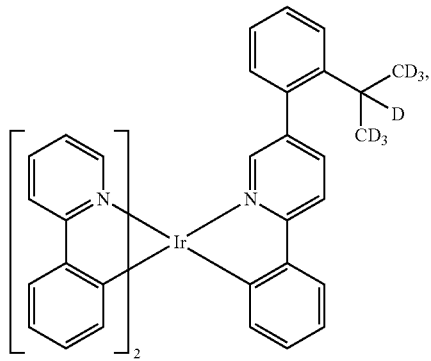
Compound 83
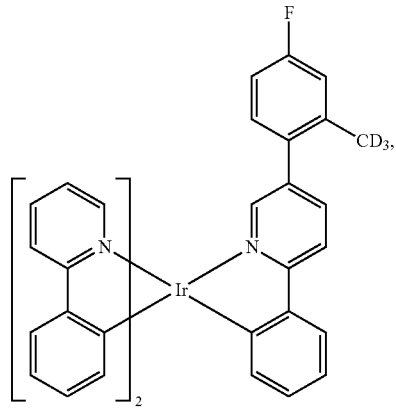
Compound 84
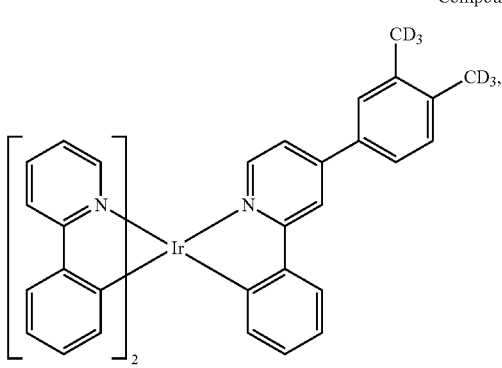
Compound 85
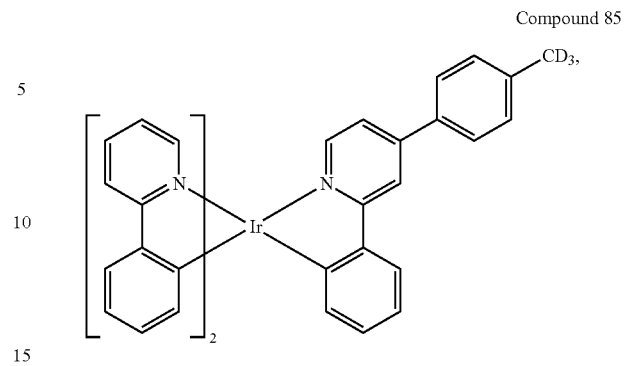
Compound 86
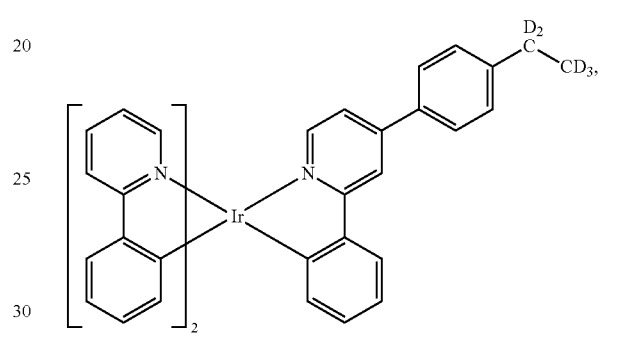
Compound 87
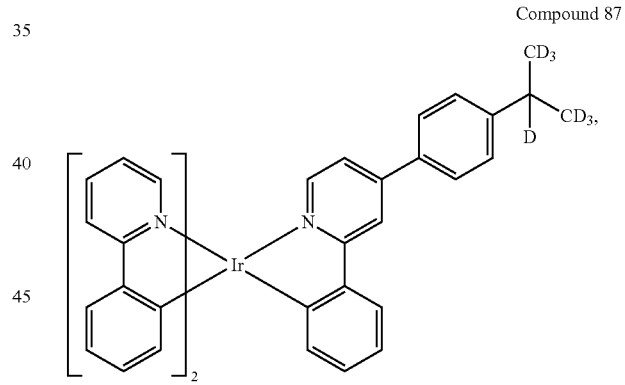
Compound 88
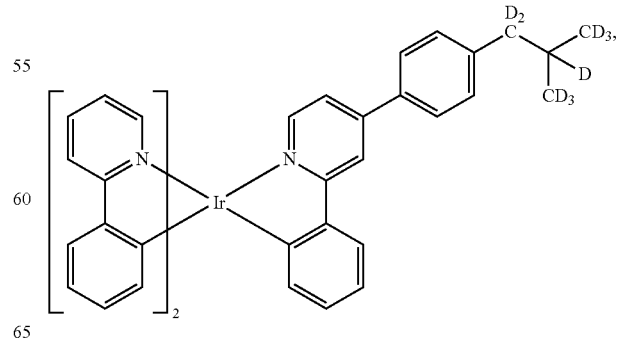

Compound 89
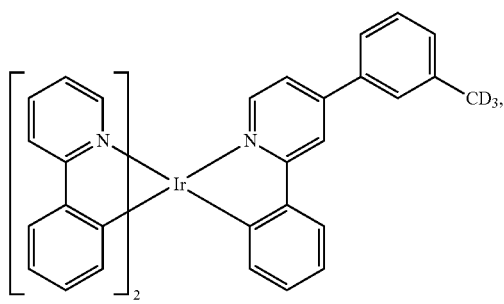
Compound 90
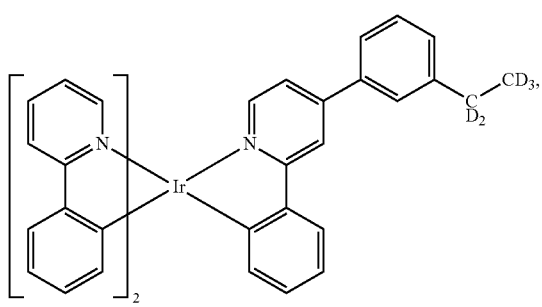
Compound 91
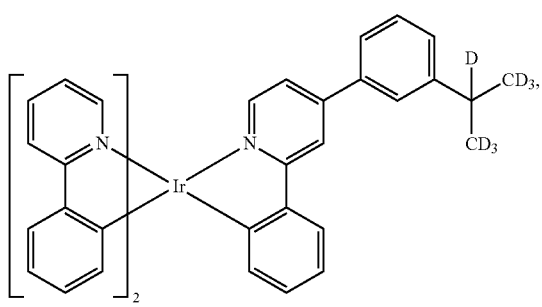
Compound 92
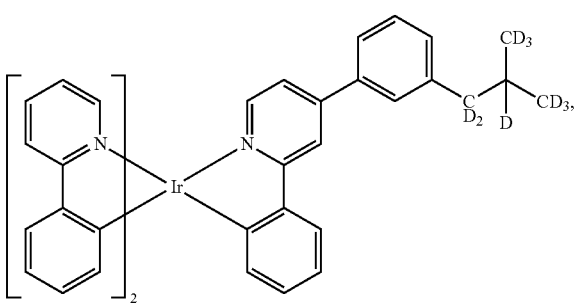
Compound 93
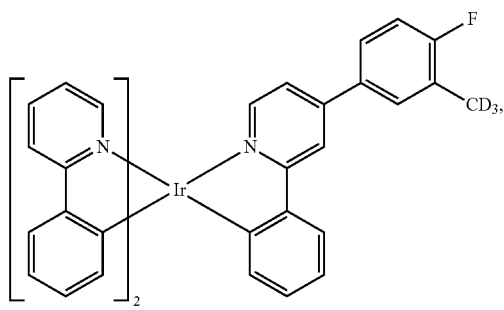
Compound 94
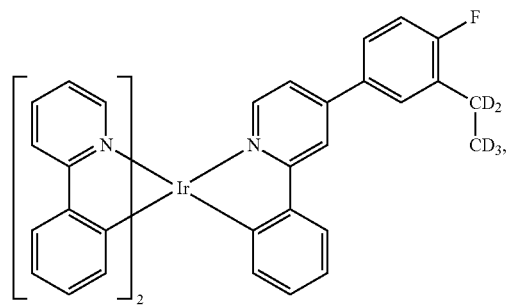
Compound 95
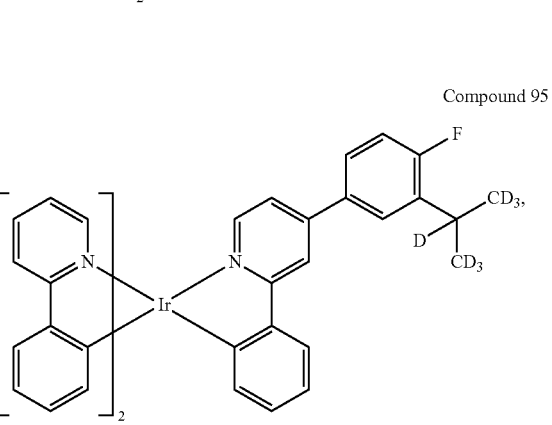
Compound 96
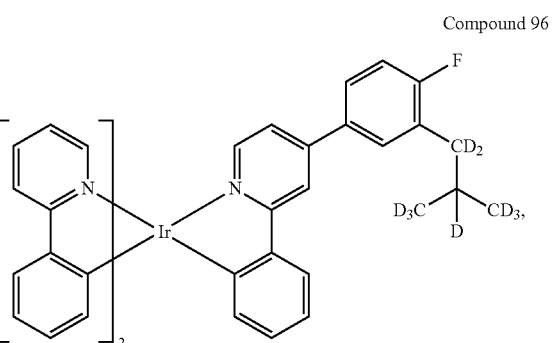
Compound 97
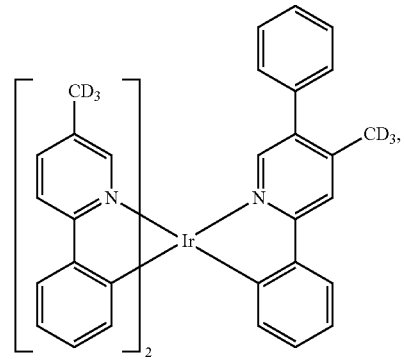

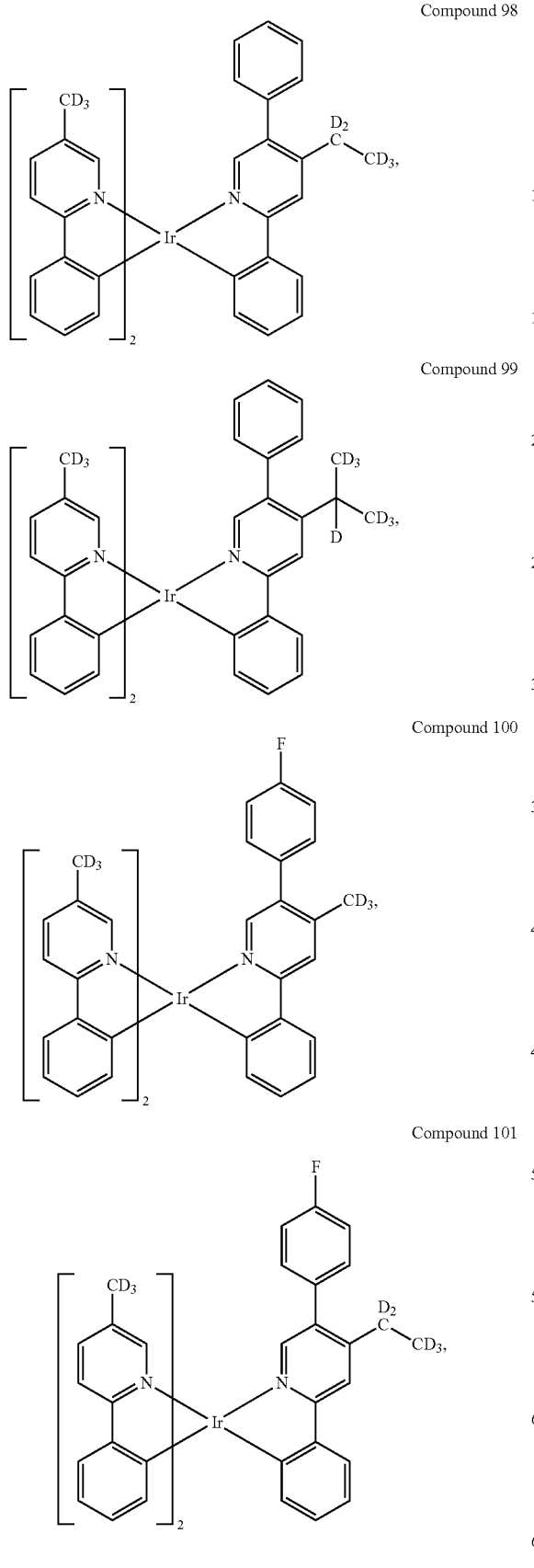
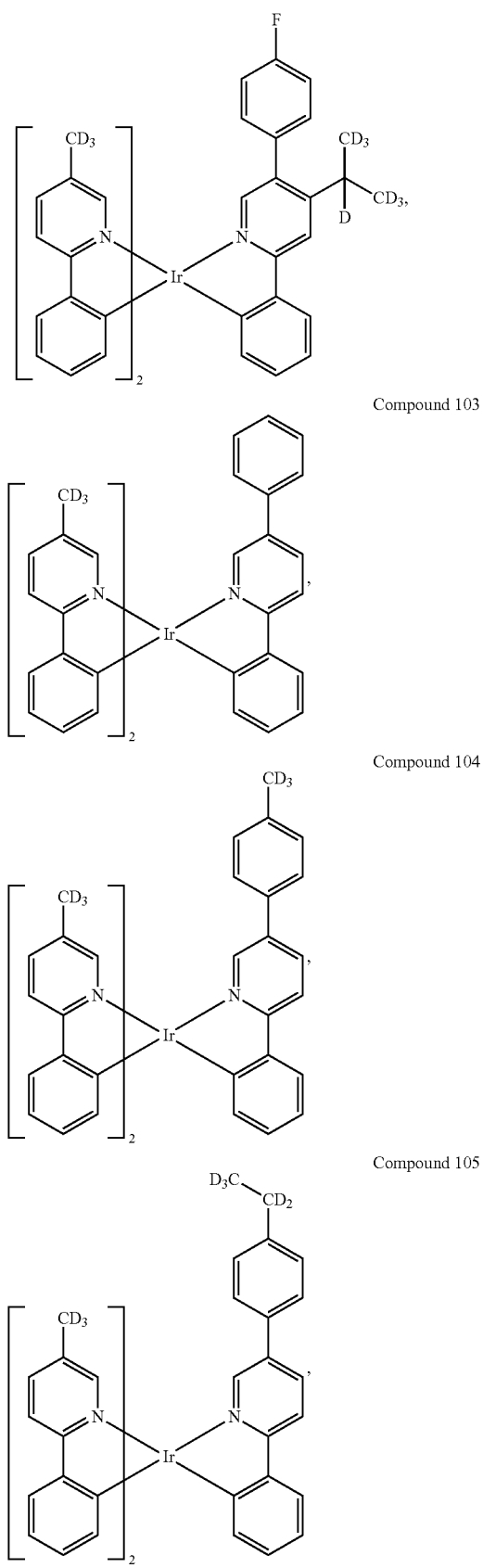

Compound 106
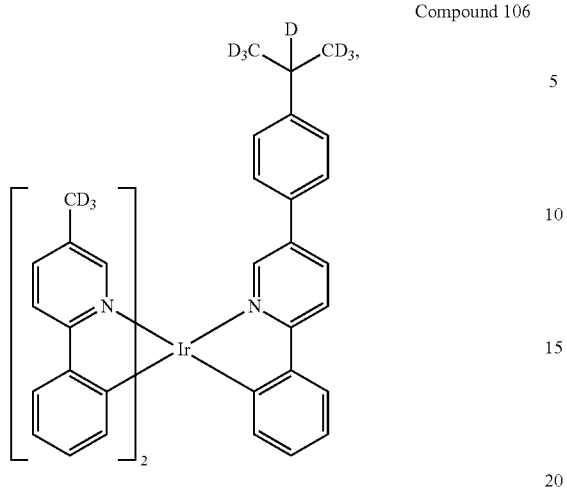
Compound 107
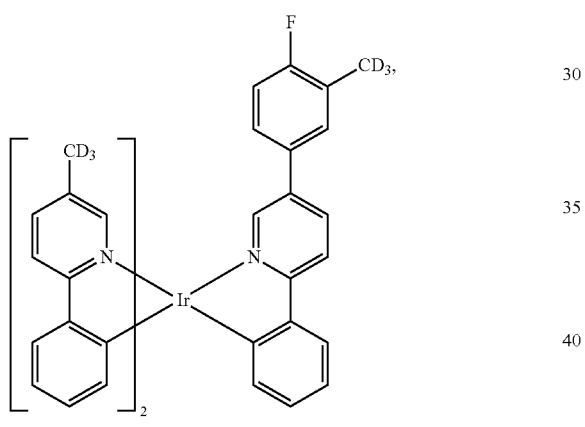
Compound 108
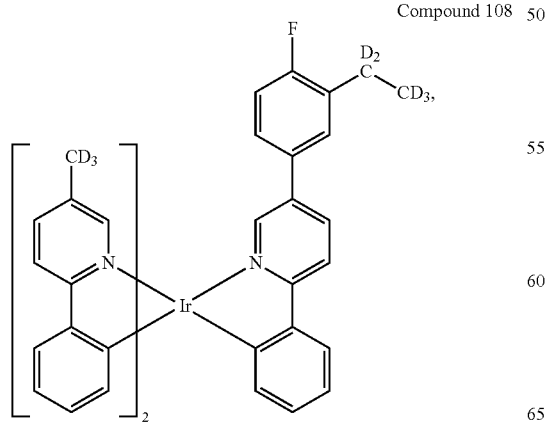
Compound 109
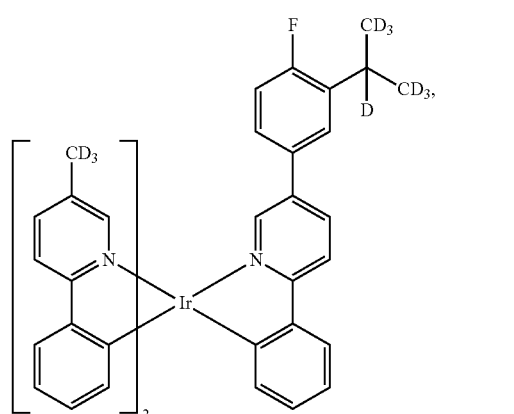
Compound 110
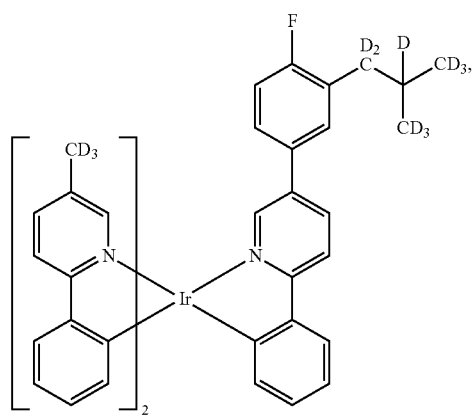
Compound 111
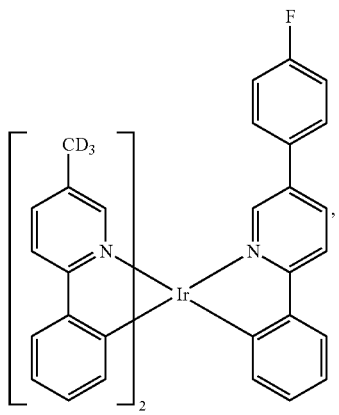

Compound 112
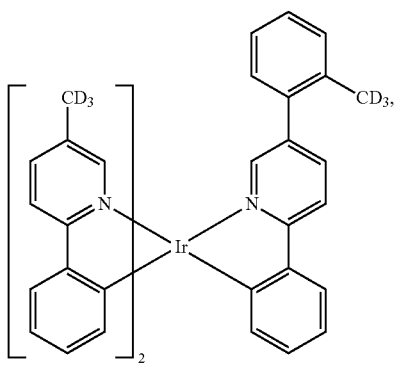
Compound 116
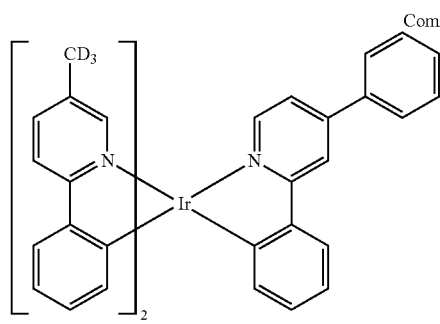
Compound 113
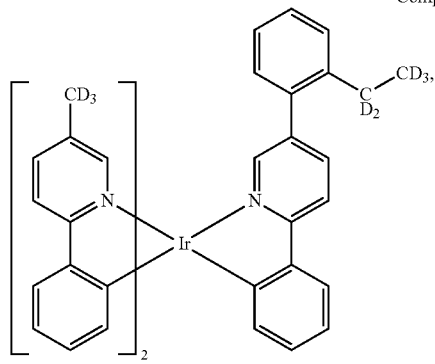
Compound 117
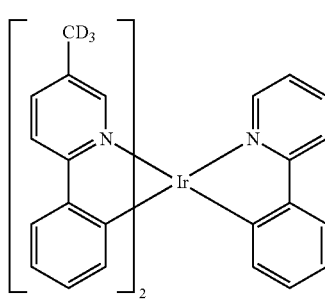
Compound 114
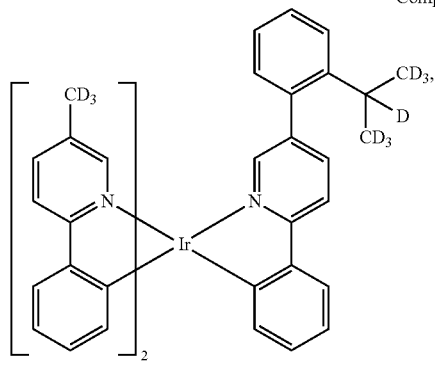
Compound 118
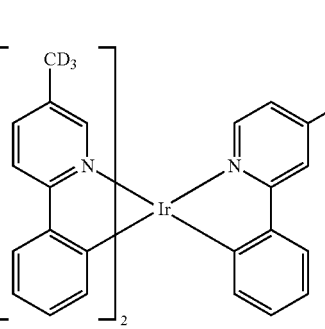
Compound 115
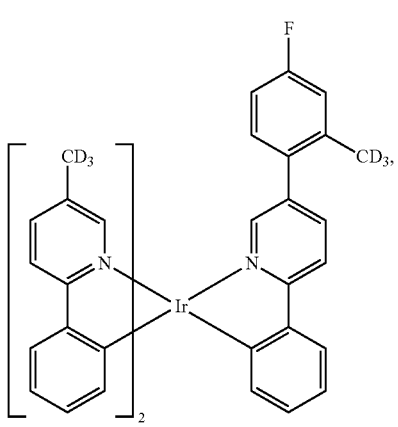
Compound 119
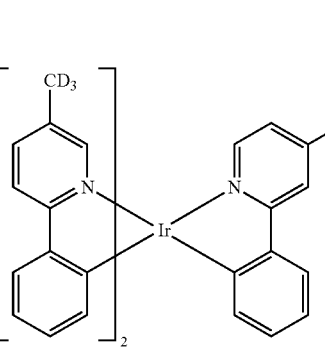

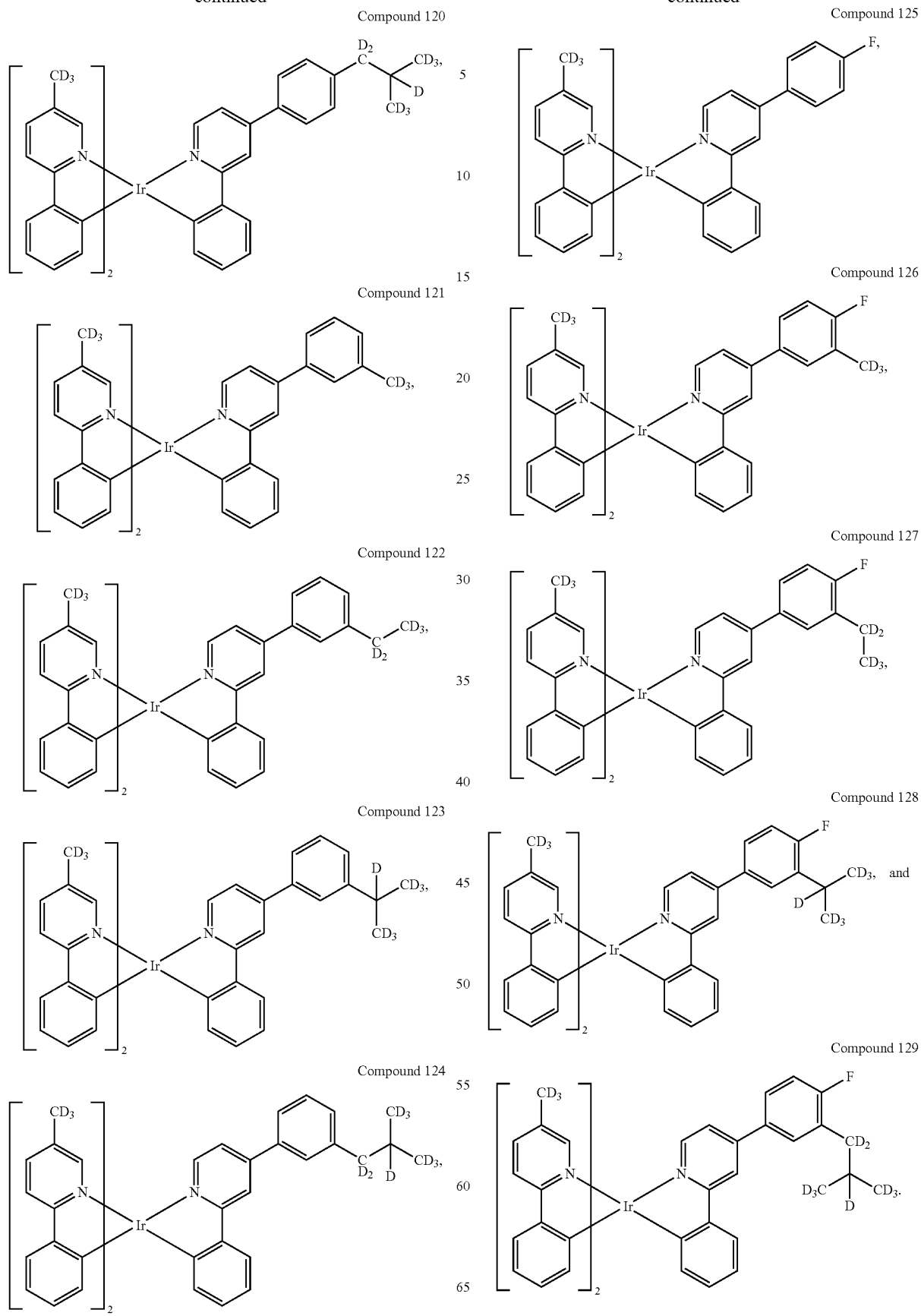

In one embodiment of the composition wherein the second compound has the structure according to Formula V and the first compound has the structure according to Formula VI defined above, the mixture of the second compound and the first compound is selected from the group consisting of: (Compound EH1 and Compound 4), (Compound EH2 and Compound 7), (Compound EH4 and Compound 3), (Compound EH5 and Compound 11), (Compound EH8 and Compound 1), (Compound EH8 and Compound 67), (Compound EH16 and Compound 21), (Compound EH28 and Compound 29), (Compound EH40 and Compound 34), and (Compound EH40 and Compound 97).

In another embodiment of the composition wherein the second compound has the structure according to Formula V and the first compound has the structure according to Formula VI defined above, the mixture of the second compound and the first compound is (Compound EH40 and Compound 97).

According to another aspect of the present disclosure, a first device comprising a first OLED is disclosed. The first OLED comprising: an anode; a cathode; and an organic layer, disposed between the anode and the cathode, comprising a first composition comprising a mixture of a first compound and a second compound, wherein the first compound has different chemical structure than the second compound;
wherein the first compound is capable of functioning as a phosphorescent emitter in an organic light emitting device at room temperature;
wherein the first compound has an evaporation temperature T1 of 150 to 350° C.;
wherein the second compound has an evaporation temperature T2 of 150 to 350° C.;
wherein the absolute value of T1–T2 is less than 20° C.;
wherein the first compound has a concentration C1 in said mixture, and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predefined distance away from the material; and
wherein the absolute value of (C1–C2)/C1 is less than 5%. Preferably the absolute value of (C1–C2)/C1 is less than 3%.

In one embodiment of the first device, the organic layer is an emissive layer. In another embodiment of the first device, the organic layer is a non-emissive layer.

In one embodiment of the first device, the organic layer further comprises a phosphorescent emitting material.

In one embodiment of the first device, the organic layer further comprises a host.

In one embodiment of the first device, the first compound functions as a phosphorescent emitting material.

In one embodiment of the first device, the first compound functions as a host.

In one embodiment of the first device, the first device further comprises a second organic light emitting device separate from the first organic light emitting device, and wherein the second organic light emitting device comprises an emitting dopant having a peak wavelength of between 400 to 500 nanometers.

In one embodiment of the first device, the first organic light emitting device comprises a first emissive layer and a second emissive layer; wherein the first emissive layer comprises the first composition; and the second emissive layer comprises an emitting dopant having a peak wavelength of between 400 to 500 nanometers.

In one embodiment of the first device, the first device is a consumer product. In another embodiment, the first device is an organic light-emitting device. In another embodiment, the first device is a lighting panel.

In one embodiment of the first device, the first composition leaves a residue corresponding to less than 5 wt % of the original charge in the sublimation crucible after the depletion of the first composition in the evaporation process. Preferably, the first composition is deposited in a vacuum system having a pressure level in the range of $1\times10^{-8}$ Torr to $1\times10^{-12}$ Torr.

According to another aspect of the present disclosure, a method for fabricating an organic light emitting device comprising a first electrode, a second electrode, and a first organic layer disposed between the first electrode and the second electrode, wherein the first organic layer comprises a first composition comprising a mixture of a first compound and a second compound is disclosed. The method comprises the following: providing a substrate having the first electrode disposed thereon; depositing the first composition over the first electrode; and depositing the second electrode over the first organic layer,
wherein the first compound has different chemical structure than the second compound,
wherein the first compound is capable of functioning as a phosphorescent emitter in an organic light emitting device at room temperature,
wherein the first compound has an evaporation temperature T1 of 150 to 350° C.,
wherein the second compound has an evaporation temperature T2 of 150 to 350° C.,
wherein the absolute value of T1–T2 is less than 20° C.,
wherein the first compound has a concentration C1 in said mixture, and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predefined distance away from the material, and wherein the absolute value of (C1–C2)/C1 is less than 5%.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

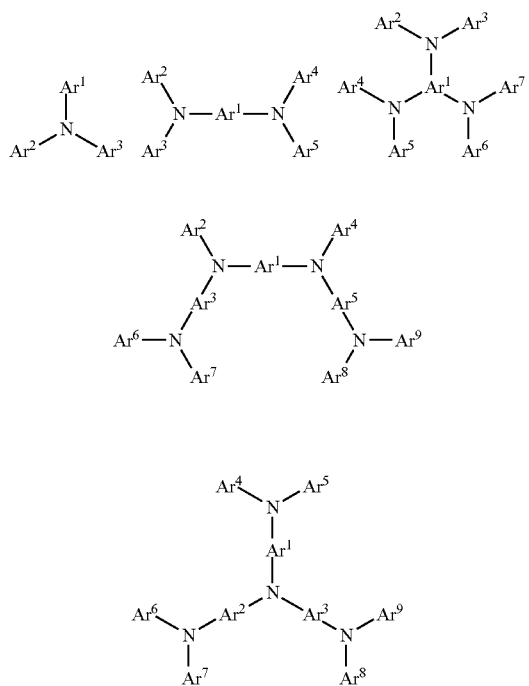

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

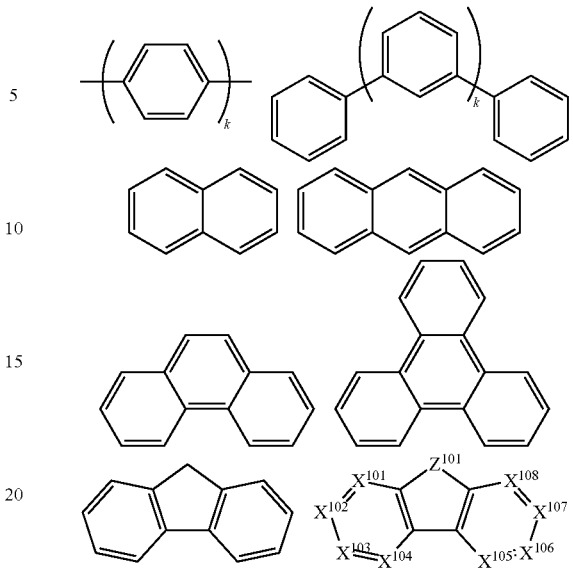

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

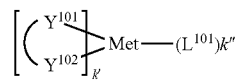

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

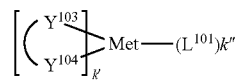

wherein Met is a metal; (Y$^{103}$-Y$^{104}$) is a bidentate ligand, Y$^{103}$ and Y$^{104}$ are independently selected from C, N, O, P, and S; L$^{101}$ is an another ligand; k' is an integer value from 1 to the maximum number of ligands that may be attached to the metal; and k'+k" is the maximum number of ligands that may be attached to the metal.

In one aspect, the metal complexes are:

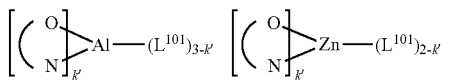

wherein (O—N) is a bidentate ligand, having metal coordinated to atoms O and N.

In another aspect, Met is selected from Ir and Pt. In a further aspect, (Y$^{103}$-Y$^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

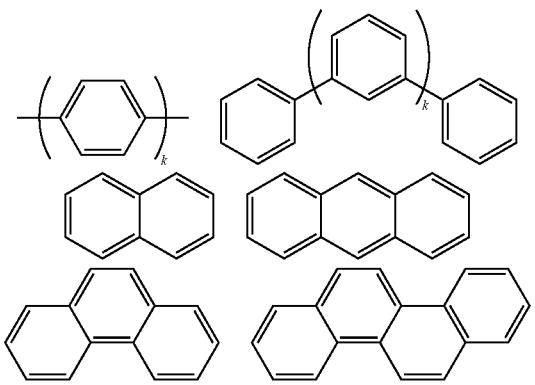

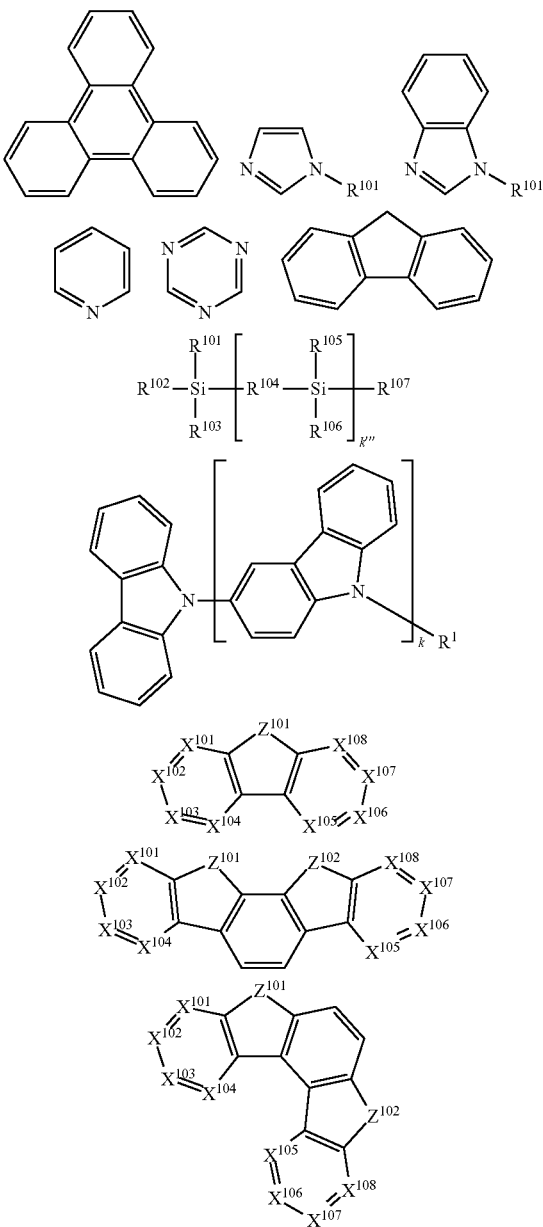

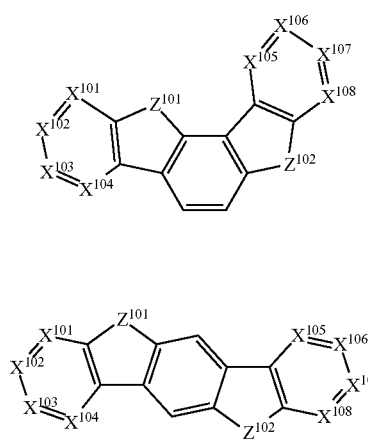

-continued

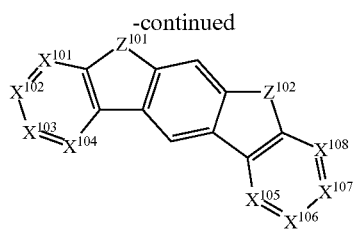

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

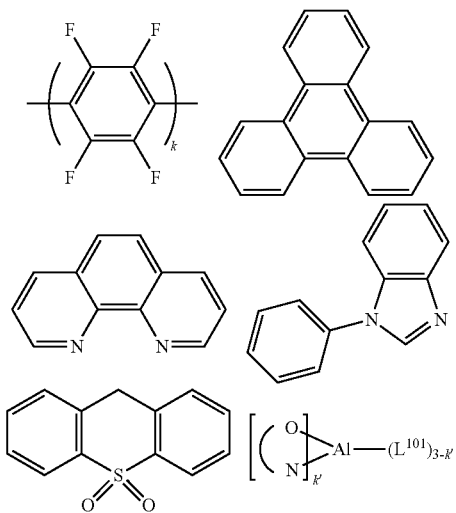

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

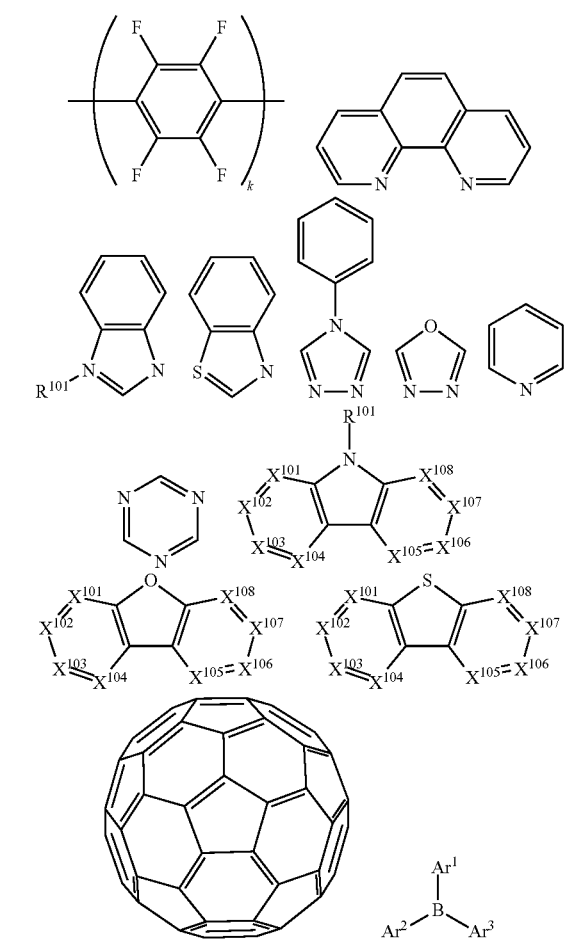

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

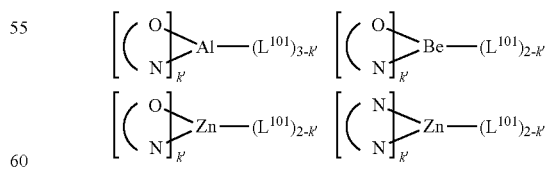

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 5 below. Table 5 lists non-limiting classes of materials, non-limiting examples of compounds for each class, and references that disclose the materials.

TABLE 5

| MATERIAL | EXAMPLES OF MATERIAL | PUBLICATIONS |
|---|---|---|
| Hole injection materials | | |
| Phthalocyanine and porphyrin compoounds | 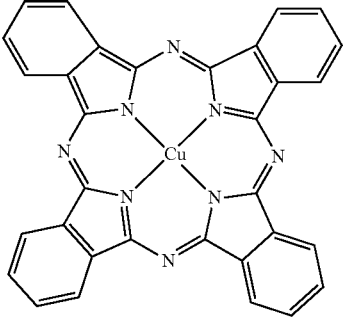 | Appl. Phys. Lett. 69, 2160 (1996) |
| Starburts triarylamines | 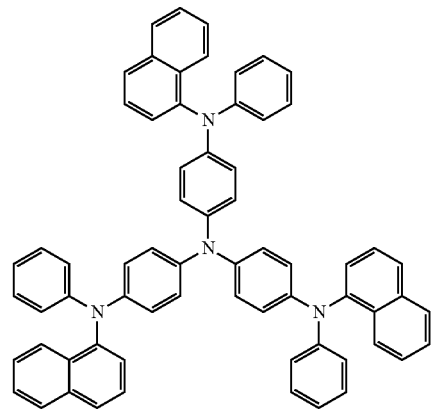 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| CF$_x$ Fluorohydrocarbon polymer | $-\!\!\operatorname{\!\!\!\!-\!\!\!\!}\!\!(CH_xF_y)\!\!\operatorname{\!\!\!\!-\!\!\!\!}_n\!\!-$ | Appl. Phys. Lett. 78, 673 (2001) |
| Conductiong polymers (e.g., PEDOT:PSS, polyaniline, polypthiophene) | 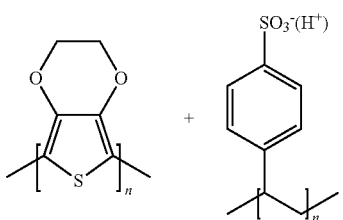 | Synth. Met. 87, 171 (1997) WO2007002683 |
| Phosphonic acid and silane SAMs | 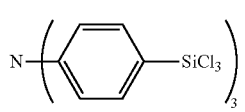 | US20030162053 |

TABLE 5-continued

| MATERIAL | EXAMPLES OF MATERIAL | PUBLICATIONS |
|---|---|---|
| Triarylamine or polythiophene polymers with conductivity dopants | 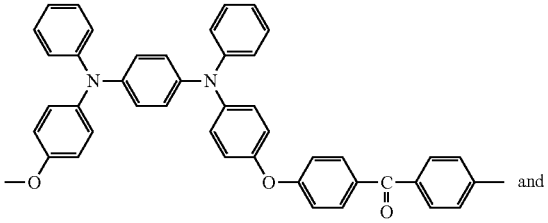 | EP1725079A1 |
| Organic compounds with conductive inorganic compounds, such as molybdenum and tungsten oxides | 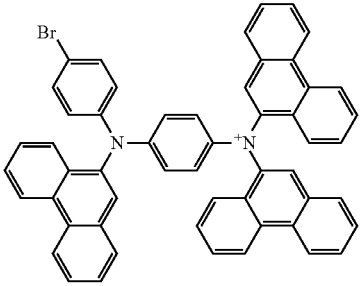 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | US20050123751<br>SID Symposium Digest, 37, 923 (2006)<br>WO2009018009 |
| n-type semiconducting organic complexes | | US20020158242 |
| Metal organometallic complexes | | US20060240279 |
| Cross-linkable compounds | | US20080220265 |

TABLE 5-continued

| MATERIAL | EXAMPLES OF MATERIAL | PUBLICATIONS |
| --- | --- | --- |
| Polythiophene based polymers and copolymers | | WO 2011075644<br>EP2350216 |

Hole transporting materials

| | | |
| --- | --- | --- |
| Triarylamines (e.g., TPD, α-NPD) | | Appl. Phys. Lett. 51, 913 (1987) |
| | | U.S. Pat. No. 5,061,569 |
| | | EP560955 |
| | | J. Mater. Chem. 3, 319 (1993) |

TABLE 5-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbaole compounds | | Adv. Mater. 6, 677 (1994), US20080124572 |

TABLE 5-continued
| MATERIAL | EXAMPLES OF MATERIAL | PUBLICATIONS |
|---|---|---|
| Triarylamine with (di)benzothiophene/ (di)benzofuran | 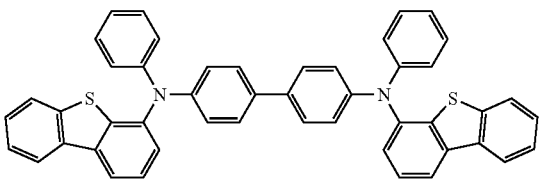 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 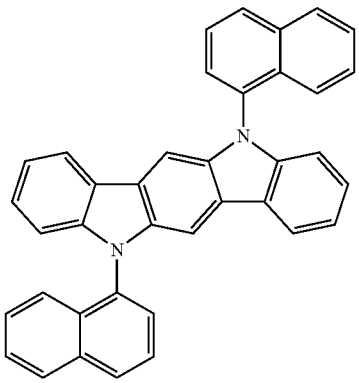 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 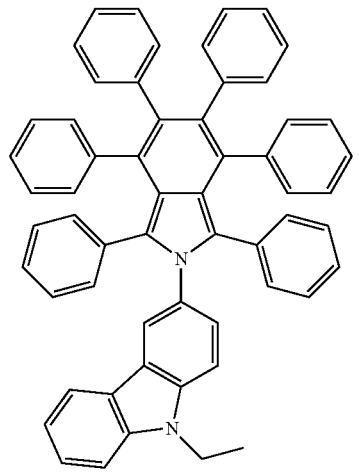 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 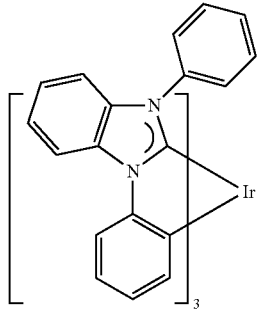 | US20080018221 |
Phosphorescent OLED host materials
Red hosts
| | | |
|---|---|---|
| Arylcarbazoles | 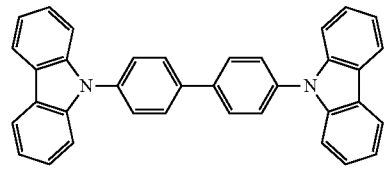 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 5-continued
| MATERIAL | EXAMPLES OF MATERIAL | PUBLICATIONS |
|---|---|---|
| Metal 8-hydroxyquinolates (e.g., Alq$_3$, BAlq) | 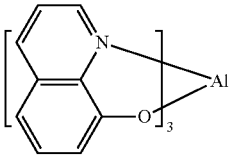 | Nature 395, 151 (1998) |
| | 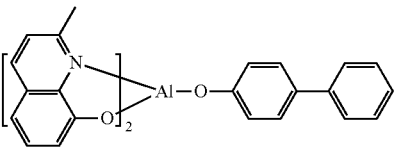 | US20060202194 |
| | 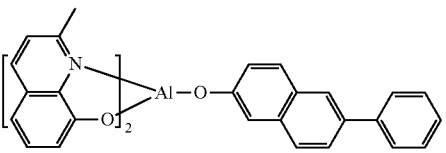 | WO2005014551 |
| | 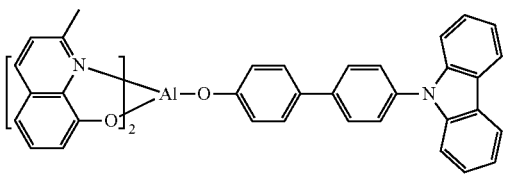 | WO2006072002 |
| Metal phenoxybenzothiazole compounds | 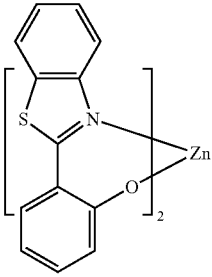 | Appl. Phys. Lett. 90, 123509 (2007) |
| Conjugated oligomers and polymers (e.g., polyfluorene) | 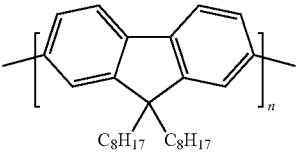 | Org. Electron. 1, 15 (2000) |
| Aromatic fused rings | 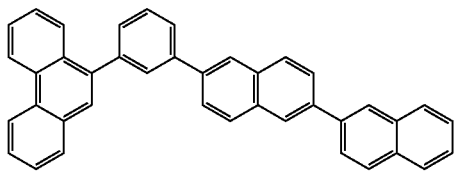 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 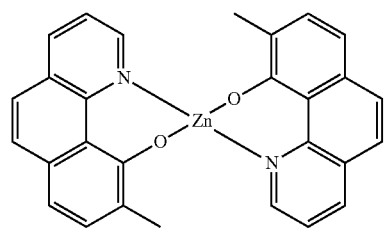 | WO2010056066 |

TABLE 5-continued
| MATERIAL | EXAMPLES OF MATERIAL | PUBLICATIONS |
|---|---|---|
| Chrysene based compounds | 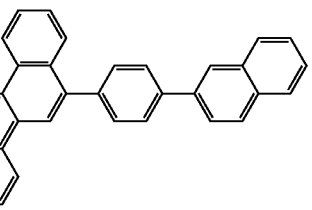 | WO2011086863 |
Green hosts
| | | |
|---|---|---|
| Arylcarbazoles | 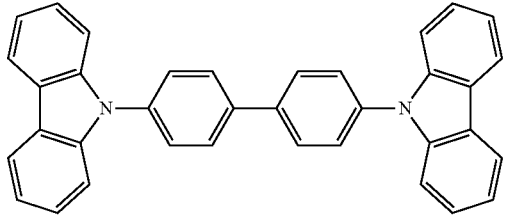 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 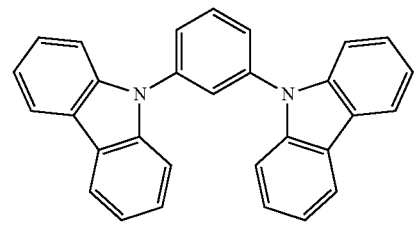 [SMILES: c1cc(-n2c3ccccc3c3ccccc32)cc(-n2c3ccccc3c3ccccc32)c1] | US20030175553 |
| | 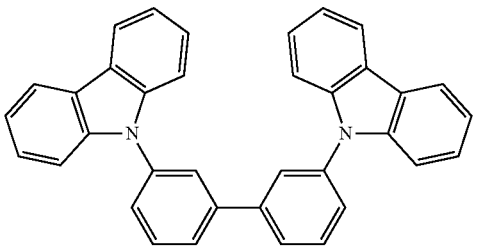 [SMILES: c1cc(-c2cccc(-n3c4ccccc4c4ccccc43)c2)cc(-n2c3ccccc3c3ccccc32)c1] | WO2001039234 |
| Aryltriphenylene compounds | 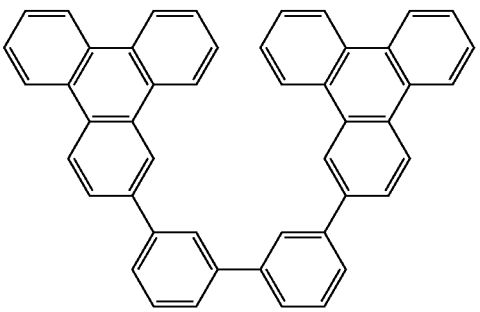 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 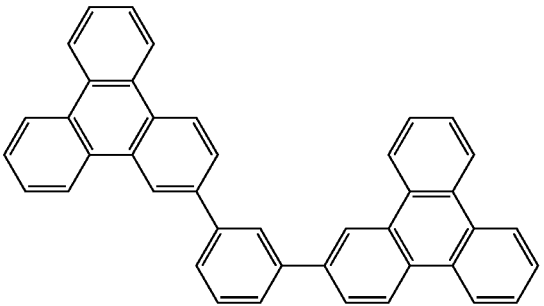 [SMILES: c1cc(-c2ccc3c4ccccc4c4ccccc4c3c2)cc(-c2ccc3c4ccccc4c4ccccc4c3c2)c1] | US20060280965 |

TABLE 5-continued
| MATERIAL | EXAMPLES OF MATERIAL | PUBLICATIONS |
|---|---|---|
| | 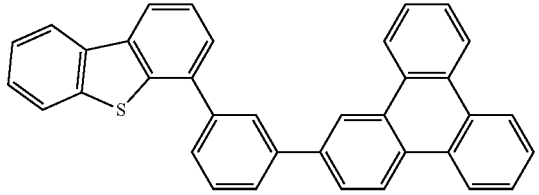 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 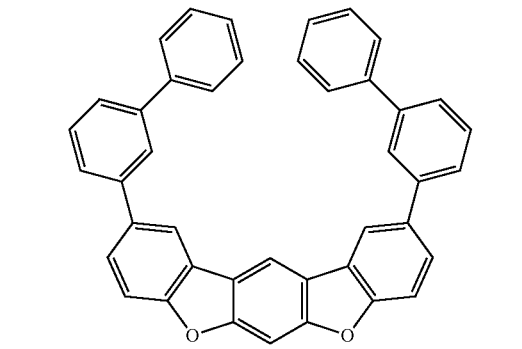 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 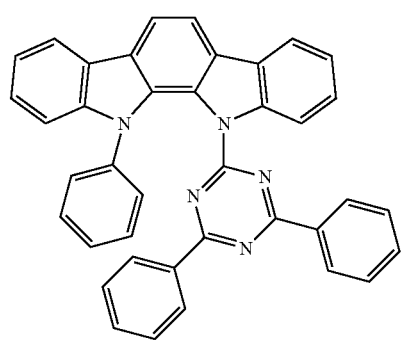 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 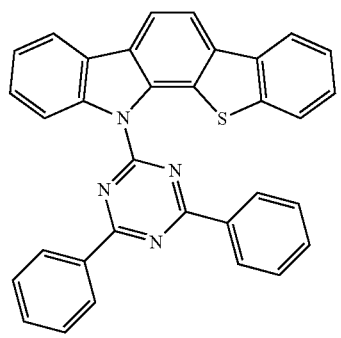 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 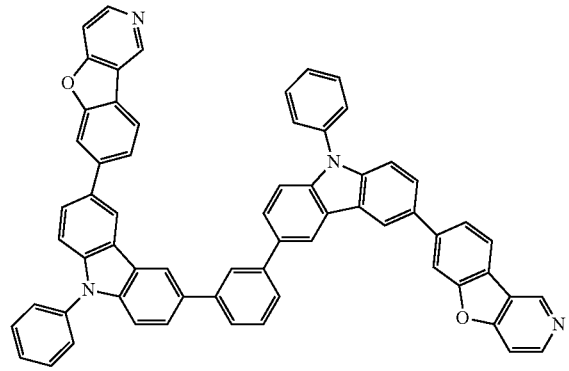 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 5-continued
| MATERIAL | EXAMPLES OF MATERIAL | PUBLICATIONS |
|---|---|---|
| | 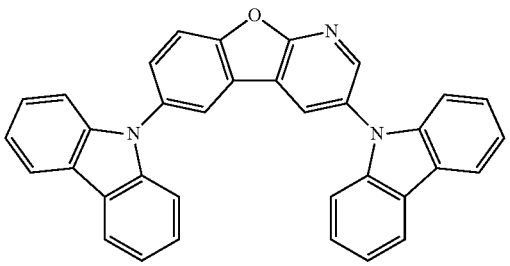 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 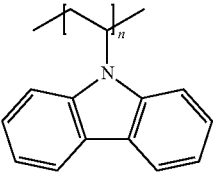 | Appl. Phys. Lett. 77, 2280 (2000) |
| Spirofluoroene compounds | 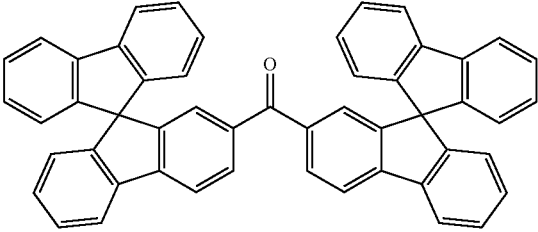 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 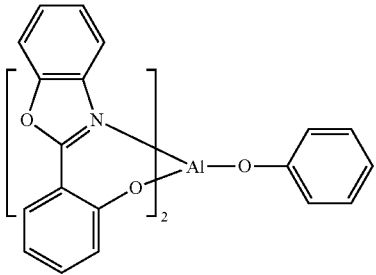 | WO2005089025 |
| | 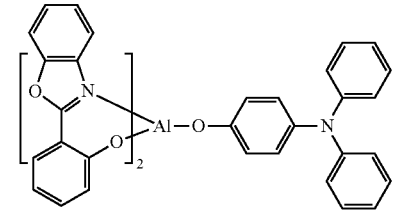 | WO2006132173 |
| | 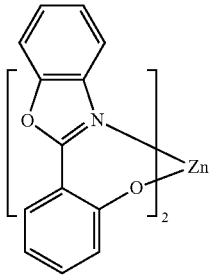 | JP200511610 |

TABLE 5-continued

| MATERIAL | EXAMPLES OF MATERIAL | PUBLICATIONS |
| --- | --- | --- |
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triaole, oxadiazole) | | J. Appl. Phys. 90, 5048 (2001) |

| MATERIAL | EXAMPLES OF MATERIAL | PUBLICATIONS |
|---|---|---|
| | 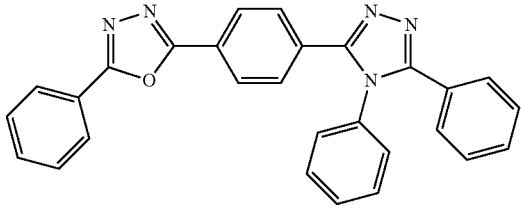 [SMILES: c1ccc(-c2nnc(-c3ccc(-c4nnc(-c5ccccc5)n4-c4ccccc4)cc3)o2)cc1] | WO2004107822 |
| Tetraphenylene complexes | 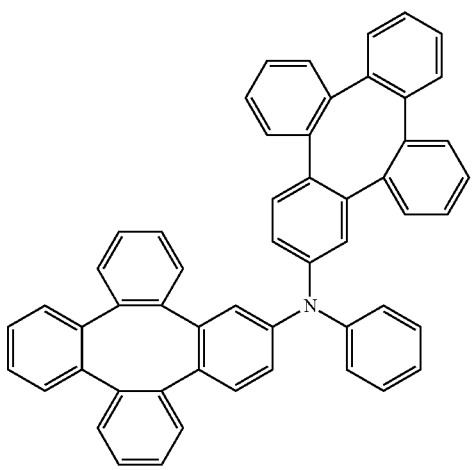 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 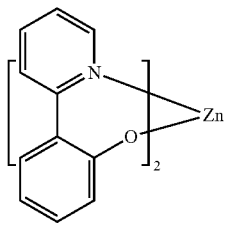 | WO2005030900 |
| Metal coordination complexes (e.g., Zn, Al with N^N ligands) | 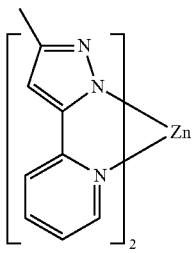 | US20040137268, US20040137267 |
Blue hosts
| MATERIAL | EXAMPLES OF MATERIAL | PUBLICATIONS |
|---|---|---|
| Arylcarbazoles | 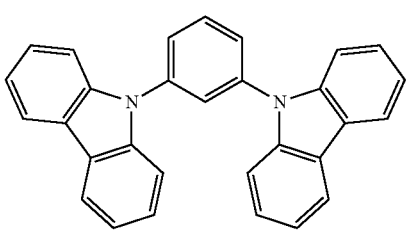 [SMILES: c1cc(-n2c3ccccc3c3ccccc32)cc(-n2c3ccccc3c3ccccc32)c1] | Appl. Phys. Lett, 82, 2422 (2003) |

TABLE 5-continued
| MATERIAL | EXAMPLES OF MATERIAL | PUBLICATIONS |
|---|---|---|
| | 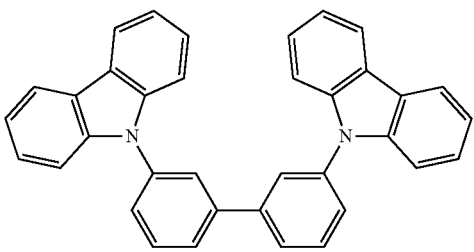 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 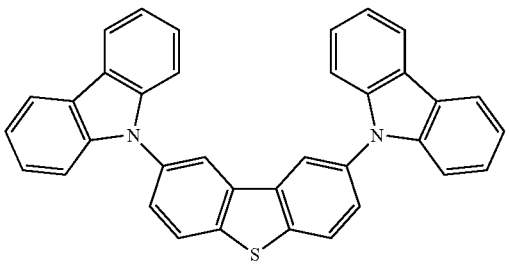 [SMILES: c1ccc2c(c1)c1ccccc1n2-c1ccc2sc3ccc(-n4c5ccccc5c5ccccc54)cc3c2c1] | WO2006114966, US20090167162 |
| | 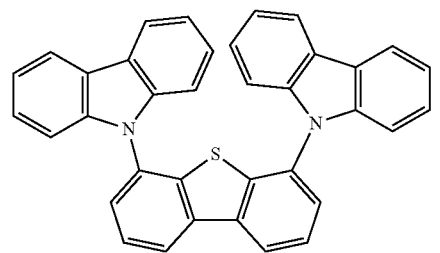 [SMILES: c1cc(-n2c3ccccc3c3ccccc32)c2sc3c(-n4c5ccccc5c5ccccc54)cccc3c2c1] | US20090167162 |
| | 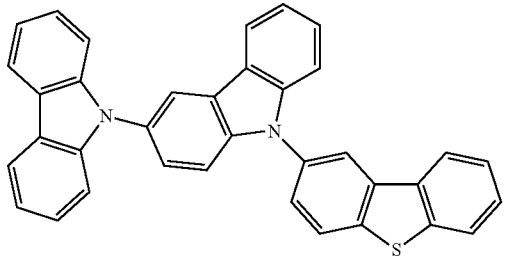 [SMILES: c1ccc2c(c1)sc1ccc(-n3c4ccccc4c4cc(-n5c6ccccc6c6ccccc65)ccc43)cc12] | WO2009086028 |
| | 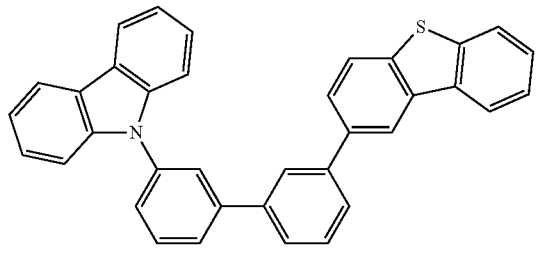 [SMILES: c1cc(-c2cccc(-n3c4ccccc4c4ccccc43)c2)cc(-c2ccc3sc4ccccc4c3c2)c1] | US20090030202, US20090017330 |
| | 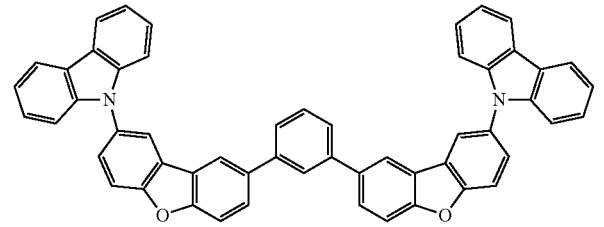 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |

TABLE 5-continued
| MATERIAL | EXAMPLES OF MATERIAL | PUBLICATIONS |
|---|---|---|
| Silicon aryl compounds | 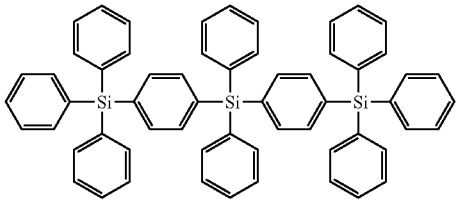 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 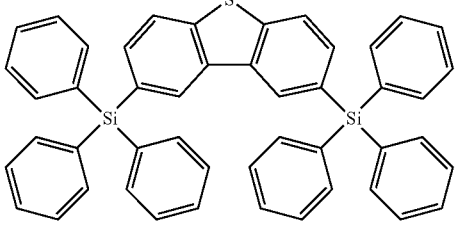 | WO2009003898 |
| Silicon/Germanium aryl compounds | 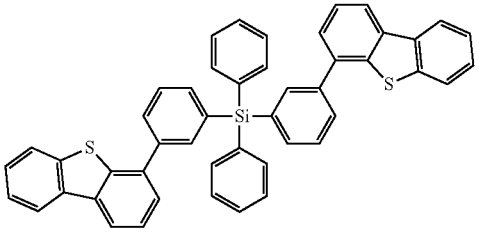 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 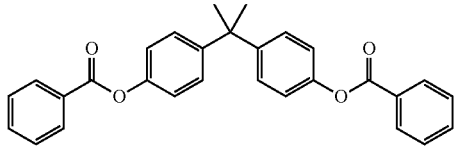 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 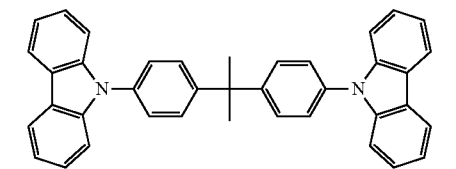 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 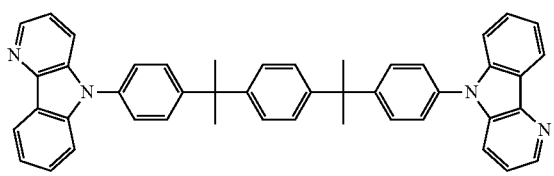 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 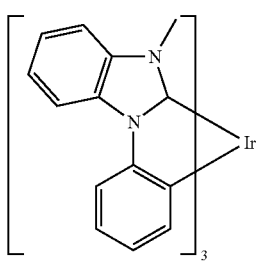 | U.S. Pat. No. 7,154,114 |
Phosphorescent dopants
Red dopants TABLE 5-continued

| MATERIAL | EXAMPLES OF MATERIAL | PUBLICATIONS |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |
| | | US20030072964 |
| | | US20030072964 |
| | | US220060202194 |

TABLE 5-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater. 19, 739 (2007) |

TABLE 5-continued
| MATERIAL | EXAMPLES OF MATERIAL | PUBLICATIONS |
|---|---|---|
| | 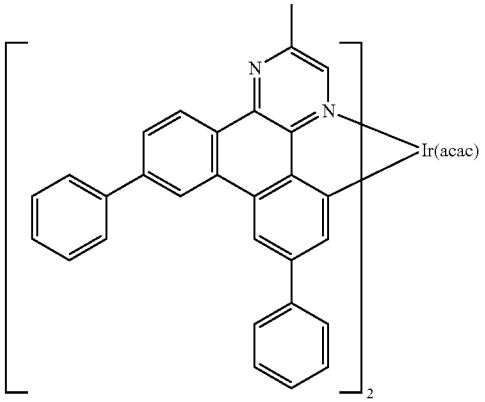 | WO2009100991 |
| | 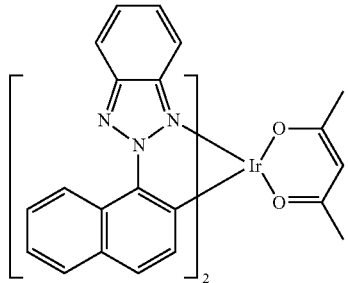 | WO2008101842 |
| | 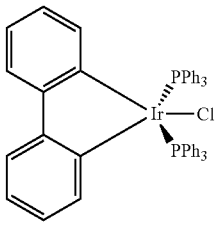 | U.S. Pat. No. 7,232,618 |
| Platinum(II) organometallic complexes | 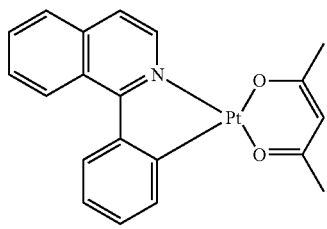 | WO2003040257 |
| | 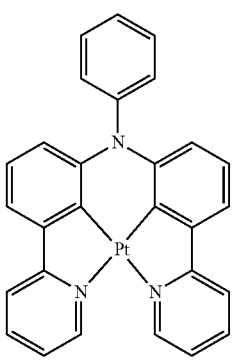 | US20070103060 |

TABLE 5-continued

| MATERIAL | EXAMPLES OF MATERIAL | PUBLICATIONS |
| --- | --- | --- |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

TABLE 5-continued

| MATERIAL | EXAMPLES OF MATERIAL | PUBLICATIONS |
|---|---|---|
| | | U.S. Pat. No. 7,332,232 |
| | | US20090108737 WO2010028151 |
| | | EP1841834B |
| | | US20060127696 |

TABLE 5-continued

| MATERIAL | EXAMPLES OF MATERIAL | PUBLICATIONS |
|---|---|---|
| | | US20090039776 |
| | | U.S. Pat. No. 6,921,915 |
| | | US20100244004 |
| | | U.S. Pat. No. 6,687,266 |
| | | Chem. Mater. 16, 2480 (2004) |

| MATERIAL | EXAMPLES OF MATERIAL | PUBLICATIONS |
|---|---|---|
| | 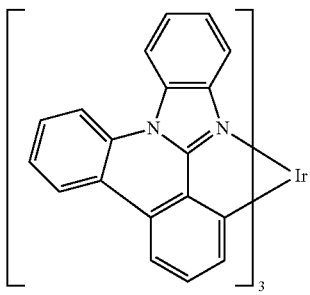 | US20070190359 |
| | 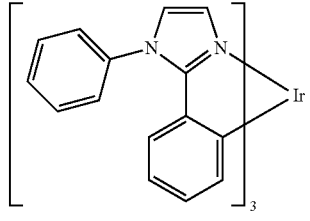 | US 20060008670 JP2007123392 |
| | 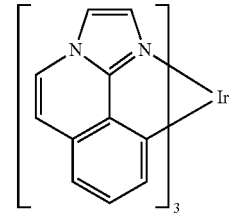 | WO2010086089, WO2011044988 |
| | 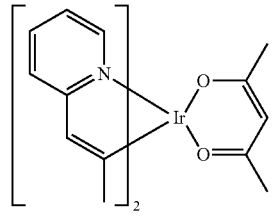 | Adv. Mater. 16, 2003 (2004) |
| | 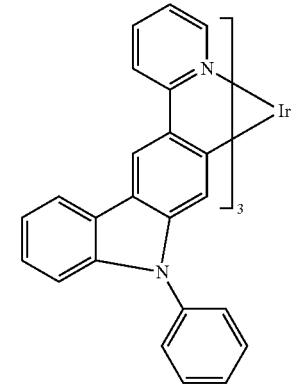 | Angew. Chem. Int. Ed. 2006, 45, 7800 |
| | 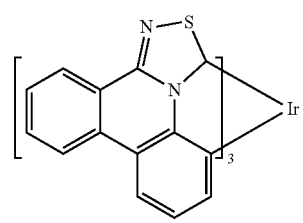 | WO2009050290 |

TABLE 5-continued
| MATERIAL | EXAMPLES OF MATERIAL | PUBLICATIONS |
|---|---|---|
| | 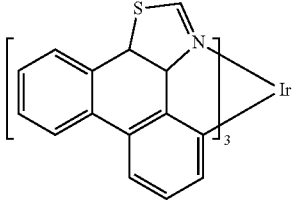 | US20090165846 |
| | 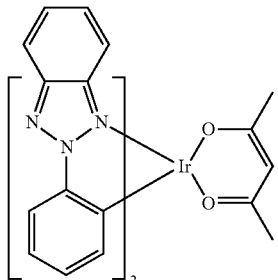 | US20080015355 |
| | 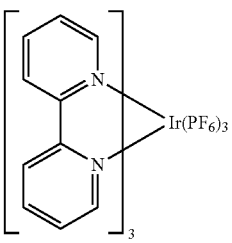 | US20010015432 |
| | 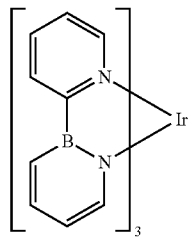 | US20100295032 |
| Monomer for polymeric metal organometallic compounds | 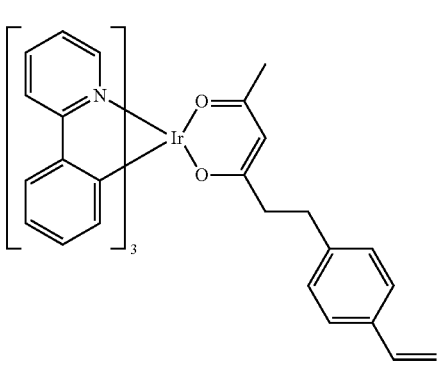 | U.S. Pat. No. 7,250,226, U.S. Pat. No. 7,396,598 |

TABLE 5-continued
| MATERIAL | EXAMPLES OF MATERIAL | PUBLICATIONS |
| --- | --- | --- |
| Pt(II) organometallic complexes, including polydenated ligands | 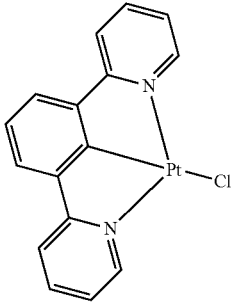 | Appl. Phys. Lett. 86, 153505 (2005) |
| | 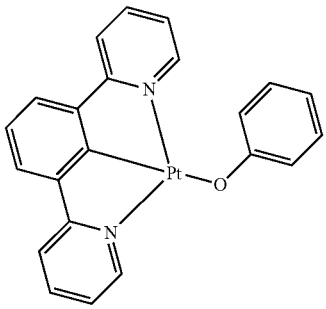 | Appl. Phys. Lett. 86, 153505 (2005) |
| | 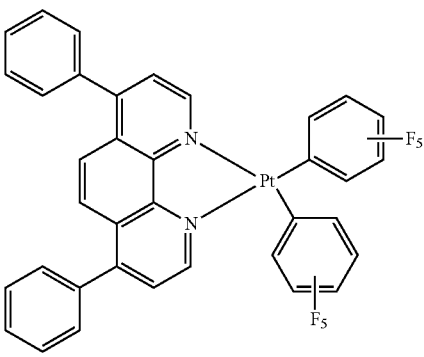 | Chem. Lett. 34, 592 (2005) |
| | 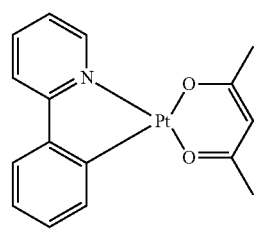 | WO2002015645 |
| | 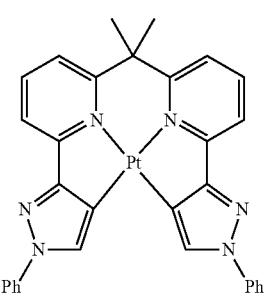 | US20060263635 |

TABLE 5-continued
| MATERIAL | EXAMPLES OF MATERIAL | PUBLICATIONS |
|---|---|---|
| | 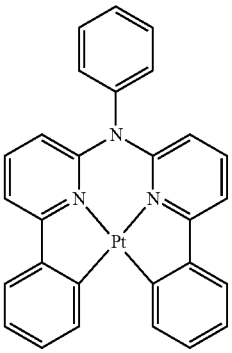 | US20060182992<br>US20070103060 |
| Cu complexes | 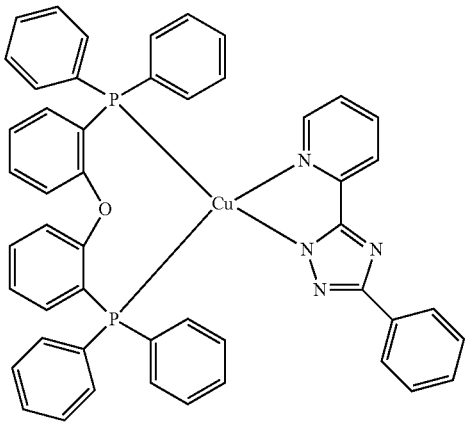 | WO2009000673 |
| | 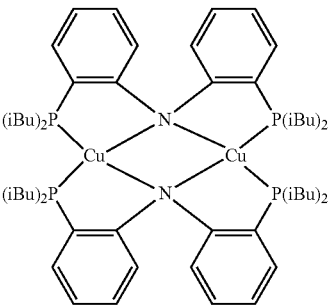 | US20070111026 |
| Gold complexes | 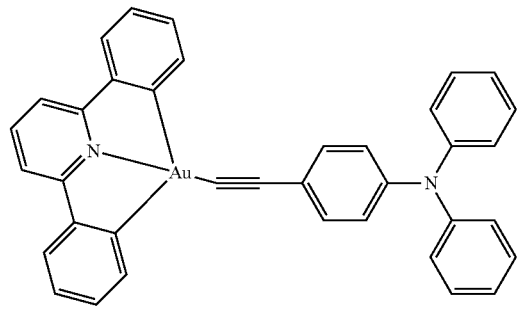 | Chem. Commun. 2906 (2005) |

TABLE 5-continued
| MATERIAL | EXAMPLES OF MATERIAL | PUBLICATIONS |
|---|---|---|
| Rhenium(III) complexes | 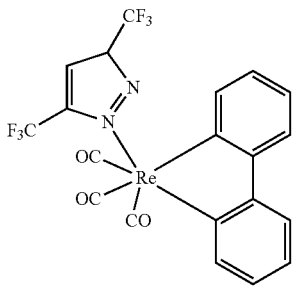 | Inorg. Chem. 42, 1248 |
| Osmium(II) complexes | | U.S. Pat. No. 7,279,704 |
| Deuterated organometallic complexes | | US20030138657 |
| Organometallic complexes with two or more metal centers | | US20030152802 |
| | 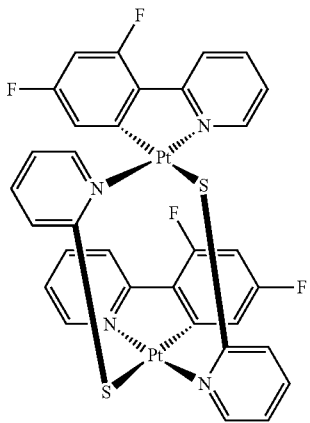 | U.S. Pat. No. 7,090,928 |
Blue dopants
| | | |
|---|---|---|
| Iridium(III) organometallic complexes | 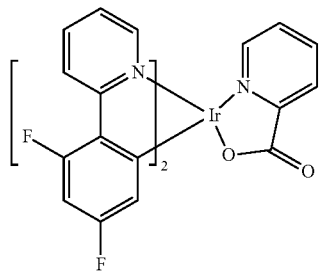 | WO2002002714 |
| | 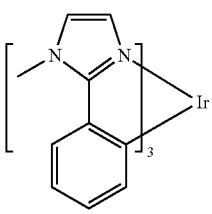 | WO2006009024 |

TABLE 5-continued
| MATERIAL | EXAMPLES OF MATERIAL | PUBLICATIONS |
|---|---|---|
| | 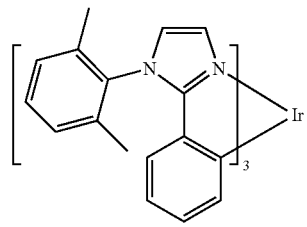 | US20060251923<br>US20110057559<br>US20110204333 |
| | 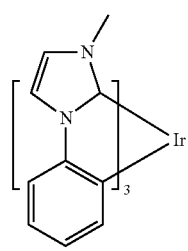 | U.S. Pat. No. 7,393,599,<br>WO2006056418,<br>US20050260441,<br>WO2005019373 |
| | 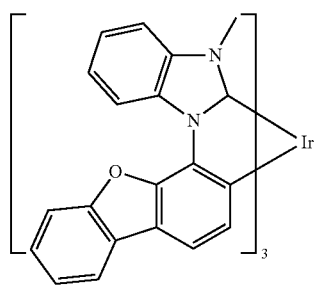 | U.S. Pat. No. 7,534,505 |
| | 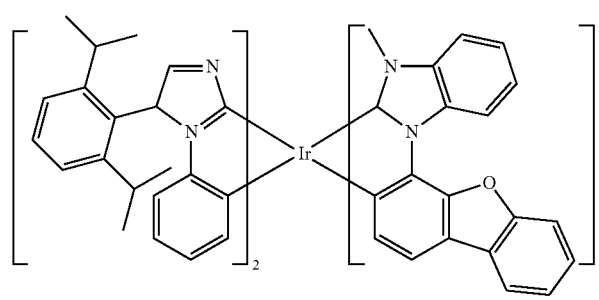 | WO2011051404 |
| | 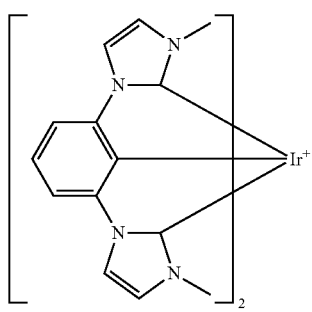 | U.S. Pat. No. 7,445,855 |

| MATERIAL | EXAMPLES OF MATERIAL | PUBLICATIONS |
|---|---|---|
| | 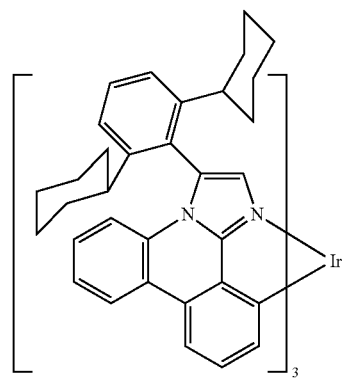 | US20070190359, US20080297033 US20100148663 |
| | 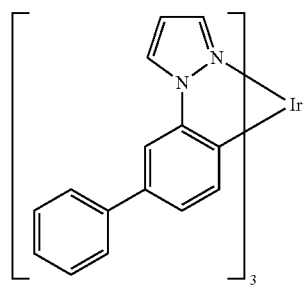 | U.S. Pat. No. 7,338,722 |
| | 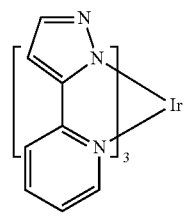 | US20020134984 |
| | 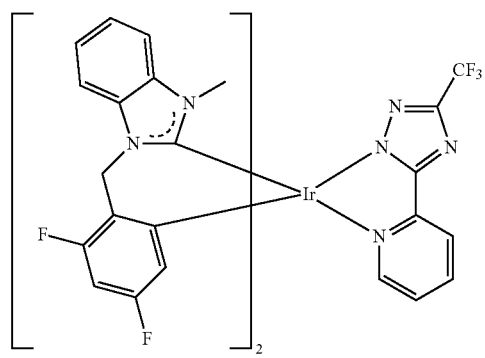 | Angew. Chem. Int. Ed. 47, 4542 (2008) |
| | 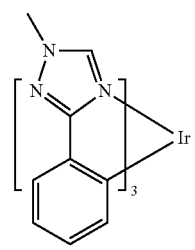 | Chem. Mater. 18, 5119 (2006) |

TABLE 5-continued
| MATERIAL | EXAMPLES OF MATERIAL | PUBLICATIONS |
|---|---|---|
| | 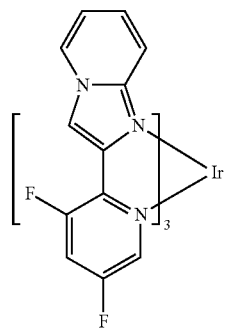 | Inorg. Chem. 46, 4308 (2007) |
| | 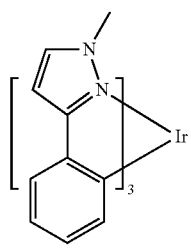 | WO2005123873 |
| | 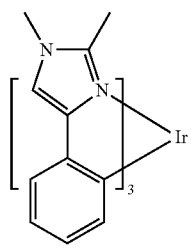 | WO2005123873 |
| | 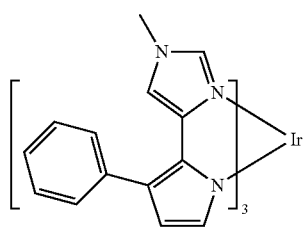 | WO2007004380 |
| | 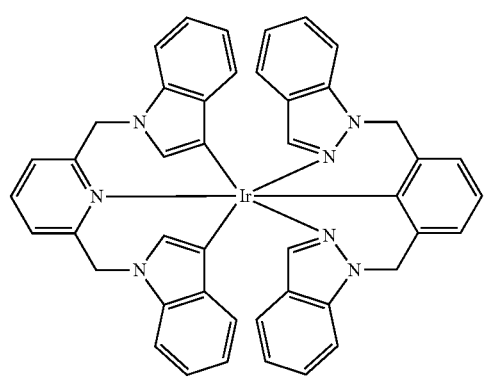 | WO2006082742 |

TABLE 5-continued
| MATERIAL | EXAMPLES OF MATERIAL | PUBLICATIONS |
|---|---|---|
| Osmium(II) complexes | 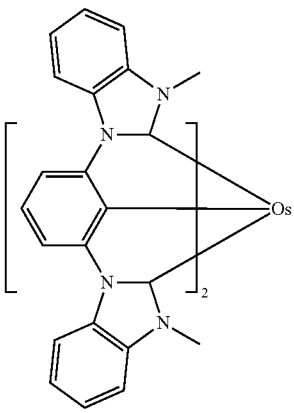 | U.S. Pat. No. 7,279,704 |
| | 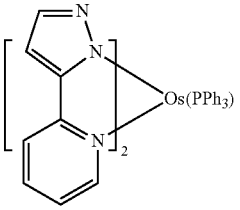 | Organometallics 23, 3745 (2004) |
| Gold complexes | 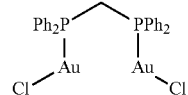 | Appl. Phys. Lett. 74, 1361 (1999) |
| Platinum(II) complexes | 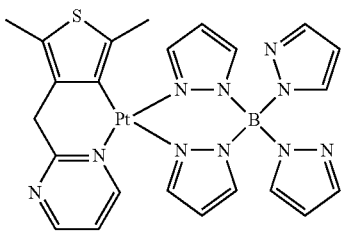 | WO2006098120, WO2006103874 |
| Pt tetradentate complexes with at least one metal-carbene bond | 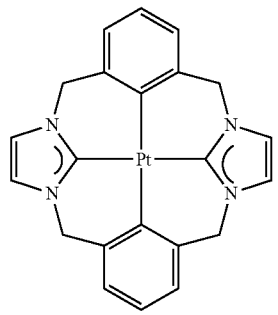 | U.S. Pat. No. 7,655,323 |
| Exciton/hole blocking layer materials | | |
| Bathocuprine compounds (e.g., BCP, BPhen) | 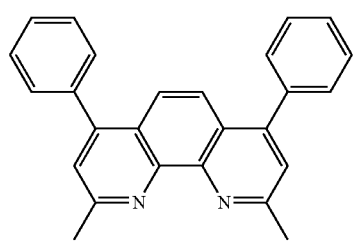 [SMILES: Cc1cc(-c2ccccc2)c2ccc3c(-c4ccccc4)cc(C)nc3c2n1] | Appl. Phys. Lett. 75, 4 (1999) |

TABLE 5-continued
| MATERIAL | EXAMPLES OF MATERIAL | PUBLICATIONS |
|---|---|---|
| | 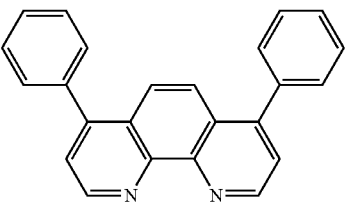 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 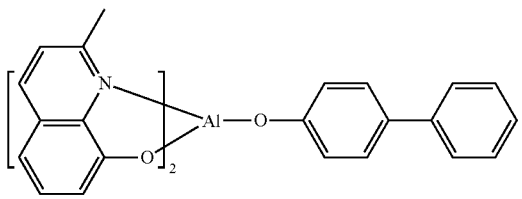 | Appl. Phys. Lett. 81, 162 (2002) |
| 5-member ring electron deficient heterocycles such as triazole, oladiazole, imidazole, benzoimidazole | 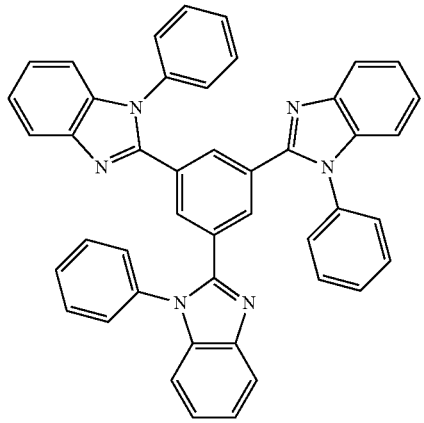 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 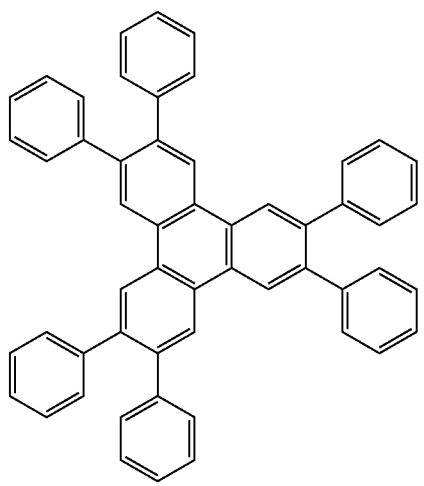 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 5-continued

| MATERIAL | EXAMPLES OF MATERIAL | PUBLICATIONS |
|---|---|---|
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

Electron transporting materials

| | | |
|---|---|---|
| Anthracene-benzoimidazole compounds | | WO2003060956 |
| | | US20090179554 |

TABLE 5-continued
| MATERIAL | EXAMPLES OF MATERIAL | PUBLICATIONS |
|---|---|---|
| Aza triphenylene derivatives | 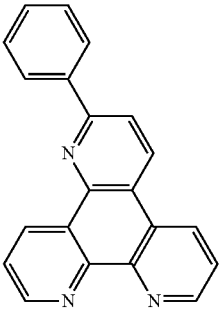 [SMILES: c1ccc(-c2ccc3c4cccnc4c4ncccc4c3n2)cc1] | US20090115316 |
| Anthracene-benzothiazole compounds | 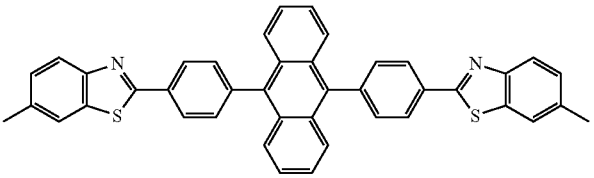 | Appl. Phys. Lett. 89, 063504 (2006) |
| Metal 8-hydroxyquinolates (e.g., Alq$_3$, Zrq$_4$) | 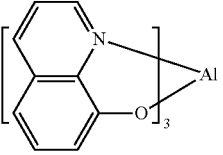 | Appl. Phys. Lett. 51, 913 (1987)<br>U.S. Pat. No. 7,230,107 |
| Metal hydroxybenoquinolates | 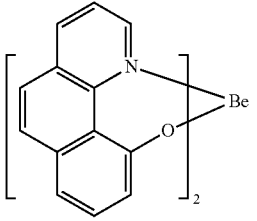 | Chem. Lett. 5, 905 (1993) |
| Bathocuprine compounds such as BCP, BPhen, etc | 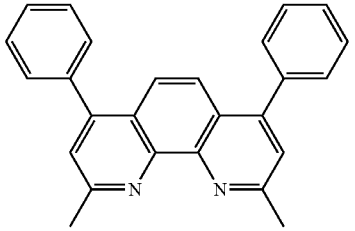 [SMILES: Cc1cc(-c2ccccc2)c2ccc3c(-c4ccccc4)cc(C)nc3c2n1] | Appl. Phys. Lett. 91, 263503 (2007) |
| | 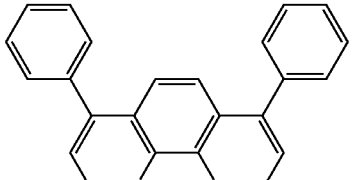 | Appl. Phys. Lett. 79, 449 (2001) |

TABLE 5-continued
| MATERIAL | EXAMPLES OF MATERIAL | PUBLICATIONS |
| --- | --- | --- |
| 5-member ring electron deficient heterocycles (e.g., triazole, oxadiazole, imidazole, benzoimidazole) | 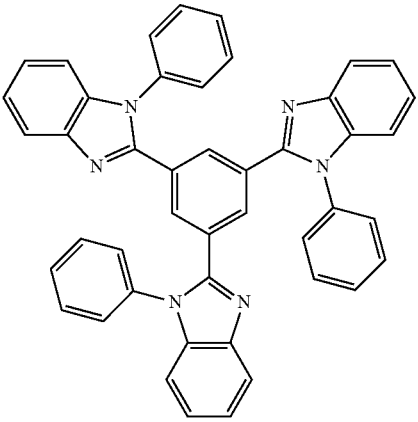 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 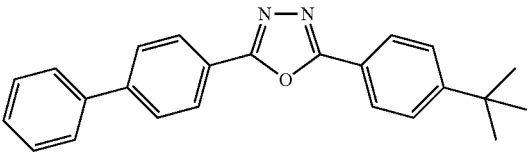 [SMILES: CC(C)(C)c1ccc(-c2nnc(-c3ccc(-c4ccccc4)cc3)o2)cc1] | Appl. Phys. Lett. 55, 1489 (1989) |
| | 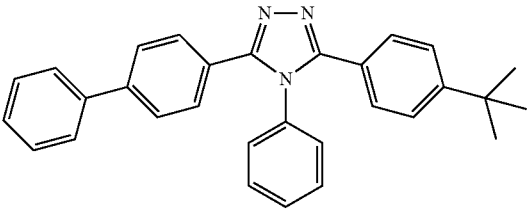 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 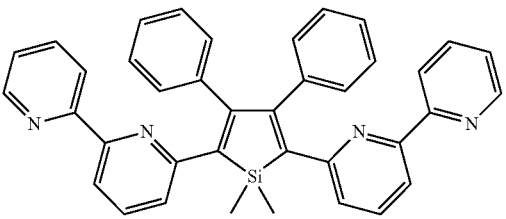 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 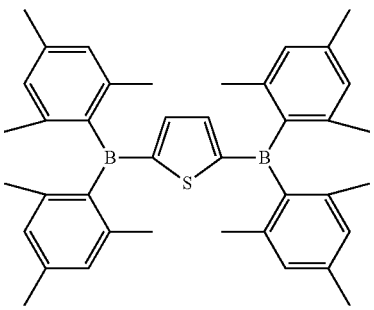 | J. Am. Chem. Soc. 120, 9714 (1998) |
| Fluorinated aromatic compounds | 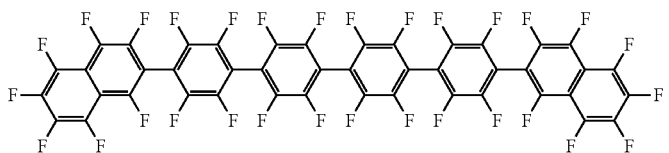 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 5-continued

| MATERIAL | EXAMPLES OF MATERIAL | PUBLICATIONS |
|---|---|---|
| Fullerene (e.g., C60) | 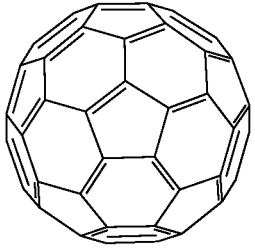 | US20090101870 |
| Triazine complexes | 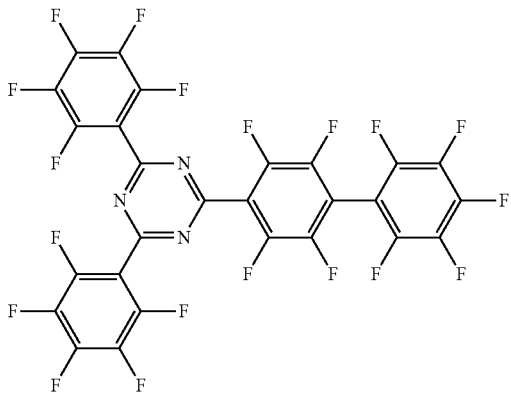 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 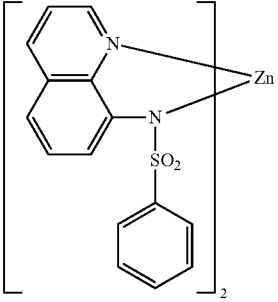 | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A premixed co-evaporation source composition comprising:

a mixture of a first compound and a second compound for co-evaporation from one sublimation crucible;

wherein the first compound has a different chemical structure than the second compound;

wherein the first compound is capable of functioning as a phosphorescent emitter in an organic light emitting device at room temperature;

wherein the first compound has an evaporation temperature T1 of 150 to 350° C.;

wherein the second compound has an evaporation temperature T2 of 150 to 350° C.;

wherein absolute value of T1–T2 is less than 20° C.;

wherein the first compound has a concentration C1 in said mixture and a concentration C2 in a film formed by evaporating the mixture in a vacuum deposition tool at a constant pressure between 1×10⁻⁶ Torr to 1×10⁻⁹ Torr, at a 2 Å/sec deposition rate on a surface position at a predefined distance away from the mixture being evaporated;

wherein absolute value of (C1−C2)/C1 is less than 5%;

wherein the first compound and the second compound each independently has the formula of Ir(L¹)₂(L²);

wherein L¹ has the formula:

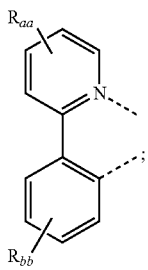

wherein L² has the formula:

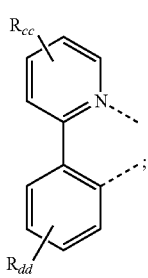

wherein L¹ is different from L²;

wherein $R_{aa}$, $R_{bb}$, and $R_{dd}$ may represent mono, di, tri, or tetra substitution, or no substitution;

wherein $R_{cc}$ represents mono-substitution;

wherein $R_{aa}$, $R_{bb}$, and $R_{dd}$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein two adjacent substituents of $R_{aa}$, $R_{bb}$, and $R_{dd}$ are optionally joined to form a fused ring or form a multidentate ligand;

wherein the $R_{cc}$ of the first compound is a 5 or 6-membered carbocyclic ring, which may be substituted; and wherein the $R_{cc}$ of the second compound is a 5 or 6-membered heterocyclic ring, which may be substituted.

2. The premixed co-evaporation source composition of claim 1, wherein the $R_{cc}$ of the first compound is benzene, which may be substituted, and the Rcc of the second compound is pyridine, which may be substituted.

3. The premixed co-evaporation source composition of claim 1, wherein each L¹ is selected from the group consisting of:

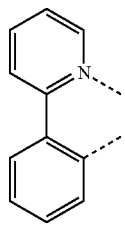

L₁₋₁

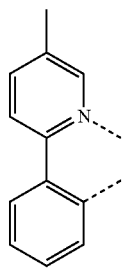

L₁₋₂

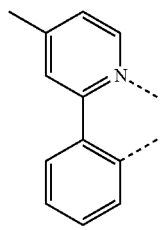

L₁₋₃

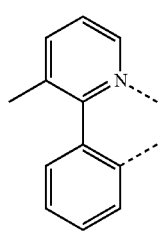

L₁₋₄

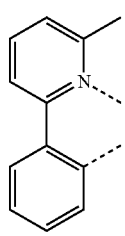

L₁₋₅

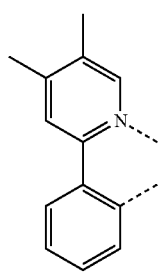

L₁₋₆

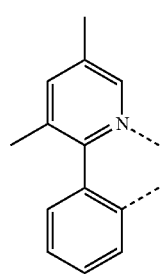 L1-7
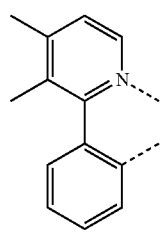 L1-8
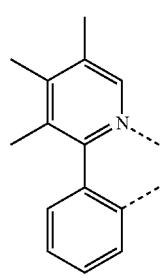 L1-9
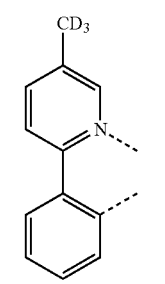 L1-10
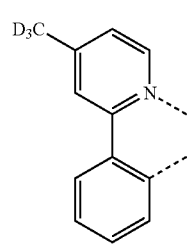 L1-11
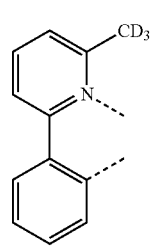 L1-12
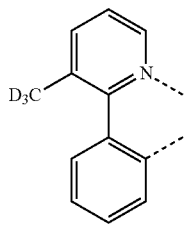 L1-13
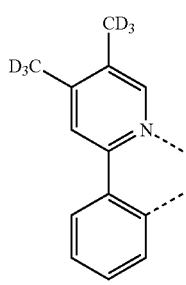 L1-14
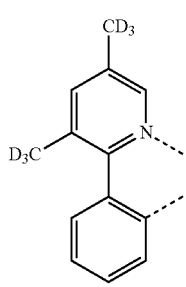 L1-15
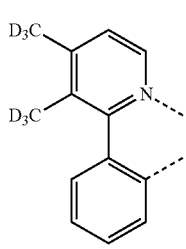 L1-16
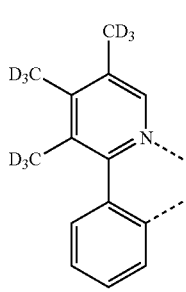 L1-17
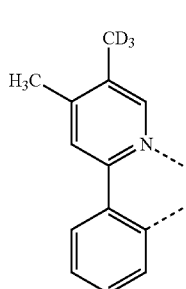 L1-18

| L1-19 | L1-25 |
| L1-20 | L1-26 |
| L1-21 | L1-27 |
| L1-22 | L1-28 |
| L1-23 | L1-29 |
| L1-24 | L1-30 |

L1-31 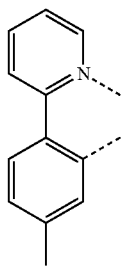
L1-32 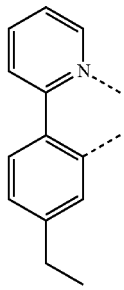
L1-33 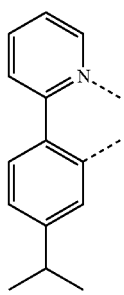
L1-34 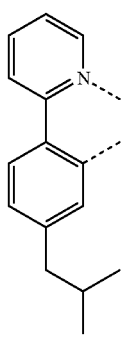
L1-35 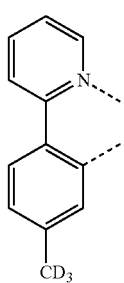
L1-36 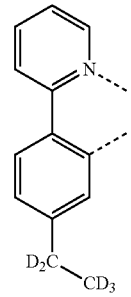
L1-37 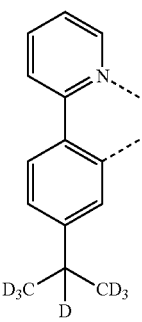
L1-38 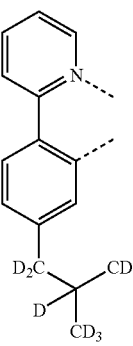
L1-39 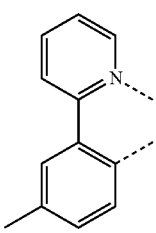
L1-40 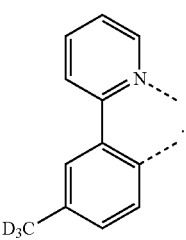
4. An organic light emitting device comprising:
an anode;
a cathode; and
an organic layer, disposed between the anode and the cathode, the organic layer comprising the premixed co-evaporation source composition according to claim 1.

5. The premixed co-evaporation source composition of claim 1, wherein $L^2$ of the first compound is selected from the group consisting of:
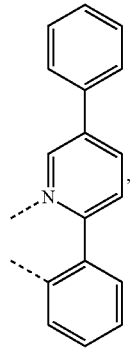
L<sub>2-1</sub>
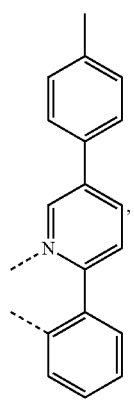
L<sub>2-2</sub>
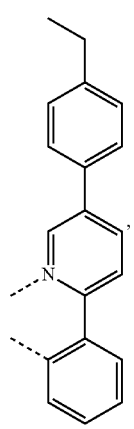
L<sub>2-3</sub>
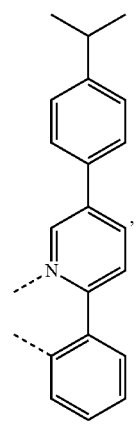
L<sub>2-4</sub>
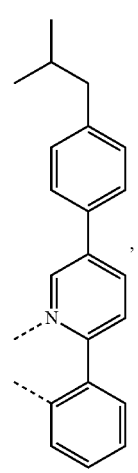
L<sub>2-5</sub>
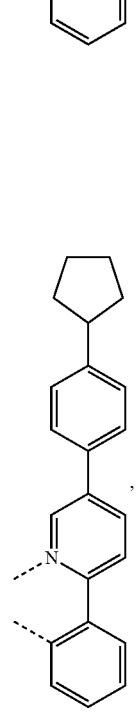
L<sub>2-6</sub>

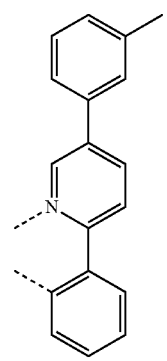 L2-7
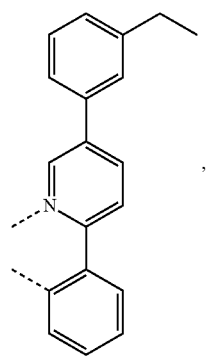 L2-8
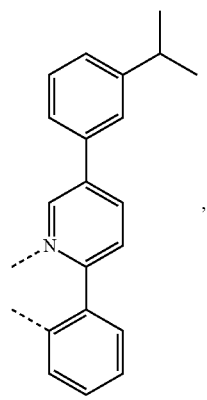 L2-9
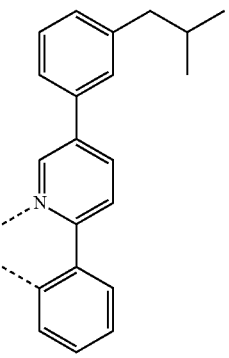 L2-10
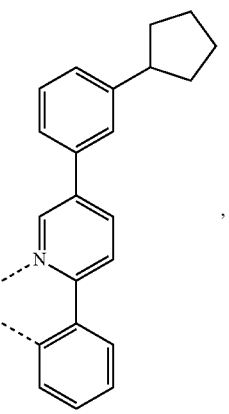 L2-11
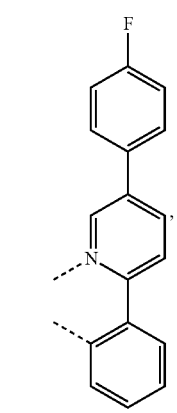 L2-12
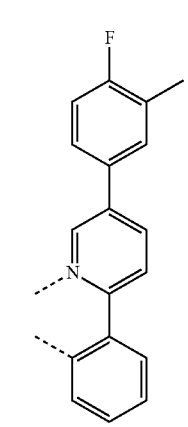 L2-13
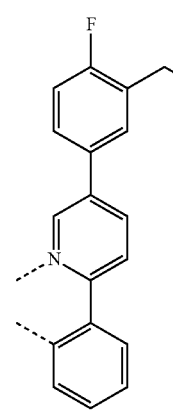 L2-14

L2-15 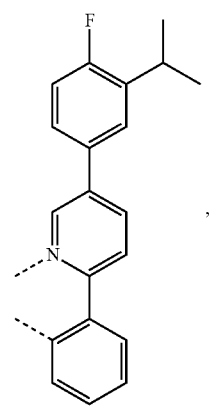
L2-16 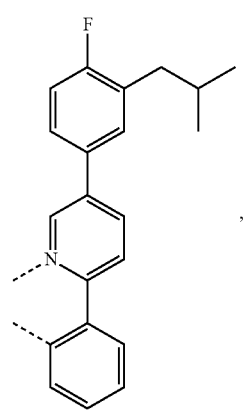
L2-17 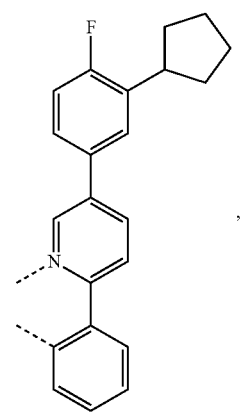
L2-18 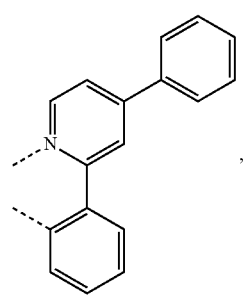
L2-19 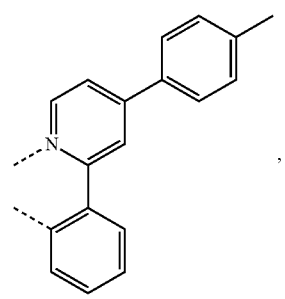
L2-20 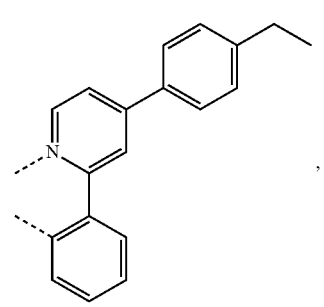
L2-21 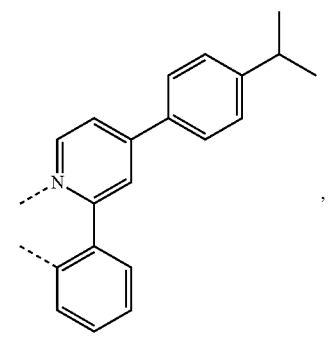
L2-22 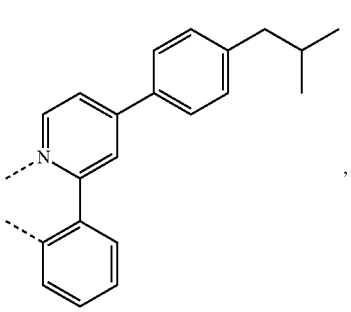
L2-23 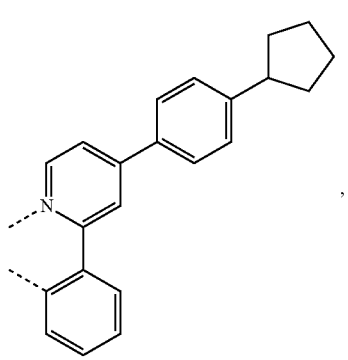

L2-24 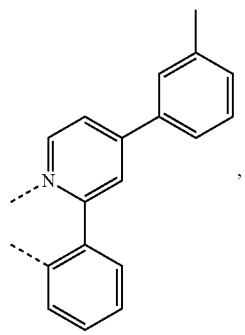,
L2-25 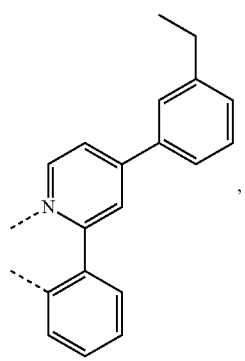,
L2-26 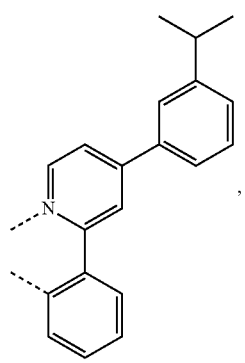,
L2-27 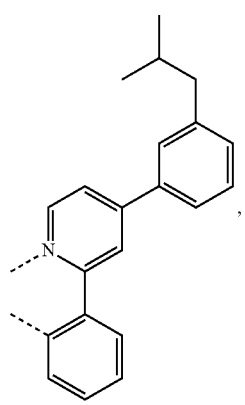,
L2-28 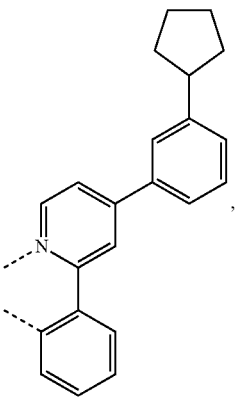,
L2-29 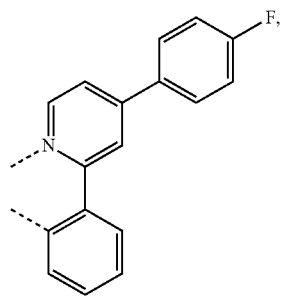,
L2-30 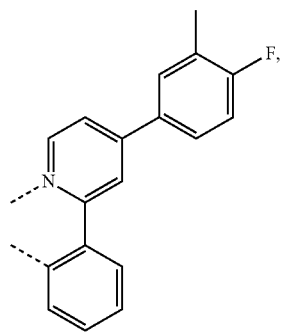,
L2-31 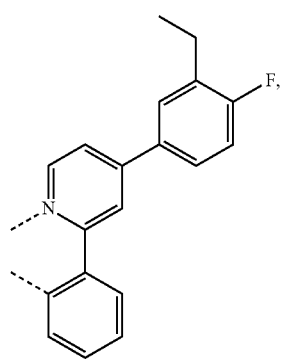,

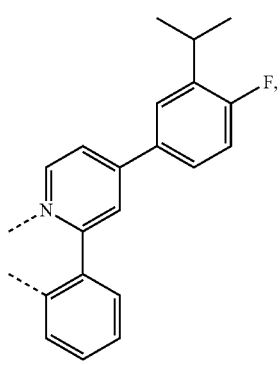
L2-32
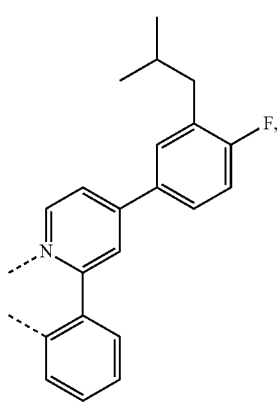
L2-33
1p;4p
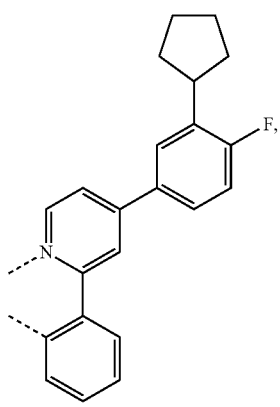
L2-34
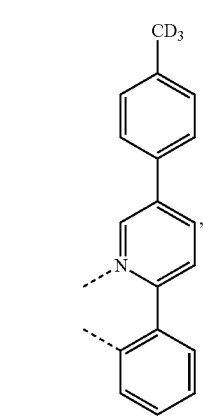
L2-82
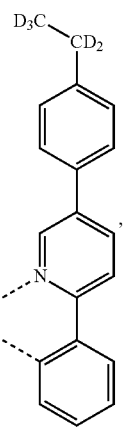
L2-83
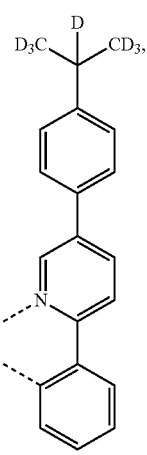
L2-84
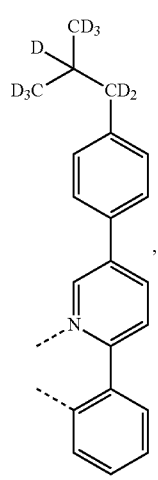
L2-85

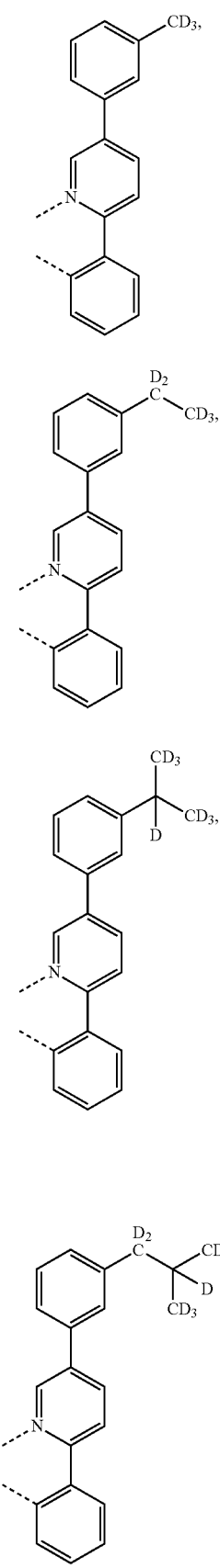
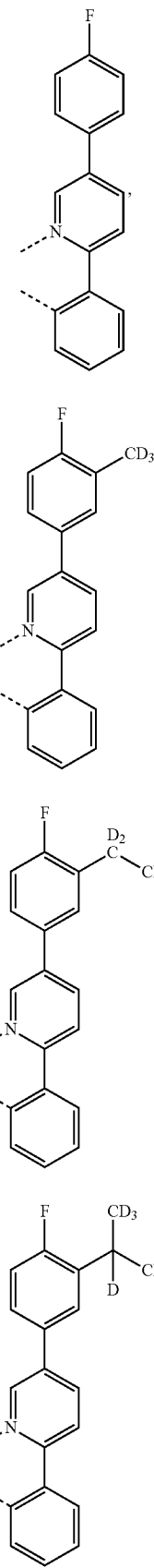

L2-94
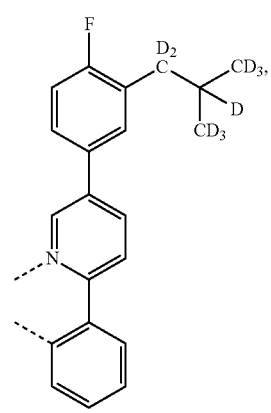
L2-95
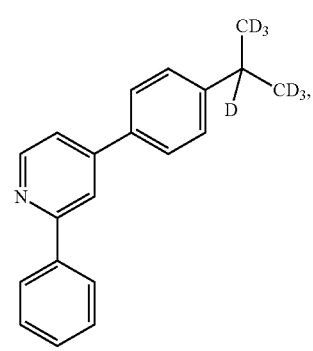
L2-96
L2-97
L2-98
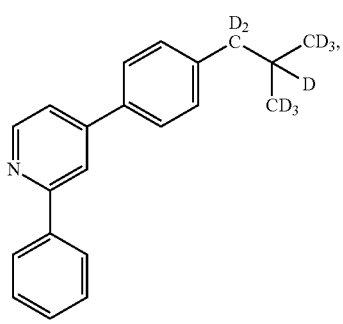
L2-99
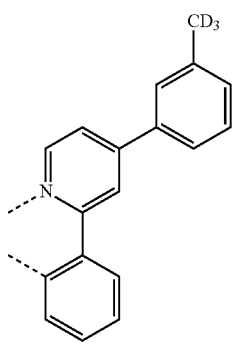
L2-100
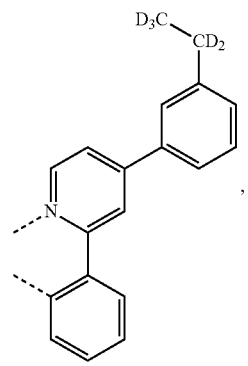
L2-101
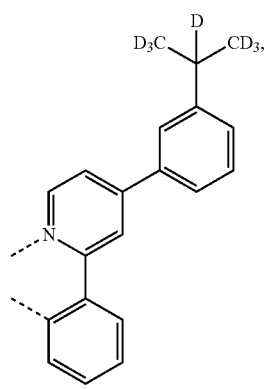

-continued
L2-102
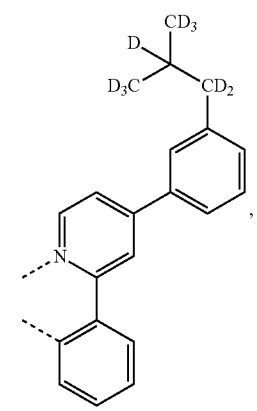
L2-103
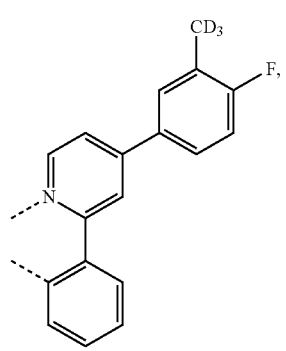
L2-104
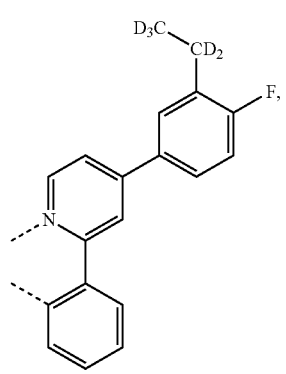
L2-105
-continued
L2-106
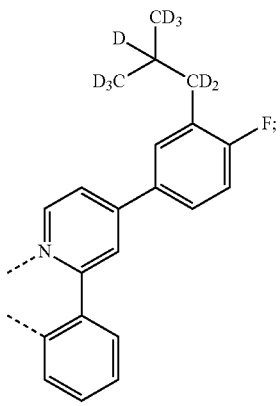
and
wherein L² of the second compound is selected from the group consisting of:
L2-35
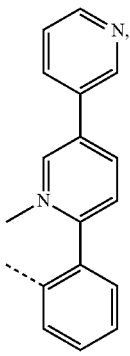
L2-36
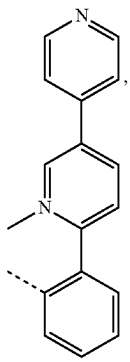
L2-37

L2-38, L2-39, L2-40, L2-41, L2-42, L2-43, L2-44, L2-45

-continued
L2-46
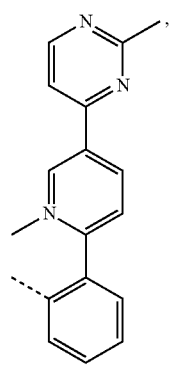
L2-47
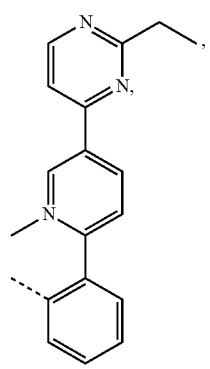
L2-48
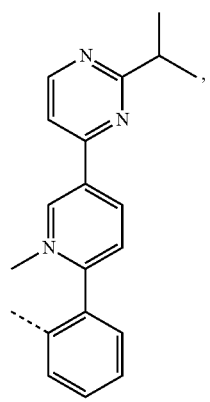
L2-49
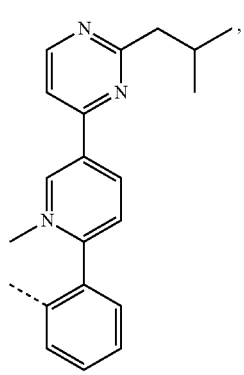
-continued
L2-50
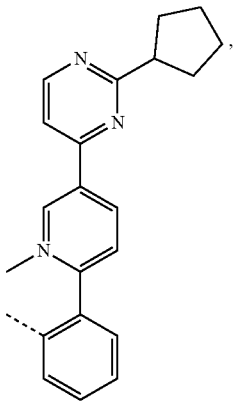
L2-51
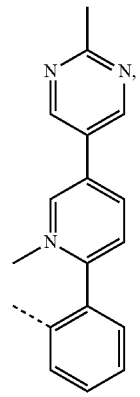
L2-52
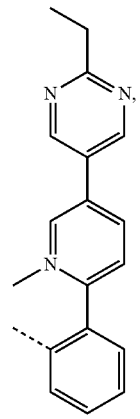
L2-53
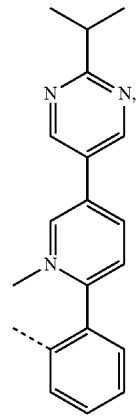

L2-54
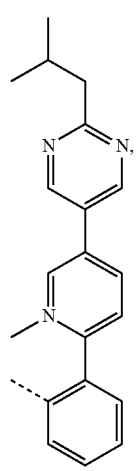
L2-55
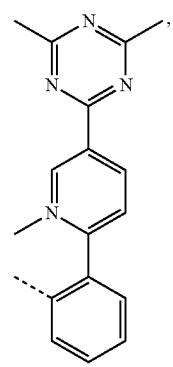
L2-56
L2-57
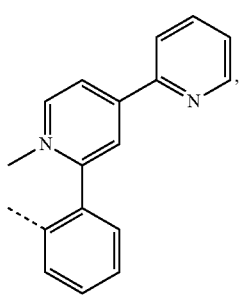
L2-58
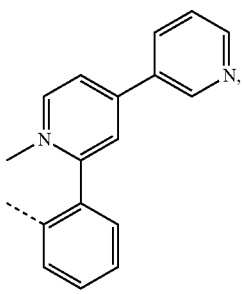
L2-59
L2-60
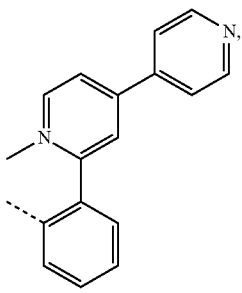
L2-61
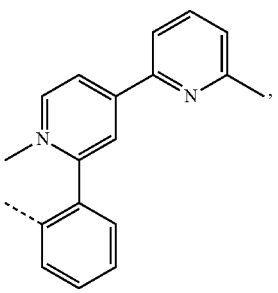

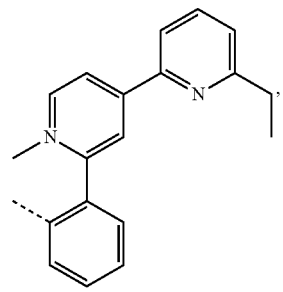 L2-62
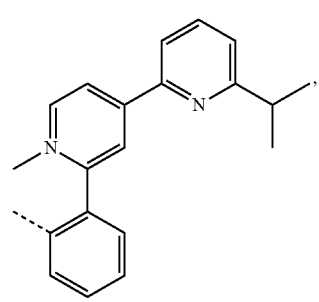 L2-63
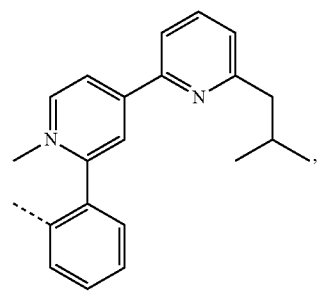 L2-64
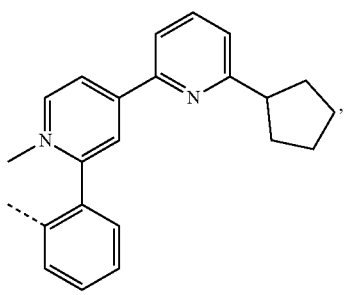 L2-65
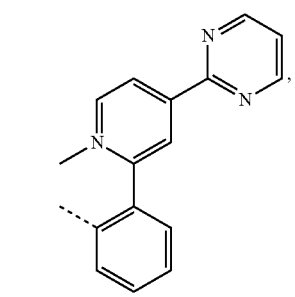 L2-66
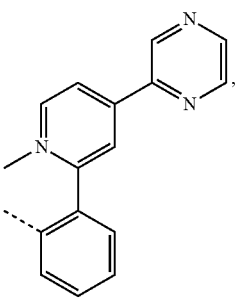 L2-67
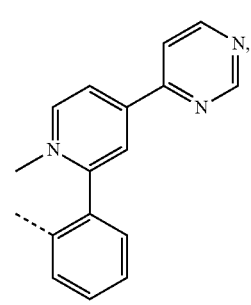 L2-68
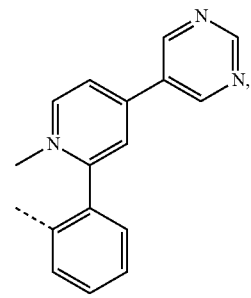 L2-69
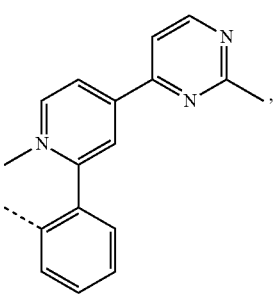 L2-70
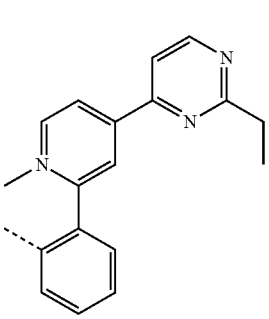 L2-71

L2-72 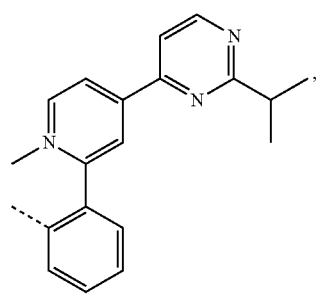
L2-73 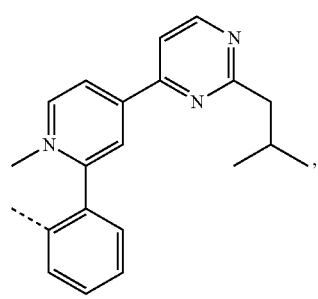
L2-74 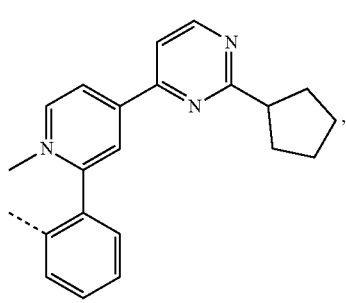
L2-75 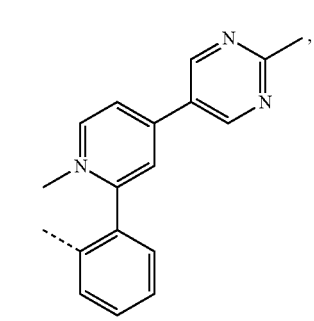
L2-76 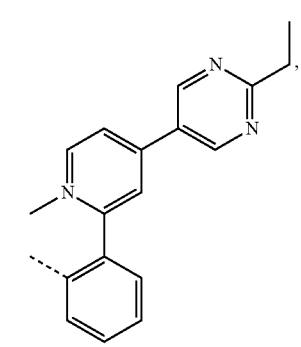
L2-77 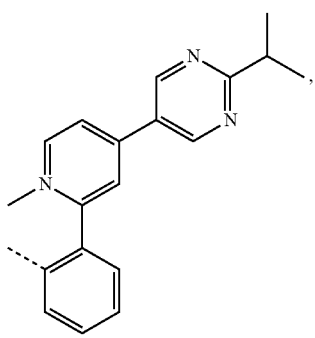
L2-78 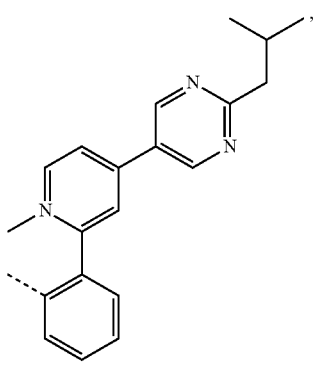
L2-79 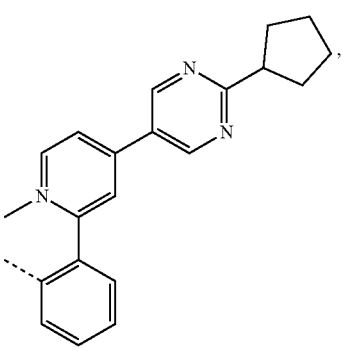
L2-80 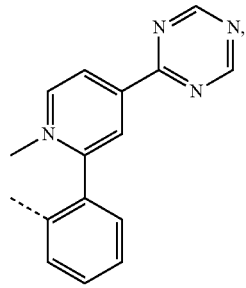

L2-81 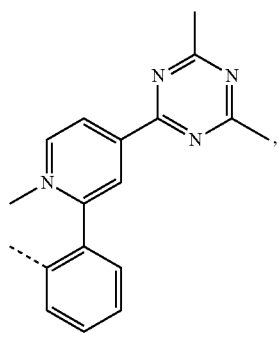
L2-107 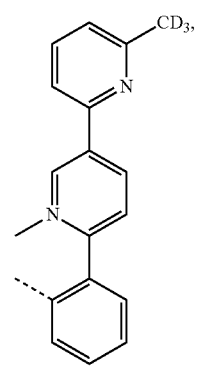
L2-108 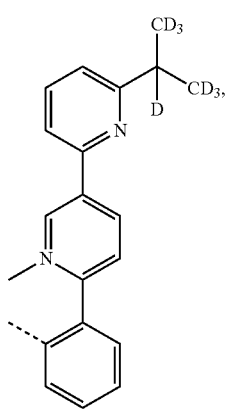
L2-109 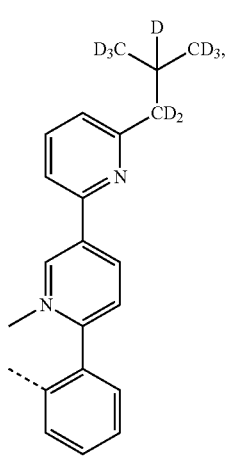
L2-110 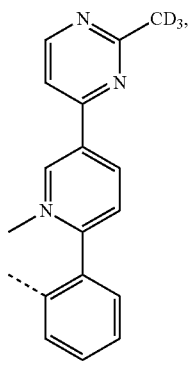
L2-111 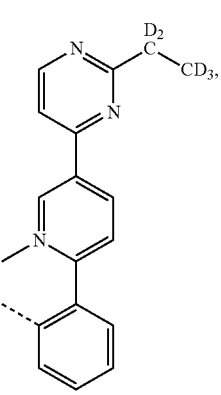
L2-112 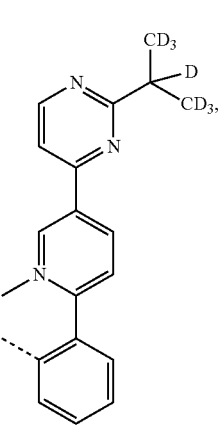
L2-113 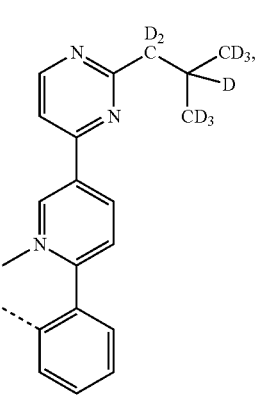

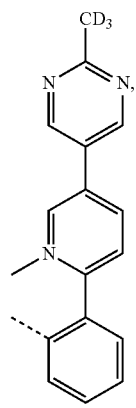
L2-114
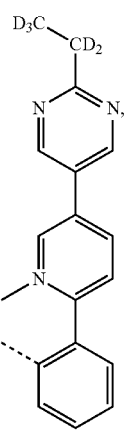
L2-115
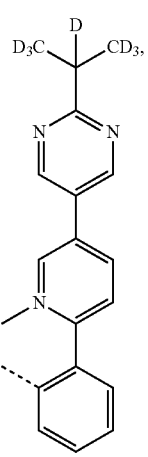
L2-116
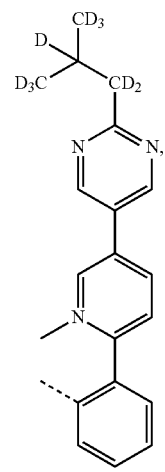
L2-117
L2-118
L2-119
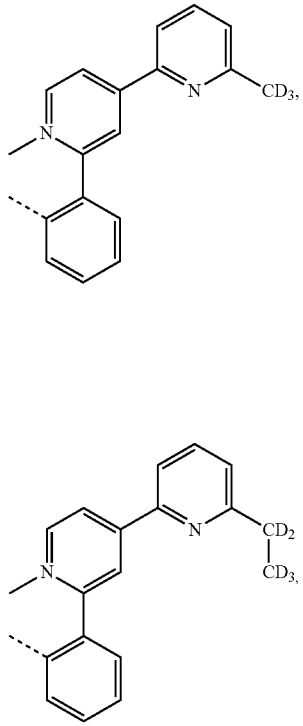
L2-120

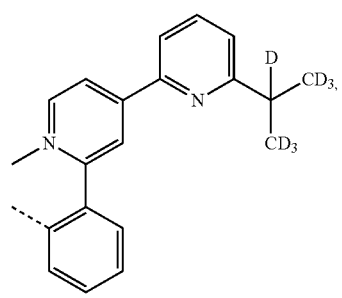 L2-121
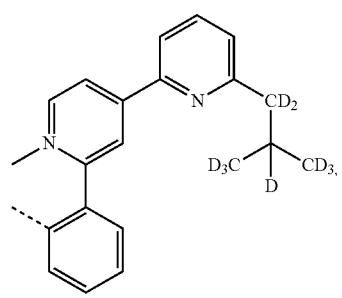 L2-122
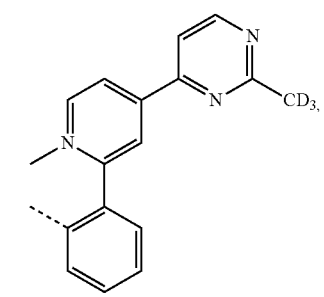 L2-123
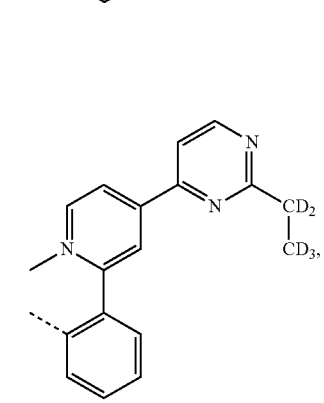 L2-124
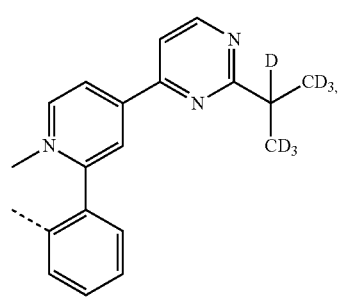 L2-125
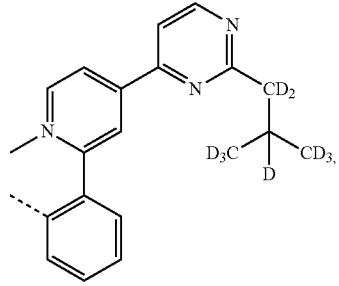 L2-126
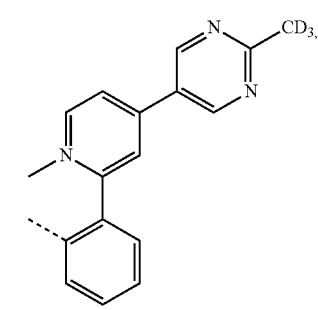 L2-127
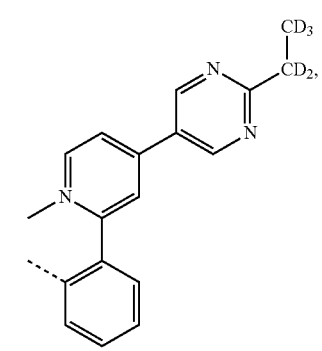 L2-128
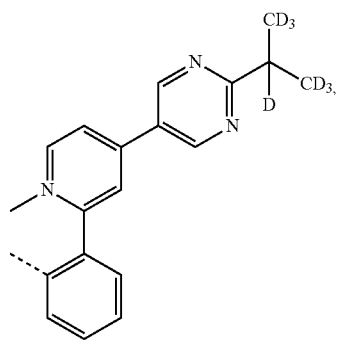 L2-129

299
-continued
L2-130
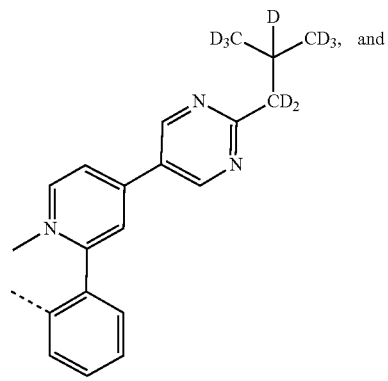
L2-131
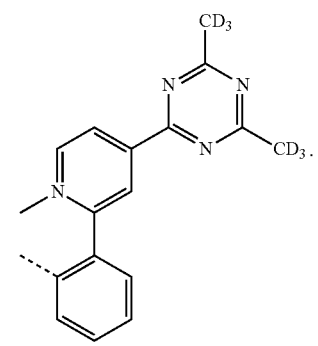
6. The premixed co-evaporation source composition of claim 1, wherein the first compound is selected from the group consisting of:
Compound 7
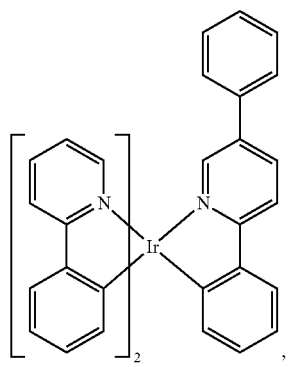
300
-continued
Compound 8
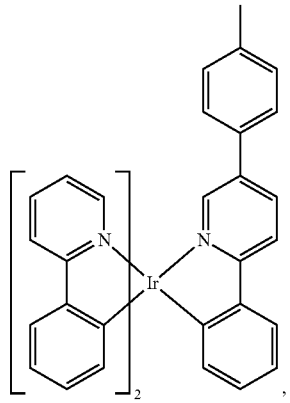
Compound 9
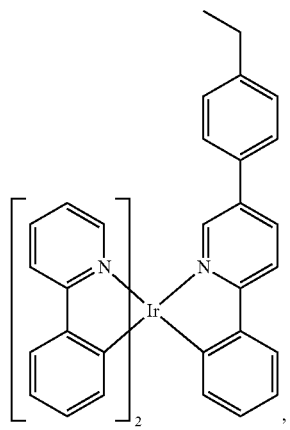
Compound 10
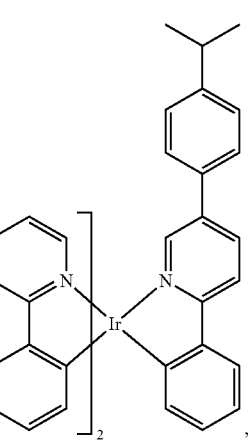

-continued
Compound 11
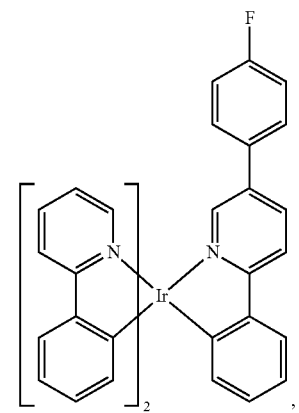
Compound 12
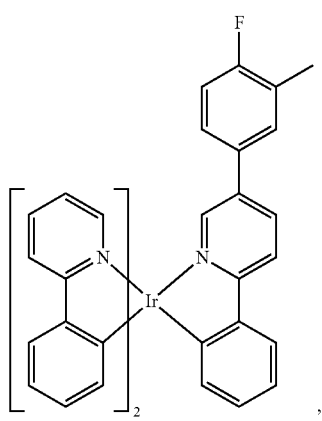
Compound 13
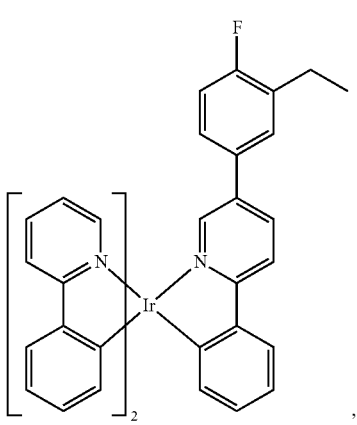
Compound 14
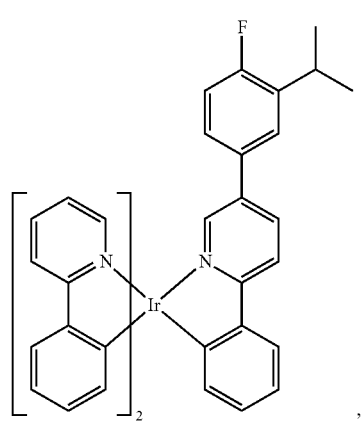
-continued
Compound 15
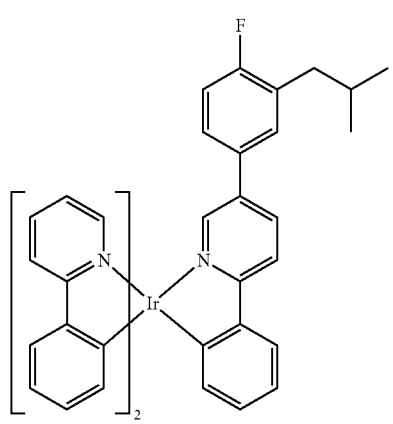
Compound 20
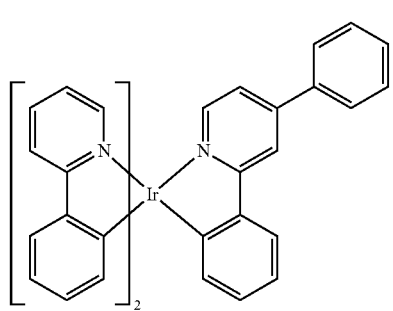
Compound 21
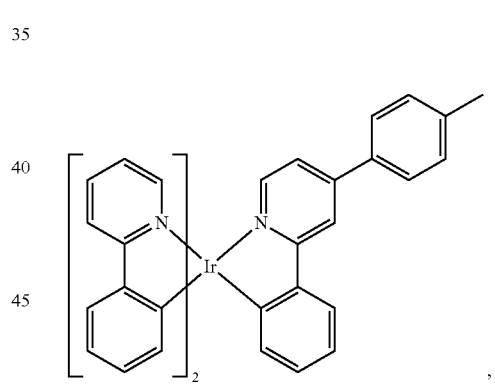
Compound 22
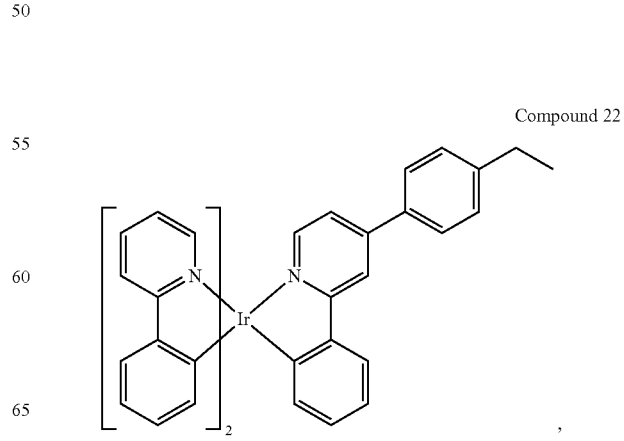

Compound 23
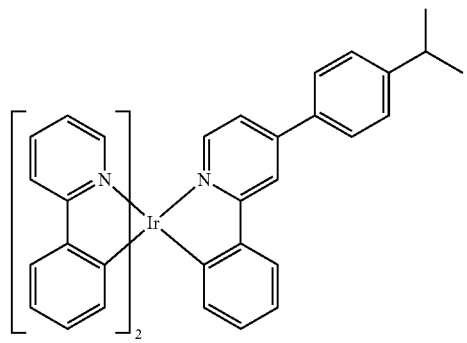
Compound 24
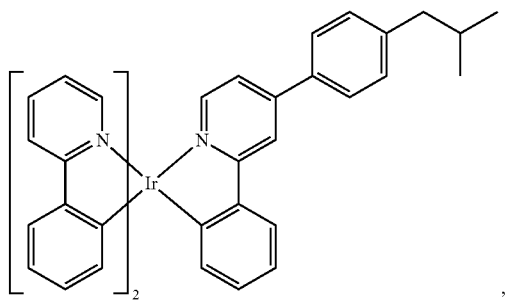
Compound 25
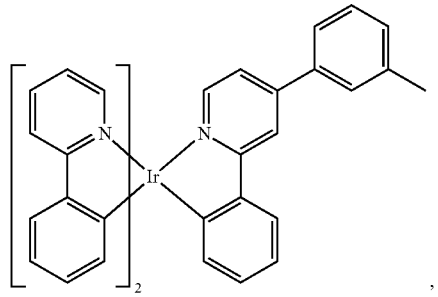
Compound 26
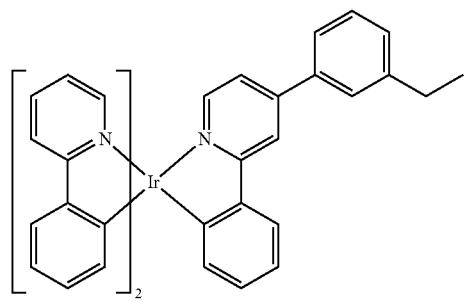
Compound 27
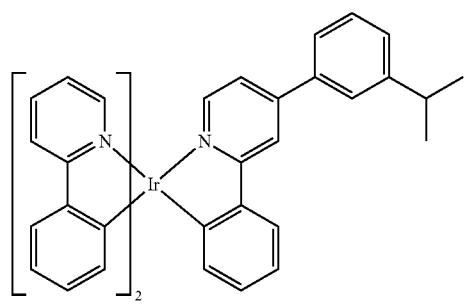
Compound 28
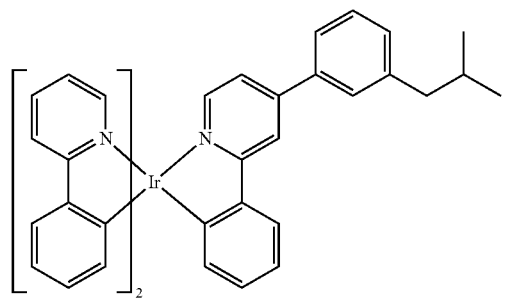
Compound 29
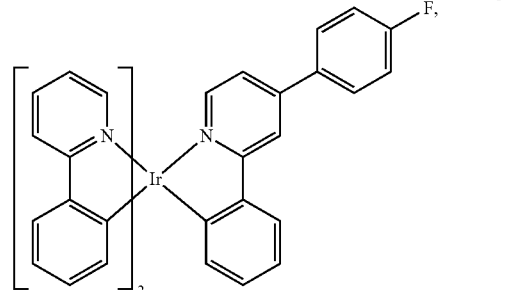
Compound 30
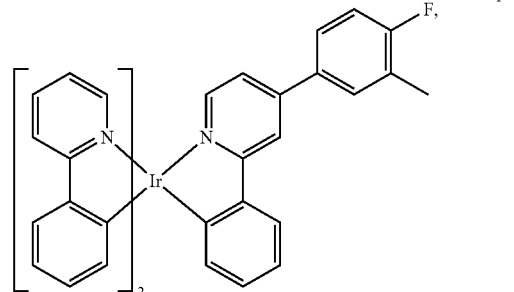
Compound 31
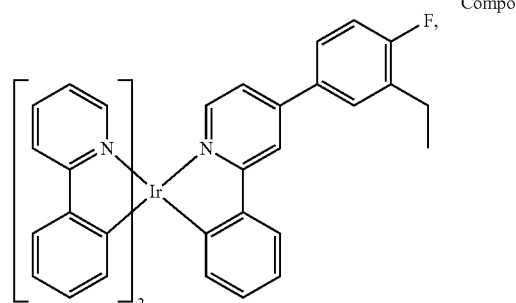
Compound 32
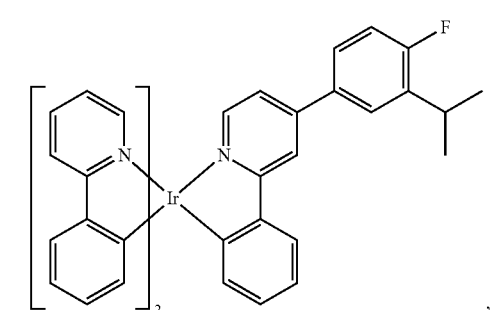

Compound 33
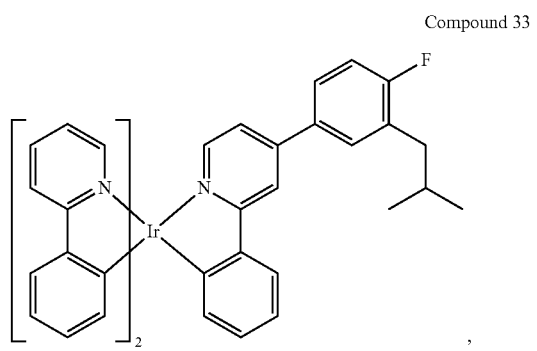
Compound 40
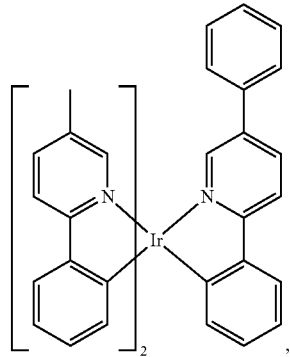
Compound 41
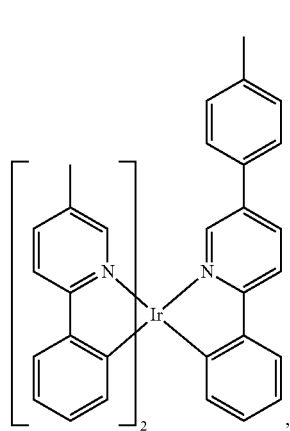
Compound 42
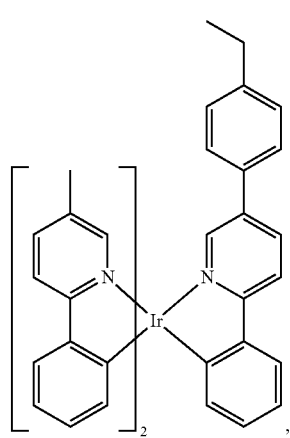
Compound 43
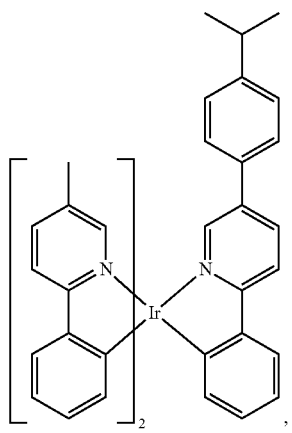
Compound 44
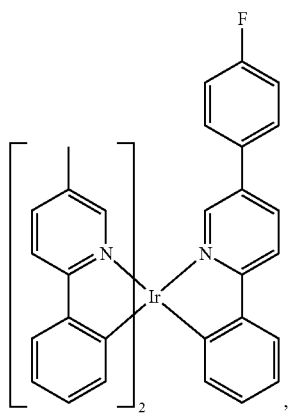
Compound 45
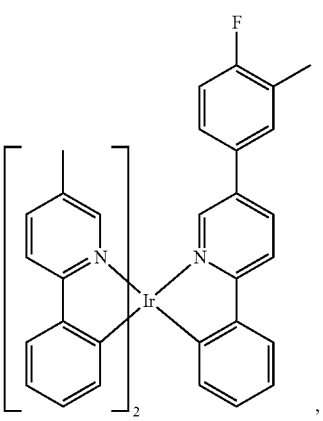

-continued
Compound 46
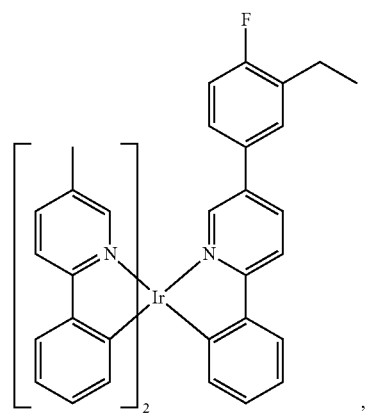,
Compound 47
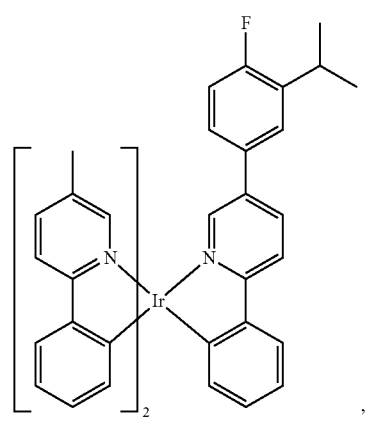,
Compound 48
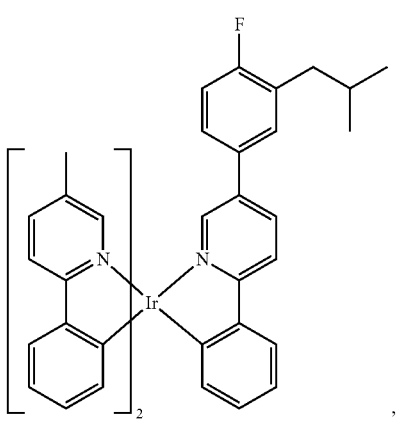,
Compound 53
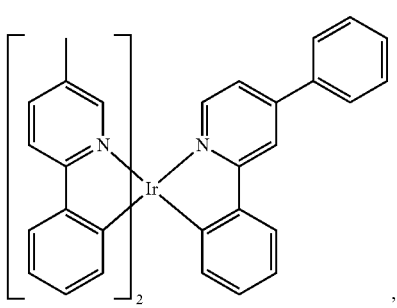,
-continued
Compound 54
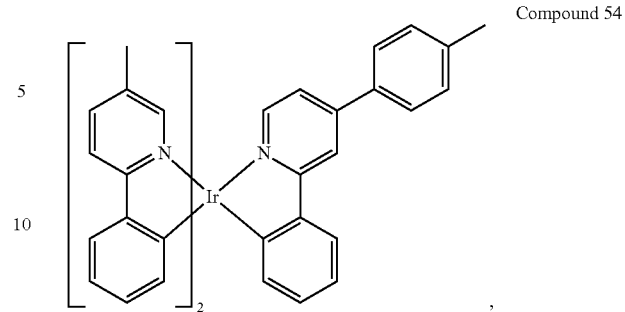,
Compound 55
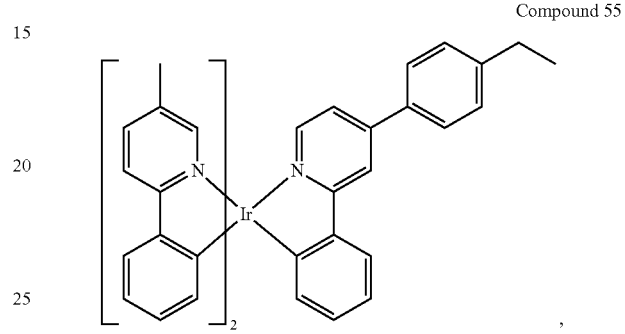,
Compound 56
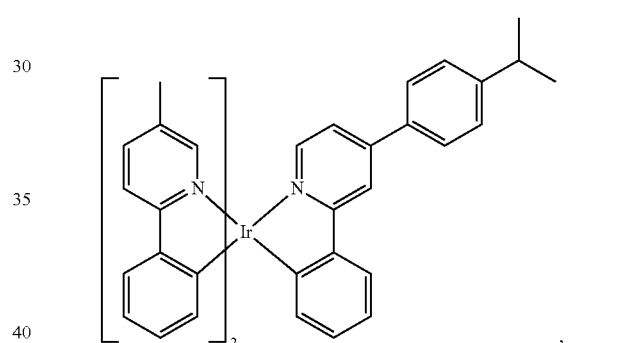,
Compound 57
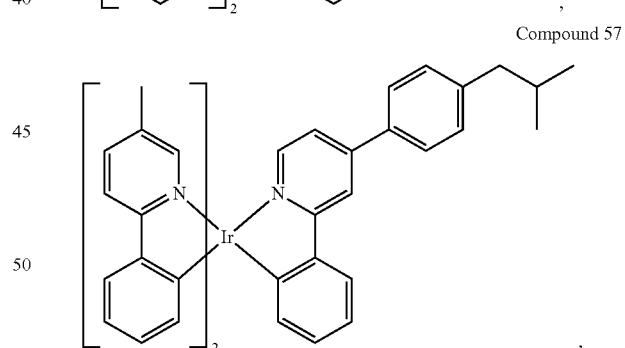,
Compound 58
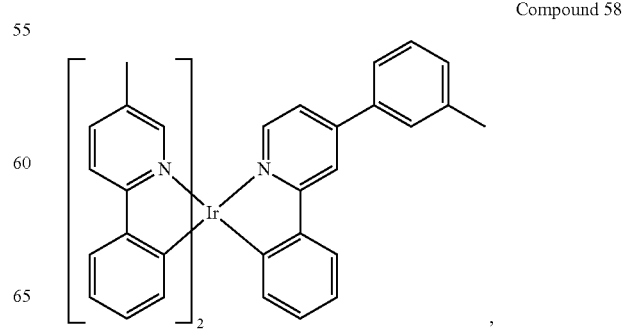, Compound 59
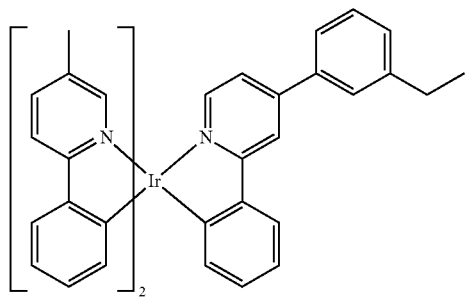
Compound 60
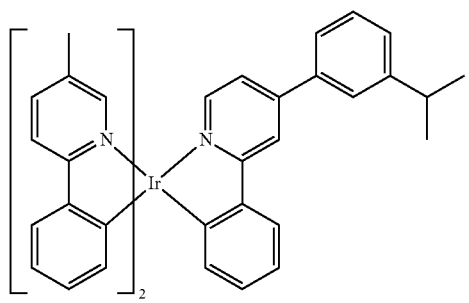
Compound 61
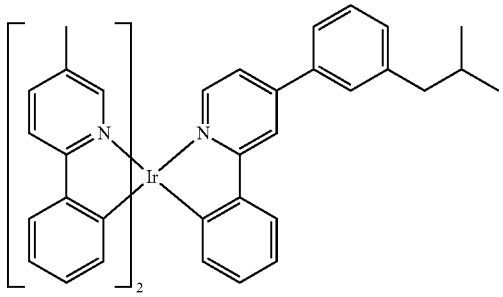
Compound 62
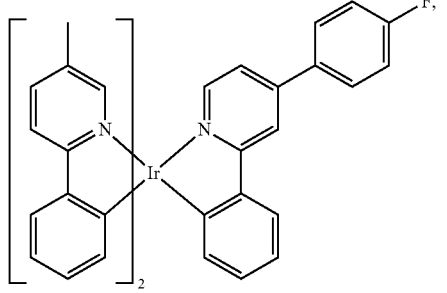
Compound 63
Compound 64
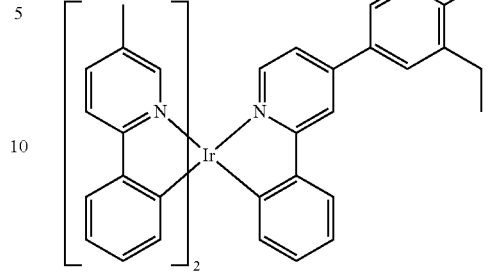
Compound 65
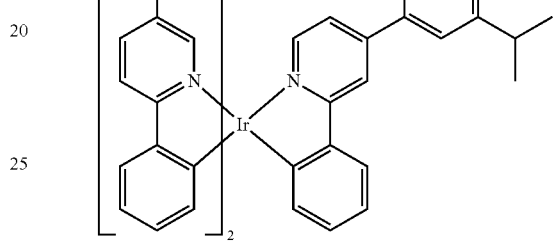
Compound 66
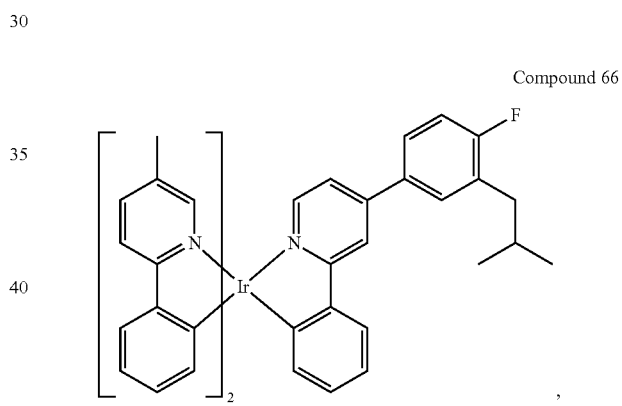
Compound 73
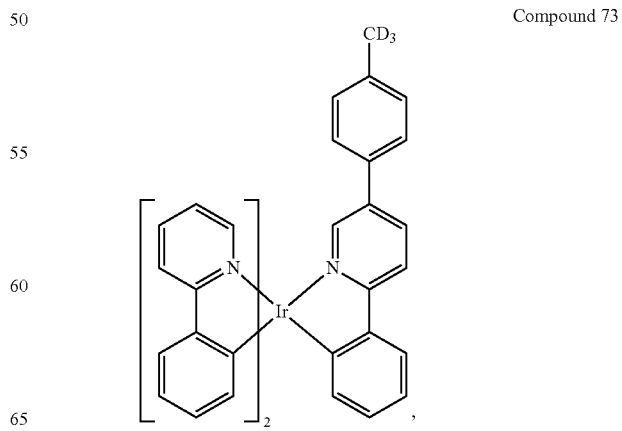

Compound 74
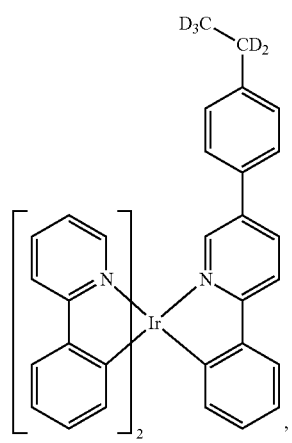
Compound 75
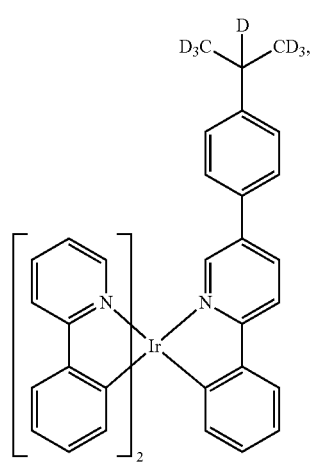
Compound 76
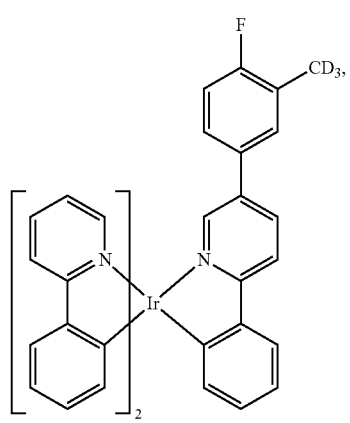
Compound 77
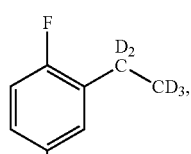
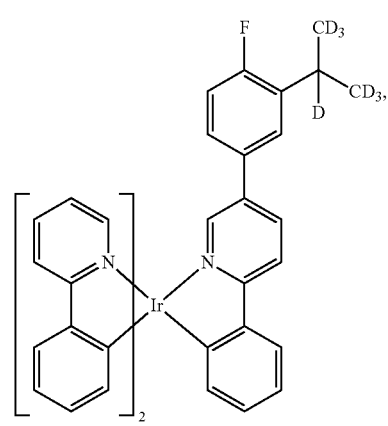
Compound 78
Compound 79
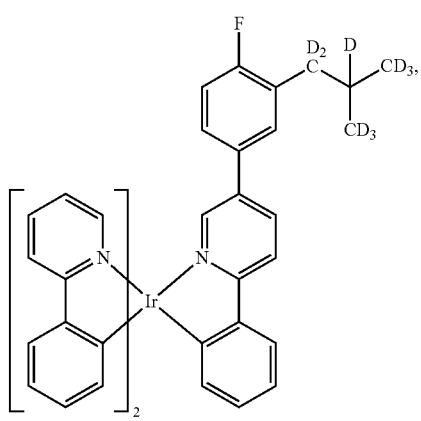
Compound 84
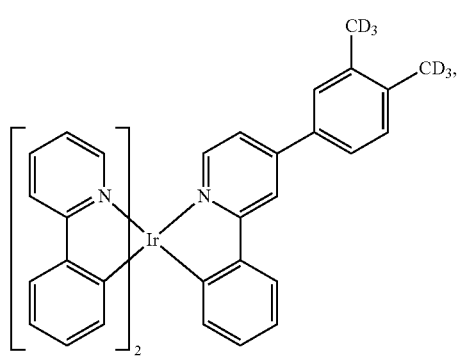

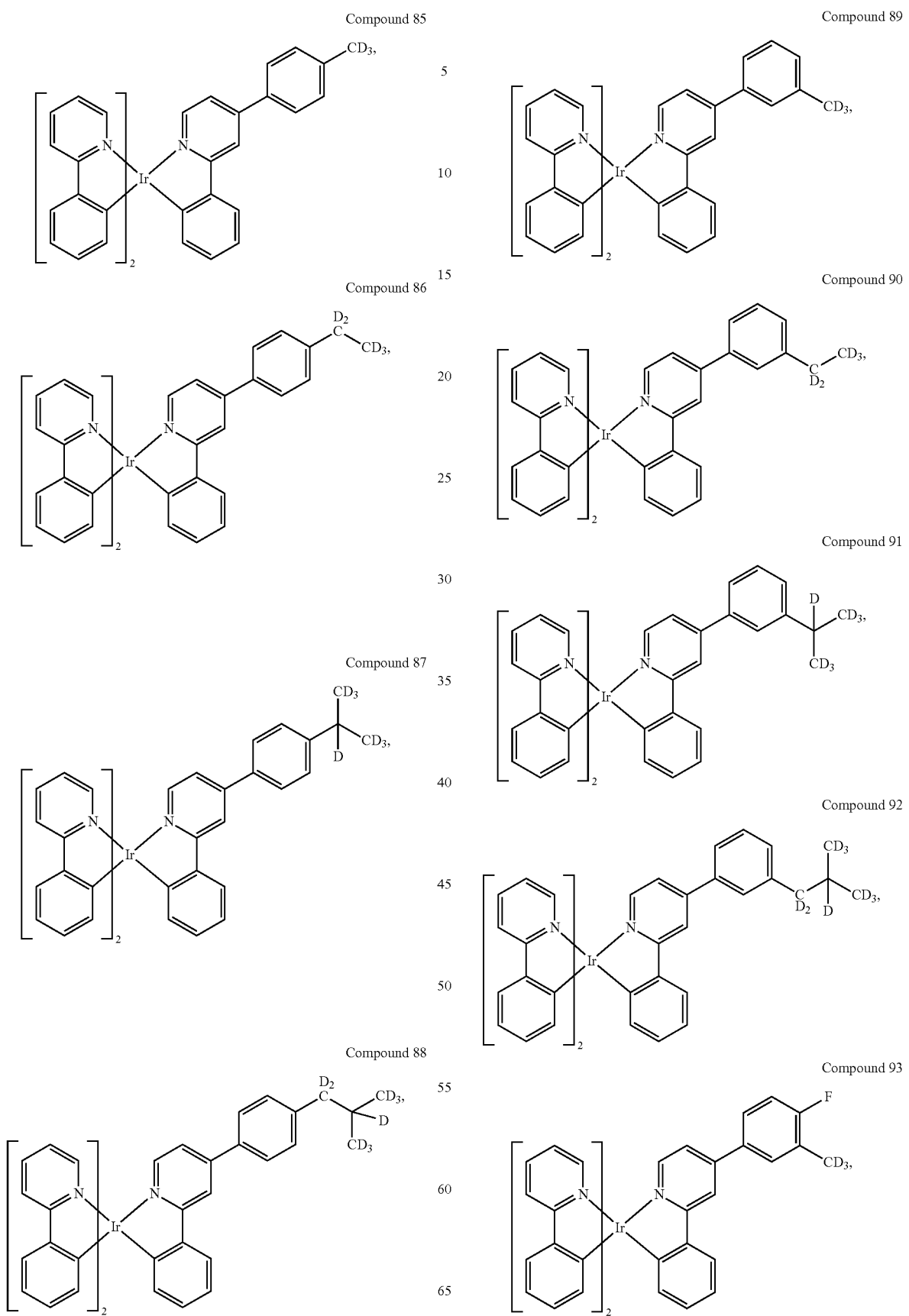

Compound 94
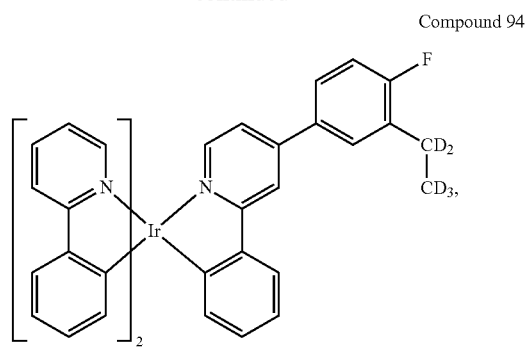
Compound 104
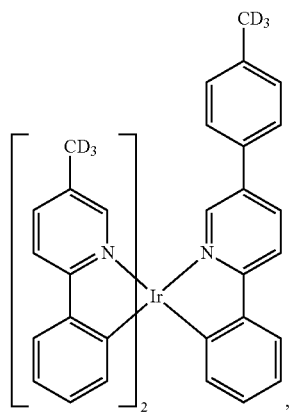
Compound 95
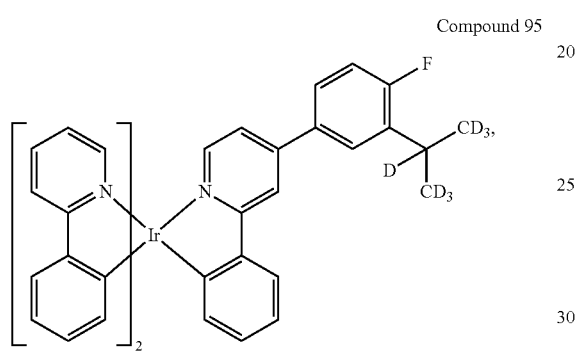
Compound 105
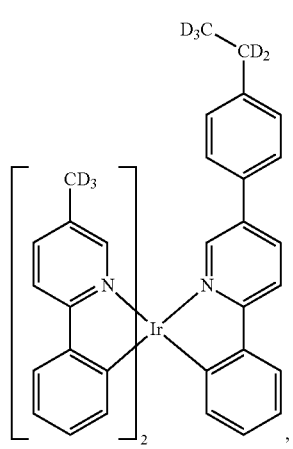
Compound 96
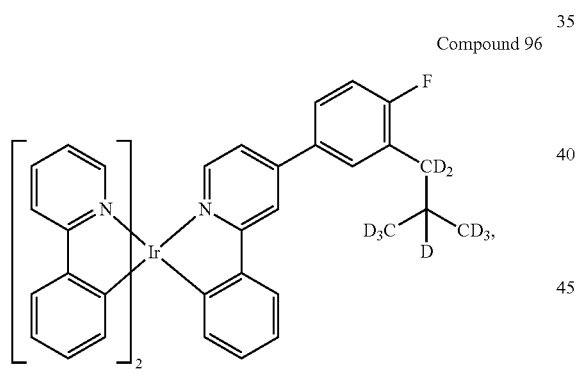
Compound 103
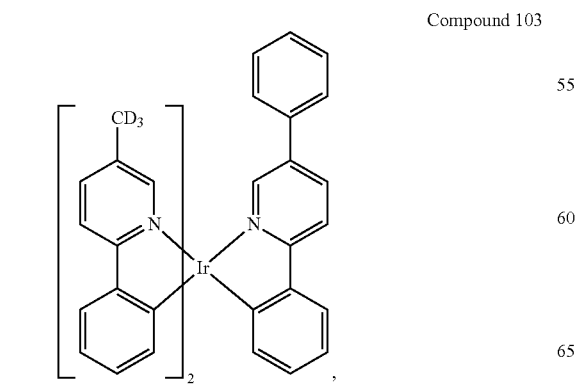
Compound 106
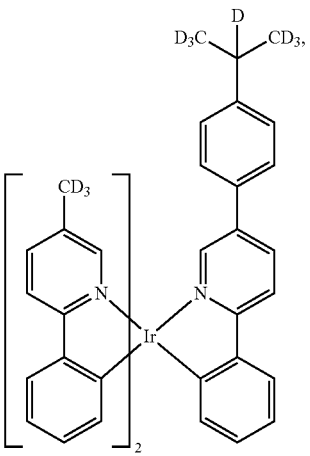

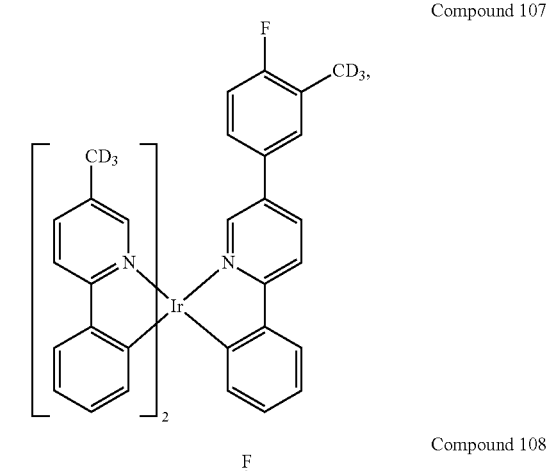
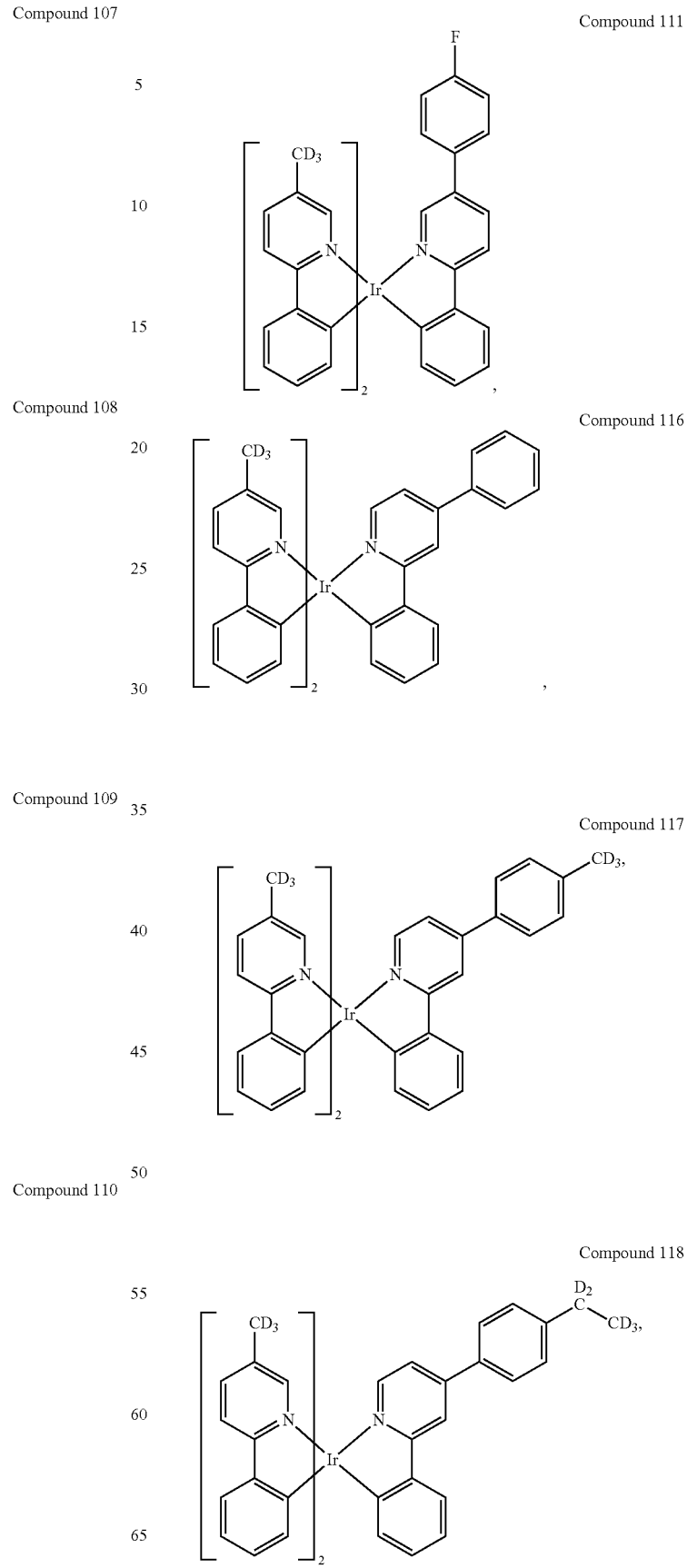

Compound 119

Compound 120

Compound 121

Compound 122

Compound 123

Compound 124

Compound 125

Compound 126

Compound 127

Compound 128
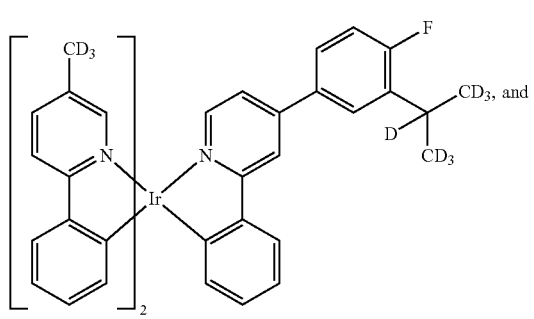
Compound 129
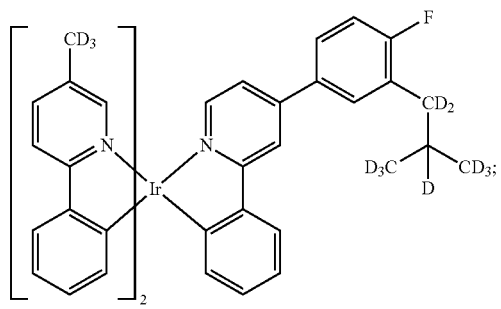
and
the second compound is selected from the group consisting of:
Compound 130
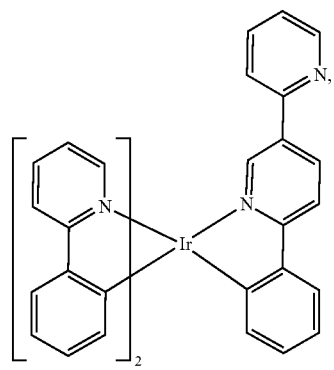
Compound 131
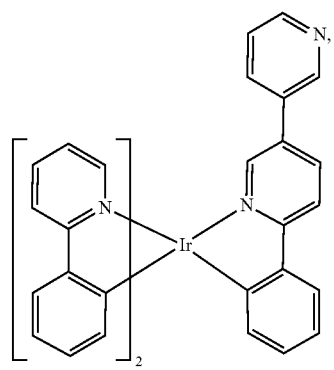
Compound 132
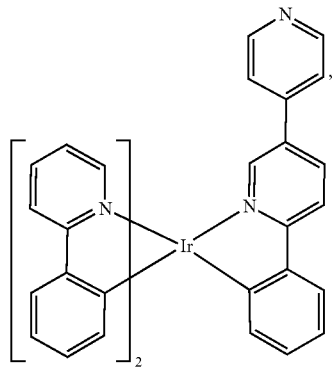
Compound 133
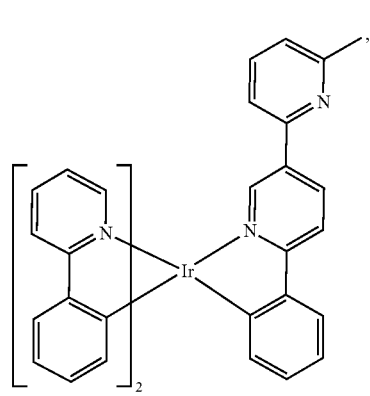
Compound 134
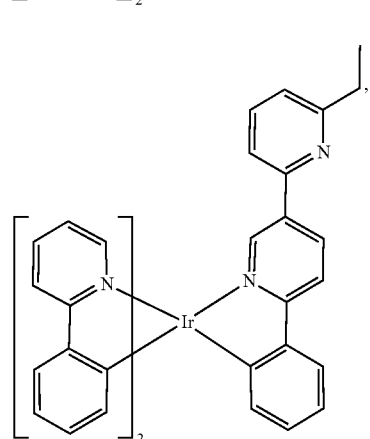
Compound 135
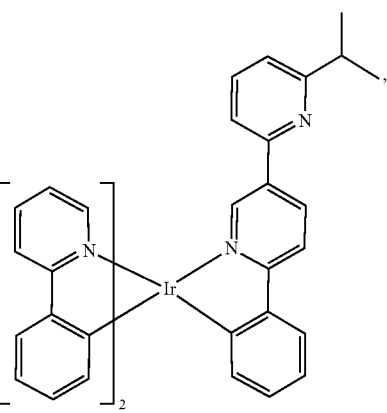

Compound 136
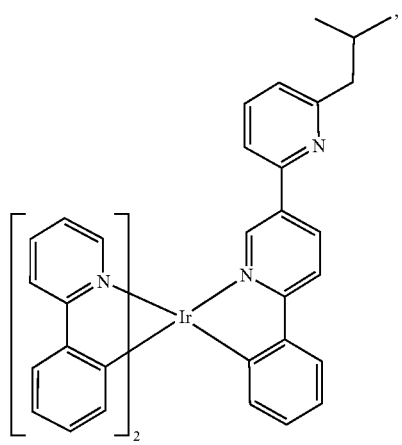
Compound 137
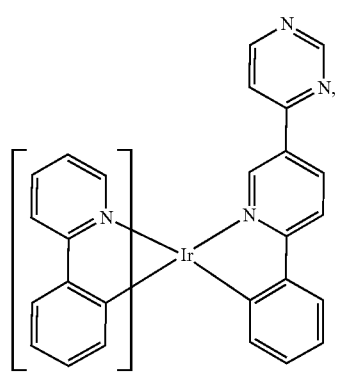
Compound 138
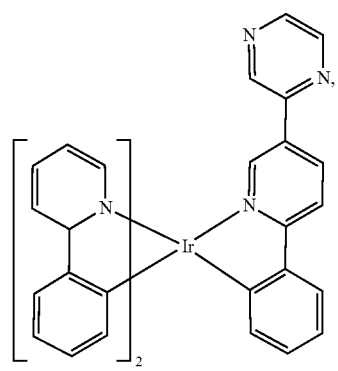
Compound 139
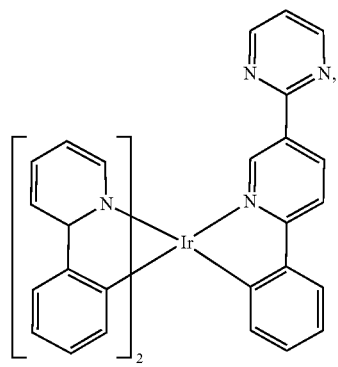
Compound 140
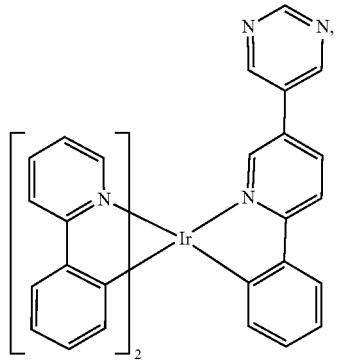
Compound 141
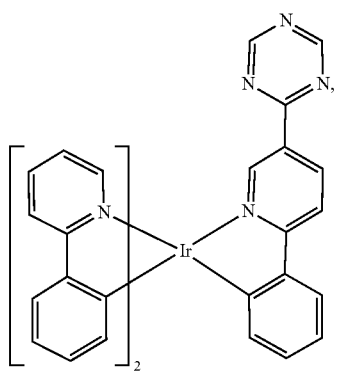
Compound 142
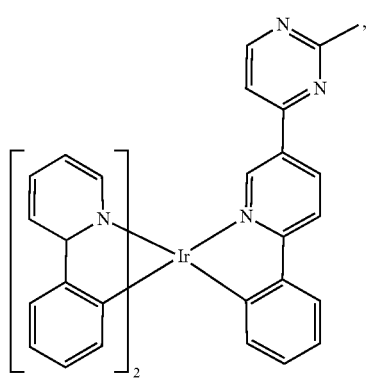
Compound 143
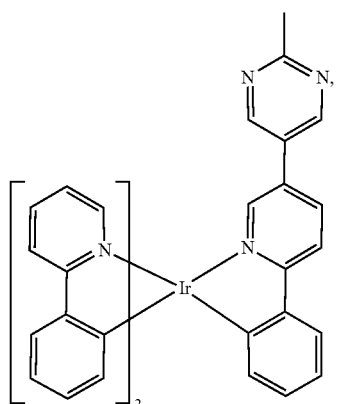

Compound 144
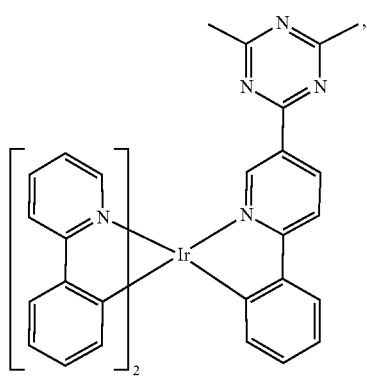
Compound 145
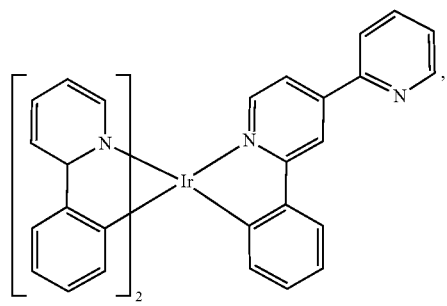
Compound 146
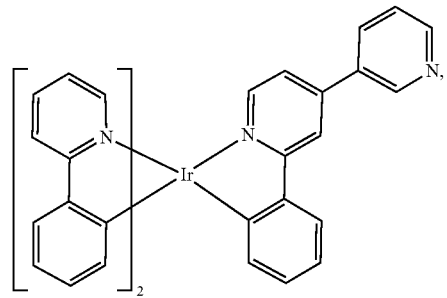
Compound 147
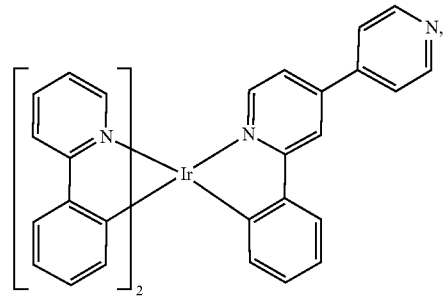
Compound 148
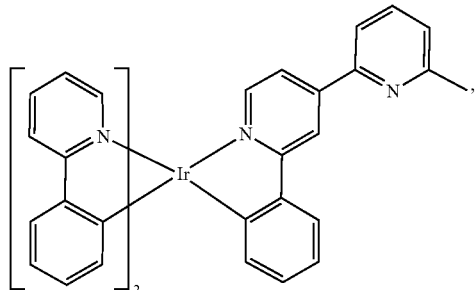
Compound 149
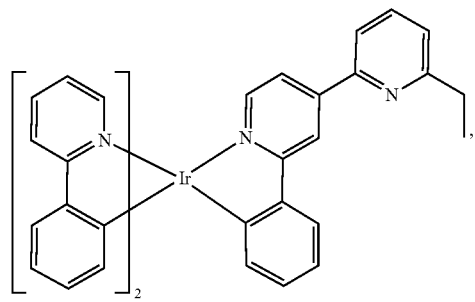
Compound 150
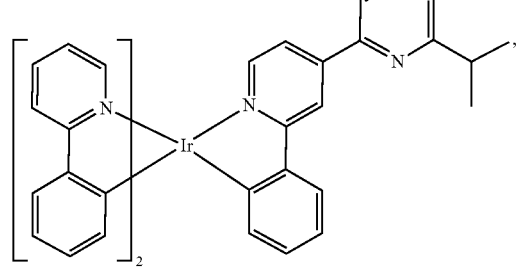
Compound 151
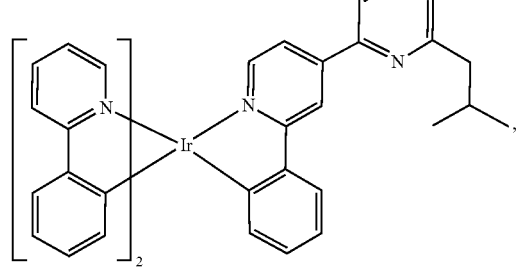
Compound 152
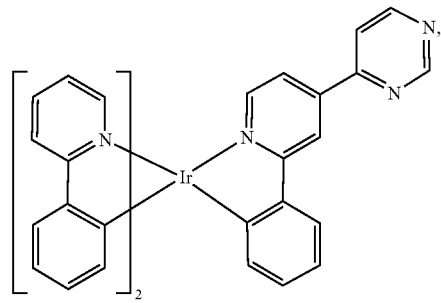

Compound 153
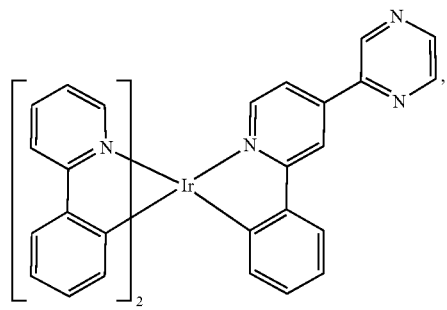
Compound 154
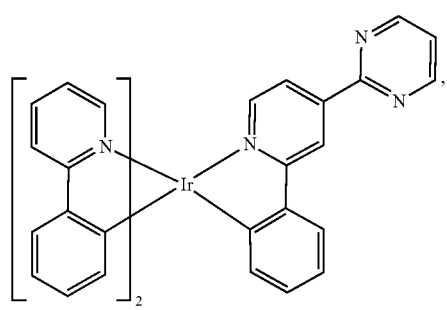
Compound 155
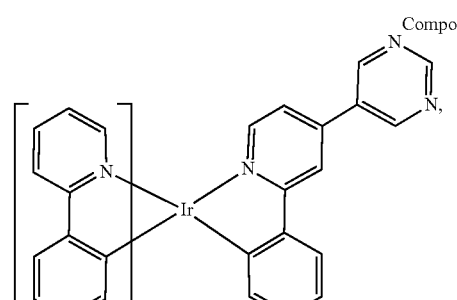
Compound 156
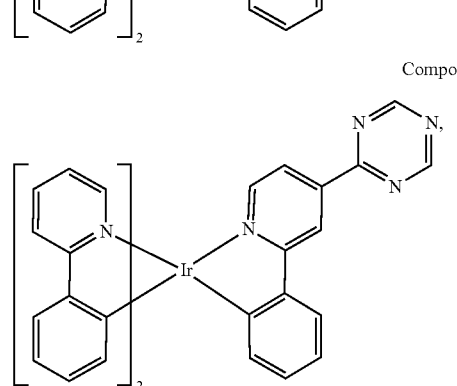
Compound 157
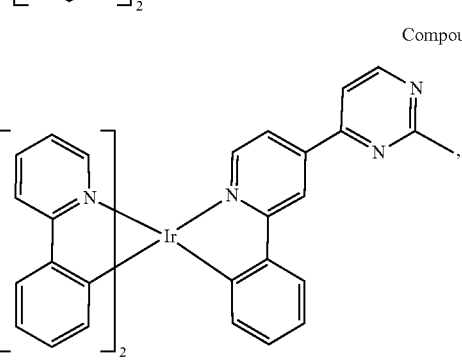
Compound 158
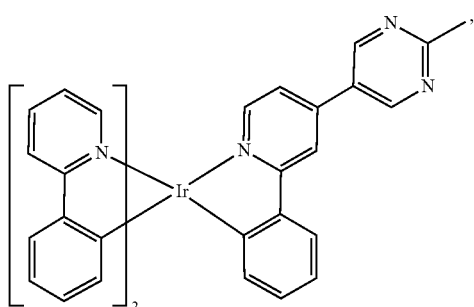
Compound 159
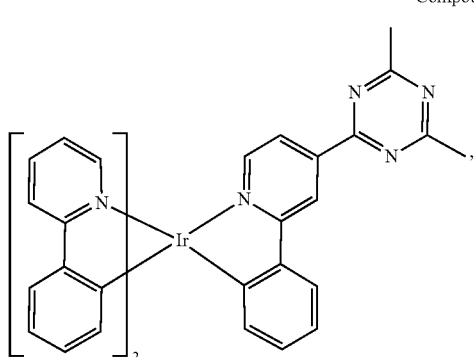
Compound 160
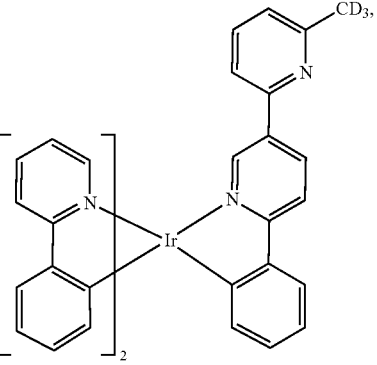
Compound 161
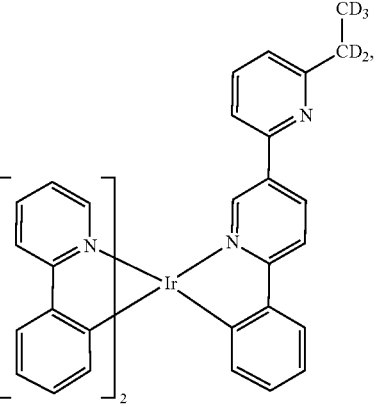

Compound 162
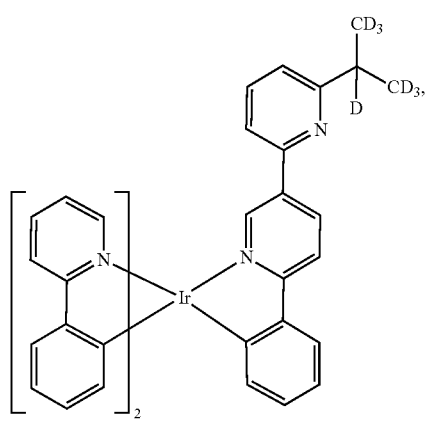
Compound 163
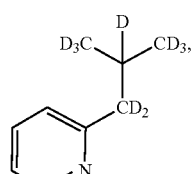
Compound 164
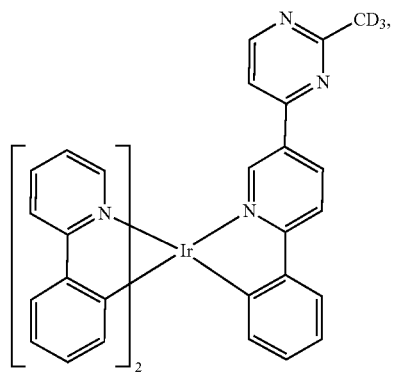
Compound 165
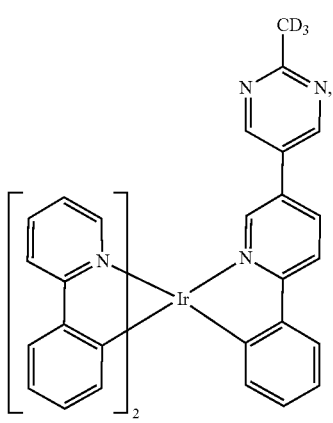
Compound 166
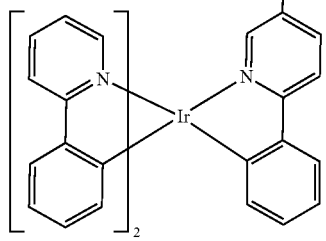
Compound 167
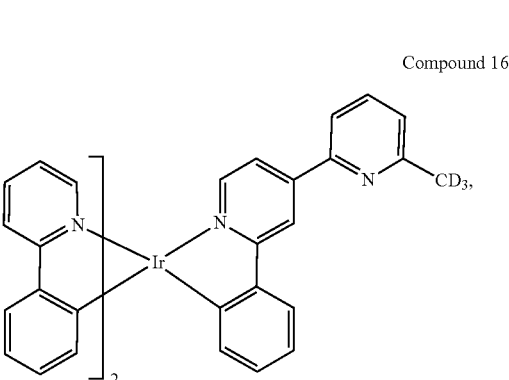
Compound 168
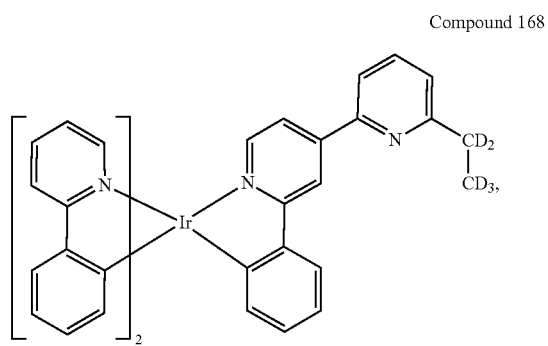

Compound 169
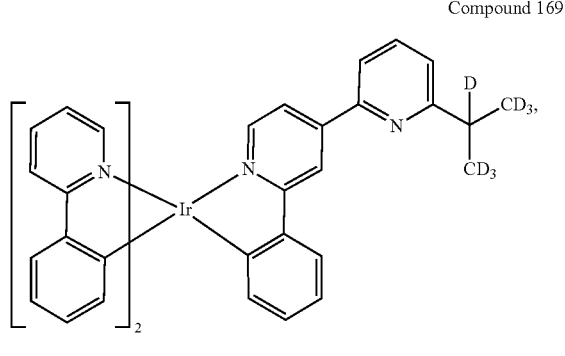
Compound 170
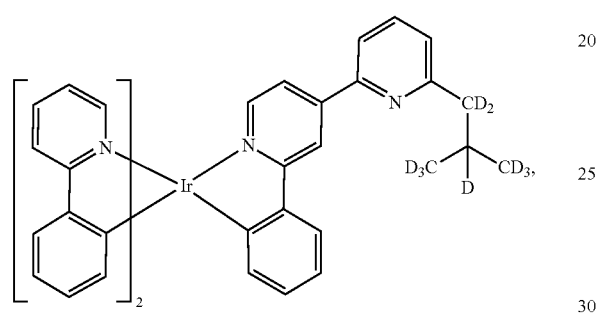
Compound 171
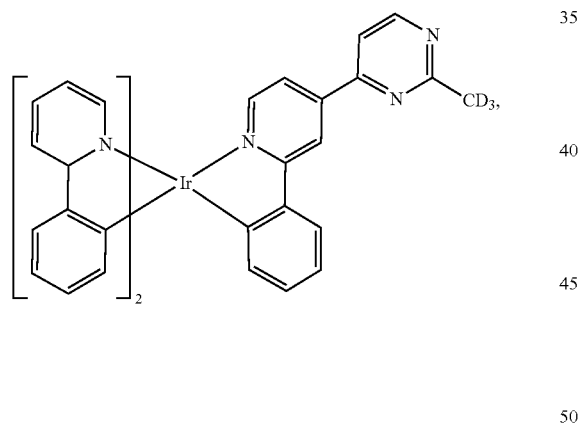
Compound 172
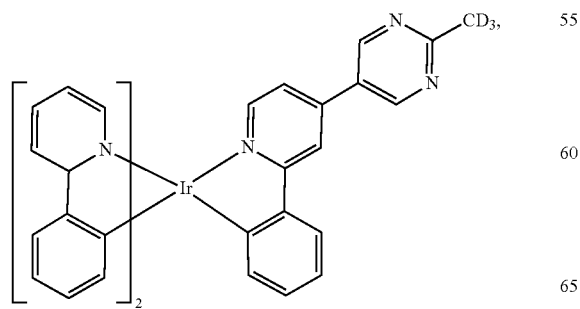
Compound 173
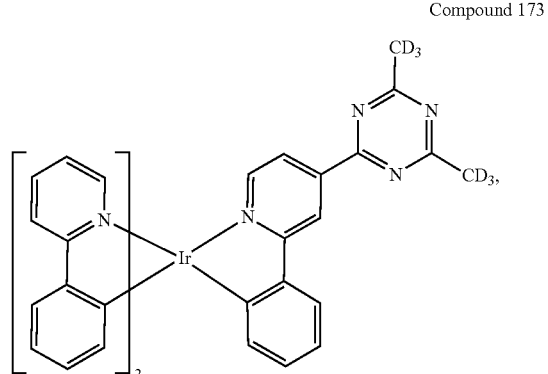
Compound 174
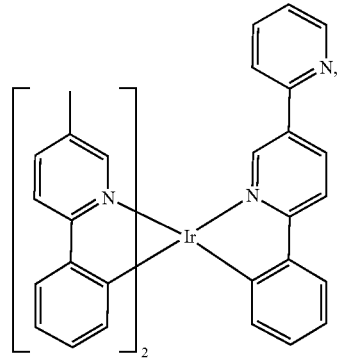
Compound 175
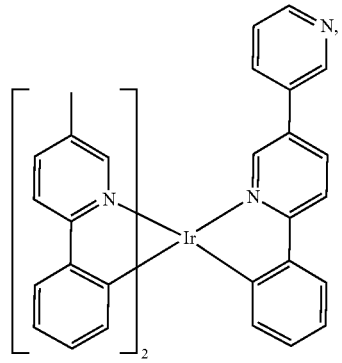
Compound 176
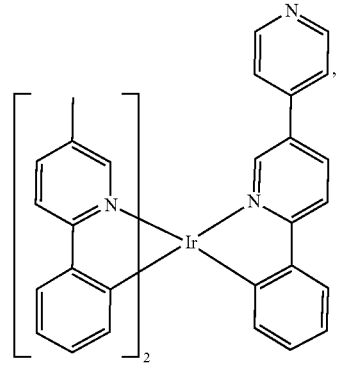

Compound 177
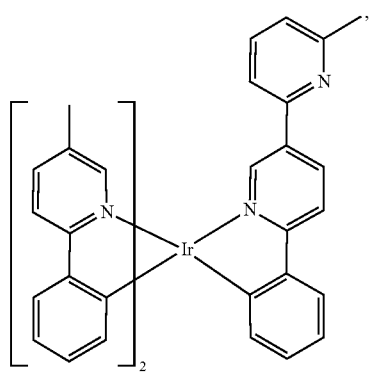
Compound 178
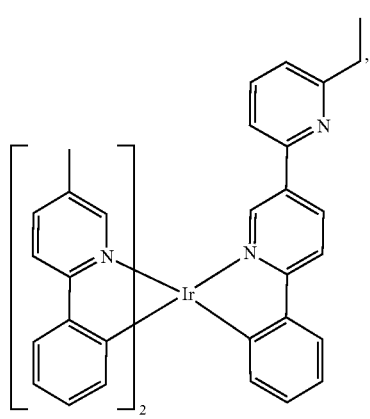
Compound 179
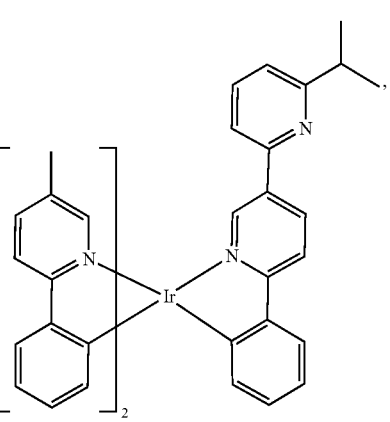
Compound 180
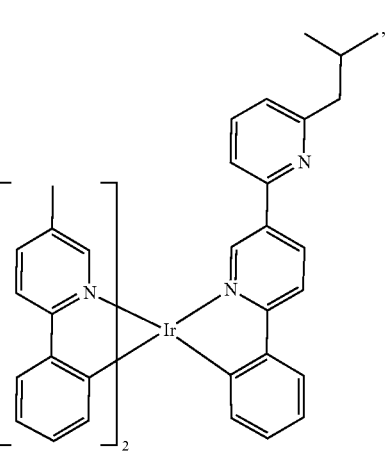
Compound 181
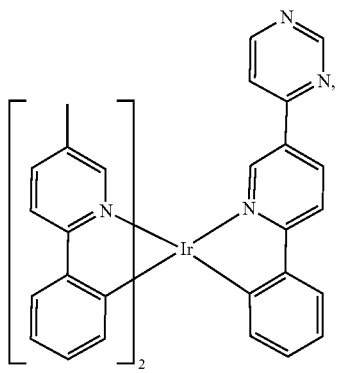
Compound 182
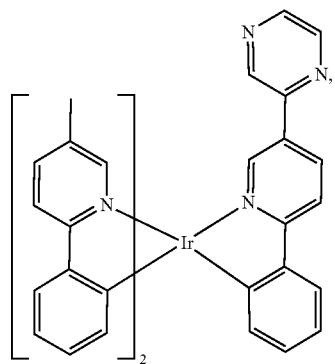
Compound 183
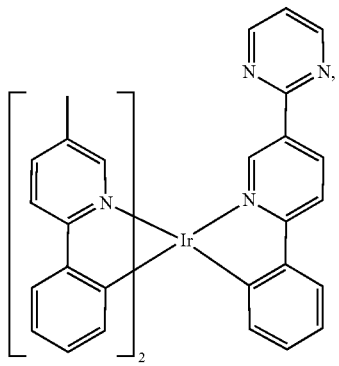
Compound 184
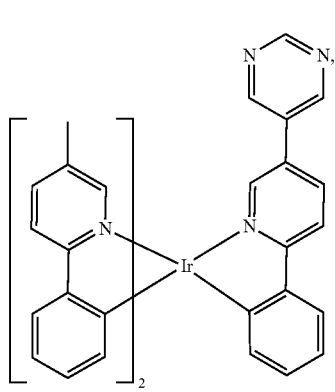

Compound 185
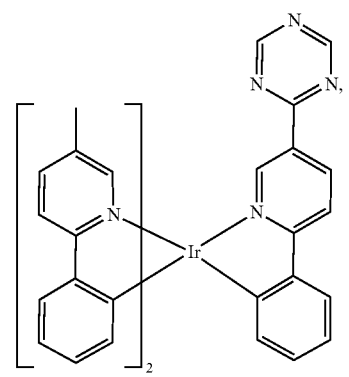
Compound 186
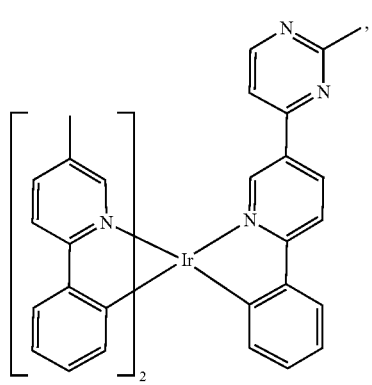
Compound 187
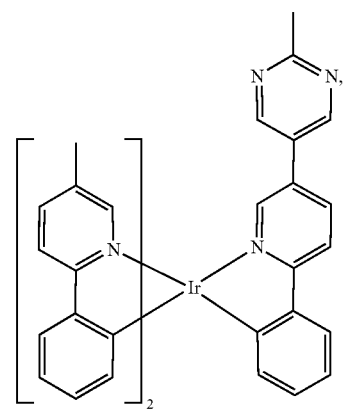
Compound 188
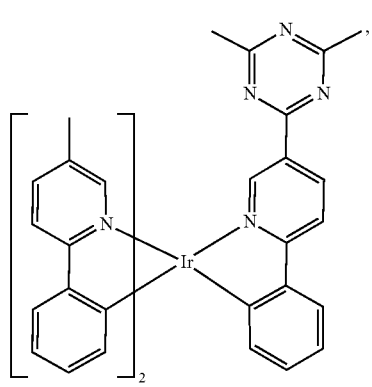
Compound 189
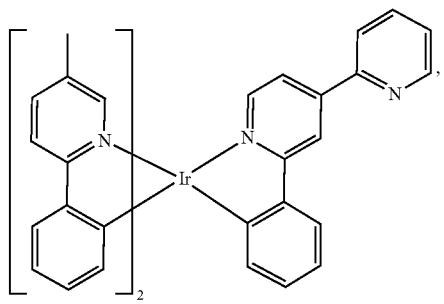
Compound 190
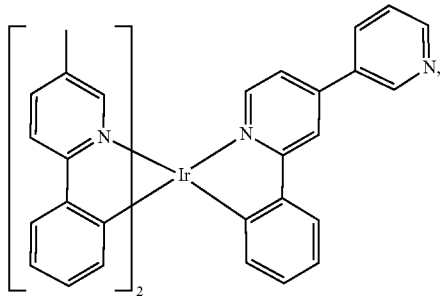
Compound 191
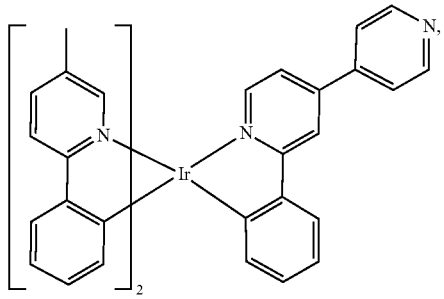
Compound 192
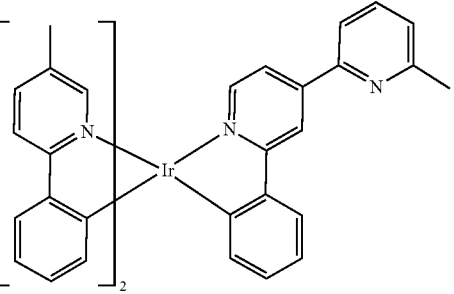
Compound 193
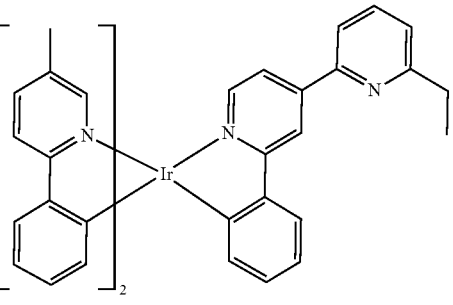

Compound 194
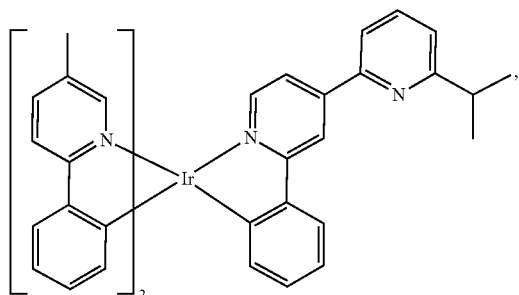
Compound 195
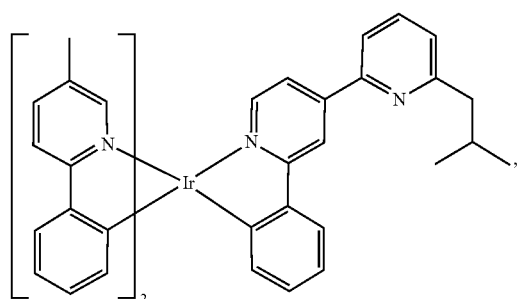
Compound 196
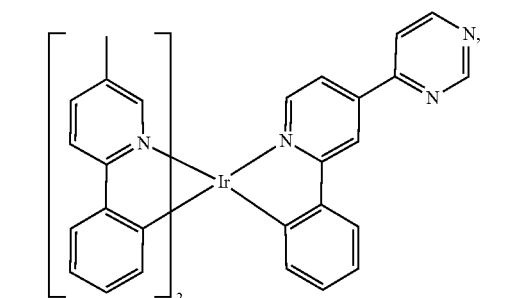
Compound 197
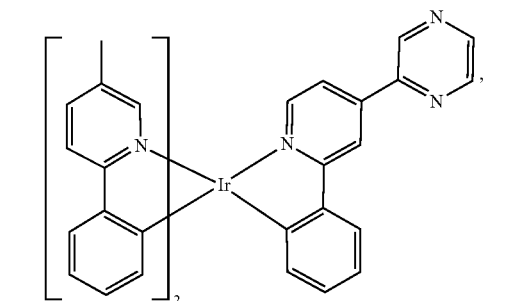
Compound 198
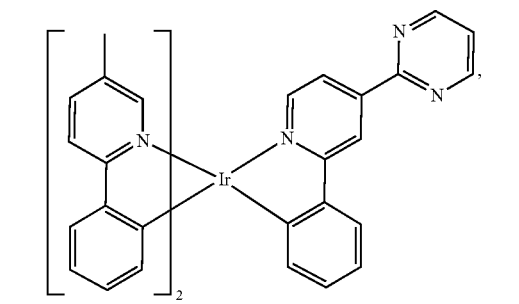
Compound 199
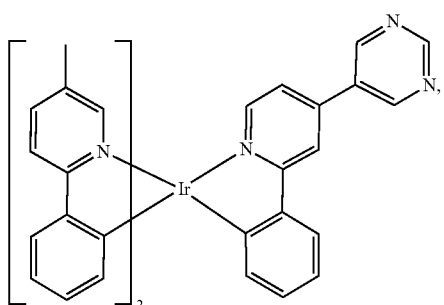
Compound 200
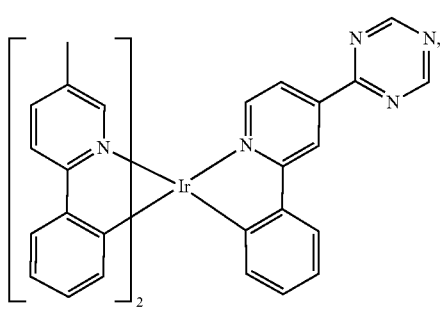
Compound 201
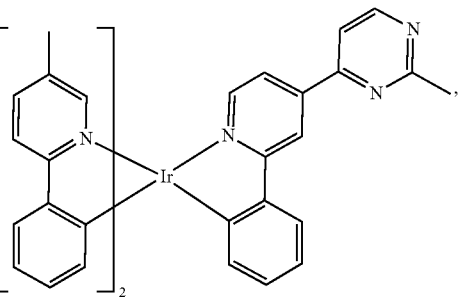
Compound 202
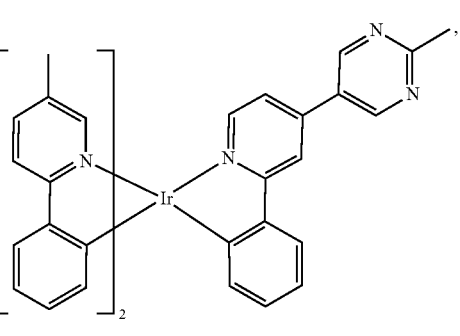

Compound 203
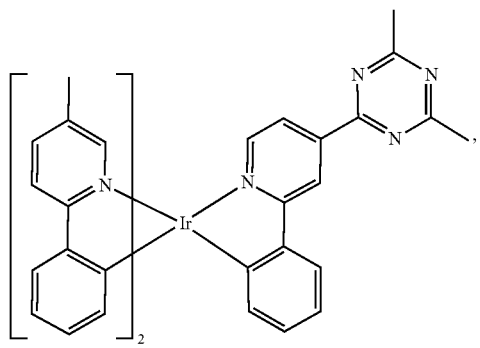
Compound 204
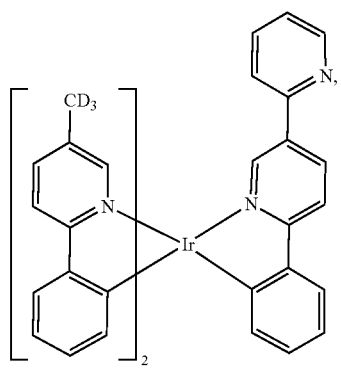
Compound 205
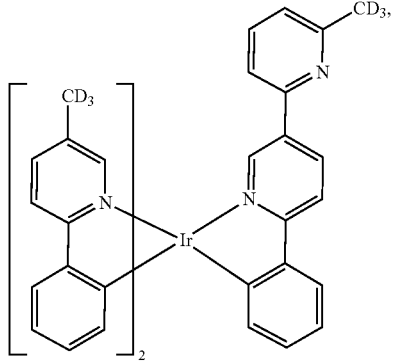
Compound 206
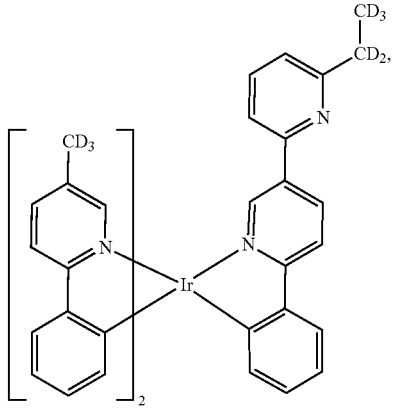
Compound 207
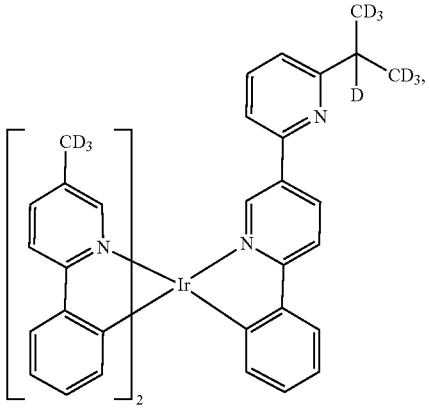
Compound 208
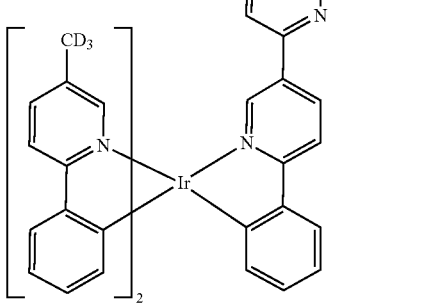
Compound 209
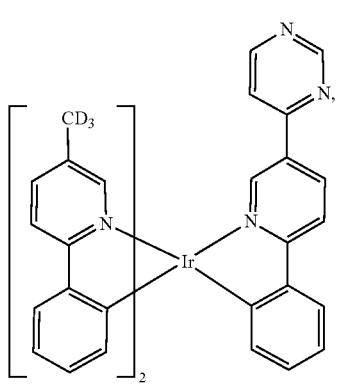
Compound 210
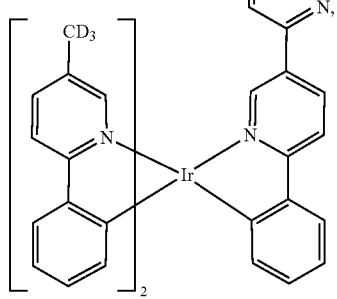

Compound 211
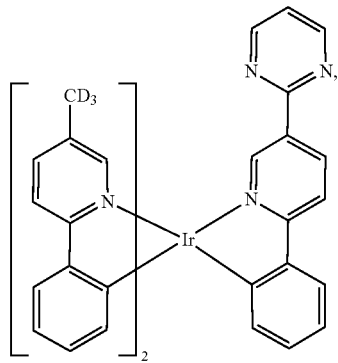
Compound 212
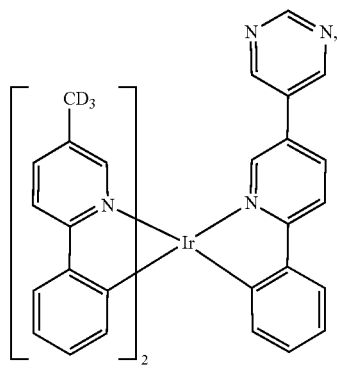
Compound 213
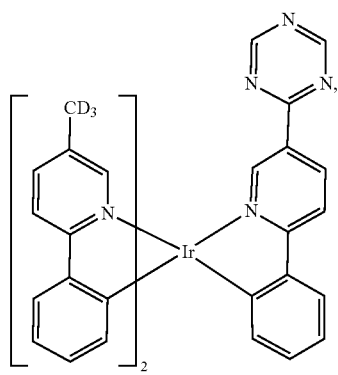
Compound 214
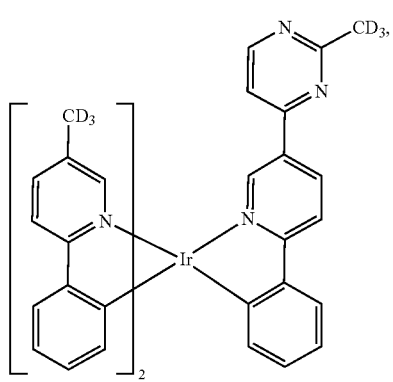
Compound 215
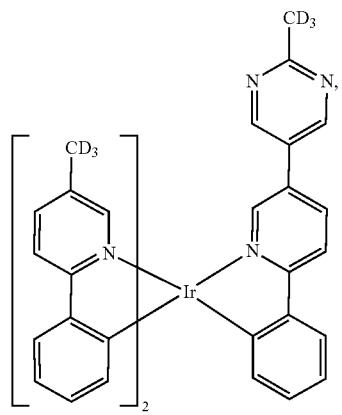
Compound 216
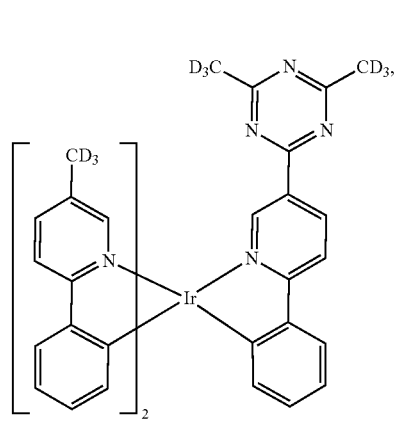
Compound 217
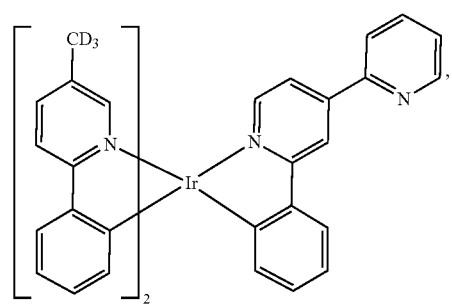
Compound 218
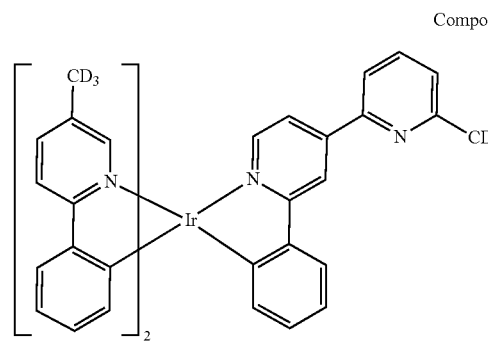

Compound 219
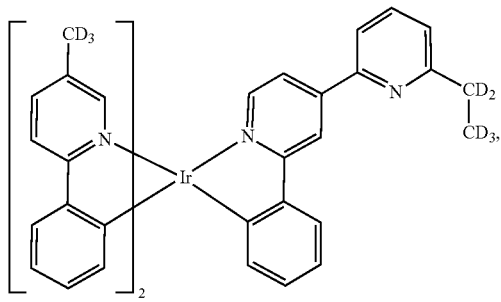
Compound 220
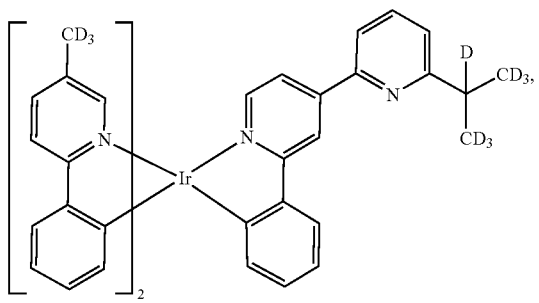
Compound 221
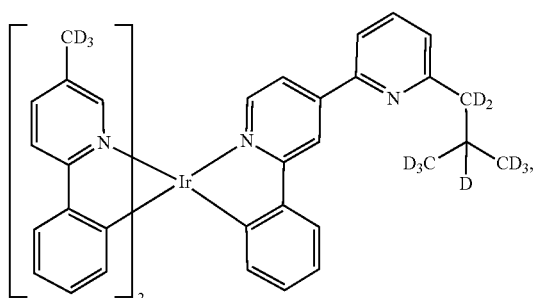
Compound 222
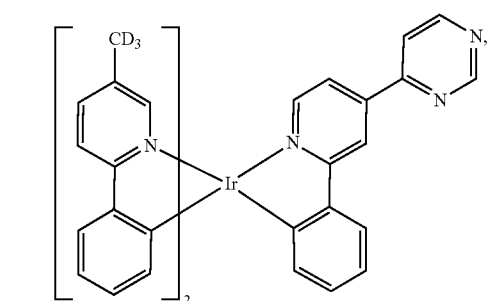
Compound 223
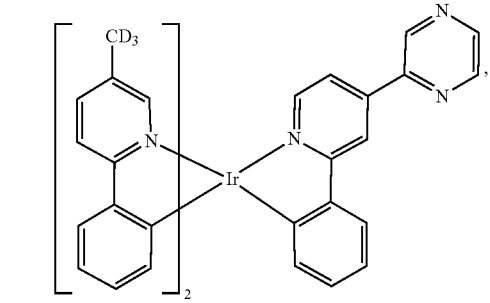
Compound 224
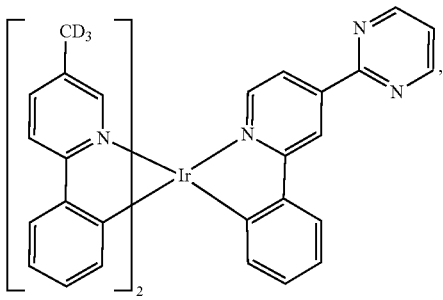
Compound 225
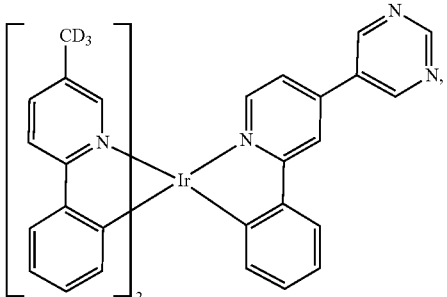
Compound 226
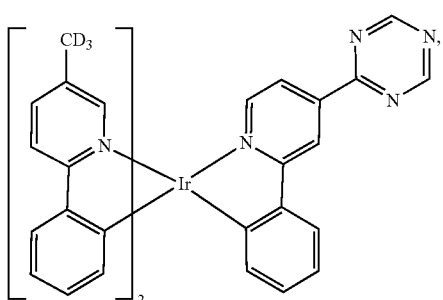
Compound 227
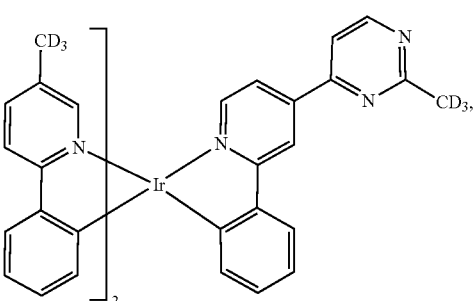
Compound 228
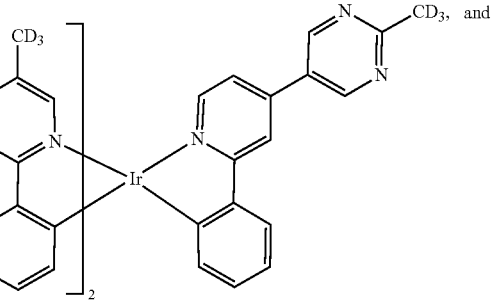

Compound 229

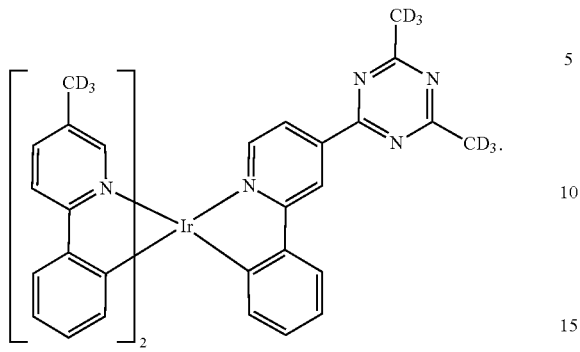

7. The premixed co-evaporation source composition of claim 6, wherein the mixture of the first compound and the second compound is selected from the group consisting of: (Compound 7 and Compound 130), (Compound 8 and Compound 131), (Compound 25 and Compound 131), (Compound 27 and Compound 135), (Compound 20 and Compound 145), (Compound 25 and Compound 148), (Compound 40 and Compound 174), (Compound 103 and Compound 204), and (Compound 116 and Compound 217).

* * * * *